United States Patent
Greenberg et al.

(12)

(10) Patent No.: US 11,452,750 B2
(45) Date of Patent: *Sep. 27, 2022

(54) ONCOLYTIC VIRAL VECTORS AND USES THEREOF

(71) Applicant: Oncorus, Inc., Cambridge, MA (US)

(72) Inventors: Kenneth P. Greenberg, Cambridge, MA (US); Mitchell H. Finer, Cambridge, MA (US)

(73) Assignee: Oncorus, Inc., Cambridge, MA (US)

( * ) Notice: Subject to any disclaimer, the term of this patent is extended or adjusted under 35 U.S.C. 154(b) by 500 days.

This patent is subject to a terminal disclaimer.

(21) Appl. No.: 16/507,789

(22) Filed: Jul. 10, 2019

(65) Prior Publication Data

US 2020/0147156 A1 May 14, 2020

Related U.S. Application Data

(63) Continuation of application No. 16/047,499, filed on Jul. 27, 2018, now Pat. No. 10,391,132, which is a continuation of application No. PCT/US2017/015417, filed on Jan. 27, 2017.

(60) Provisional application No. 62/287,619, filed on Jan. 27, 2016.

(51) Int. Cl.
*A61K 35/763* (2015.01)
*A61P 35/00* (2006.01)
*C12N 15/113* (2010.01)

(52) U.S. Cl.
CPC ............ *A61K 35/763* (2013.01); *A61P 35/00* (2018.01); *C12N 15/113* (2013.01); *C12N 15/1133* (2013.01); *C12N 2310/113* (2013.01); *C12N 2310/141* (2013.01); *C12N 2320/30* (2013.01); *C12N 2330/51* (2013.01); *C12N 2710/16621* (2013.01); *C12N 2710/16632* (2013.01); *C12N 2710/16662* (2013.01)

(58) Field of Classification Search
None
See application file for complete search history.

(56) References Cited

U.S. PATENT DOCUMENTS

| | | | |
|---|---|---|---|
| 5,059,538 A | 10/1991 | Nozaki et al. | |
| 5,399,363 A | 3/1995 | Liversidge et al. | |
| 5,466,468 A | 11/1995 | Schneider et al. | |
| 5,543,158 A | 8/1996 | Gref et al. | |
| 5,641,515 A | 6/1997 | Ramtoola | |
| 5,658,724 A | 8/1997 | DeLuca | |
| 5,780,045 A | 1/1998 | McQuinn et al. | |
| 5,725,871 A | 3/1998 | Illum | |
| 5,756,353 A | 5/1998 | Debs | |
| 5,759,814 A | 6/1998 | Burke et al. | |
| 5,804,212 A | 9/1998 | Illum | |
| 5,804,413 A | 9/1998 | DeLuca | |
| 5,837,532 A | 11/1998 | Preston et al. | |
| 5,849,571 A | 12/1998 | Glorioso et al. | |
| 5,849,572 A | 12/1998 | Glorioso et al. | |
| 5,879,934 A | 3/1999 | DeLuca | |
| 5,998,174 A | 12/1999 | Glorioso et al. | |
| 6,071,742 A | 6/2000 | Tracy et al. | |
| 6,261,552 B1 | 7/2001 | DeLuca | |
| 6,469,155 B1 | 10/2002 | Fiume et al. | |
| 6,653,447 B1 | 11/2003 | Cosman et al. | |
| 7,078,029 B2 | 7/2006 | DeLuca | |
| 7,473,418 B2 | 1/2009 | Yu et al. | |
| 7,514,252 B2 | 4/2009 | Chiocca et al. | |
| 7,531,167 B2 | 5/2009 | Glorioso, III et al. | |
| 8,129,167 B2 | 3/2012 | Cosman | |
| 8,546,553 B2 | 10/2013 | Terns et al. | |
| 8,957,036 B2 | 2/2015 | Cascio et al. | |
| 8,980,246 B2 | 3/2015 | Kirn | |
| 9,157,071 B2 | 10/2015 | Capmadelli et al. | |
| 9,226,977 B2 | 1/2016 | Kirn | |
| 9,593,347 B2 | 3/2017 | Glorioso, III et al. | |
| 9,919,062 B2 | 3/2018 | Kirn | |
| 10,172,893 B2 | 1/2019 | Uchida et al. | |
| 10,188,686 B2 | 1/2019 | Uchida et al. | |
| 10,201,575 B2 | 2/2019 | Uchida et al. | |
| 2002/0037575 A1 | 3/2002 | Speck | |
| 2002/0187126 A1 | 12/2002 | Blaho et al. | |
| 2008/0008686 A1 | 1/2008 | Yao | |
| 2008/0289058 A1 | 11/2008 | Cascio et al. | |
| 2009/0136452 A1 | 5/2009 | Zhou et al. | |
| 2010/0041737 A1 | 2/2010 | Naldini et al. | |

(Continued)

FOREIGN PATENT DOCUMENTS

AU 2012322999 B2 8/2017
AU 2017206231 B2 2/2019

(Continued)

OTHER PUBLICATIONS

Jenkins et al., "Deletion of the Herpes simplex 1 internal repeat sequences affects pathogenicity in the mouse," Frontiers in Bioscience, Oct. 1996, 1:a59-68.

(Continued)

*Primary Examiner* — Robert M Kelly
(74) *Attorney, Agent, or Firm* — Cooley LLP

(57) ABSTRACT

The present disclosure relates to recombinant viral vectors for the treatment and prevention of cancer. Oncolytic viral vectors incorporate one or more of the following features: viral replication restriction by insertion of tumor-suppressive microRNA (miRNA) target sequences into the viral genome; disruption of oncogenic miRNA function; cancer microenvironment remodeling; and cancer cell targeting by incorporation of protease-activated antibodies into the viral particle.

31 Claims, 39 Drawing Sheets

Specification includes a Sequence Listing.

(56) References Cited

U.S. PATENT DOCUMENTS

| | | |
|---|---|---|
| 2010/0076057 A1 | 3/2010 | Sontheimer et al. |
| 2010/0093617 A1 | 4/2010 | Barrangou et al. |
| 2010/0104578 A1 | 4/2010 | Shafren |
| 2010/0233141 A1 | 9/2010 | Polach et al. |
| 2010/0257638 A1 | 10/2010 | Cai et al. |
| 2011/0213017 A1 | 9/2011 | Cascio et al. |
| 2011/0217739 A1 | 9/2011 | Terns et al. |
| 2011/0300538 A1 | 12/2011 | Barrangou et al. |
| 2012/0277120 A1 | 11/2012 | Serber et al. |
| 2013/0011828 A1 | 1/2013 | Barrangou et al. |
| 2013/0071430 A1 | 3/2013 | Nakamura et al. |
| 2013/0096186 A1 | 4/2013 | Glorioso, III et al. |
| 2013/0156808 A1 | 6/2013 | Jonjic |
| 2013/0288251 A1 | 10/2013 | Horvath et al. |
| 2014/0255313 A1 | 9/2014 | Vasiljeva et al. |
| 2015/0017121 A1 | 1/2015 | Becher et al. |
| 2016/0153000 A1 | 6/2016 | Glorioso et al. |
| 2016/0175462 A1 | 6/2016 | Zhang et al. |
| 2016/0250267 A1 | 9/2016 | Evnin |
| 2017/0000832 A1 | 1/2017 | Shafren et al. |
| 2017/0035819 A1 | 2/2017 | Uchida et al. |
| 2017/0081384 A1 | 3/2017 | Cascio et al. |
| 2017/0157188 A1 | 6/2017 | Silvestre et al. |
| 2017/0107537 A1 | 7/2017 | Glorioso, III et al. |
| 2017/0189514 A1 | 7/2017 | Glorioso, III et al. |
| 2017/0274025 A1 | 9/2017 | Uchida et al. |
| 2017/0274057 A1 | 9/2017 | Jonjic |
| 2018/0169241 A1 | 6/2018 | Cantwell |
| 2018/0169271 A1 | 6/2018 | Cantwell et al. |
| 2018/0215794 A1 | 8/2018 | Russell et al. |
| 2018/0318365 A1 | 11/2018 | Yeung et al. |
| 2018/0339004 A1 | 11/2018 | Greenberg et al. |
| 2019/0070233 A1 | 3/2019 | Yeung et al. |
| 2019/0201493 A1 | 7/2019 | Becher et al. |
| 2019/0026241 A1 | 8/2019 | Uchida et al. |
| 2020/0206285 A1 | 7/2020 | Finer |
| 2020/0405792 A1 | 12/2020 | Zhou et al. |

FOREIGN PATENT DOCUMENTS

| | | |
|---|---|---|
| CA | 2850575 A1 | 4/2013 |
| EP | 2591796 A1 | 5/2013 |
| EP | 2766035 B1 | 3/2018 |
| EP | 3351261 A1 | 7/2018 |
| EP | 3441084 A1 | 2/2019 |
| JP | 2001-508294 | 6/2001 |
| JP | 2003-518080 | 6/2003 |
| JP | 2009-060907 A | 3/2009 |
| KR | 2003-0047667 A | 6/2003 |
| WO | WO 91/02788 A1 | 3/1991 |
| WO | WO 96/04394 A1 | 2/1996 |
| WO | WO 98/15637 A1 | 4/1998 |
| WO | WO 99/06583 A1 | 2/1999 |
| WO | WO 2005/092374 A2 | 10/2005 |
| WO | WO 2006/017914 A1 | 2/2006 |
| WO | WO 2007/025097 A2 | 3/2007 |
| WO | WO 2008/021207 A2 | 2/2008 |
| WO | WO 2008/141151 A2 | 11/2008 |
| WO | WO 2008/143875 A1 | 11/2008 |
| WO | WO 2009/111892 A1 | 9/2009 |
| WO | WO 2009/144755 A1 | 12/2009 |
| WO | WO 2009/148488 A2 | 12/2009 |
| WO | WO 2009/150431 A1 | 12/2009 |
| WO | WO 2010/011961 A2 | 1/2010 |
| WO | WO 2010/054108 A2 | 5/2010 |
| WO | WO 2010/054154 A2 | 5/2010 |
| WO | WO 2010/135242 A1 | 11/2010 |
| WO | WO 2011/125469 A1 | 10/2011 |
| WO | WO 2011/130749 A2 | 10/2011 |
| WO | WO 2012/006181 A2 | 1/2012 |
| WO | WO 2012/054726 A1 | 4/2012 |
| WO | WO 2012/149470 A1 | 11/2012 |
| WO | WO 2012/164565 A1 | 12/2012 |
| WO | WO 2013/053775 A1 | 4/2013 |
| WO | WO 2013/098244 A1 | 7/2013 |
| WO | WO 2013/109604 A1 | 7/2013 |
| WO | WO 2013/126794 A1 | 8/2013 |
| WO | WO 2013/141680 A1 | 9/2013 |
| WO | WO 2013/142578 A1 | 9/2013 |
| WO | WO 2015/009952 A1 | 1/2015 |
| WO | WO 2015/066042 A1 | 5/2015 |
| WO | WO 2016/141320 A2 | 9/2016 |
| WO | WO 2017/118864 A1 | 7/2017 |
| WO | WO 2017/118865 A1 | 7/2017 |
| WO | WO 2017/118866 A1 | 7/2017 |
| WO | WO 2017/118867 A1 | 7/2017 |
| WO | WO 2017/132552 A1 | 8/2017 |
| WO | WO 2017/156349 A1 | 9/2017 |
| WO | WO 2018/026872 A1 | 2/2018 |
| WO | WO 2018/027316 A1 | 2/2018 |
| WO | WO 2018/049248 A1 | 3/2018 |
| WO | WO 2018/049261 A1 | 3/2018 |
| WO | WO 2018/085461 A1 | 5/2018 |
| WO | WO 2018/118819 A2 | 6/2018 |
| WO | WO 2018/118967 A1 | 6/2018 |
| WO | WO 2018/127713 A1 | 7/2018 |
| WO | WO 2019/023483 A1 | 1/2019 |

OTHER PUBLICATIONS

Junejo et al., "Deletions and Duplication in Internal Inverted Repeat Sequence of Long Region/Unique Sequence of Long Region (IRL/UL) of Herpes Simplex Virus Type-i (HSV-i) Genome are not Evidently Associated with Intracranial and Foot-Pad Pathogenicity in Mouse Model," J. Pak. Med. Assoc., 45(4), pp. 95-98, 1995.

Wollman et al., "Oncolytic Virus Therapy for Glioblastoma Multiforme: Concepts and Candidates," Cancer J., Jan.-Feb. 2012;18(1):69-81.

U.S. Appl. No. 61/562,738, filed Nov. 22, 2011, Jonjic.

Cherenkova et al., "Generation of recombinant adenoviruses and lentiviruses expressing angiogenic and neuroprotective factors using Gateway cloning technology," Cell Transplantology and Tissue Engineering, 2012, vol. 7, No. 3, 164-168 (with English abstract).

Gibson et al., "Enzymatic assembly of DNA molecules up to several hundred kilobases," Nature Methods 2009;6(5):343-345.

Loakes et al., "5-Nitroindole as an universal base analogue," Nucleic Acids Research, 1994, 22(20): 4039-4043.

López-Otin et al., "Emerging roles of proteases in tumour suppression," Nat Rev Cancer, 2007, 7(10):800-808.

NCBI Reference Sequence: NC_001806.2, Human herpesvirus 1 strain 17, complete genome, Aug. 13, 2018, 62 pages.

Nichols et al., "A universal nucleoside for use at ambiguous sites in DNA primers," Nature, Jun. 1994, vol. 369, pp. 492-493.

Richard et al., "The pUL37 tegument protein guides alpha-herpesvirus retrograde axonal transport to promote neuroinvasion," PLoS Pathogens, 2017, 13(12), e1006741, 32 pages.

Slavuljica et al., "Recombinant mouse cytomegalovirus expressing a ligand for the NKG2d receptor is attenuated and has improved vaccine properties," J. Clin. Invest., 120(12): 4532-4545 (Dec. 2010).

Stamenkovic et al., "Extracellular matrix remodelling: the role of matrix metalloproteinases," Journal of Pathology, 2003, 200: 448-464.

Takenaga et al., "Microparticle resins as a potential nasal drug delivery system for insulin," Journal of Controlled Release, Mar. 1998, vol. 52, Issues 1-2, pp. 81-87.

Tocchi et al., "Functional interactions between matrix metalloproteinases and glycosaminoglycans," FEBS Journal (2013) 280:2332-2341.

Wahid et al., "MicroRNAs: Synthesis, mechanism, function, and recent clinical trials," Biochimica et Biophysica Acta, 2010, 1803: 1231-1243.

Watkins, Jr. and Santalucia, Jr., "Nearest-neighbor thermodynamics of deoxyinosine pairs in DNA duplexes," Nucleic Acids Research, 2005, 33(19): 6258-6267.

Zhang et al., "Abstract 3669: IDH mutant glial cell resistance to natural killer cell cytotoxicity," Cancer Research, 74, 3669 (Oct. 1, 2014).

Extended European Search Report for European Application No. 20184441.2, dated Jan. 12, 2021, 7 pages.

(56) References Cited

OTHER PUBLICATIONS

Baertsch et al., "MicroRNA-mediated multi-tissue detargeting of oncolytic measles virus," Cancer Gene Therapy (2014) 21, 373-380.
Henke et al., "microRNA-122 stimulates translation of hepatitis C virus RNA," EMBO J. (2008) 27:3300-3310.
U.S. Patent Office, International Search Report in International Patent Application No. PCT/US2017/037531, 4 pp. (dated Sep. 29, 2017).
U.S. Patent Office, Written Opinion in International Patent Application No. PCT/US2017/037531, 4 pp. (dated Sep. 29, 2017).
U.S. Appl. No. 60/917,752, filed May 14, 2007, Cascio et al.
U.S. Appl. No. 61/325,137, filed Apr. 16, 2010, Glorioso et al.
U.S. Appl. No. 61/847,405, filed Jul. 17, 2013, Glorioso et al.
Adamiak et al., "Herpes Simplex Virus Type 2 Glycoprotein G is Targeted by the Sulfated Oligo- and Polysaccharide Inhibitors of Virus Attachment to Cells," Journal of Virology, 81 (24), 13424-13434 (2007).
Aghi et al., "Oncolytic herpes virus with defective ICP6 specifically replicates in quiescent cells with homozygous genetic mutations in p16.," Oncogene, 27: 4249-4254 (2008).
Akimoto et al., "A new delivery system for 5-fluorouracil using prodrug and converting enzyme," J. Ophthalmol., 86(5): 581-586 (2002).
Amelio et al., "A Chromatin Insulator-Like Element in the Herpes Simplex Virus Type 1 Latency-Associated Transcript Region Binds CCCTC-Binding Factor and Displays Enhancer-Blocking and Silencing Activities," J. of Virology, 80(5): 2358-2368 (Mar. 2006).
Anderson et al., "Pseudotyping of Glycoprotein D-Deficient Herpes Simplex Virus Type 1 with Vesicular Stomatitis Virus Glycoprotein G Enable Mutant Virus Attachment and Entry," Journal of Virology, 74(5): 2481-2487 (Mar. 2000).
Asano et al., "Humanization of the Bispecific Epidermal Growth Factor Receptor X CD3 Diabody and Its Efficacy as a Potential Clinical Reagent," Clin. Cancer Res., 12(13): 4036-4042 (Jul. 1, 2006).
Assi et al., "Gene Therapy for Brain Tumors: Basic Developments and Clinical Implementation," Neurosci. Lett. 527(2): 71-77 (2012).
Baek et al., "Bispecific Adapter-Mediated Retargeting of a Receptor-Restricted HSV-1 Vector to CEA-Bearing Tumor Cells," Molecular Therapy, 19(3): 507-514 (Mar. 2011).
Barrangou et al., "CRISPR Provides Acquired Resistance Against Viruses in Prokaryotes," Science 315, 1709 (2007).
Bennett et al., "Comparison of safety, delivery, and efficacy of two oncolytic herpes viruses (G207 and NV1020) for peritoneal cancer," Cancer Gene Therapy, 9: 935-945 (2002).
Broberg et al., "Immune Response to Herpes Simplex Virus and γ134.5 Deleted HSV Vectors," Current Gene Therapy, 5: 523-530 (2005).
Brouns et al., "Small CRISPR RNAs Guide Antiviral Defense in Prokaryotes," Science, Aug. 15, 2008; 321(5891): 960-964.
Bzik et al., "Nucleotide Sequence of a Region of the Herpes Simplex Virus Type 1 gB Glycoprotein Gene: Mutations Affecting Rate of Virus Entry and Cell Fusion," Virology, 37: 185-190 (1984).
Cai et al., "Linker-Insertion Nonsense and Restriction-Site Deletion Mutations of the gB Glycoprotein Gene of Herpes Simplex Virus Type 1," Journal of Virology, 61(3): 714-721 (Mar. 1987).
Camacho et al., "Phase 1 clinical trial of anti-CTLA4 human monoclonal antibody CP-675,206 in patients (pts) with advanced solid malignancies," J. Clin. Oncol., 22(145): Abstract No. 2505 (2004) (antibody CP-675206), 4 pages.
Campadelli-Fiume et al., "Rethinking herpes simplex virus: the way to oncolytic agents," Rev. Med. Viral., 21: 213-226 (2011).
Cao et al., "A functional study of miR-124 in the developing neural tube," Genes & Development, 21: 531-536 (2007).
Cattaneo et al., "Reprogrammed viruses as cancer therapeutics: targeted, armed and shielded" Nature Reviews. Microbiology, 6(7): 529-540 (2008).
Cawood et al., "Use of Tissue-Specific MicroRNA to Control Pathology of Wild-Type Adenovirus without Attenuation of Its Ability to Kill Cancer Cells," PloS Pathogens, 5(5): 1-10 (May 2009).
Cheadle et al., "Cloning and expression of the variable regions of mouse myeloma protein MOPC315 in E. coli: recovery of active FV fragments.," Mol Immunol (1992) 29(1): 21-30.
Cocchi et al., "The Ectodomain of a Novel Member of the Immunoglobulin Subfamily Related to the Poliovirus Receptor Has the Attributes of a Bona Fide Receptor for Herpes Simplex Virus Types 1 and 2 in Human Cells," Journal of Virology, 72(12): 9992-10002 (Dec. 1998).
Cocchi et al., "The Herpes Simplex Virus JMP Mutant Enters Receptor-Negative J Cells through a Novel Pathway Independent of the Known Receptors nectin1, HveA, and nectin2," Journal of Virology, 78(9): 4720-4729 (May 2004).
Cong et al., "Multiplex Genome Engineering Using CRISPR/Cas Systems," Science, Feb. 15, 2013; 339(6121): 819-823.
Conner et al., "A strategy for systemic delivery of the oncolytic herpes virus HSV1716: redirected tropism by antibody-binding sites incorporated on the virion surface as a glycoprotein D fusion protein," Gene Therapy, 15: 1579-1592 (2008).
Connolly et al., "Potential Nectin-1 Binding Site on Herpes Simplex Virus Glycoprotein D," Journal of Virology, 79(2): 1282-1295 (Jan. 2005).
Connolly et al., Structure-Based Analysis of the Herpes Simplex Virus Glycoprotein D Binding Site Present on Herpevirus Entry Mediator HveA (HVEM), Journal of Virology 76(21):10894-10904 (Nov. 2002).
Currier et al., "Efficacy and Safety of the Oncolytic Herpes Simplex Virus rRp450 Alone and Combined With Cyclophosphamide," Molecular Therapy, 16(5): 879-885 (2008).
Deltcheva et al., "CRISPR RNA maturation by trans-encoded small RNA and hostfactor RNase III," Nature, Mar. 31, 2011; 471 (7340): 602-607.
Deluca et al., "Nucleotide Sequences of Herpes Simplex Virus Type 1 (HSV-1) Affecting Virus Entry, Cell Fusion, and Production of Glycoprotein gB (VP7)," Virology, 122: 411-423 (1982).
Delwar et al., "Tumour-specific triple-regulated oncolytic herpes virus to target glioma," Oncotarget, 2016, vol. 7, No. 19, pp. 28658-28669.
Desai et al., "Incorporation of the Green Fluorescent Protein into the Herpes Simplex Virus Type 1 Capsid," Journal of Virology, 72(9): 7563-7568 (Sep. 1998).
Dmitrieva et al., "Chondroitinase ABC I-mediated spread and antitumor efficacy," Clin. Cancer Res., 17(6): 1362-1372 (2011).
Doronina et al.,"Site-specific release of nascent chains from ribosomes at a sense codon.," Molecular and Cellular Biology, 28(13): 4227-4239 (2008).
Edge et al., "A let-7 MicroRNA-sensitive Vesicular Stomatitis Virus Demonstrates Tumor-specific Replication," Molecular Therapy, 16(8): 1437-1443 (Aug. 2008).
Eisenring et al., "IL-12 initiates tumor rejection via lymphoid tissue-inducer cells bearing the natural cytotoxicity receptor NKp46," Nat Immunol., 2010;11(11):1030-8.
Esko et al., "Animal Cell Mutants Defective in Glycosaminoglycan biosynthesis," Proc. Natl. Acad. Sci. USA, 82: 3197-3201 (May 1985).
European Patent Office, European Search Report in European Patent Application No. 17155129 (dated May 30, 2017), 8 pages.
Fecci et al., "Systemic CTLA-4 Blockade Ameliorates Glioma-Induced Changes to the CD4+ T Cell Compartment without Affecting Regulatory T-Cell Function," Clin Cancer Res., 2007;13(7):2158-2167.
Frampton et al., "Equine Herpesvirus 1 Enters Cells by Two Different Pathways, and Infection Requires the Activation of the Cellular Kinase ROCK1," Journal of Virology, 81(20): 10879-10889 (2007).
Friedman et al., "Herpes Simplex Virus Oncolytic Therapy for Pediatric Malignancies "Molecular Therapy, 17(7): 1125-1135 (2009).
Fu et al., "Construction of an oncolytic herpes simplex virus that precisely targets hepatocellular carcinoma cells," Mol. Ther 20:339-46 (2012).

(56) References Cited

OTHER PUBLICATIONS

Fujioka et al., "Interleukin-18 protects mice against acute herpes simplex virus type 1 infection," Journal of Virology, 73(3): 2401-2409 (1999).
Fuller et al., "Anti-glycoprotein D Antibodies That Permit Adsorption but Block Infection by Herpes Simplex Virus 1 Prevent Virion-cell Fusion at the Cell Surface," Proc. Natl. Acad. Sci. USA, 84: 5454-5458 (Aug. 1987).
Fuller et al., "Neutralizing Antibodies Specific for Glycoprotein H of Herpes Simplex Virus Permit Viral Attachment to Cells but Prevent Penetration," Journal of Virology, 63(8): 3435-3443 (Aug. 1989).
Garneau et al., "The CRISPR/Cas bacterial immune system cleaves bacteriophage and plasmid DNA," Nature, vol. 468, Nov. 4, 2010, pp. 67-72.
Gasiunas et al., "Cas9-crRNA ribonucleoprotein complex mediates specific DNA cleavage for adaptive immunity in bacteria," PNAS, Sep. 25, 2012, vol. 109, No. 39, pp. 15539-15540.
Gaur et al., "Characterization of microRNA expression levels and their biological correlates in human cancer cell lines," Cancer Res., 67(6): 2456-2468 (2007).
Geraghty et al., "Entry of Alphaherpesviruses Mediated by Poliovirus Receptor-Related Protein 1 and Poliovirus Receptor," Science, 280: 1618-1620 (Jun. 5, 1998).
Gierasch et al., "Construction and Characterization of Bacterial Artificial Chromosomes Containing HSV-1 Strains 17 and KOS," Journal of Virological Methods, 135: 197-206 (2006).
Grandi et al., Design and application of oncolytic HSV vectors for glioblastoma therapy, Golemis; Protein-Protein Interactions: A Molecular Cloning Manual; Cold Spring Harbor Laboratory Press, 2002 Expert Rev. Neurother., 9(4): 505-517 (2009).
Grossman et al., "Survival of Patients with Newly Diagnosed Glioblastoma Treated with Radiation and Temozolomide in Research Studies in the United States," Clinical Cancer Research, 16: 2443-2449 (2010).
Gubanova et al., "Oncolytic viruses in the therapy of gliomas," Mol Biol (Mosk), 46(6), pp. 874-886 (Nov.-Dec. 2012), ISSN: 0026-8984 (English abstract).
Hale et al., "RNA-Guided RNA Cleavage by a CRISPR RNA-Cas Protein Complex," Cell 139, 945-956, Nov. 25, 2009.
He et al., "Targeting Glioblastoma Stem Cells: Cell Surface Markers," Current Medicinal Chemistry, 19: 6050-6055 (2012).
Highlander et al., "Identification of mar Mutations in Herpes Simplex Virus Type 1 Glycoprotein B Which Alter Antigenic Structure and Function in Virus Penetration," Journal of Virology, 63(2): 730-738 (Feb. 1989).
Hodi et al., "Improved Survival with Ipilimumab in Patients with Metastatic Melanoma," The New England Journal of Medicine, 363(8): 711-723 (2010).
Hong et al. "Ectopic matrix metalloproteinase 9 expression in human brain tumor cells enhances oncolytic HSV vector infection," Gene Therapy 17:1200-1205 (2010).
Iorio et al., "microRNA involvement in human cancer," Carcinogenesis, 33(6): 1126-1133 (2012).
Ishida et al., "Enhanced cytotoxicity with a novel system combining the paclitaxel-2'-ethylcarbonate prodrug and an HSV amplicon with an attenuated replication-competent virus, HF10 as a helper virus," Cancer Letters, 288: 17-27 (2010).
Jackson et al., "Crystal structure of the CRISPR RNA-guided surveillance complex from *Escherichia coli*," Science, Sep. 19, 2014; 345(6203): 1473-1479.
Jackson et al, "Insertion Mutations in Herpes Simplex Virus 1 Glycoprotein H Reduce Cell Surface Expression, Slow the Rate of Cell Fusion, or Abrogate Functions in Cell Fusion and Viral Entry," Journal of Virology, 84(4): 2038-2046 (Feb. 2010).
Jinek et al., "A Programmable Dual-RNA-Guided DNA Endonuclease in Adaptive Bacterial Immunity," Science Aug. 17, 2012: vol. 337, Issue 6096, pp. 816-821.
Jinek et al., "RNA-programmed genome editing in human cells," eLife 2013;2:e00471, 9 pages.
Kaji et al., "Virus-free induction of pluripotency and subsequent excision of reprogramming factors," Nature, 458(7239): 771-775 (2009).
Kambara et al., "An oncolytic HSV-1 mutant expressing ICP34.5 under control of a nestin promoter increases survival of animals even when symptomatic from a brain tumor," Cancer Res., 65(7): 2832-2839 (2005).
Karpowicz et al., "E-Cadherin Regulates Neural Stem Cell Self-Renewal," The Journal of Neuroscience, 29(121: 3885-3896 (2009).
Karsy et al., "Current Progress on Understanding MicroRNAs in Glioblastoma Multiforme.," Genes & Cancer, 3(1): 3-15 (2012).
Katoh et al., "Hedgehog signaling, epithelial-to-mesenchymal transition and miRNA (review)," International Journal of Molecular Medicine, 22: 271-275 (2008).
Kaur et al., "Oncolytic HSV-1 Virotherapy: Clinical Experience and Opportunities for Progress," Curr Pharm Biotechnol., Jul. 2012; 13(9): 1842-1851.
Kelly et al., "Attenuation of Vesicular Stomatitis Virus Encephalitis through MicroRNA Targeting," Journal of Virology, Feb. 2010, vol. 84, No. 3, pp. 1550-1562.
Kelly et al., "Engineering microRNA responsiveness to decrease virus pathogenicity," Nature Medicine, Nov. 2008, vol. 14, No. 11, pp. 1277-1283.
Kosovsky et al., "Herpes Simplex Virus 1 (HSV-1) Strain HSZP Glycoprotein B Gene: Comparison of Mutations among Strains Differing in Virulence," Virus Genes, 20(1): 27-33 (2000).
Krisky et al., "Rapid method for construction of recombinant HSV gene transfer vectors," Gene Therapy, 4: 1120-1125 (1997).
Krisky et al., "Deletion of multiple immediate-early genes from herpes simplex virus reduces cytotoxicity and permits long-term gene expression in neurons," Gene Therapy 5:1593-1603 (1998).
Krummenacher et al., "Effects of Herpes Simplex Virus on Structure and Function of Nectin-1/HveC," Journal of Virology, 76(5): 2424-2433 (Mar. 2002).
Kuan et al., "Increased Binding Affinity Enhances Targeting of Glioma Xenografts by EGFRVIII-Specific scFv," Int. J. Cancer, 88: 962-969 (2000).
Kumar et al., "Impaired microRNA processing enhances cellular transformation and tumorigenesis," Nature Genetics, 39(5): 673-677 (2007).
Kwon et al., "Soluble V Domain of Nectin-1/HveC Enables Entry of Herpes Simplex Virus Type 1 (HSV-1) into HSY-Resistant Cells by Binding to Viral Glycoprotein D," Journal of Virology, 80(1): 138-148 (Jan. 2006).
Lavon et al., "Gliomas display a microRNA expression profile reminiscent of neural precursor cells," Neuro-Oncology, 12(5): 422-433 (2010).
Lee et al., "MicroRNA Regulation of Oncolytic Herpes Simplex Virus-1 for Selective Killing of Prostate Cancer Cells," Clin. Cancer Res., 15(16): 5126-5135 (2009).
Lee et al., "Transcriptional and Translational Dual-regulated Oncolytic Herpes Simplex Virus Type 1 for Targeting Prostate Tumors," Molecular Therapy, 2010; 18(5):929-935.
Li et al., "Identification of Functional Domains in Herpes Simplex Virus 2 Glycoprotein B," Journal of Virology, 3792-3800 (Apr. 2006).
Li et al., "MicroRNA-145 regulates oncolytic herpes simplex virus-1 for selective killing of human non-small cell lung cancer cells", Virology Journal 10(1): 241 (2013), 9 pages.
Ligas et al., "A Herpes Simplex Virus Mutant in Which Glycoprotein D Sequences Are Replaced by 13-Galactosidase Sequences Binds to but Is Unable To Penetrate into Cells," Journal of Virology, 62(5): 1486-1494 (May 1988).
Lilley et al., "Multiple Immediate-Early Gene-Deficient Herpes Simplex Virus Vectors Allowing Efficient Gene Delivery to Neurons in Culture and Widespread Gene Delivery to the Central Nervous System In Vivo," J. of Virology, 75:9: 4343-4356 (May 2001).
Ma et al., "A novel HBV antisense RNA gene delivery system targeting hepatocellular carcinoma," World J Gastroenterol 9:463-467 (2003).
MacDonald et al., "Genome Sequence of Herpes Simplex Virus 1 Strain KOS," Journal of Virology, 86(11): 6371-6372 (Jun. 2012).

(56) References Cited

OTHER PUBLICATIONS

Mali et al., "RNA-Guided Human Genome Engineering via Cas9," Science, Feb. 15, 2013; 339(6121): 823-826.
Mammoto et al., "Role of Collagen Matrix in Tumor Angiogenesis and Glioblastoma Multiforme Progression," The American Journal of Pathology, 183(4): 1293-1305 (2013).
Manickan et al., "Genetic immunization against herpes simplex virus. Protection is mediated by CD4+ T lymphocytes," The Journal of Immunology, 155: 259-265 (1995).
Markert et al., "Conditionally replicating herpes simplex virus mutant, G207 for the treatment of malignant glioma: results of a phase I trial.," Gene Therapy, 7: 867-874 (2000).
Marraffini and Sontheimer, "CRISPR Interference Limits Horizontal Gene Transfer in Staphylococci by Targeting DNA," Science, Dec. 19, 2008; 322(5909): 1843-1845.
Mazzacurati et al., "Use of miRNA response sequences to block off-target replication and increase the safety of an unattenuated, glioblastoma-targeted oncolytic HSV.," Molecular Therapy, 23(1): 99-107 (2015).
McGeoch et al., "The Complete DNA Sequence of the Long Unique Region in the Genome of Herpes Simplex Virus Type 1," J. Gen. Virol. (1988), 69, 1531-1574.
McKee et al., "Degradation of fibrillar collagen in a human melanoma xenograft improves the efficacy of an oncolytic herpes simplex virus vector."Cancer Research, 66(5): 2509-2513 (2006).
Menotti et al., "Construction of a Fully Retargeted Herpes Simplex Virus 1 Recombinant Capable of Entering Cells Solely via Human Epidermal Growth Factor Receptor 2," Journal of Virology, 82(20): 10153-10161 (Oct. 2008).
Menotti, L., et al., "Inhibition of human tumor growth in mice by an oncolytic herpes simplex virus designed to target solely HER-2-positive cells," PNAS 106:9039-9044 (2009).
Metz et al., "Bispecific antibody derivatives with restricted binding functionalities that are activated by proteolytic processing," Protein Engineering, Design & Selection vol. 25 No. 10 pp. 571-580, 2012.
Miao et al., "EphA2 promotes infiltrative invasion of glioma stem cells in vivo through cross-talk with Akt and regulates stem cell properties," Oncogene, 34(5): 558-567 (2015).
Miest et al.,"New viruses for cancer therapy: meeting clinical needs," Nature Reviews. Microbiology, 12(1): 23-34 (2014).
Miller et al., "Development of a Syngenic Murine 816 Cell Line-Derived Melanoma Susceptible to Destruction by Neuroattenuated HSV-1," Molecular Therapy, 3(2): 160-168 (Feb. 2001).
Milne et al., "Glycoprotein D Receptor-Dependent, Low-pH-Independent Endocytic Entry of Herpes Simplex Virus Type 1," Journal of Virology, 79(11): 6655-6663 (Jun. 2005).
Mohyeldin et al., "Gene and viral therapy for glioblastoma: a review of clinical trials and future directions," The Cancer Journal, 18(1): 82-88 (2012).
Mok et al., "Matrix Metalloproteinases-1 and -8 Improve the Distribution and Efficacy of an Oncolytic Virus," Cancer Res., 67(22): 10664-10668 (2007).
Montgomery et al., "Herpes Simplex Virus-1 Entry into Cells Mediated by a Novel Member of the TNF/NGF Receptor Family," Cell 87:427-436 (1996).
Muggeridge, "Characterization of Cell-cell Fusion Mediated by Herpes Simplex Virus 2 glycoproteins gB, gD, gH and gL in Transfected Cells," Journal of General Virology, 81: 2017-2027 (2000).
Mullokandov et al. "High-throughput assessment of microRNA activity and function using microRNA sensor and decoy libraries," Nature methods 9:840-846 (2012).
Mulepati et al., "Crystal structure of a CRISPR RNA-guided surveillance complex bound to a ssDNA target," Science, Sep. 19, 2014; 345(6203): 1479-1484.
Nakano et al., "Mechanism of HSV infection through soluble adapter-mediated virus bridging to the EGF receptor," Virology, 413: 12-18 (2011).
Navaratnarajah et al., "Targeted Entry of Enveloped Viruses: Measles and Herpes Simplex Virus ," Curr. Opin. Viral., 2(1): 43-49 (2012).

NCBI, "Chain A, Glycoprotein B From Herpes Simplex Virus Type 1" Database Entrez-Nucleotide, Accession No. 4L1R_A (Jun. 26, 2013). Retrieved on Mar. 5, 2018, 5 pages.
NCBI, "glycoprotein B [Human herpesvirus 1]," Database Entrez-Nucleotide, Accession No. AAA91805 (Mar. 8, 1996). Retrieved on Mar. 5, 2018, 1 page.
NCBI, "glycoprotein B [Human herpesvirus 1]," Database Entrez-Nucleotide, Accession No. AAF70301 (May 16, 2000). Retrieved on Mar. 5, 2018, 1 page.
NCBI, "glycoprotein B [Human herpesvirus 2]," Database Entrez-Nucleotide, Accession No. ABU45427 (Nov. 29, 2007). Retrieved on Mar. 5, 2018, 2 pages.
NCBI, "Herpes Simplex Virus Type 1 Gene for Glycoprotein gH," Database GenBank Accession No. X03896 (Apr. 18, 2005). Retrieved on Mar. 5, 2018, 3 pages.
NCBI, "Human Herpesvirus 1 Complete Genome," Database GenBank Accession No. X14112 (Oct. 23, 2008). Retrieved on Mar. 5, 2018, 70 pages.
NCBI, "Human Herpesvirus 1 Strain KOS Glycoprotein B Gene," Database GenBank Accession No. AF311740 (Jan. 24, 2001). Retrieved on Mar. 5, 2018, 2 pages.
Nduom et al., "Glioblastoma Cancer Stem-like Cells—Implications for Pathogenesis and Treatment," Cancer., 18(1): 100-106 (2012).
Nicola and Strauss., "Cellular and Viral Requirements for Rapid Endocytic Entry of Herpes Simplex Virus," Journal of Virology, 78(14): 7508-7517 (Jul. 2004).
Nicola et al., "Roles for Endocytosis and Low pH in Herpes Simplex Virus Entry into HeLa and Chinese Hamster Ovary Cells," Journal of Virology, 77(9): 5324-5332 (May 2003).
O'Day et al., "Efficacy and safety of ipilimumab monotherapy in patients with pretreated advanced melanoma: a multicenter single-arm phase II study," Annals of Oncology, 2010 21:1712-1717.
Ocana et al., "A new regulatory loop in cancer-cell invasion," Molecular Biology Organization, 9(6): 521-522 (2008).
Omidfar et al., "Production of a Novel Camel Single-Domain Antibody Specific for the Type III Mutant EGFR," Tumor Biology, 25: 296-305 (2004).
Omidfar et al., "Production and Characterization of a New Antibody Specific for the Mutant EGF Receptor, EGFRvlll, in Camelus bactrianus," Tumor Biology, 25:179-187 (2004).
Opalinska et al., "Nucleic-Acid Therapeutics: Basic Principles and Recent Applications," Nature Reviews, 1: 503-514 (2002).
Parker et al., "Oncolytic viral therapy of malignant glioma," Neurotherapeutics: The Journal of the American Society for Experimental NeuroTherapeutics, 6: 558-569 (2009).
Patriarca et al., "Epithelial cell adhesion molecule expression (CD326) in cancer: a short review," Cancer Treatment Reviews, 38: 68-75 (2012).
Payne et al., "The pathobiology of collagens in glioma," Mol. Cancer Res., (2013) 11:1129-1140.
Pertel et al., "Cell Fusion Induced by Herpes Simplex Virus Glycoproteins gB, gD, and gH-gL Requires a gD Receptor but Not Necessarily Heparan Sulfate," Virology, 279: 313-324 (2001).
Peters et al., "Designing herpes viruses as oncolytics," Molecular Therapy—Oncolytics (2015) 2, 15010, 14 pages.
Qi et al., "Repurposing CRISPR as an RNA-Guided Platform for Sequence-Specific Control of Gene Expression," Cell 152, 1173-1183, Feb. 28, 2013.
Raag and Whitlow, "Single-chain Fvs.," FASEB (1995) 9(1):73-80.
Ran et al., "Genome engineering using the CRISPR-Cas9 system," Nature Protocols Nov. 2013;8(11):2281-2308.
Rauch et al., "Mutations in Herpes Simplex Virus Glycoprotein D Distinguish Entry of Free Virus from Cell-Cell Spread," Journal of Virology, 74(24): 11437-11446 (Dec. 2000).
Riddick et al., "Integration and analysis of genome-scale data from gliomas," Nature Reviews—Neurology, 7: 439-450 (2011).
Saharkhiz-Langroodi and Holland, Identification of the Fusion-from-without Determinants of Herpes Simplex Virus Type 1 Glycoprotein B, Virology 227, 153-159 (1997).
Sapranauskas et al., "The *Streptococcus thermophilus* CRISPR/Cas system provides immunity in *Escherichia coli*," Nucleic Acids Research, 2011, vol. 39, No. 21, pp. 9275-9282.

(56) References Cited

OTHER PUBLICATIONS

Schaffer et al., "Temperature-Sensitive Mutants of Herpes Simplex Virus Type 1: Isolation, Complementation and Partial Characterization," Virology, 52: 57-71 (1973).
Segal, "Bacteria herald a new era of gene editing," eLife 2013;2:e00563, 3 pages.
Sethi et al., "Protection of Mice from Fatal Herpes Simplex Virus Type 1 Infection by Adoptive Transfer of Cloned Virus-specific and H-2-restricted Cytotoxic T Lymphocytes," J. Gen. Viral., 64: 443-447 (1983).
Shi et al., "hsa-mir-181a and hsa-mir-181b function as tumor suppressors in human glioma cells," Brain Research, 1236: 185-193 (2008).
Shogan et al., "Virucidal Activity of a GT-Rich Oligonucleotide against Herpes Simplex Virus Mediated by Glycoprotein B," Journal of Virology, 80(10): 4740-4747 (May 2006).
Silber et al., "miR-124 and miR-137 inhibit proliferation of glioblastoma multiforme cells and induce differentiation of brain tumor stem cells," BMC Medicine, 6(14): 1-17 (2008).
Simmons et al., "Local secretion of anti-CTLA-4 enhances the therapeutic efficacy of a cancer immunotherapy with reduced evidence of systemic autoimmunity," Cancer Immunol Immunother., 2008;57(8):1263-1270.
Sinkunas et al., "In vitro reconstitution of Cascade-mediated CRISPR immunity in *Streptococcus thermophilus*," The EMBO Journal (2013) 32, 385-394.
Smith, "Relationship Between the Envelope and the Infectivity of Herpes Simplex Virus," Herpes Virus Envelopes, 814-816 (1964).
Struyf et al., "Mutations in the N-Terminal Domains of Nectin-1 and Nectin-2 Reveal Differences in Requirements for Entry of Various Alphaherpesviruses and for Nectin-Nectin Interactions," Journal of Virology, 76(24): 12940-12950 (Dec. 2002).
Szymczak et al., "Development of 2A peptide-based strategies in the design of multicistronic vectors," Expert Opin. Biol. Ther., 5(5): 627-638 (2005).
Thomas et al., "Equine Herpesvirus 1 Gene 12 Can Substitute for vmw65 in the Growth of Herpes Simplex Virus (HSV) Type 1, Allowing the Generation of Optimized Cell Lines for the Propagation of HSV Vectors with Multiple Immediate-Early Gene Defects," J. of Virology, 73(9): 7399-7 409 (Sep. 1999).
Tischer et al., "Two-step red-mediated recombination for versatile high-efficiency markerless DNA manipulation in *Escherichia coli.*," BioTechniques, 40(2): 191-196 (2006).
Todo, "Oncolytic Virus Therapy Using Genetically Engineered Herpes Simplex Viruses," Cell, 15(3): 151-159 (2002).
Topalian et al., "Safety, Activity, and Immune Correlates of Anti-PD-1 Antibody in Cancer," The New England Journal of Medicine, 366(26): 2443-2454 (2012).
Triozzi et al., "Phase I Study of the Intratumoral Administration of Recombinant Canarypox Viruses Expressing B7.1 and Interleukin 12 in Patients with Metastatic Melanoma," Clin Cancer Res 2005;11(11):4168-4175.
Tsvitov et al., "Characterization of Soluble Glycoprotein D-mediated Herpes Simplex Virus Type 1 Infection," Virology, 360: 477-491 (2007).
Turner et al., "Glycoproteins gB, gD, and gHgL of Herpes Simplex Virus Type 1 Are Necessary and Sufficient To Mediate Membrane Fusion in a Cos Cell Transfection System," Journal of Virology, 72(1): 873-875 (Jan. 1998).
Uchida et al., "A Double Mutation in Glycoprotein gB Compensates for Ineffective gD-Dependent initiation of Herpes Simplex Virus Type 1 Infection," Journal of Virology, 84(23): 12200-12209 (Dec. 2010).
Uchida et al., "Co-engineering of HSV-1 gB and gD Enables Efficient Retargeted Infection," 29th Annual Meeting of the American Society for Virology, slides of oral presentation, 38 pages, Bozeman, MT (Jul. 17-21, 2010).

Uchida et al., "Co-engineering of HSV-1 Glycoproteins B and D Enables Highly Efficient Retargeted Infection," 29th Annual Meeting of the American Society for Virology, abstract, 1 page, Bozeman, MT (Jul. 17-21, 2010).
Uchida et al., "Effective Treatment of an Orthotopic Xenograft Model of Human Glioblastoma Using an EGFR-retargeted Oncolytic Herpes Simplex Virus," Molecular Therapy 21(3):561-569 (2012).
Uchida et al., "Fully Retargeted HSV-1 Infection Directed by Re-Engineered Glycoprotein D (gD) Is Augmented by Hyperactive gB Mutations," Molecular Therapy, 18(Supp. 1): S249, Abstract 640 (May 2010).
Uchida et al., "Generation of Herpes virus Entry Mediator (HVEM)-Restricted Herpes Simplex Virus Type 1 Mutant Viruses: Resistance of HVEM-Expressing Cells and Identification of Mutations That Rescue Nectin-1 Recognition," Journal of Virology, 83(7): 2951-2961 (Apr. 2009).
Uchida et al., "Hyperactive gB Mutations Augment Fully Retargeted HSV Infection," 13$^{th}$ Annual Meeting of the American Society of Gene & Cell Therapy, slides of oral presentation, 34 pages, Washington, DC (May 19-22, 2010).
Uchida et al., "Hyperactive gB Mutations Augment Fully Retargeted HSV Infection," 35th Annual International Herpes Virus Workshop, poster presentation, 1 page, Salt Lake City, UT (Jul. 24-29, 2010).
Uchida et al., "Hyperactive Glycoprotein B (gB) Mutations Augment Fully Retargeted Herpes Simplex Virus (HSV) Infection," 101 Annual Meeting of the American Association for Cancer Research, poster presentation, 1 page, Washington, DC (Apr. 18, 2010).
Uchida et al., "Hyperactive Glycoprotein B Mutations Augment Fully Retargeted HSV Infection," 35th Annual International Herpes Virus Workshop, abstract, 1 page, Salt Lake City, UT (Jul. 24-29, 2010).
Uchida et al., "Identification of Mutations in HSV-1 Envelope Glycoprotein B That Enhance Retargeted Infection," Proceedings of the American Association for Cancer Research, 51: 139, Abstract 584 (Apr. 2010).
Uchida et al., "Novel Mutations in gB and gH Circumvent the Requirement for Known gD Receptors in Herpes Simplex Virus 1 Entry and Cell-to-Cell Spread," Journal of Virology, 87(3): 1430-1442 (Feb. 2013).
Ushijima et al., "Determination and Analysis of the DNA Sequence of Highly Attenuated Herpes Simplex Virus Type 1 Mutant HF10, a Potential Oncolylic Virus," Microbes and Infection, 9: 142-149 (2007).
Varghese et al., "Oncolytic herpes simplex virus vectors for cancer virotherapy," Cancer Gene Therapy, 9(12): 967-978 (2002).
Verhaak et al., "An integrated genomic analysis identifies clinically relevant subtypes of glioblastoma characterized by abnormalities in PDGFRA, IDH1, EGFR and NF1," Cancer Cell, 17: 98-110 (2010).
Visvanathan et al., "The microRNA miR-124 antagonizes the anti-neural REST/SCP1 pathway during embryonic CNS development," Genes & Development, 21: 744-749 (744).
Voeks et al., "Gene therapy for prostate cancer delivered by ovine adenovirus and mediated by purine nucleoside phosphorylase and fludarabine in mouse models," Gene Therapy, 9(12): 759-768 (2002).
Wakimoto et al., "Effects of innate immunity on herpes simplex virus and its ability to kill tumor cells," Gene Therapy, 10: 983-990 (2003).
Warner et al., "A Cell Surface Protein with Herpesvirus Entry Activity (HveB) Confers Susceptibility to Infection by Mutants of Herpes Simplex Virus Type 1, Herpes Simples Virus Type 2, and Pseudorabies Virus," Virology, 246: 179-189 (1998).
Wikstrand et al., "Monoclonal Antibodies against EGFRvlll Are Tumor Specific and React with Breast and Lung Carcinomas and Malignant Gliomas," Cancer Research, 55: 3140-3148 (Jul. 15, 1995).
Wong et al., "Targeted oncolytic herpes simplex viruses for aggressive cancers," Current Pharmaceutical Biotechnology, 13: 1786-1794 (2012).
Xia et al., "Loss of Brain-enriched miR-124 MicroRNA Enhances Stem-like Traits and Invasiveness of Glioma Cells," The Journal of Biological Chemistry, 287(13): 9962-9971 (2012).

(56) References Cited

OTHER PUBLICATIONS

Yan et al. "Effective small RNA destruction by the expression of a short tandem target mimic in *Arabidopsis*," The Plant Cell 24:415-427 (2012).

Yin et al., "The treatment of glioblastomas: A systematic update on clinical Phase III trials," Critical Reviews in Oncology/Hematology, 87: 265-282 (2013).

Yun, "Overcoming the extracellular matrix barrier to improve intratumoral spread and therapeutic potential of oncolytic virotherapy," Current Opinion in Molecular Therapeutics, 10(4): 356-361 (2008).

Zaharoff et al., "Intratumoral Immunotherapy of Established Solid Tumors with Chitosan/IL-12," J Immunother. 2010;33(7):697-705.

Zetsche et al., "Cpf1 Is a Single RNA-Guided Endonuclease of a Class 2 CRISPR-Cas System," Cell 163, 759-771, Oct. 22, 2015.

Zhang et al., "MicroRNA-128 inhibits glioma cells proliferation by targeting transcription factor E2F3a," J. Mol Med., 87: 43-51 (2009).

Zhong et al., "Induction, Selection and Expansion of Acute Myeloid Leukemia Reactive Autologous T Cells for Adoptive Immunotherapy," Blood, Nov. 2005, 106(11):1061.

Zhou and Roizman, "Construction and properties of a herpes simplex virus 1 designed to enter cells solely via the IL-13α2 receptor," PNAS 103(14):5508-5513 (2006).

Extended European Search Report issued by the European Patent Office for Application No. 14859119.1, dated Apr. 19, 2017, 10 pages.

International Preliminary Report on Patentability issued by the International Searching Authority for Application No. PCT/US2011/032923, dated Oct. 16, 2012, 8 pages.

International Search Report and Written Opinion issued by the International Searching Authority for Application No. PCT/US2011/032923, dated Mar. 28, 2012 12 pages.

International Preliminary Report on Patentability issued by the International Searching Authority for Application No. PCT/US2014/062676, dated May 3, 2016, 5 pages.

International Search Report and Written Opinion issued by the International Searching Authority for Application No. PCT/US2014/062676, dated Dec. 23, 2014, 9 pages.

International Search Report and Written Opinion of the International Searching Authority for International Application No. PCT/US2018/43938, dated Dec. 14, 2018, 16 pages.

Supplementary Partial European Search Report for European Application No. 18837388.0, dated Aug. 3, 2021, 9 pages.

Kennedy et al., "Design of an Interferon-Resistant Oncolytic HSV-1 Incorporating Redundant Safety Modalities for Improved Tolerability," Molecular Therapy: Oncolytics, Sep. 2020, vol. 18, pp. 476-490.

Liu et al, "ICP34.5 deleted herpes simplex virus with enhanced oncolytic, immune stimulating, and anti-tumour properties", Gene Ther., 2003, 10/4, 292-303.

Tarasova M.V., et al., "Oncolytic viruses in the treatment of gliomas, study guide," Novosibirsk, 2015, 30 pages, (with partial English translation).

Zhang et al., "Intravesical treatment of advanced urothelial bladder cancers with oncolytic HSV-1 co-regulated by differentially expressed microRNAs," Gene Therapy (2016) 23, 460-468.

All non-Schwannoma = non-cancerous tissue
BM = non-cancerous bone marrow

FIG. 10

| Tissue | miR-451a Norm | CA |
|---|---|---|
| Bladder | 1402.9 | 21.1 |
| Breast | 2262.1 | 3.9 |
| Colon | 3606.9 | 22.0 |
| Glioma | 4269.7 | 16.7 |
| H & N | 11919.8 | 10.3 |
| Lung | 31442.0 | 10.5 |
| Pancreatic | 1035.8 | 13.3 |

FIG. 11

| Tissue | miR-1 Norm | CA |
|---|---|---|
| Bladder | 175.0 | 0.8 |
| Breast | 3.0 | 0.3 |
| Colon | 149.3 | 1.6 |
| Glioma | 75.2 | 1.0 |
| H & N | 2846.6 | 2.6 |
| Lung | 73.3 | 1.4 |
| Pancreatic | 4.1 | 0.4 |

FIG. 12

| Tissue | miR-559 Norm | CA |
|---|---|---|
| Bladder | 14.0 | 0.4 |
| Breast | 88.4 | 0.9 |
| Colon | 40.8 | 2.1 |
| Glioma | 162.7 | 0.4 |
| H & N | 71.2 | 2.2 |
| Lung | 548.3 | 0.1 |
| Pancreatic | 13.3 | 0.5 |

FIG. 13

| Tissue | 145-5p Norm | CA |
|---|---|---|
| Bladder | 971.5 | 39.8 |
| Breast | 406.1 | 106.6 |
| Colon | 1177.3 | 0.5 |
| Glioma | 2399.2 | 7.2 |
| H & N | 690.9 | 30.4 |
| Lung | 1547.5 | 1.0 |
| Pancreatic | 81.7 | 0.5 |

FIG. 14

| 143-3p | | |
|---|---|---|
| Tissue | Norm | CA |
| Bladder | 489028.8 | 14904.6 |
| Breast | 125943.9 | 91543.1* |
| Colon | 509955.6 | 193.9 |
| Glioma | 514114.8 | 1248.6 |
| H & N | 331034.2 | 20706.2 |
| Lung | 436136.8 | 390.9 |
| Pancreatic | 25557.0 | 269.8 |

| miR-143-3p Breast counts | | miR-143-3p H & N counts | |
|---|---|---|---|
| BT-549 | 132.1 | FaDu | 144.5 |
| DU4475 | 20.1 | SCC-15 | 214.2 |
| HCC-1395 | 503387.3 | SCC-25 | 123445.7 |
| HCC-1806 | 39.7 | SCC9 | 242.2 |
| HCC1143 | 1011.5 | A253 | 54.6 |
| HCC1187 | 4737.7 | Detroit-562 | 136.4 |
| HCC1599 | 1858.7 | | |
| HCC1937 | 33.2 | | |
| HCC38 | 21.9 | | |
| HCC70 | 174.9 | | |
| Hs-578T | 495642.8 | | |
| BT-20 | 46.9 | | |

* Circled wells indicate reduced GFP expression levels

* Circled wells indicate reduced GFP expression levels

FIG. 32

| Construct | ICP27 miRNA site | ICP4 miRNA site |
|---|---|---|
| ONCR-003 | None | 124 |
| ONCR-010 | 122, 34a, Let7 | 124 |
| ONCR-011 | 125a-5p | 124 |
| ONCR-012 | 143-3p | 124 |
| ONCR-013 | 145-5p | 124 |
| ONCR-014 | 199a-5p | 124 |
| ONCR-015 | 1-3p | 124 |
| ONCR-016 | 133a-3p | 124 |
| ONCR-017 | 223-3p | 124 |
| ONCR-018 | 451a | 124 |
| ONCR-019 | 126-3p | 124 |
| ONCR-020 | 127a-3p | 124 |
| ONCR-021 | 133b | 124 |
| ONCR-022 | 134-3p | 124 |

FIG. 33
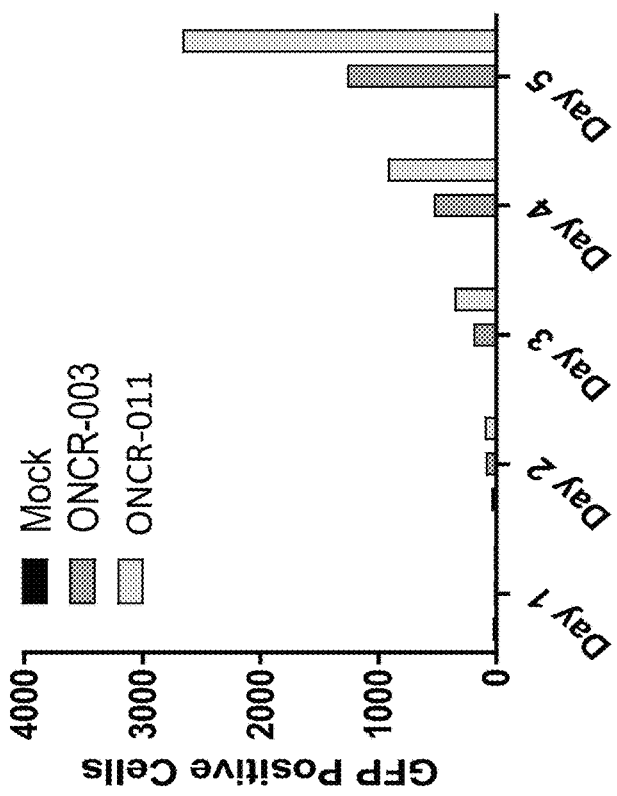
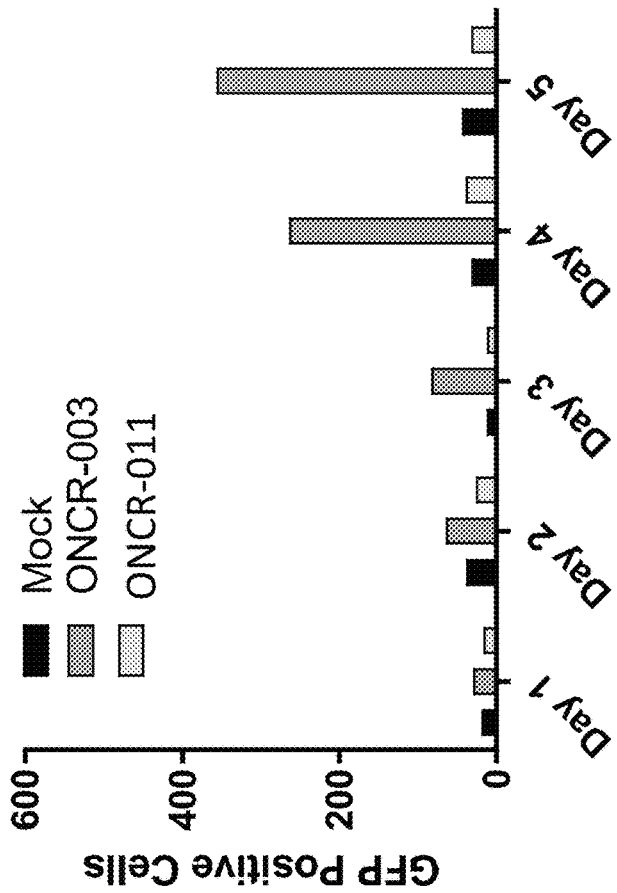

gB:NT: virus entry-enhancing double mutation in gB gene

BAC: loxP-flanked choramphenicol-resistance and lacZ sequences

Δjoint: deletion of the complete internal repeat region including one copy of the ICP4 gene ICP4:TmiRNA: insertion of miRNA target sequences (e.g. let-7, miR-34a, miR-101, miR-125b, miR-145, etc.) into the 3' UTR of the remaining ICP4 gene (also may be placed in 5' UTR)

gB:NT: virus entry-enhancing double mutation in gB gene

BAC: loxP-flanked choramphenicol-resistance and lacZ sequences

Δjoint: deletion of the complete internal repeat region including one copy of the ICP4 gene ICP27:TmiRNA: insertion of miRNA target sequences (e.g. let-7, miR-34a, miR-101, miR-125b, miR-145, etc.) into the 3' UTR of the ICP27 gene (also may be placed in 5' UTR)

FIG. 41 gB:NT: virus entry-enhancing double mutation in gB gene

BAC: loxP-fl gB:NT: virus entry-enhancing double mutation in gB gene

BAC: loxP-flan gB:NT: virus entry-enhancing double mutation in gB gene

BAC: loxP-flanked choramphenicol-resistance and lacZ sequences

Δjoint: deletion of the complete internal repeat region including one copy of the ICP4 gene UL19:TmiRNA & ICP4:TmiRNA: insertion of miRNA target sequences (e.g. let-7, miR-34a, miR-101, miR-125b, miR-145, etc.) into the 3' UTR of the UL19 and ICP4 genes (also may be placed in 5' UTR)

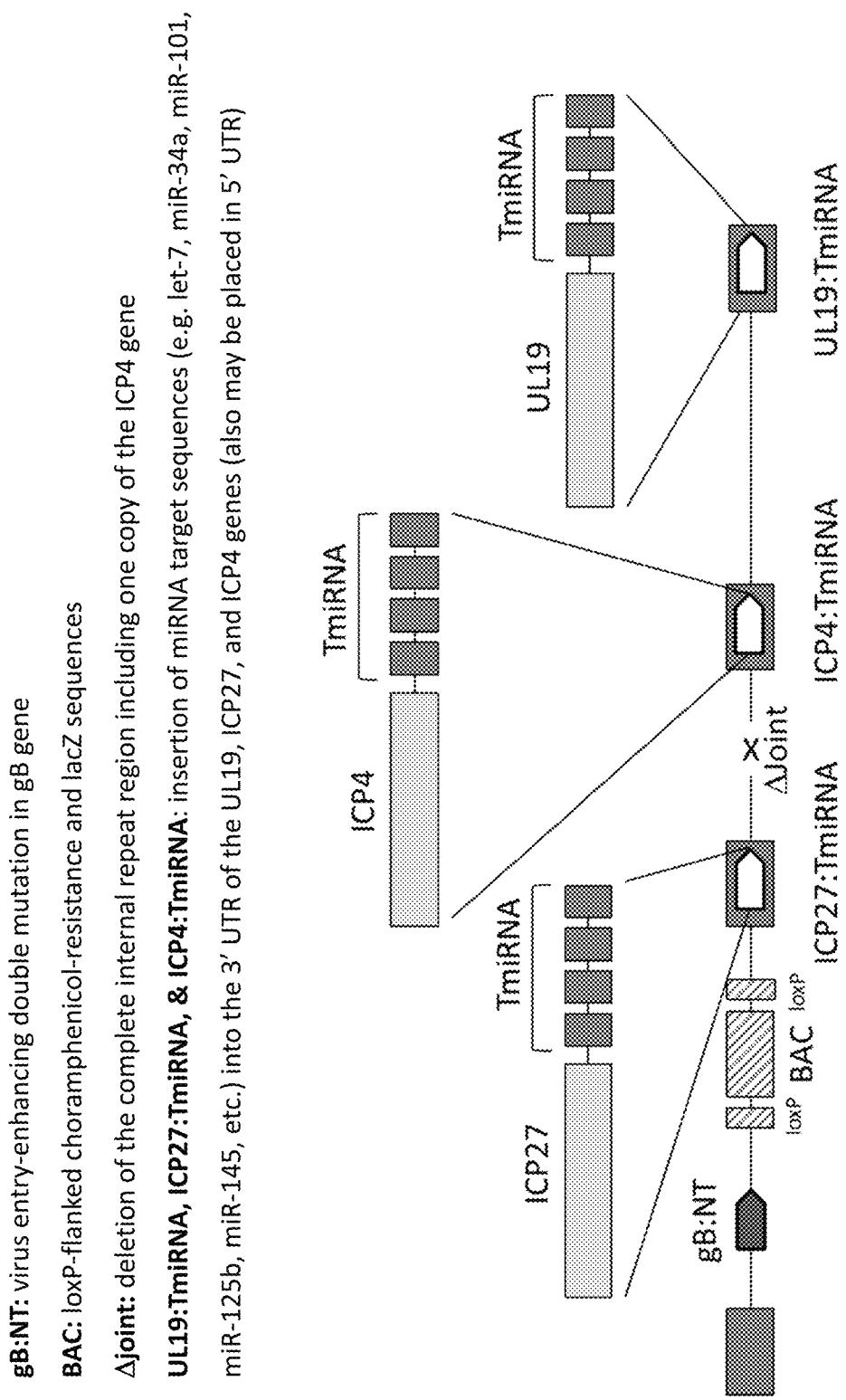

FIG. 44 gB:NT: virus entry-enhancing double mutation in gB gene

BAC: loxP-flanked choramphenicol-resistance and lacZ sequences

Δjoint: deletion of the complete internal repeat region including one copy of the ICP4 gene

UL19:TmiRNA, ICP27:TmiRNA, & ICP4:TmiRNA: insertion of miRNA target sequences (e.g. let-7, miR-34a, miR-101, miR-125b, miR-145, etc.) into the 3' UTR of the UL19, ICP27, and ICP4 genes (also may be placed in 5' UTR)

FIG. 45 gB:NT: virus entry-enhancing double mutation in gB gene

BAC: loxP-flanked choramphenicol-resistance and lacZ sequences

Δjoint: deletion of the complete internal repeat region including one copy of the ICP4 gene ICP4:TmiRNA: insertion of tumor suppressor miRNA target sequences (e.g. let-7, miR-34a, miR-101, miR-125b, miR-145) into the 3' UTR of the remaining ICP4 gene (also may be placed in 5' UTR)

Pol II promoter: Constitutive (CAG, UbC, EF1α, PGK) or cell-specific (e.g. TRPV1, Nav1.7, hSYN)

Endonuclease: CRISPR associated endonuclease (e.g. SpCas9, SaCas9, FnCpf1, FnCas9, etc.)

Poly(A): polyadenylation signal (e.g. bGH)

gRNA: Single crRNA-trRNA fusion (DR-crRNA-DR-trRNA); crRNA targeted to oncogenic microRNA (e.g. miR-17, miR-21, miR-155)

Pol III promoter: E.g. U6, H1, 7SK

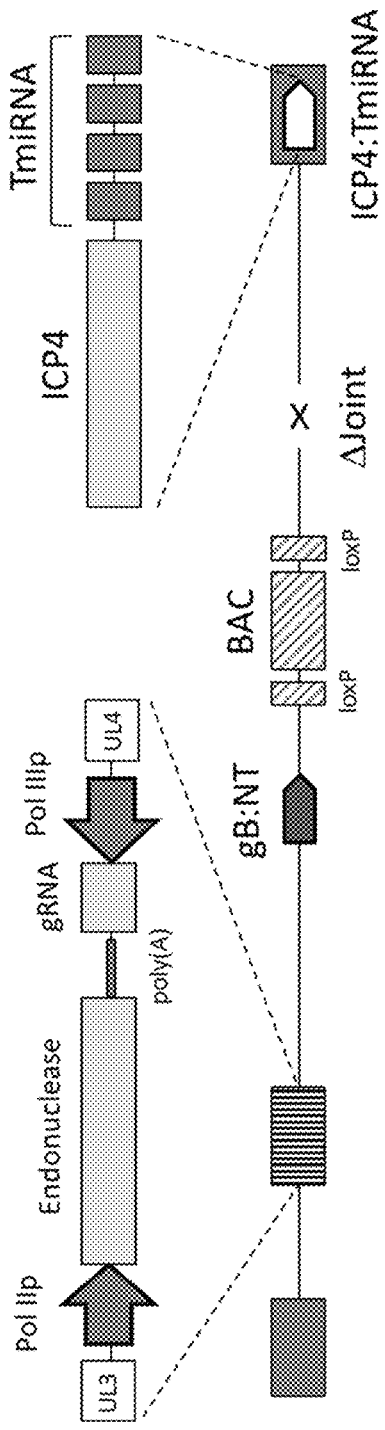

FIG. 46 gB:NT: virus entry-enhancing double mutation in gB gene

BAC: loxP-flanked choramphenicol-resistance and lacZ sequences

ΔJoint: deletion of the complete internal repeat region including one copy of the ICP4 gene ICP4:TmiRNA: insertion of tumor suppressor miRNA target sequences (e.g. let-7, miR-34a, miR-101, miR-125b, miR-145) into the 3' UTR of the remaining ICP4 gene (also may be placed in 5' UTR)

Pol II promoter: Constitutive (CAG, U gB:NT: virus entry-enhancing double mutation in gB gene
BAC: loxP-flanked choramphenicol-resistance

FIG. 48 gB:NT: virus entry-enhancing double mutation in gB gene

BAC: loxP-flanked choramphenicol-resistance and lacZ sequences

Δjoint: deletion of the complete internal repeat region including one copy of the ICP4 gene

ICP4:TmiRNA: insertion of miR-124 target sequence cassette into the 3' UTR of the remaining ICP4 gene (also may be placed in 5' UTR)

ICP27:TmiRNA: insertion of miR-451a, miR-145-5p, and miR-559 target sequence cassettes into the 3' UTR of the ICP-27 gene (also may be placed in 5' UTR)

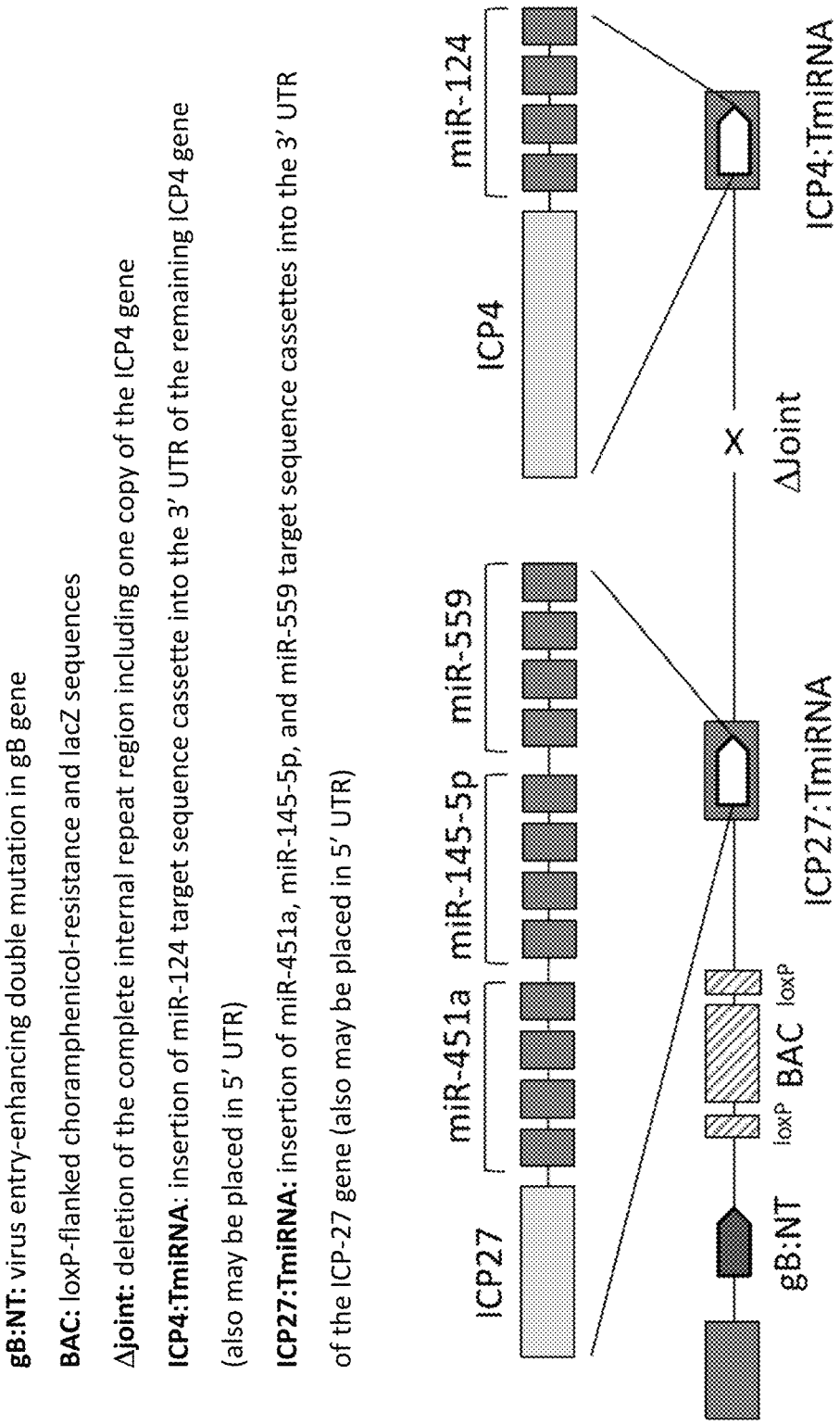

FIG. 49

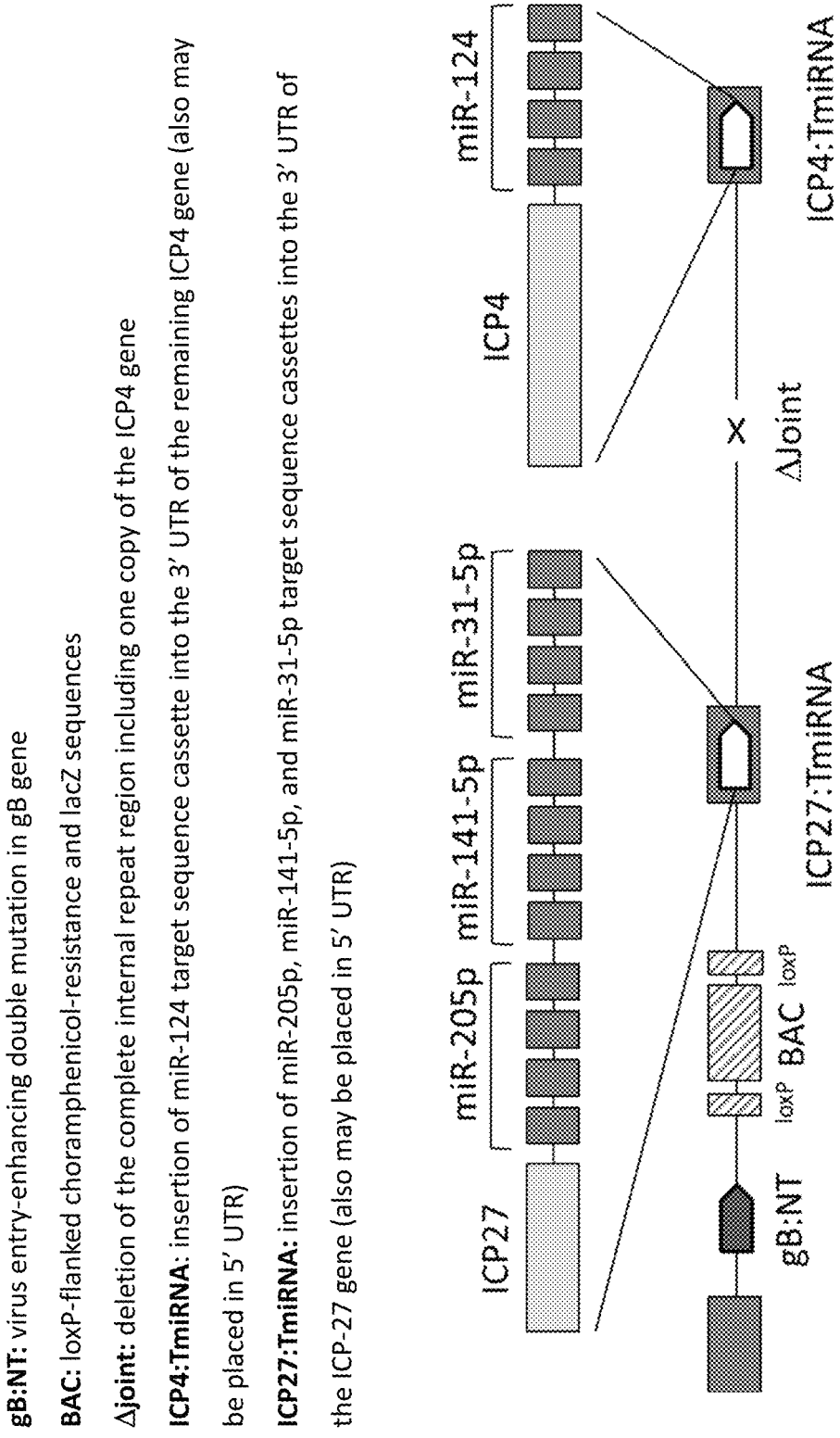

gB:NT: virus entry-enhancing double mutation in gB gene

BAC: loxP-flanked choramphenicol-resistance and lacZ sequences

Δjoint: deletion of the complete internal repeat region including one copy of the ICP4 gene

ICP4:TmiRNA: insertion of miR-124 target sequence cassette into the 3' UTR of the remaining ICP4 gene (also may be placed in 5' UTR)

ICP27:TmiRNA: insertion of miR-205p, miR-141-5p, and miR-31-5p target sequence cassettes into the 3' UTR of the ICP-27 gene (also may be placed in 5' UTR)

ONCOLYTIC VIRAL VECTORS AND USES THEREOF

CROSS REFERENCE TO RELATED APPLICATIONS

This application is a continuation of U.S. patent application Ser. No. 16/047,499, filed Jul. 27, 2018, now U.S. Pat. No. 10,391,132, which is a continuation of International Patent Application No. PCT/US2017/015417, filed Jan. 27, 2017, which claims the benefit of priority to U.S. Provisional Patent Application No. 62/287,619, filed Jan. 27, 2016, the contents of which are incorporated by reference herein in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ONCR_001_02US_SeqList.txt. The text file is 5 KB, was created on May 20, 2019, and is being submitted electronically via EFS-Web.

FIELD OF THE INVENTION

The present disclosure relates to recombinant viral vectors for the treatment and prevention of cancer. The viral vectors utilize one or more of the following aspects: viral replication restriction by insertion of tumor-suppressive microRNA (miRNA) target sequences into the viral genome; disruption of oncogenic miRNA function; cancer microenvironment remodeling; and/or cancer cell targeting by incorporation of protease-activated antibodies into the viral particle.

BACKGROUND OF THE INVENTION

Current targeted cancer therapeutics are efficacious in only a narrow range of cancers due to the heterogeneity of tumor protein expression profiles. Furthermore, many cancer treatments, including existing viral vectors, chemotherapy, radiation, and surgery lack the specificity to selectively treat cancerous cells, while maintaining the health and viability of normal, non-cancerous cells and can produce undesirable off-target effects. As such, there is a need in the art for cancer therapies that are broadly efficacious in multiple cancers and are capable of selectively eliminating cancerous cells.

Oncolytic viruses are viruses that preferentially infect cancer cells and have been used in multiple pre-clinical and clinical studies for cancer treatment. Use of oncolytic viruses carries the risk of non-specific viral infection of healthy cells, leading to the death of non-cancerous cells and tissues. However, genetic manipulation of the viruses to exploit pathways, proteins, and genes that are differentially expressed in normal vs. cancerous tissue can increase the specificity of these viruses and limit off-target infection and cell death.

MicroRNAs (miRNAs or miRs) are small non-coding endogenous RNAs that regulate gene expression by directing their target messenger RNAs for degradation or translational repression. miRNAs are intimately associated with normal cellular processes and therefore, deregulation of miRNAs contributes to a wide array of diseases including cancer. Many miRNA genes are located in cancer associated genomic regions, or in fragile sites, further strengthening the evidence that miRNAs play a pivotal role in cancer. miRNAs are differentially expressed in cancer tissues compared to normal tissues and can have a causative relationship to tumorigenesis. By exploiting this differential miRNA expression in diverse tumor types, the cancer therapeutics described herein possess a broad spectrum safety and efficacy profile, wherein oncolytic viral replication is regulated based on the expression of a particular miRNA or group of miRNAs. Further, the oncolytic viruses described herein may also express proteins that facilitate viral spread throughout a tumor, such as those altering the expression of genes and proteins that regulate the extracellular matrix, thereby increasing their therapeutic efficacy.

SUMMARY OF THE INVENTION

The invention relates to recombinant viral vectors that are useful for the treatment and prevention of cancer. The oncolytic viral vectors comprise the following aspects individually or in combination: restricting viral vector replication to cancer or tumor cells by inserting tumor-suppressive microRNA (miR) target sequences into the viral genome; incorporation of one or more genes into the viral genome whose product(s) disrupt the function of oncogenic miRNA and/or the cancer extracellular matrix; and highly selective targeting of the vectors to cancer/tumor cells by incorporating protease-activated antibodies into the viral particle.

In some embodiments, the present invention provides for a recombinant oncolytic virus comprising one or more copies of one or more tumor-suppressive micro-RNA (miR) target sequences inserted into a locus of one or more viral genes required for viral replication. In some embodiments, the virus is a herpes simplex virus, an adenovirus, a polio virus, a vaccinia virus, a measles virus, a vesicular stomatitis virus, an orthomyxovirus, a parvovirus, a maraba virus or a coxsackievirus. In some embodiments, the virus is a herpes simplex virus and wherein the one or more viral genes required for viral replication is selected from the group consisting of UL1, UL5, UL6, UL7, UL8, UL9, UL11, UL12, UL14, UL15, UL17, UL18, UL19, UL20, UL22, UL25, UL26, UL26.5, UL27, UL28, UL29, UL30, UL31, UL32, UL33, UL34, UL35, UL36, UL37, UL38, UL39, UL40, UL42, UL48, UL49, UL52, UL53, UL54, ICP0, ICP4, ICP22, ICP27, ICP47, gamma-34.5, US3, US4, US5, US6, US7, USB, US9, US10, US11, and US12. In some embodiments, the tumor-suppressive miR target sequence is a target sequence for a miR selected from Table 3. In some embodiments, the one or more tumor-suppressive miR target sequences is incorporated into the 5' untranslated region (UTR) or 3' UTR of the one or more viral genes required for viral replication.

In some embodiments, the present invention provides for a recombinant oncolytic virus comprising one or more copies of one or more tumor-suppressive micro-RNA (miR) target sequences inserted into a locus of one or more viral genes required for viral replication, wherein replication of the virus is reduced or attenuated in a first cell compared to replication of the virus in a second cell. In some embodiments, the first cell has an increased expression of a tumor-suppressive miR capable of binding to the one or more tumor-suppressive miR target sequences compared to the expression of the tumor-suppressive miR in the second cell. In some embodiments, the expression level of the tumor-suppressive miR in the first cell is at least 5% greater than the expression level of the tumor-suppressive miR in the second cell. In some embodiments, the second cell has a reduced expression of a tumor-suppressive miR capable of binding to the one or more tumor-suppressive miR target sequences compared to the expression of the tumor-suppressive miR in the first cell. In some embodiments, the expression level of the tumor-suppressive miR in the second cell is at least 5% less than the expression level of the tumor-suppressive miR in the first cell. In some embodiments, the second cell is a cancerous cell.

In some embodiments, the present invention provides for a recombinant oncolytic virus comprising one or more copies of one or more tumor-suppressive micro-RNA (miR) target sequences inserted into a locus of one or more viral genes required for viral replication, wherein the tumor-suppressive miR target sequences are target sequences for miR-124, miR-451a, miR-143-3p, and miR-559. In further embodiments, the oncolytic virus is used for the treatment of pancreatic, lung, and/or colon cancer. In some embodiments, the oncolytic virus comprises the tumor-suppressive miR target sequences for miR-124, miR-451, miR-143-3p, miR-1, and miR-559. In some embodiments, the oncolytic virus comprises the tumor-suppressive miR target sequences for miR-124, miR-451, miR-145-5p, and miR-559. In further embodiments, the oncolytic virus is used for the treatment of a tumor derived from any type of cancer. In some embodiments, the oncolytic virus comprises the tumor-suppressive miR target sequences for miR-205p, miR-141-5p, miR-31-5p, and miR-124. In further embodiments, the oncolytic virus is used for the treatment of schwannoma. In further embodiments, the tumor-suppressive miR target sequences are inserted into the ICP4, ICP27, UL19, and/or UL30 locus.

In some embodiments, the present invention provides for a recombinant oncolytic virus comprising one or more copies of one or more tumor-suppressive micro-RNA (miR) target sequences inserted into a locus of one or more viral genes required for viral replication, wherein the tumor-suppressive miR target sequence is a target sequence for miR-136-3p, miR-432-5p, miR-1-3p, miR-127-3p, miR-379-5p, miR-493-5p, miR-223-5p, miR-223-5p, miR-136-5p, miR-451a, miR-487b-3p, miR-370-3p, miR-410-3p, miR-431-3p, miR-4485-3p, miR-4485-5p, miR-127-5p, miR-409-3p, miR-338-3p, miR-559, miR-411-5p, miR-133a-5p, miR-143-3p, miR-376b-3p, miR-758-3p, miR-1, miR-101, miR-1180, miR-1236, miR-124-3p, miR-125b, miR-126, miR-1280, miR-133a, miR-133b, miR-141, miR-143, miR-144, miR-145, miR-155, miR-16, miR-18a, miR-192, miR-195, miR-200a, miR-200b, miR-200c, miR-203, miR-205, miR-214, miR-218, miR-23b, miR-26a, miR-29c, miR-320c, miR-34a, miR-370, miR-409-3p, miR-429, miR-451b, miR-490-5p, miR-493, miR-576-3p, and/or miR-99a. In further embodiments, the oncolytic virus is used for treating bladder cancer.

In some embodiments, the tumor-suppressive miR target sequence is a target sequence for miR-1251-5p, miR-219a-5p, miR-219a-2-3p, miR-124-3p, miR-448, miR-138-2-3p, miR-490-5p, miR-129-1-3p, miR-1264, miR-3943, miR-490-3p, miR-383-5p, miR-133b, miR-129-2-3p, miR-128-2-5p, miR-133a-3p, miR-129-5p, miR-1-3p, miR-885-3p, miR-124-5p, miR-759, miR-7158-3p, miR-770-5p, miR-135a-5p, miR-885-5p, let-7g-5p, miR-100, miR-101, miR-106a, miR-124, miR-124a, miR-125a, miR-125a-5p, miR-125b, miR-127-3p, miR-128, miR-129, miR-136, miR-137, miR-139-5p, miR-142-3p, miR-143, miR-145, miR-146b-5p, miR-149, miR-152, miR-153, miR-195, miR-21, miR-212-3p, miR-219-5p, miR-222, miR-29b, miR-31, miR-3189-3p, miR-320, miR-320a, miR-326, miR-330, miR-331-3p, miR-340, miR-342, miR-34a, miR-376a, miR-449a, miR-483-5p, miR-503, miR-577, miR-663, miR-7, miR-7-5p, miR-873, let-7a, let-7f, miR-107, miR-122, miR-124-5p, miR-139, miR-146a, miR-146b, miR-15b, miR-16, miR-181a, miR-181a-1, miR-181a-2, miR-181b, miR-181b-1, miR-181b-2, miR-181c, miR-181d, miR-184, miR-185, miR-199a-3p, miR-200a, miR-200b, miR-203, miR-204, miR-205, miR-218, miR-23b, miR-26b, miR-27a, miR-29c, miR-328, miR-34c-3p, miR-34c-5p, miR-375, miR-383, miR-451, miR-452, miR-495, miR-584, miR-622, miR-656, miR-98, miR-124-3p, miR-181b-5p, miR-200b, and/or miR-3189-3p. In further embodiments, the oncolytic virus is used for treating brain cancer.

In some embodiments, the tumor-suppressive miR target sequence is a target sequence for miR-10b-5p, miR-126-3p, miR-145-3p, miR-451a, miR-199b-5p, miR-5683, miR-3195, miR-3182, miR-1271-5p, miR-204-5p, miR-409-5p, miR-136-5p, miR-514a-5p, miR-559, miR-483-3p, miR-1-3p, miR-6080, miR-144-3p, miR-10b-3p, miR-6130, miR-6089, miR-203b-5p, miR-4266, miR-4327, miR-5694, miR-193b, let-7a, let-7a-1, let-7a-2, let-7a-3, let-7b, let-7c, let-7d, let-7e, let-7f-1, let-7f-2, let-7g, let-7i, miR-100, miR-107, miR-10a, miR-10b, miR-122, miR-124, miR-1258, miR-125a-5p, miR-125b, miR-126, miR-127, miR-129, miR-130a, miR-132, miR-133a, miR-143, miR-145, miR-146a, miR-146b, miR-147, miR-148a, miR-149, miR-152, miR-153, miR-15a, miR-16, miR-17-5p, miR-181a, miR-1826, miR-183, miR-185, miR-191, miR-193a-3p, miR-195, miR-199b-5p, miR-19a-3p, miR-200a, miR-200b, miR-200c, miR-205, miR-206, miR-211, miR-216b, miR-218, miR-22, miR-26a, miR-26b, miR-300, miR-30a, miR-31, miR-335, miR-339-5p, miR-33b, miR-34a, miR-34b, miR-34c, miR-374a, miR-379, miR-381, miR-383, miR-425, miR-429, miR-450b-3p, miR-494, miR-495, miR-497, miR-502-5p, miR-517a, miR-574-3p, miR-638, miR-7, miR-720, miR-873, miR-874, miR-92a, miR-98, miR-99a, mmu-miR-290-3p, and/or mmu-miR-290-5p. In further embodiments, the oncolytic virus is used for treating breast cancer.

In some embodiments, the tumor-suppressive miR target sequence is a target sequence for miR-143, miR-145, miR-17-5p, miR-203, miR-214, miR-218, miR-335, miR-342-3p, miR-372, miR-424, miR-491-5p, miR-497, miR-7, miR-99a, miR-99b, miR-100, miR-101, miR-15a, miR-16, miR-34a, miR-886-5p, miR-106a, miR-124, miR-148a, miR-29a, and/or miR-375. In further embodiments, the oncolytic virus is used for treating cervical cancer.

In some embodiments, the tumor-suppressive miR target sequence is a target sequence for miR-133a-5p, miR-490-5p, miR-124-3p, miR-137, miR-655-3p, miR-376c-3p, miR-369-5p, miR-490-3p, miR-432-5p, miR-487b-3p, miR-342-3p, miR-223-3p, miR-136-3p, miR-136-3p, miR-143-5p, miR-1-3p, miR-214-3p, miR-143-3p, miR-199a-3p, miR-199b-3p, miR-451a, miR-127-3p, miR-133a-3p, miR-145-5p, miR-145-3p, miR-199a-5p, let-7a-1, let-7a-2, let-7a-3, let-7b, let-7c, let-7d, let-7e, let-7f-1, let-7f-2, let-7g, let-7i, miR-100, miR-101, miR-126, miR-142-3p, miR-143, miR-145, miR-192, miR-200c, miR-21, miR-214, miR-215, miR-22, miR-25, miR-302a, miR-320, miR-320a, miR-34a, miR-34c, miR-365, miR-373, miR-424, miR-429, miR-455, miR-484, miR-502, miR-503, miR-93, miR-98, miR-186, miR-30a-5p, miR-627, let-7a, miR-1, miR-124, miR-125a, miR-129, miR-1295b-3p, miR-1307, miR-130b, miR-132, miR-133a, miR-133b, miR-137, miR-138, miR-139, miR-139-5p, miR-140-5p, miR-148a, miR-148b, miR-149, miR-150-5p, miR-154, miR-15a, miR-15b, miR-16, miR-18a, miR-191, miR-193a-5p, miR-194, miR-195, miR-196a, miR-198, miR-199a-5p, miR-203, miR-204-5p, miR-206, miR-212, miR-218, miR-224, miR-24-3p, miR-26b, miR-27a, miR-28-3p, miR-28-5p, miR-29b, miR-30a-3p, miR-30b, miR- 328, miR-338-3p, miR-342, miR-345, miR-34a-5p, miR-361-5p, miR-375, miR-378, miR-378a-3p, miR-378a-5p, miR-409-3p, miR-422a, miR-4487, miR-483, miR-497, miR-498, miR-518a-3p, miR-551a, miR-574-5p, miR-625, miR-638, miR-7, miR-96-5p, miR-202-3p, miR-30a, and/or miR-451. In further embodiments, the oncolytic virus is used for treating colon or colorectal cancer.

In some embodiments, the tumor-suppressive miR target sequence is a target sequence for miR-101, miR-130a, miR-130b, miR-134, miR-143, miR-145, miR-152, miR-205, miR-223, miR-301a, miR-301b, miR-30c, miR-34a, miR-34c, miR-424, miR-449a, miR-543, and/or miR-34b inserted into the 5' UTR or 3' UTR of one or more viral genes required for viral replication. In further embodiments, the oncolytic virus is used for treating endometrial cancer.

In some embodiments, the tumor-suppressive miR target sequence is a target sequence for miR-125b, miR-138, miR-15a, miR-15b, miR-16, miR-16-1, miR-16-1-3p, miR-16-2, miR-181a, miR-181b, miR-195, miR-223, miR-29b, miR-34b, miR-34c, miR-424, miR-10a, miR-146a, miR-150, miR-151, miR-155, miR-2278, miR-26a, miR-30e, miR-31, miR-326, miR-564, miR-27a, let-7b, miR-124a, miR-142-3p, let-7c, miR-17, miR-20a, miR-29a, miR-30c, miR-720, miR-107, miR-342, miR-34a, miR-202, miR-142-5p, miR-29c, miR-145, miR-193b, miR-199a, miR-214, miR-22, miR-137, and/or miR-197 inserted into the 5' UTR or 3' UTR of one or more viral genes required for viral replication. In further embodiments, the oncolytic virus is used for treating hematologic cancer.

In some embodiments, the tumor-suppressive miR target sequence is a target sequence for miR-1, miR-145, miR-1826, miR-199a, miR-199a-3p, miR-203, miR-205, miR-497, miR-508-3p, miR-509-3p, let-7a, let-7d, miR-106a*, miR-126, miR-1285, miR-129-3p, miR-1291, miR-133a, miR-135a, miR-138, miR-141, miR-143, miR-182-5p, miR-200a, miR-218, miR-28-5p, miR-30a, miR-30c, miR-30d, miR-34a, miR-378, miR-429, miR-509-5p, miR-646, miR-133b, let-7b, let-7c, miR-200c, miR-204, miR-335, miR-377, and/or miR-506 inserted into the 5' UTR or 3' UTR of one or more viral genes required for viral replication. In further embodiments, the oncolytic virus is used for treating kidney cancer.

In some embodiments, the tumor-suppressive miR target sequence is a target sequence for let-7a-1, let-7a-2, let-7a-3, let-7b, let-7c, let-7d, let-7e, let-7f, let-7f-1, let-7f-2, let-7g, let-7i, miR-1, miR-100, miR-101, miR-105, miR-122, miR-122a, miR-1236, miR-124, miR-125b, miR-126, miR-127, miR-1271, miR-128-3p, miR-129-5p, miR-130a, miR-130b, miR-133a, miR-134, miR-137, miR-138, miR-139, miR-139-5p, miR-140-5p, miR-141, miR-142-3p, miR-143, miR-144, miR-145, miR-146a, miR-148a, miR-148b, miR-150-5p, miR-15b, miR-16, miR-181a-5p, miR-185, miR-188-5p, miR-193b, miR-195, miR-195-5p, miR-197, miR-198, miR-199a, miR-199a-5p, miR-199b, miR-199b-5p, miR-200a, miR-200b, miR-200c, miR-202, miR-203, miR-204-3p, miR-205, miR-206, miR-20a, miR-21, miR-21-3p, miR-211, miR-212, miR-214, miR-217, miR-218, miR-219-5p, miR-22, miR-223, miR-26a, miR-26b, miR-29a, miR-29b-1, miR-29b-2, miR-29c, miR-302b, miR-302c, miR-30a, miR-30a-3p, miR-335, miR-338-3p, miR-33a, miR-34a, miR-34b, miR-365, miR-370, miR-372, miR-375, miR-376a, miR-377, miR-422a, miR-424, miR-424-5p, miR-433, miR-4458, miR-448, miR-450a, miR-451, miR-485-5p, miR-486-5p, miR-497, miR-503, miR-506, miR-519d, miR-520a, miR-520b, miR-520c-3p, miR-582-5p, miR-590-5p, miR-610, miR-612, miR-625, miR-637, miR-675, miR-7, miR-877, miR-940, miR-941, miR-98, miR-99a, miR-132, and/or miR-31 inserted into the 5' UTR or 3' UTR of one or more viral genes required for viral replication. In further embodiments, the oncolytic virus is used for treating liver cancer. In further embodiments, the liver cancer is hepatocellular carcinoma.

In some embodiments, the tumor-suppressive miR target sequence is a target sequence for miR-143-3p, miR-126-3p, miR-126-5p, miR-1266-3p, miR-6130, miR-6080, miR-511-5p, miR-143-5p, miR-223-5p, miR-199b-5p, miR-199a-3p, miR-199b-3p, miR-451a, miR-142-5p, miR-144, miR-150-5p, miR-142-3p, miR-214-3p, miR-214-5p, miR-199a-5p, miR-145-3p, miR-145-5p, miR-1297, miR-141, miR-145, miR-16, miR-200a, miR-200b, miR-200c, miR-29b, miR-381, miR-409-3p, miR-429, miR-451, miR-511, miR-99a, let-7a-1, let-7a-2, let-7a-3, let-7b, let-7c, let-7d, let-7e, let-7f-1, let-7f-2, let-7g, let-7i, miR-1, miR-101, miR-133b, miR-138, miR-142-5p, miR-144, miR-1469, miR-146a, miR-153, miR-15a, miR-15b, miR-16-1, miR-16-2, miR-182, miR-192, miR-193a-3p, miR-194, miR-195, miR-198, miR-203, miR-217, miR-218, miR-22, miR-223, miR-26a, miR-26b, miR-29c, miR-33a, miR-34a, miR-34b, miR-34c, miR-365, miR-449a, miR-449b, miR-486-5p, miR-545, miR-610, miR-614, miR-630, miR-660, miR-7515, miR-9500, miR-98, miR-99b, miR-133a, let-7a, miR-100, miR-106a, miR-107, miR-124, miR-125a-3p, miR-125a-5p, miR-126, miR-126*, miR-129, miR-137, miR-140, miR-143, miR-146b, miR-148a, miR-148b, miR-149, miR-152, miR-154, miR-155, miR-17-5p, miR-181a-1, miR-181a-2, miR-181b, miR-181b-1, miR-181b-2, miR-181c, miR-181d, miR-184, miR-186, miR-193b, miR-199a, miR-204, miR-212, miR-221, miR-224, miR-27a, miR-27b, miR-29a, miR-30a, miR-30b, miR-30c, miR-30d, miR-30d-5p, miR-30e-5p, miR-32, miR-335, miR-338-3p, miR-340, miR-342-3p, miR-361-3p, miR-373, miR-375, miR-4500, miR-4782-3p, miR-497, miR-503, miR-512-3p, miR-520a-3p, miR-526b, miR-625*, and/or miR-96 inserted into the 5' UTR or 3' UTR of one or more viral genes required for viral replication. In further embodiments, the oncolytic virus is used for treating lung cancer.

In some embodiments, the tumor-suppressive miR target sequence is a target sequence for let-7b, miR-101, miR-125b, miR-1280, miR-143, miR-146a, miR-146b, miR-155, miR-17, miR-184, miR-185, miR-18b, miR-193b, miR-200c, miR-203, miR-204, miR-205, miR-206, miR-20a, miR-211, miR-218, miR-26a, miR-31, miR-33a, miR-34a, miR-34c, miR-376a, miR-376c, miR-573, miR-7-5p, miR-9, and/or miR-98 inserted into the 5' UTR or 3' UTR of one or more viral genes required for viral replication. In further embodiments, the oncolytic virus is used for treating melanoma.

In some embodiments, the tumor-suppressive miR target sequence is a target sequence for let-7d, miR-218, miR-34a, miR-375, miR-494, miR-100, miR-124, miR-1250, miR-125b, miR-126, miR-1271, miR-136, miR-138, miR-145, miR-147, miR-148a, miR-181a, miR-206, miR-220a, miR-26a, miR-26b, miR-29a, miR-32, miR-323-5p, miR-329, miR-338, miR-370, miR-410, miR-429, miR-433, miR-499a-5p, miR-503, miR-506, miR-632, miR-646, miR-668, miR-877, and/or miR-9 inserted into the 5' UTR or 3' UTR of one or more viral genes required for viral replication. In further embodiments, the oncolytic virus is used for treating oral cancer.

In some embodiments, the tumor-suppressive miR target sequence is a target sequence for let-7i, miR-100, miR-124, miR-125b, miR-129-5p, miR-130b, miR-133a, miR-137, miR-138, miR-141, miR-145, miR-148a, miR-152, miR-153, miR-155, miR-199a, miR-200a, miR-200b, miR-200c, miR-212, miR-335, miR-34a, miR-34b, miR-34c, miR-409-3p, miR-411, miR-429, miR-432, miR-449a, miR-494, miR-497, miR-498, miR-519d, miR-655, miR-9, miR-98, miR-101, miR-532-5p, miR-124a, miR-192, miR-193a, and/or miR-7 inserted into the 5' UTR or 3' UTR of one or more viral genes required for viral replication. In further embodiments, the oncolytic virus is used for treating ovarian cancer.

In some embodiments, the tumor-suppressive miR target sequence is a target sequence for miR-216a-5p, miR-802, miR-217, miR-145-3p, miR-143-3p, miR-451a, miR-375, miR-214-3p, miR-216b-3p, miR-432-5p, miR-216a-3p, miR-199b-5p, miR-199a-5p, miR-136-3p, miR-216b-5p, miR-136-5p, miR-145-5p, miR-127-3p, miR-199a-3p, miR-199b-3p, miR-559, miR-129-2-3p, miR-4507, miR-1-3p, miR-148a-3p, miR-101, miR-1181, miR-124, miR-1247, miR-133a, miR-141, miR-145, miR-146a, miR-148a, miR-148b, miR-150*, miR-150-5p, miR-152, miR-15a, miR-198, miR-203, miR-214, miR-216a, miR-29c, miR-335, miR-34a, miR-34b, miR-34c, miR-373, miR-375, miR-410, miR-497, miR-615-5p, miR-630, miR-96, miR-132, let-7a, let-7a-1, let-7a-2, let-7a-3, let-7b, let-7c, let-7d, let-7e, let-7f-1, let-7f-2, let-7g, let-7i, miR-126, miR-135a, miR-143, miR-144, miR-150, miR-16, miR-200a, miR-200b, miR-200c, miR-217, miR-218, miR-337, miR-494, and/or miR-98 inserted into the 5' UTR or 3' UTR of one or more viral genes required for viral replication. In further embodiments, the oncolytic virus is used for treating pancreatic cancer.

In some embodiments, the tumor-suppressive miR target sequence is a target sequence for let-7a-3p, let-7c, miR-100, miR-101, miR-105, miR-124, miR-128, miR-1296, miR-130b, miR-133a-1, miR-133a-2, miR-133b, miR-135a, miR-143, miR-145, miR-146a, miR-154, miR-15a, miR-187, miR-188-5p, miR-199b, miR-200b, miR-203, miR-205, miR-212, miR-218, miR-221, miR-224, miR-23a, miR-23b, miR-25, miR-26a, miR-26b, miR-29b, miR-302a, miR-30a, miR-30b, miR-30c-1, miR-30c-2, miR-30d, miR-30e, miR-31, miR-330, miR-331-3p, miR-34a, miR-34b, miR-34c, miR-374b, miR-449a, miR-4723-5p, miR-497, miR-628-5p, miR-642a-5p, miR-765, and/or miR-940 inserted into the 5' UTR or 3' UTR of one or more viral genes required for viral replication. In further embodiments, the oncolytic virus is used for treating prostate cancer.

In some embodiments, the tumor-suppressive miR target sequence is a target sequence for miR-101, miR-183, miR-204, miR-34a, miR-365b-3p, miR-486-3p, and/or miR-532-5p inserted into the 5' UTR or 3' UTR of one or more viral genes required for viral replication. In further embodiments, the oncolytic virus is used for treating retinoblastoma.

In some embodiments, the tumor-suppressive miR target sequence is a target sequence for miR-143-3p, miR-133b, miR-1264, miR-448, miR-1298-5p, miR-490-5p, miR-138-2-3p, miR-144-3p, miR-144-5p, miR-150-5p, miR-129-1-3p, miR-559, miR-1-3-p, miR-143-5p, miR-223-3p, miR-3943, miR-338-3p, miR-124-3p, miR-219a-5p, miR-219a-2-3p, miR-451a, miR-142-5p, miR-133a-3p, miR-145-5p, and/or miR-145-3p. In further embodiments, the oncolytic virus is used for treating glioblastoma.

In some embodiments, the tumor-suppressive miR target sequence is a target sequence for miR-143-3p, miR-223-3p, miR-6080, miR-208b-3p, miR-206, miR-133a-5p, miR-133b, miR-199a-5p, miR-199b-5p, miR-145-3p, miR-145-5p, miR-150-5p, miR-142-3p, miR-144-3p, miR-144-5p, miR-338-3p, miR-214-3p, miR-559, miR-133a-3p, miR-1-3p, miR-126-3p, miR-142-5p, miR-451a, miR-199a-3p, and/or miR-199b-3p. In further embodiments, the oncolytic virus is used for treating head and neck cancer.

In some embodiments, the tumor-suppressive miR target sequence is a target sequence for miR-133b, miR-208b-3p, miR-6130, miR-141-5p, miR-31-3p, miR-1293, miR-129-2-3p, miR-129-5p, miR-124-3p, miR-219a-5p, miR-219a-2-3p, miR-490-3p, miR-488-3p, miR-935, miR-124-5p, miR-122-3p, miR-122-5p, miR-1-3p, miR-133a-3p, miR-375, miR-141-3p, miR-31-5p, miR-205-5p, miR-200c-3p, and/or miR-203a-3p. In further embodiments, the oncolytic virus is used for treating a Schwannoma.

In some embodiments, the present invention provides for recombinant oncolytic viruses comprising one or more of (a) one or more tumor-suppressive micro-RNA (miR) target sequences inserted into a locus of one or more viral genes required for viral replication; (b) one or more polynucleotides encoding one or more proteins or oligonucleotides, wherein the proteins or oligonucleotides reduce the expression or inhibit the function of a miR, a gene, or a TIMP; (c) at least one protease-activated antibody; and/or (d) a polynucleotide encoding at least one protease activated antibody. In some embodiments, the miR is an oncogenic miR or a microenvironment remodeling miR. In some embodiments, the oncogenic miR is selected from the miRs listed in Table 4. In some embodiments, the gene is an oncogenic gene. In some embodiments, the oncogenic gene is selected from the genes listed in Table 7. In some embodiments, the microenvironment remodeling miR is selected from the miRs listed in Table 5. In some embodiments, the TIMP is selected from TIMP1, TIMP2, TIMP3 and TIMP4. In some embodiments, the oligonucleotide of (b) is an shRNA or a decoy oligonucleotide.

In some embodiments, the present invention provides for recombinant oncolytic viruses comprising one or more of (a) one or more tumor-suppressive micro-RNA (miR) target sequences inserted into a locus of one or more viral genes required for viral replication; (b) one or more polynucleotides encoding one or more proteins or oligonucleotides, wherein the proteins or oligonucleotides reduce the expression or inhibit the function of a miR, a gene, or a TIMP; (c) at least one protease-activated antibody; and/or (d) a polynucleotide encoding at least one protease activated antibody, wherein the protein is a nuclease, a bispecific T-cell engager (BiTE), an anti-immunosuppressive protein, or an immunogenic antigen. In some embodiments, the nuclease is selected from a Clustered Regulatory Interspaced Short Palindromic Repeats (CRISPR)-associated endonuclease, a zinc-finger nuclease (ZFN) or a Transcription activator-like effector nuclease (TALEN). In some embodiments, the CRISPR-associated endonuclease is selected from SpCas9, SpCas9-HF1, SpCas9-HF2, SpCas9-HF3, SpCas9-HF4, SaCas9, FnCpf, FnCas9, eSpCas9, C2C1, C2C3, Cpf1, Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4. In further embodiments, the oncolytic virus further comprises a heterologous polynucleotide encoding an tracr-RNA (trRNA) and a crispr-RNA (crRNA), wherein the crRNA is targeted to a genomic DNA sequence encoding a miR or a TIMP and wherein the trRNA facilitates binding and activation of a CRISPR-associated endonuclease.

In some embodiments, the anti-immunosuppressive protein is an anti-regulatory T-cell (Treg) protein or an anti-myeloid-derived suppressor cell (MDSC) protein. In some embodiments, the anti-immunosuppressive protein is a VHH-derived blocker or a VHH-derived BiTE.

In some embodiments, the protein induces an anti-tumor immune response. In further embodiments, the protein is selected from EpCAM, folate, IFNβ, anti-CTLA-4, anti-PD1, A2A, anti-FGF2, anti-FGFR/FGFR2b, anti-SEMA4D, CCL5, CD137, CD200, CD38, CD44, CSF-1R, CXCL10, CXCL13, endothelin B Receptor, IL-12, IL-15, IL-2, IL-21, IL-35, ISRE7, LFA-1, NG2 (also known as SPEG4), a SMAD protein, STING, TGFβ, and VCAM1.

In some embodiments, the present invention provides for recombinant oncolytic viruses comprising one or more of (a) one or more tumor-suppressive micro-RNA (miR) target sequences inserted into a locus of one or more viral genes required for viral replication; (b) one or more polynucleotides encoding one or more proteins or oligonucleotides, wherein the proteins or oligonucleotides reduce the expression or inhibit the function of a miR, a gene, or a TIMP; (c) at least one protease-activated antibody; and/or (d) a polynucleotide encoding at least one protease activated antibody, wherein the at least one protease-activated antibody is incorporated into a viral glycoprotein envelope. In some embodiments, the protease-activated antibody is activated by a protease selected from a cysteine cathepsin, an aspartic cathepsin, a kallikrein (hK), a serine protease, a caspase, a matrix metalloproteinase (MMP), and a disintegrin metalloproteinase (ADAM). In some embodiments, the protease is selected from cathepsin K, cathepsin B, cathepsin L, cathepsin E, cathepsin D, hK1, PSA (hK3), hK10, hK15, uPA, uPAR, MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19, MMP-20, MMP-21, MMP-23A, MMP-23B, MMP-24, MMP-25, MMP-26, MMP-27, MMP-28, or a protease listed in Table 6.

In some embodiments, the protease-activated antibody binds to a protein expressed more highly by a cancer cell or in a cancer microenvironment than by a non-cancer cell or in a non-cancer microenvironment. In some embodiments, the protease-activated antibody binds NKG2D, c-met, HGFR, CD8, heparan sulfate, VSPG4 (also known as NG2), EGFR, EGFRvIII, CD133, CXCR4, carcinoembryonic antigen (CEA), CLC-3, annexin II, human transferrin receptor, or EpCAM.

In some embodiments, the miR target sequence and/or the one or more polynucleotides is inserted into a gene locus of the viral genome. In some embodiments, the virus is a herpes simplex virus and wherein the at least one polynucleotide is inserted into or between one or more viral gene loci selected from the group consisting of the internal repeat joint region (comprising one copy each of the diploid genes ICP0, ICP34.5, LAT, ICP4, and the ICP47 promoter), ICP0, LAT, UL1, UL5, UL6, UL7, UL8, UL9, UL11, UL12, UL14, UL15, UL17, UL18, UL19, UL20, UL22, UL25, UL26, UL26.5, UL27, UL28, UL29, UL30, UL31, UL32, UL33, UL34, UL35, UL36, UL37, UL38, UL39, UL40, UL42, UL48, UL49, UL52, UL53, UL54, ICP0, ICP4, ICP22, ICP27, ICP47, gamma-34.5, US3, US4, US5, US6, US7, US8, US9, US10, US11, and US12.

In some embodiments, the invention provides for a nucleic acid molecule encoding an oncolytic virus described herein. In some embodiments, the invention provides for a viral stock of an oncolytic virus described herein. In some embodiments, the invention provides for a composition comprising an oncolytic virus described herein and a pharmaceutically-acceptable carrier.

In some embodiments, the invention provides a method of killing a cancerous cell, comprising exposing the cancerous cell to an oncolytic virus described herein or compositions thereof under conditions sufficient for the oncolytic virus to infect and replicate within said cancerous cell, and wherein replication of the oncolytic virus within the cancerous cell results in cell death. In some embodiments, the cancerous cell has a reduced expression of a tumor-suppressive miR capable of binding to the one or more tumor-suppressive miR-target sequences compared to the expression of the tumor-suppressive miR in a non-cancerous cell. In some embodiments, the expression level of the tumor-suppressive miR in the cancerous cell is at least 5% less than the expression level the tumor-suppressive miR in the non-cancerous cell. In some embodiments, replication of the oncolytic virus is increased or maintained in cancerous cells with a reduced expression of the tumor-suppressive miR capable of binding to the one or more tumor-suppressive miR-target sequences. In some embodiments, viral replication is at least 5% greater in the cancerous cells compared to the viral replication in the non-cancerous cell. In some embodiments, the cell is in vivo. In some embodiments, the cell is within a tumor.

In some embodiments, the invention provides a method of treating cancer in a subject in need thereof, comprising administering an oncolytic virus described herein or compositions thereof to the subject. In some embodiments, the subject is a mouse, a rat, a rabbit, a cat, a dog, a horse, a non-human primate, or a human. In some embodiments, the oncolytic virus or compositions thereof are administered intravenously, subcutaneously, intratumorally, intramuscularly, or intranasally. In some embodiments, the cancer is selected from lung cancer, breast cancer, ovarian cancer, cervical cancer, prostate cancer, testicular cancer, colorectal cancer, colon cancer, pancreatic cancer, liver cancer, gastric cancer, head and neck cancer, thyroid cancer, malignant glioma, glioblastoma, melanoma, B-cell chronic lymphocytic leukemia, diffuse large B-cell lymphoma (DLBCL), and marginal zone lymphoma (MZL). In some embodiments, lung cancer is small cell lung cancer or non-small cell lung cancer. In some embodiments, liver cancer is hepatocellular carcinoma (HCC).

BRIEF DESCRIPTION OF THE DRAWINGS

FIG. 10 illustrates downregulation of miR-451a expression in all tumor types (CA) compared to non-cancerous tissue (Norm).

FIG. 11 illustrates downregulation of miR-1 expression in all tumor types (CA), moderate expression of miR-1 in non-cancerous tissue (Norm), and high expression of miR-1 in non-cancerous head and neck tissue (H&N).

FIG. 12 illustrates downregulation of miR-559 expression in all tumor types (CA), low expression of miR-559 in non-cancerous tissue (Norm), and high expression of miR-559 in non-cancerous lung tissue.

FIG. 13 illustrates downregulation of miR-145-5p expression in all tumor types (CA) and high expression of miR-145-5p in the majority of non-cancerous tissue (Norm).

FIG. 14 illustrates downregulation of miR-143-3p expression in colon lung, and pancreatic tumor types (CA) and high expression of miR-143-3p in the majority of non-cancerous tissue (Norm).

FIG. 15A shows a schematic of a pTetR tet repressor plasmid that induces expression of an miRNA expression plasmid. FIG. 15B shows a schematic of a pTF-002 miRNA expression plasmid containing a tet-inducible mCherry and miRNA expression cassette.

FIG. 15C shows a schematic of a pTF-004 miRNA attenuation reporter enabling the read-out of destabilized GFP (dsGFP).

FIG. 32 shows miR-attenuated HSV constructs with target sequences for various miRNAs inserted into the ICP27 and ICP4 genes.

FIG. 33 illustrates HSV attenuation by miR-125 in non-cancerous (post-mitotic lung) and cancerous (A253) cells.

FIG. 41 shows a schematic of a UL19-TmiRNA-attenuated HSV vector for the treatment of cancer or benign hyper-proliferative disorders.

FIG. 44 shows a schematic of an UL19-TmiRNA, ICP27-TmiRNA, and ICP4-TmiRNA-attenuated HSV vector for the treatment of cancer or benign hyper-proliferative disorders.

FIG. 45 shows a schematic of an ICP4-TmiRNA-attenuated, genome-editing HSV vector for the treatment of cancer.

FIG. 46 shows a schematic of an ICP4-TmiRNA-attenuated, genome-editing, microenvironment-remodeling HSV vector for the treatment of cancer.

FIG. 48 shows a schematic of an ICP4-TmiRNA and ICP27-TmiRNA-attenuated HSV vector for the treatment of multiple cancer types.

FIG. 49 shows a schematic of an ICP4-TmiRNA and ICP27-TmiRNA-attenuated HSV vector for the treatment of schwannoma.

DETAILED DESCRIPTION OF THE INVENTION

Figure 1:
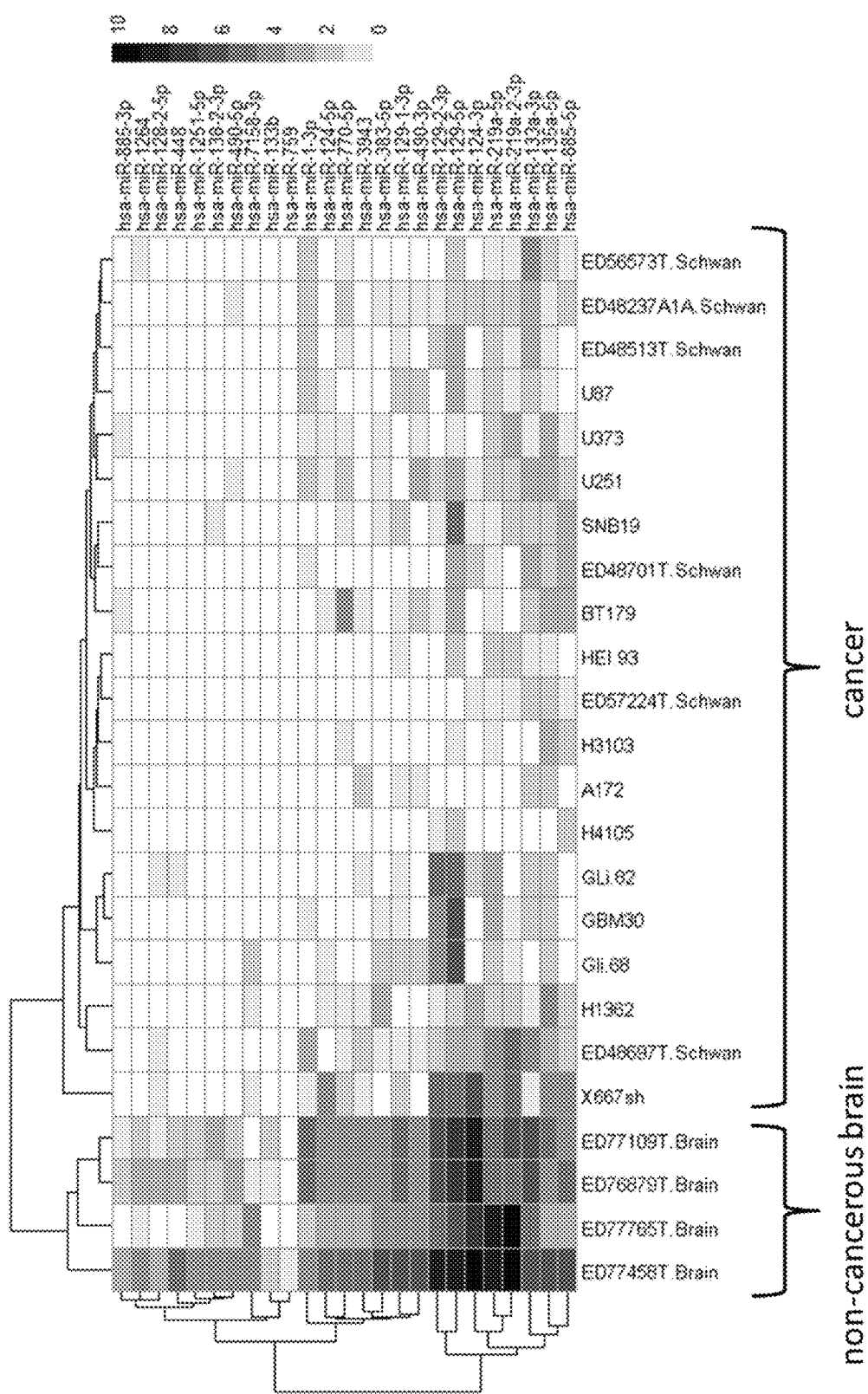
FIG. 1 illustrates a heat map of an miRNA expression profile in cancerous and non-cancerous brain tissue corresponding to 25 selected miRNAs.
Figure 2:
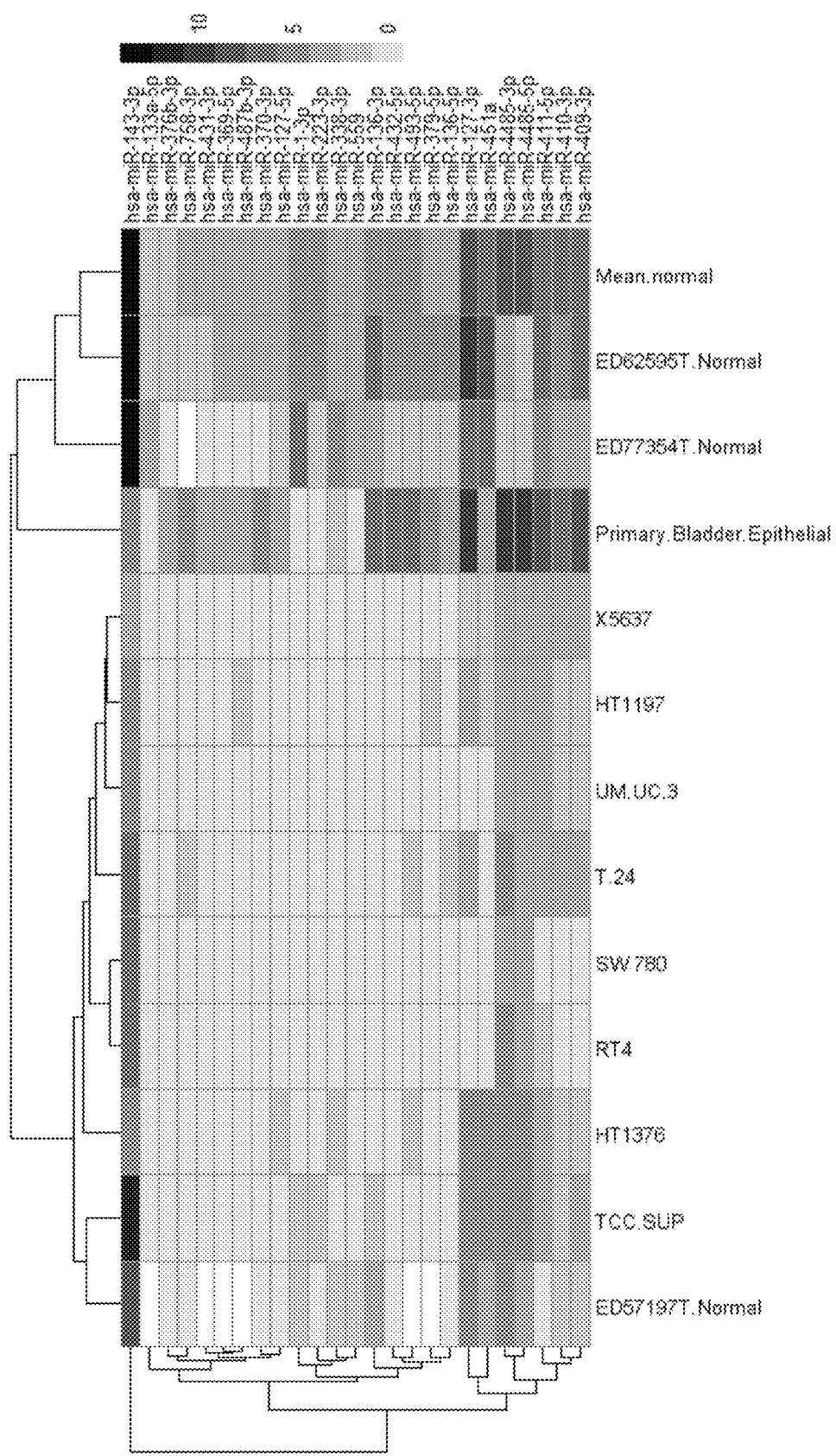
FIG. 2 illustrates a heat map of an miRNA expression profile in cancerous and non-cancerous bladder tissue corresponding to 25 selected miRNAs.
Figure 3:
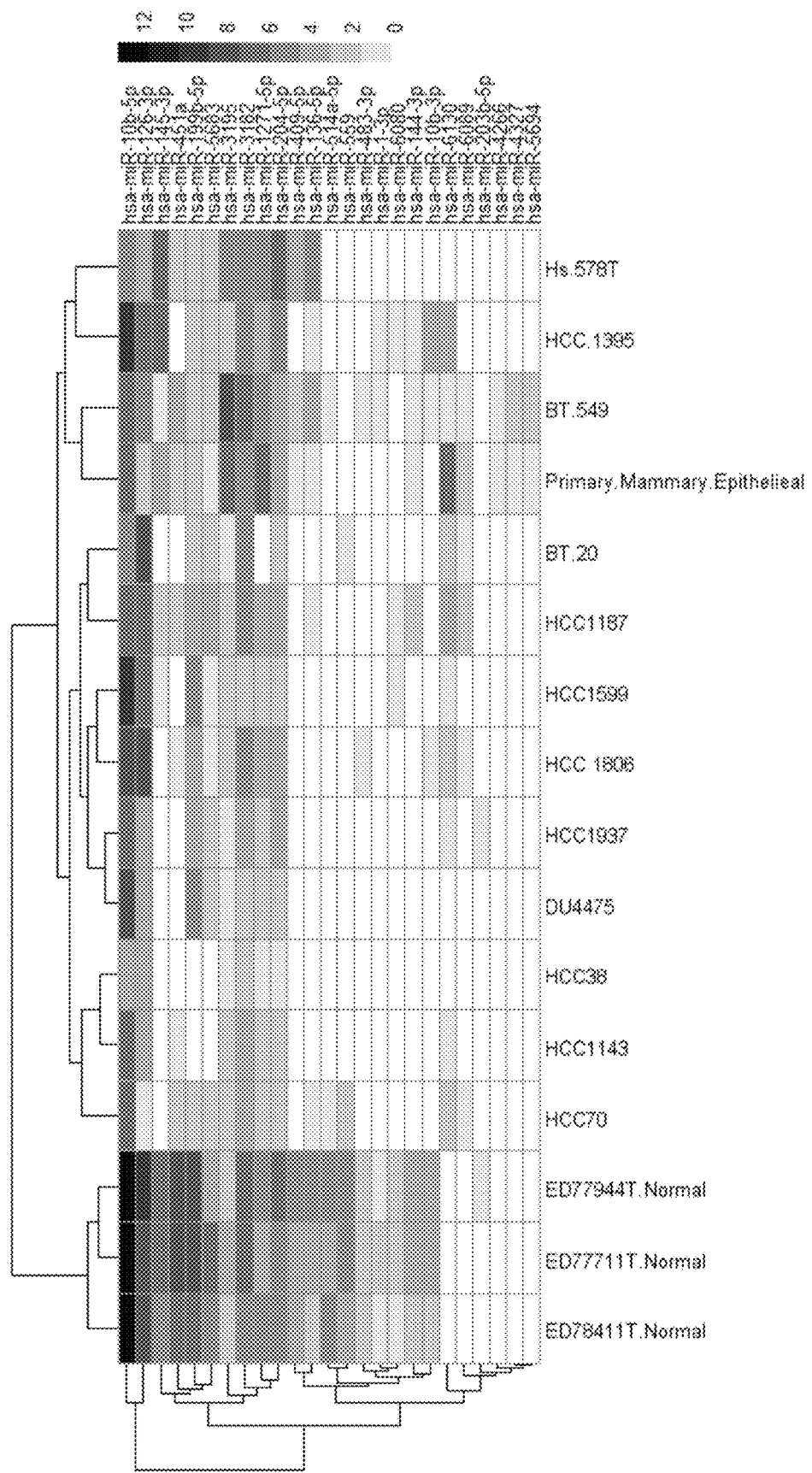
FIG. 3 illustrates a heat map of an miRNA expression profile in cancerous and non-cancerous breast tissue corresponding to 25 selected miRNAs.
Figure 4:
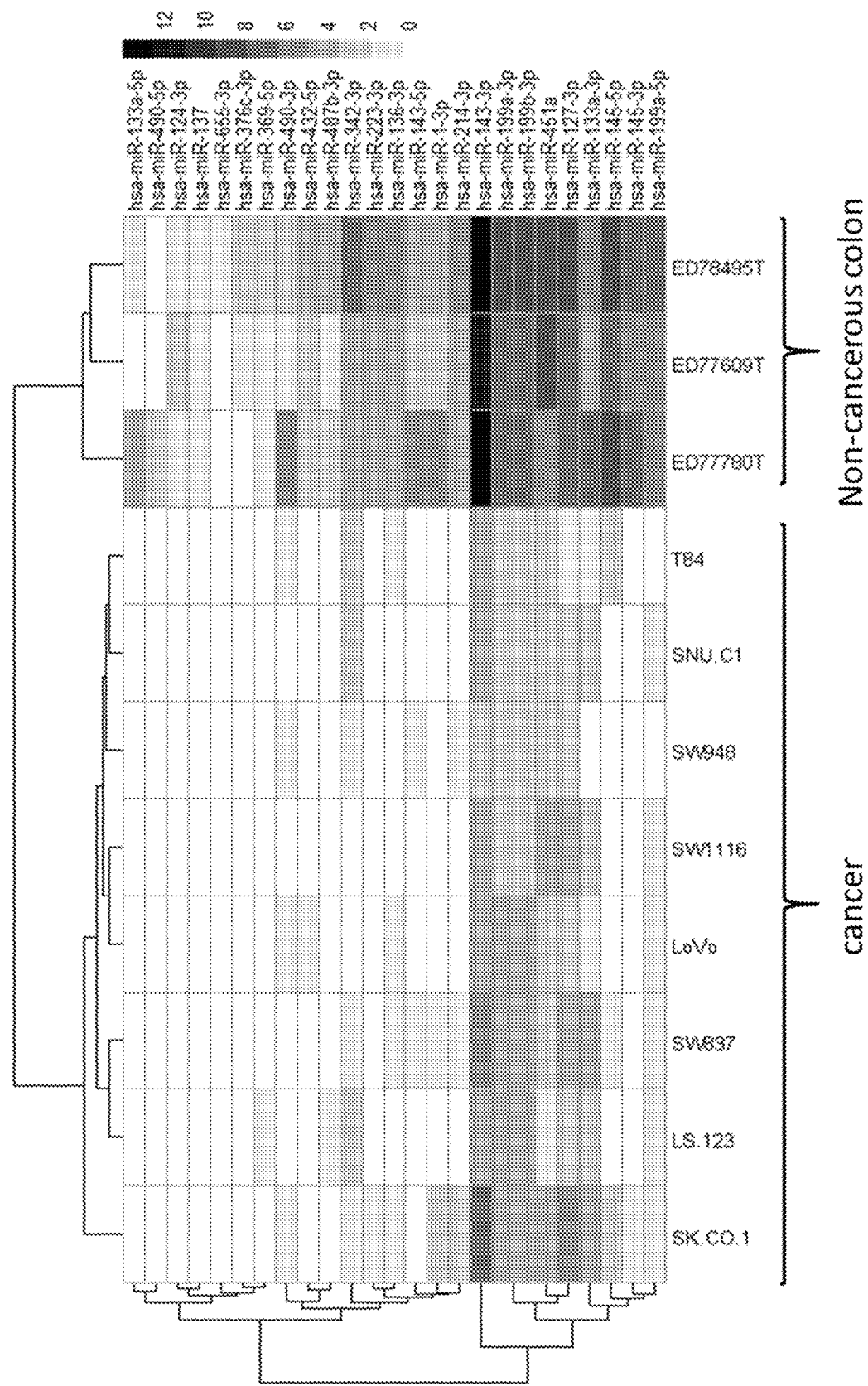
FIG. 4 illustrates a heat map of an miRNA expression profile in cancerous and non-cancerous colon tissue corresponding to 25 selected miRNAs.
Figure 5:
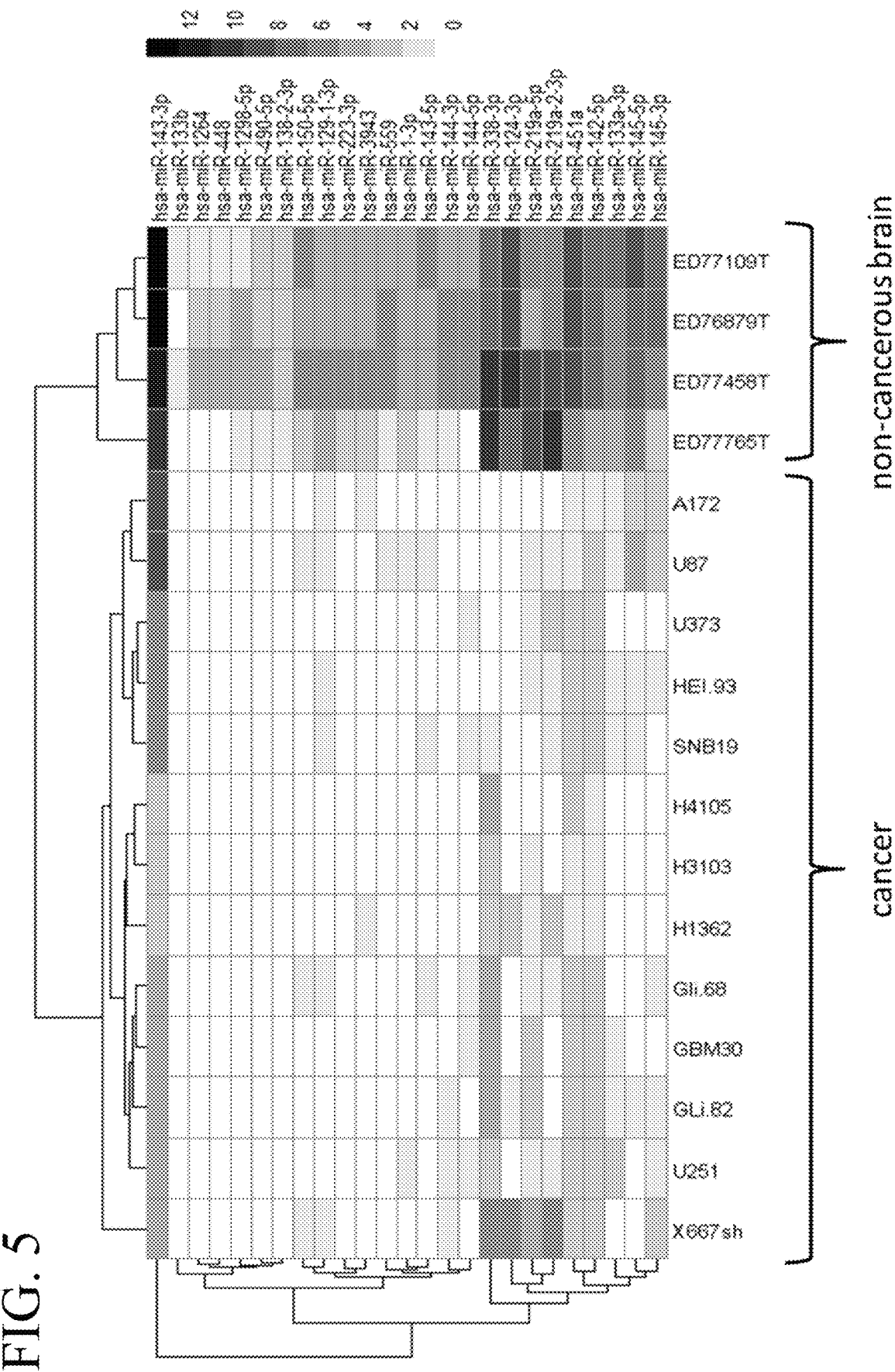
FIG. 5 illustrates a heat map of an miRNA expression profile in glioblastoma and non-cancerous brain tissue corresponding to 25 selected miRNAs.
Figure 6:
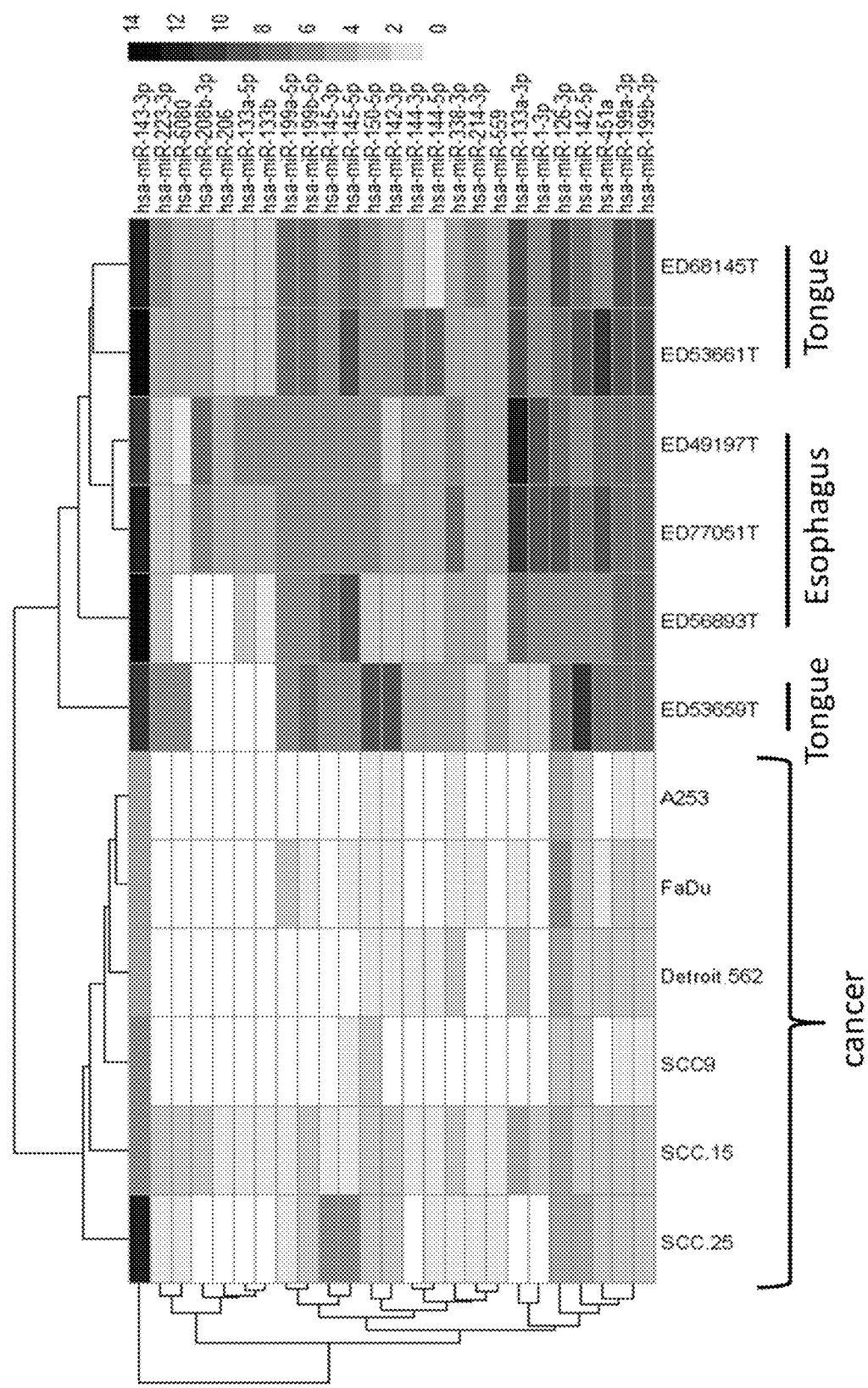
FIG. 6 illustrates a heat map of an miRNA expression profile in cancerous and non-cancerous head and neck tissue corresponding to 25 selected miRNAs.
Figure 7:
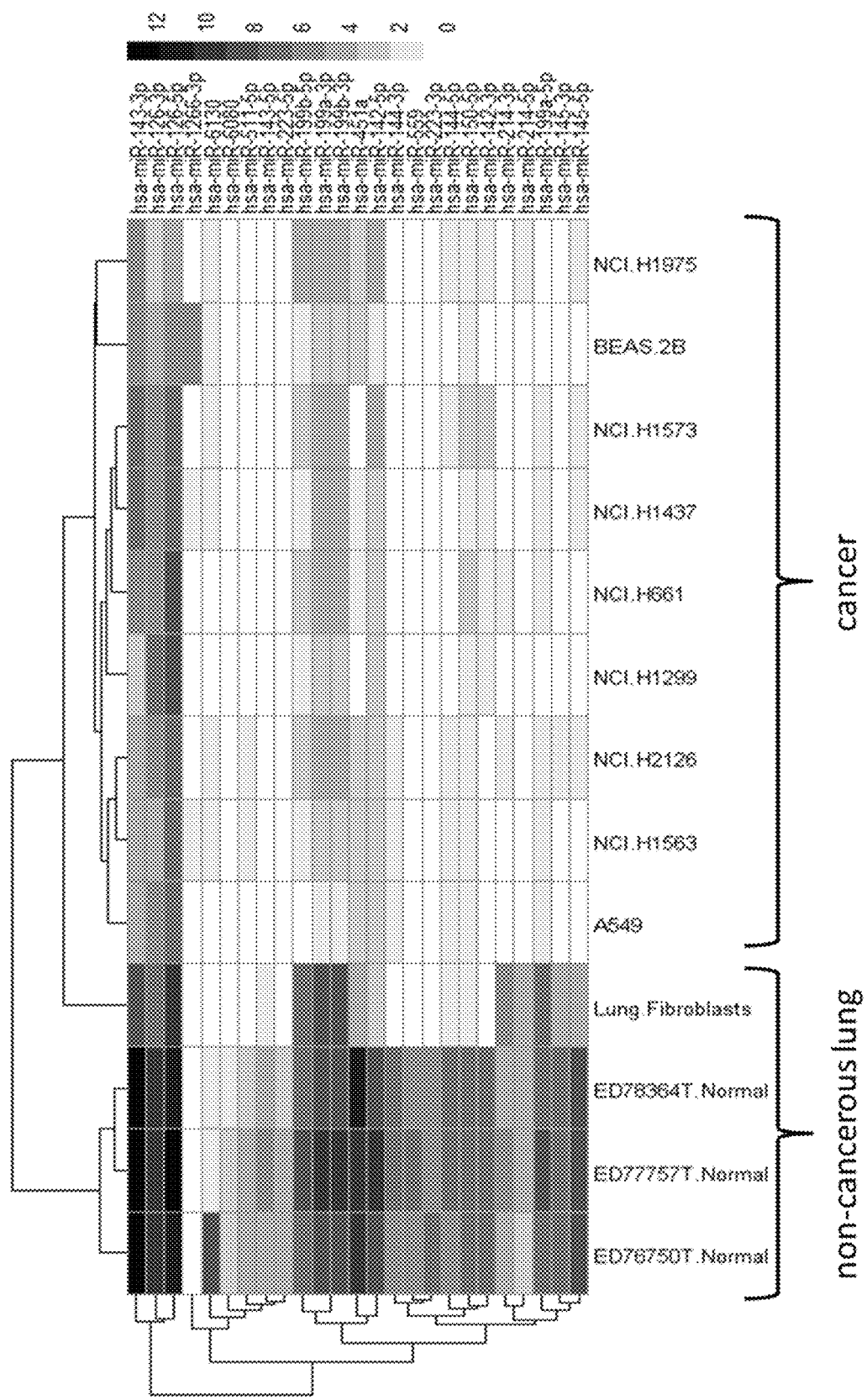
FIG. 7 illustrates a heat map of an miRNA expression profile in cancerous and non-cancerous lung tissue corresponding to 25 selected miRNAs.
Figure 8:
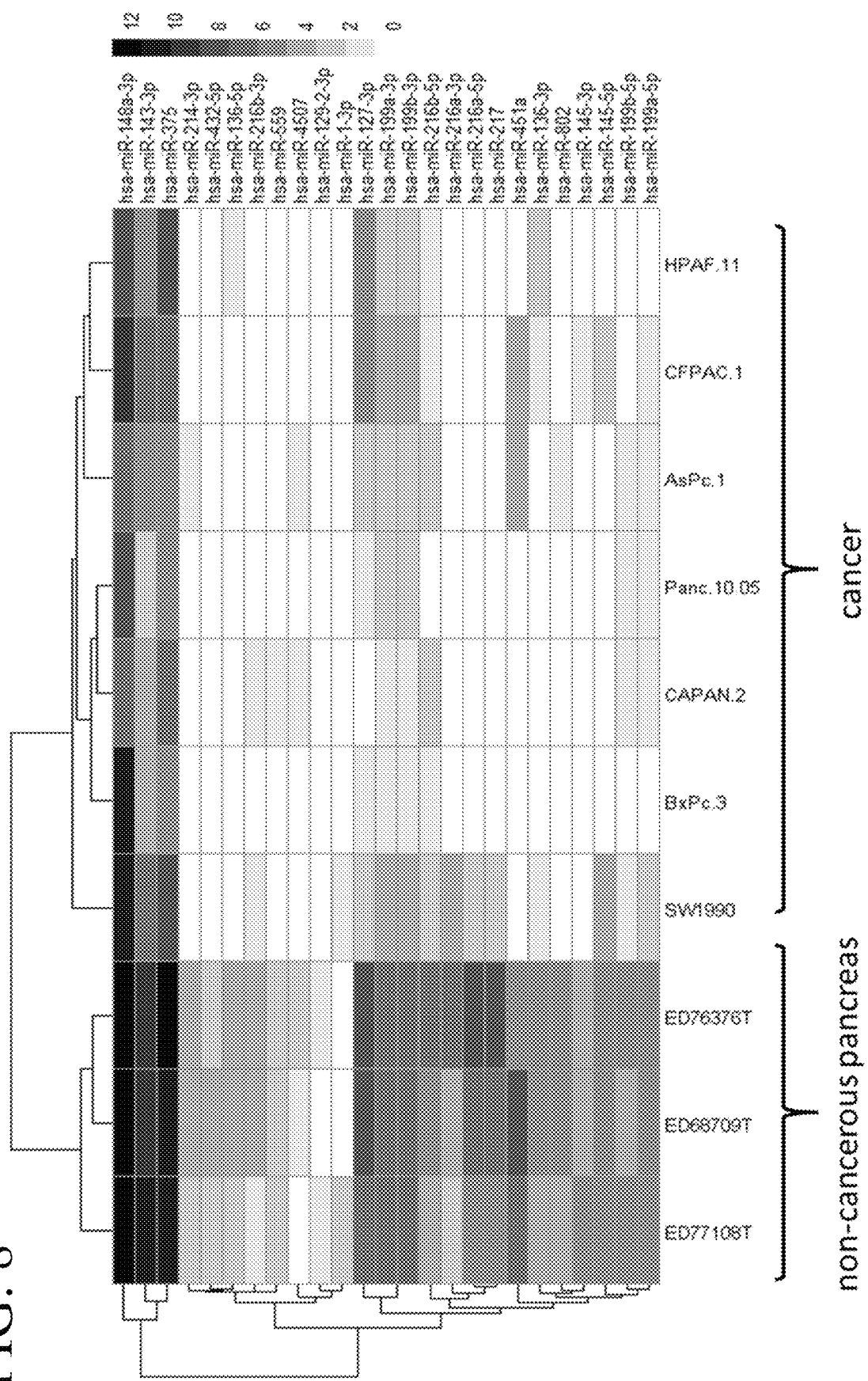
FIG. 8 illustrates a heat map of an miRNA expression profile in cancerous and non-cancerous pancreatic tissue corresponding to 25 selected miRNAs.
Figure 9:
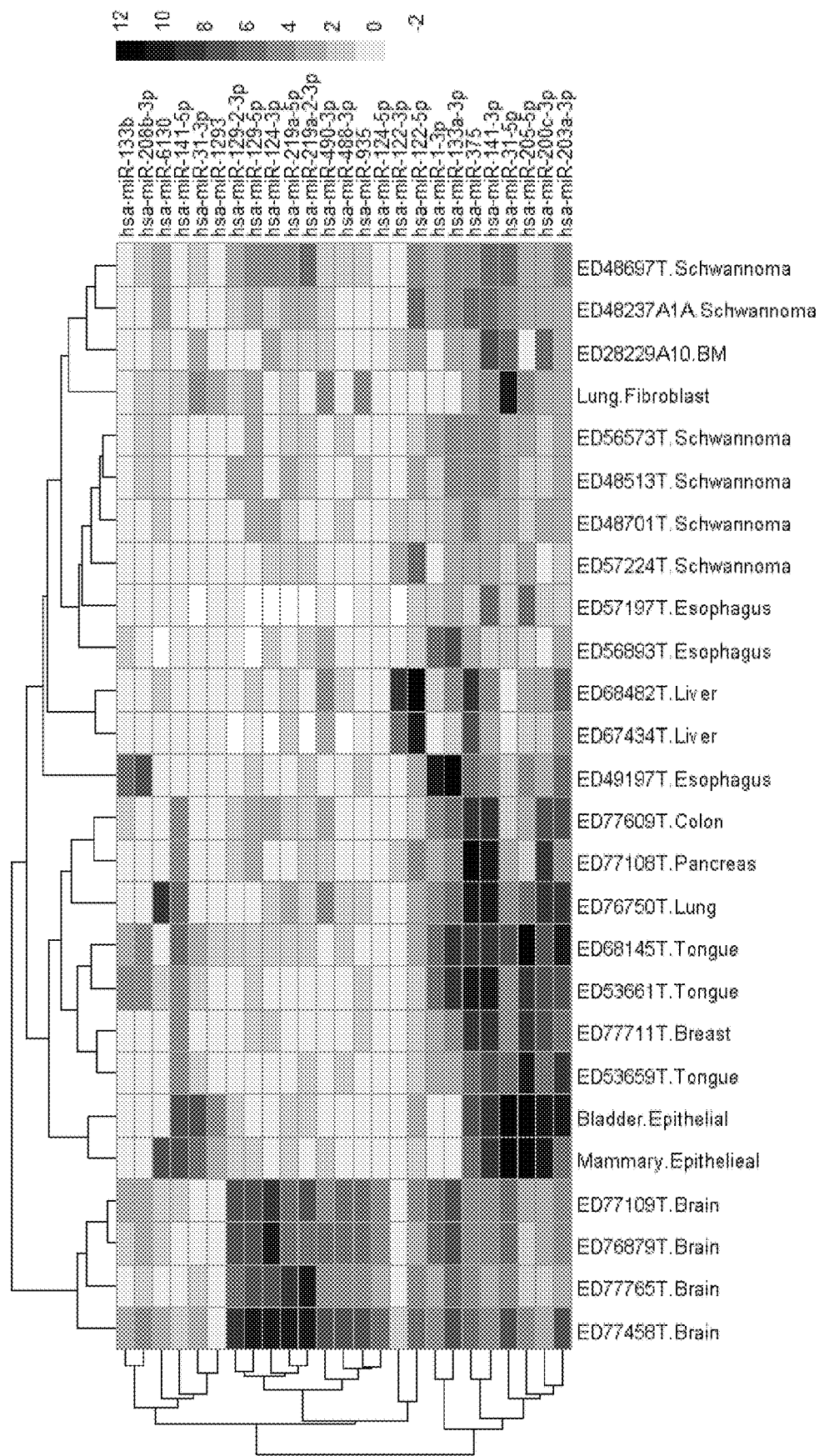
FIG. 9 illustrates a heat map of an miRNA expression profile in schwannoma and non-schwannoma tissue corresponding to 25 selected miRNAs.
Figure 15A:
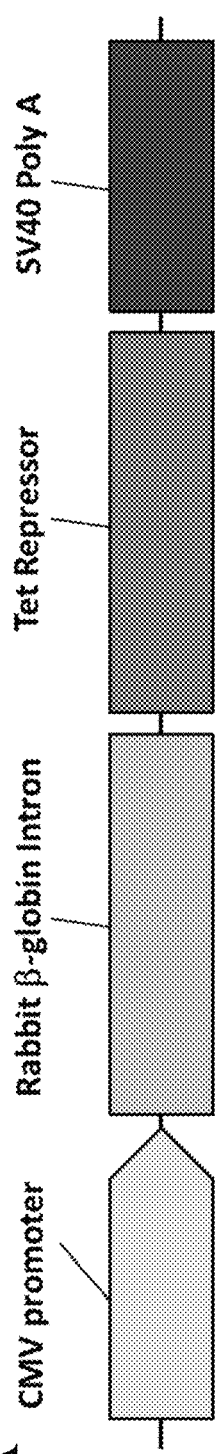
FIG. 15A-FIG. 15C illustrate a miRNA expression and attenuation reporter gene system described in Example 2.
Figure 15B:
Figure 15C:
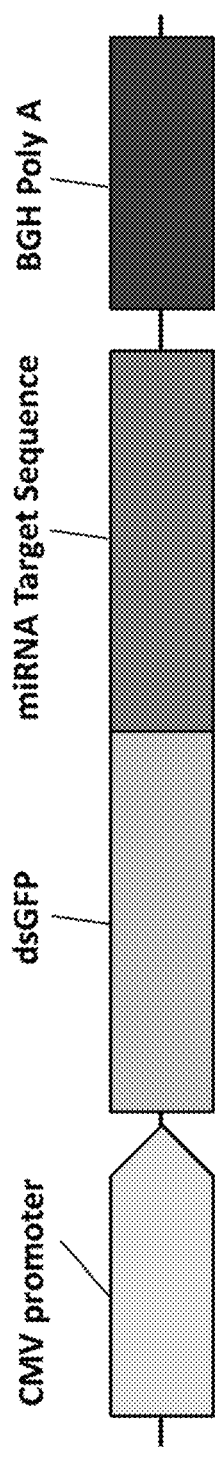

In some aspects, the present invention utilizes differential miRNA expression profiles to effectively restrict viral vector replication to tumor cells. In some embodiments, the viral vectors described herein also disrupt the expression of specific miRNAs for reduced tumor proliferation, metastasis, and/or remodeling of the tumor microenvironment to enable enhanced viral spread. In some embodiments, the viral vectors described herein encompass the use of surface molecules on viral vectors to facilitate targeting to tumor cells. These aspects can be applied individually or in combination to develop viral vectors potentially capable of treating a wide array of cancer types with a single viral vector. As such, the invention further encompasses recombinant oncolytic viral vectors for use in the treatment and prevention of diseases and disorders (e.g., cancer). In some embodiments, this invention utilizes endogenous microRNA (miRNA) to enable a safe and efficacious recombinant viral vector suitable to treat a broad array of cancers.

The section headings used herein are for organizational purposes only and are not to be construed as limiting the subject matter described. All documents, or portions of documents, cited herein, including but not limited to patents, patent applications, articles, books, and treatises, are hereby expressly incorporated by reference in their entirety for any purpose. In the event that one or more of the incorporated documents or portions of documents define a term that contradicts that term's definition in the application, the definition that appears in this application controls. However, mention of any reference, article, publication, patent, patent publication, and patent application cited herein is not, and should not be taken as an acknowledgment, or any form of suggestion, that they constitute valid prior art or form part of the common general knowledge in any country in the world.

In the present description, any concentration range, percentage range, ratio range, or integer range is to be understood to include the value of any integer within the recited range and, when appropriate, fractions thereof (such as one tenth and one hundredth of an integer), unless otherwise indicated. It should be understood that the terms "a" and "an" as used herein refer to "one or more" of the enumerated components unless otherwise indicated. The use of the alternative (e.g., "or") should be understood to mean either one, both, or any combination thereof of the alternatives. As used herein, the terms "include" and "comprise" are used synonymously. As used herein, "plurality" may refer to one or more components (e.g., one or more miRNA target sequences).

Oncolytic Viruses

In some embodiments, the present invention provides for recombinant oncolytic viruses, wherein one or more copies of one or more tumor-suppressive micro-RNA (miR) target sequences are inserted into a locus of one or more viral genes required for viral replication. As used herein, the term "oncolytic virus" refers to a virus that has been modified to, or naturally, preferentially infect cancer cells. Examples of oncolytic viruses are known in the art including, but not limited to, herpes simplex virus, an adenovirus, a polio virus, a vaccinia virus, a measles virus, a vesicular stomatitis virus, an orthomyxovirus, a parvovirus, a maraba virus or a coxsackievirus. In some embodiments, the oncolytic viruses described herein are incorporated into a viral vector. The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. A viral vector may sometimes be referred to as a "recombinant virus" or a "virus." The terms "oncolytic virus" and "oncolytic vector" are used interchangeably herein. In particular embodiments, the recombinant viral vector is a herpes simplex virus capable of tumor-selective vector replication as described in International PCT Publication No. WO 2015/066042, which is incorporated by reference in its entirety.

The terms "microRNA," "miRNA," and "miR" are used interchangeably herein and refer to small non-coding endogenous RNAs that regulate gene expression by directing their target messenger RNAs (mRNA) for degradation or translational repression. miRs are differentially expressed in a broad array of disease states, including multiple types of cancer. In some aspects, cancer cells of a given cancer type or tissue demonstrate differential expression of miRs compared to non-cancerous control cells. As used herein, the term "oncomiR" refers to miRs that are associated (either positively or negatively) with carcinogenesis, malignant transformation, or metastasis. In some aspects, the expression level of a particular oncomiR is associated with the development or maintenance of a particular cancer. Such miRs are referred to herein as "oncogenic miRs."

In some embodiments, the expression of an oncogenic miR is increased in cancerous cells or tissues compared to non-cancerous controls. For example, the expression of an oncogenic miR in a cancerous cell may be increased by at least 5% compared to the expression of the oncogenic miR in a non-cancerous cell or tissue. In some embodiments, the expression of an oncogenic miR is increased by at least 5%, 10%, 15%, 20%, 25%, 30%, 35%, 40%, 45%, 50%, 60%, 70%, 80%, 90%, 100%, 150%, 200%, 300%, 400%, 500%, 1000% or more compared to the expression of the oncogenic miR in a non-cancerous cell or tissue. In some aspects, a cancerous cell or tissue may express an oncogenic miR that is not expressed in non-cancerous control cells or tissues. In some embodiments, the expression of an oncogenic miR is increased in cancerous cells or tissues compared to cancerous cells derived from a different cancer type. For example, the expression of an oncogenic miR in a cancerous cell may be increased by at least 5% compared to cancerous cells derived from a different cancer type. In some embodiments, the expression of an oncogenic miR is increased by at least 5%, 10%, 15%, 20%, 25%, 30%, 35%, 40%, 45%, 50%, 60%, 70%, 80%, 90%, 100%, 150%, 200%, 300%, 400%, 500%, 1000% or more compared to cancerous cells derived from a different cancer type. Examples of oncogenic miR-NAs that are frequently over-expressed in cancer tissues include, but are not limited to, miR-21, miR-155 and miR-17-92. Additional examples of oncogenic miRs are listed in Table 4.

In some embodiments, the expression of a particular oncomiR is associated with the prevention and/or delay of carcinogenesis and/or metastasis. Such oncomiRs are referred to herein as "tumor-suppressor miRs" or "tumor-suppressive miRs," as their expression prevents or suppresses the development of cancer. In some embodiments, under-expression of tumor-suppressive miRs can lead to cancer. As such, in some aspects, tumor-suppressive miRs are expressed in healthy cells and are not expressed in cancerous cells. In some aspects, the expression of a particular tumor-suppressive miR is increased in a healthy cell compared to a cancerous cell. For example, the expression of a tumor-suppressive miR in a healthy (e.g., non-cancerous) cell may be increased by at least 5% compared to the expression of a tumor-suppressive miR a cancerous cell. In some embodiments, the expression of a tumor-suppressive miR is increased by at least 5%, 10%, 15%, 20%, 25%, 30%, 35%, 40%, 45%, 50%, 60%, 70%, 80%, 90%, 100%, 150%, 200%, 300%, 400%, 500%, 1000% or more compared to the expression of the tumor-suppressive miR in a cancerous cell. In some embodiments, the expression of a tumor-suppressive miR is increased in normal cells or tissues compared to normal cells derived from a different tissue type or location in the body. For example, the expression of a tumor-suppressive miR in a normal cell may be increased by at least 5% compared to normal cells derived from a different tissue type or location in the body. In some embodiments, the expression of a tumor-suppressive miR in a normal cell is increased by at least 5%, 10%, 15%, 20%, 25%, 30%, 35%, 40%, 45%, 50%, 60%, 70%, 80%, 90%, 100%, 150%, 200%, 300%, 400%, 500%, 1000% or more compared to normal cells derived from a different tissue type or location in the body. Examples of tumor-suppressive miRNAs include, but are not limited to, miR-15a, miR-16-1, miR-34, as well as miRNAs of the let-7 family. Additional examples of tumor-suppressive miRs are listed in Table 3 and Table 8.

Cancer pathogenesis is a heterogeneous and multigenic process. As such, activation of particular pathways and the expression of particular genes may lead to cancer development in one context, and result in distinct or opposing results when activated or expressed in a different context. Therefore, the characterization of a particular gene or miR as an "oncogene" or "oncogenic miR" or as a "tumor-suppressor" or "tumor-suppressive miR" is not a binary distinction and is often context dependent. For example, miR-152b functions as an oncogenic miR in the vast majority of hematologic malignancies, but functions as a tumor-suppressive miR in many solid tumors. Further, a particular miR may be highly expressed in both cancerous and non-cancerous cells. For example, miR-155 is highly expressed in normal cells, playing an essential role in macrophage polarization, and is also highly expressed in cancer cells. As such, the development of the miR-attenuated, genome-editing, and microenvironment-remodeling oncolytic viruses described herein is based on the differential expression of a particular miR or group of miRs in one cell population or tissue compared to another cell population or tissue. One of skill in the art will understand that the term tumor-suppressive miR generally refers to a miR that is more highly expressed in a non-cancerous cell or tissue compared to a cancerous cell or tissue, and that the term oncogenic miR generally refers to a miR that is more highly expressed in a cancerous cell or tissue compared to a non-cancerous cell or tissue. One of skill in the art will further understand that a miR characterized as a tumor-suppressive miR in one type of cancer may or more may not function as a tumor-suppressive miR in a different type of cancer, and that a miR characterized as an oncogenic miR in one type of cancer may or more may not function as an oncogenic miR in a different type of cancer.

Table 1 shows the relationship between 12 select oncomiRs (9 tumor suppressors and 3 oncogenic miRNAs) and numerous cancers. A list of 3,410 oncomiR-cancer relationships is shown in Table 2. miRNAs regulate many transcripts of proteins that are involved in the control of cellular proliferation and apoptosis. Regulated proteins include conventional proto-oncoproteins and tumor suppressors such as Ras, Myc, Bcl2, PTEN and p53. Aberrant expression of miRNAs therefore often is involved in development of cancer and can therapeutically be corrected by either inhibiting oncogenic miRNAs or replacing the depleted tumor suppressor miRNA. Further, the differential expression of particular oncomiRs in cancerous vs. non-cancerous cells can be exploited as a means to target cancer therapeutics specifically to cancer cells. As such, in some embodiments, the oncolytic viral vectors described herein can comprise the following properties individually or in combination: insertion of tumor-suppressive miRNA target sequences into the viral genome, thereby restricting viral vector replication to cancer or tumor cells; one or more polynucleotides incorporated into the viral genome whose product(s) disrupt the function of an oncogenic miRNA and/or the cancer extracellular matrix; and/or protease-activated antibodies incorporated into the viral particle in order to highly selectively target the vectors to cancer and/or tumor cells.

One aspect of the invention comprises a recombinant oncolytic virus (or viral vector) comprising a plurality of copies of one or more tumor-suppressive miRNA target sequences (e.g., an miRNA selected from the miRNAs listed in Table 3 or Table 8) inserted into a locus of one or more viral genes required for viral replication. In certain embodiments, a recombinant oncolytic virus may comprise tumor-suppressive miRNA target sequences inserted into a locus of at least one, at least two, at least three, at least four, at least five, at least six, at least seven, at least eight, at least nine, or at least ten viral genes required for viral replication. Tumor-suppressor miRNAs expressed in normal (non-cancerous) cells can bind to such target sequences and suppress expression of the viral gene containing the miRNA target sequence, thereby limiting viral replication in healthy, non-cancerous cells. Such recombinant oncolytic viruses and/or vectors are referred to herein as "miR-attenuated" or "replication-restricted" as they result in reduced or attenuated viral replication in cell that express a tumor-suppressive miR capable of binding to the incorporated tumor-suppressive miR target sequence compared to cells that do not express, or have reduced expression of, the tumor-suppressive miR. By incorporating tumor-suppressive miRNAs into key genes required for viral replication, viral replication can be conditionally suppressed in normal diploid cells expressing the tumor-suppressive miRNAs and can proceed normally in cells that do not express the tumor-suppressive miRNAs. In such embodiments, healthy, non-cancerous cells are protected from the normal cells from lytic effects of infection by the recombinant viral vector.

In certain embodiments, the one or more tumor-suppressive miRNA target sequences is incorporated into the 5' untranslated region (UTR) and/or 3' UTR of one or more viral genes required for viral replication. In normal diploid cells, tumor-suppressive miRNAs can bind to the engineered 3' or 5' non coding sequence which comprises a tumor-suppressive miRNA target sequence, but these tumor-suppressive miRNAs are lacking in transformed or malignant cells. Thus, viral replication can proceed in cells that lack, or have reduced expression of, the tumor-suppressive miRNAs. In some embodiments, at least one tumor-suppressive miR target sequence is incorporated into one or more viral genes required for replication. In some embodiments, the oncolytic viral vector may comprise multiple copies of an identical tumor-suppressive miR target sequence incorporated into one viral gene required for replication. For example, 1, 2, 3, 4, 5, 6, 7, 8, 9, 10 or more copies of a tumor-suppressive miR target sequence may be incorporated into a viral gene required for replication. In particular embodiments, 2 to 6 copies of a tumor-suppressive miR target sequence are incorporated into the 3' or 5' UTR of a viral gene required for replication. In further embodiments, 4 copies of a tumor-suppressive miR target sequence are incorporated into the 3' or 5' UTR of a viral gene required for replication. In some embodiments, the oncolytic viral vector may comprise multiple copies of the same tumor-suppressive miR target sequence incorporated into a plurality of viral genes required for replication. For example, 1, 2, 3, 4, 5, 6, 7, 8, 9, 10 or more copies of a tumor-suppressive miR target sequence may be incorporated into 1, 2, 3, 4, 5, 6, 7, 8, 9, 10, or more genes required for viral replication. In particular embodiments, 2 to 6 copies of a tumor-suppressive miR target sequence are incorporated into the 3' or 5' UTR of two or more viral genes required for replication. In further embodiments, at least 4 copies of a tumor-suppressive miR target sequence are incorporated into the 3' or 5' UTR of two or more viral genes required for replication.

In some embodiments, the oncolytic viral vector may comprise target sequences for more than one tumor-suppressive miR incorporated into one viral gene required for replication. For example, target sequences for 1, 2, 3, 4, 5, 6, 7, 8, 9, 10 or more different tumor-suppressive miRs may be incorporated into a single gene required for viral replication. In some embodiments, the oncolytic viral vector may comprise target sequences for more than one tumor-suppressive miR incorporated into a plurality of viral genes required for replication. For example, target sequences for 1, 2, 3, 4, 5, 6, 7, 8, 9, 10 or more different tumor-suppressive miRs may be incorporated into 1, 2, 3, 4, 5, 6, 7, 8, 9, 10, or more genes required for viral replication. In some embodiments, the oncolytic viral vector may comprise multiple target sequences (e.g., at least 1, 2, 3, 4, 5, 6, 7, 8, 9, 10 copies of one target sequence) for at least two different tumor-suppressive miRs (e.g., at least 1, 2, 3, 4, 5, 6, 7, 8, 9, 10 different tumor-suppressive miRs). In such embodiments, the multiple target sequences for a first tumor-suppressive miR may be incorporated into a first gene required for replication, the multiple target sequences for a second tumor-suppressive miR may be incorporated into a second gene required for replication, the multiple target sequences for a third tumor-suppressive miR may be incorporated into a third gene required for replication, etc. In particular embodiments, the oncolytic viral vectors described herein comprise at least 2 to at least 8 copies of first tumor-suppressive miR target sequence incorporated into the 3' or 5' UTR of a first gene required for replication, at least 2 to at least 8 copies of second tumor-suppressive miR target sequence incorporated into the 3' or 5' UTR of a second gene required for replication, and at least 2 to at least 8 copies of third tumor-suppressive miR target sequence incorporated into the 3' or 5' UTR of a third gene required for replication.

In some embodiments, the miR-attenuated oncolytic viruses described herein result in reduced viral replication in a cell that expresses a tumor-suppressive miR capable of binding to one or more of the incorporated miR-target sequences. "Viral replication" refers to the total number of viral replication cycles that occur in a particular cell or population of cells during a given amount of time. In some embodiments, viral replication can be measured directly by assessing the total viral titer present over the course of the given amount of time, or by assessing the number of viral genome copies present (e.g., by sequencing). In some embodiments, the viral vector may additionally comprise a detectable label, such as a fluorescent reporter. In such embodiments, viral replication may be assessed by measuring the fluorescence intensity of the reporter, or the number of cells that express the reporter. In some embodiments, viral replication can be measured indirectly by assessing the number of viable cells over the course of the given amount of time. For example, the level of viral replication would be expected to inversely correlate with the number of viable cells over time.

"Reduced viral replication" as used herein, refers to a level of viral replication that is lower in a first cell or first population of cells compared to a second cell or a second population of cells. In some embodiments, the level of viral replication in the first cell or first population of cells is reduced by at least 5% compared to the level of viral replication in the second cell or population of cells. In some embodiments, the level of viral replication in the first cell or first population of cells is reduced by at least 5%, 6%, 7%, 8%, 9%, 10%, 15%, 20%, 25%, 30%, 35%, 40%, 50%, 60%, 70%, 80%, 90% or more compared to the level of viral replication in the second cell or population of cells. In some embodiments, viral replication in the first cell or first population of cells is completely inhibited compared to the viral replication in the second cell or population of cells.

In some embodiments, the reduced viral replication in the first cell or first population of cells correlates with the expression of a tumor-suppressive miR capable of binding to the one or more miR-target sequences incorporated into one or more viral genes required for replication. In some embodiments, expression of a tumor-suppressive miR corresponding to the incorporated miR-target sequence therefore inhibits or reduces the expression of the replication gene, thereby inhibiting or reducing viral replication. In some embodiments, the second cell or second population of cells does not express, or has a reduced expression level, of the tumor-suppressive miR. In some embodiments, absent or reduced expression of a tumor-suppressive miR (e.g., in a cancer cell) corresponding to the incorporated miR-target sequence allows for viral replication to proceed. In some embodiments, the expression level of the tumor-suppressive miR in the second cell or population of cells is at least 5% lower than the expression level of the tumor-suppressive miR in the first cell or population. In some embodiments, the expression level of the tumor-suppressive miR in the second cell or population of cells is reduced at least 5%, 6%, 7%, 8%, 9%, 10%, 15%, 20%, 25%, 30%, 35%, 40%, 50%, 60%, 70%, 80%, 90% or more compared to the expression level of the tumor-suppressive miR in the first cell or population. In some embodiments, the second cell does not express the tumor-suppressive miR. In particular embodiments, the first cell is a non-cancerous cell and the second cell is a cancerous cell.

In some aspects, the multiple copies (e.g., at least 2, at least 3, at least 4, at least 5, at least 6, or more copies) of a tumor-suppressive miRNA target sequence are inserted into a locus in the viral genome in tandem. In such embodiments, the multiple copies of the target sequence may be separated by a linker sequence or a space sequence. In some embodiments, the linker and/or spacer sequence comprises 4 or more nucleotides. For example, a space or linker sequence may comprise 4, 5, 6, 7, 8, 9, 10, 15, 20, 25, or more nucleotides. In some embodiments, the linker sequence or the spacer sequence comprises about 5 to about 20 nucleotides. In further embodiments, the linker sequence or the spacer sequence comprises about 8 to about 16 nucleotides. As an illustrative embodiment, and not meant to limit the present invention in any way, an oncolytic virus may comprise at least one, at least two, at least three, at least four, at least five, at least six, at least seven, at least eight, at least nine, or at least ten of one or more of the following subunits inserted in tandem into a locus of one or more viral genes required for viral replication: (a) target sequence for a first tumor-suppressive miRNA—linker or spacer sequence—target sequence for the first tumor-suppressive miRNA; or (b) target sequence for a first tumor-suppressive miRNA—linker or spacer sequence—target sequence for a second tumor-suppressive miRNA. In some embodiments, the miRNA target sequence is the reverse complement of the miRNA.

In some embodiments, an oncolytic virus is a herpes simplex virus (HSV), and the viral gene required for viral replication UL1, UL5, UL6, UL7, UL8, UL9, UL11, UL12, UL14, UL15, UL17, UL18, UL19, UL20, UL22, UL25, UL26, UL26.5, UL27, UL28, UL29, UL30, UL31, UL32, UL33, UL34, UL35, UL36, UL37, UL38, UL39, UL40, UL42, UL48, UL49, UL52, UL53, UL54, ICP0, ICP4, ICP22, ICP27, ICP47, gamma-34.5, US3, US4, US5, US6, US7, USB, US9, US10, US11, and/or US12. In some embodiments, an oncolytic virus is a herpes simplex virus (HSV), and the one or more tumor-suppressive miRNA target sequences is incorporated into one or more of ICP0, ICP4, UL19, and ICP27 genes. In certain embodiments, an oncolytic viral vector is an HSV that comprises one or more tumor suppressive miRNA target sequences (e.g., any of the tumor-suppressive miRs listed in Table 3) incorporated into the 5' or 3' UTR of one or more genes (e.g., UL1, UL5, UL6, UL7, UL8, UL9, UL11, UL12, UL14, UL15, UL17, UL18, UL19, UL20, UL22, UL25, UL26, UL26.5, UL27, UL28, UL29, UL30, UL31, UL32, UL33, UL34, UL35, UL36, UL37, UL38, UL39, UL40, UL42, UL48, UL49, UL52, UL53, UL54, ICP0, ICP4, ICP22, ICP27, ICP47, gamma-34.5, US3, US4, US5, US6, US7, USB, US9, US10, US11, or US12) that are required for viral replication (e.g., FIGS. 39-49).

In some embodiments, a replication-restricted viral vector (e.g., a miR-attenuated viral vector) comprises at least one let-7 target sequence and is used to treat lung cancer. In some embodiments, a replication-restricted viral vector comprises at least one miR-15a and/or at least one miR-16A target sequences and is used to treat B-cell chronic lymphocytic leukemia. In some embodiments, a replication-restricted viral vector comprises at least one miR-125b, at least one miR-145, at least one miR-21, and/or at least one miR-155 target sequences and is used to treat breast cancer. In other embodiments, a replication-restricted viral vector comprises at least one miR-143 and/or at least one miR-145 target sequences and is used to treat colorectal cancer. In certain embodiments, a replication-restricted viral vector comprises at least one miR-181a, at least one miR-181b, and/or at least one miR-181c target sequences and is used to treat glioblastoma. In some embodiments, a replication-restricted viral vector comprises at least one miR-199a*, at least one miR-195, at least one miR-199a, at least one miR-200a, and/or at least one miR-125a target sequences and is used to treat liver cancer (e.g., hepatocellular carcinoma).

In particular embodiments, a replication-restricted viral vector comprises at least one miR-451a target sequence, at least one miR-143-3p target sequence, at least one miR-559 target sequence, and at least one miR-124 target sequence and is used for the treatment of pancreatic, lung, and/or colon cancer. In such embodiments, the target sequences for miR-451a, miR-143-3p, miR-559, and miR-124 are incorporated into two or more genes required for viral replication (e.g., ICP4 and ICP27). In further particular embodiments, a replication-restricted viral vector comprises at least one miR-451a target sequence, at least one miR-145-5p target sequence, at least one miR-559 target sequence, and at least one miR-124 target sequence and is used for the treatment of any type of cancer described herein. In such embodiments, the target sequences for miR-451a, miR-145-5p, miR-559, and miR-124 are incorporated into two or more genes required for viral replication (e.g., ICP4 and ICP27). In further particular embodiments, a replication-restricted viral vector comprises at least one miR-205p target sequence, at least one miR-141-5p target sequence, at least one miR-31-5p target sequence, and at least one miR-124 target sequence and is used for the treatment of schwannoma. In such embodiments, the target sequences for miR-205p, miR-141-5p, miR-31-5p, and miR-124 are incorporated into two or more genes required for viral replication (e.g., ICP4 and ICP27).

In some embodiments, a recombinant oncolytic virus comprises a plurality of copies of one or more tumor-suppressive miRNA target sequences for miR-136-3p, miR-432-5p, miR-1-3p, miR-127-3p, miR-379-5p, miR-493-5p, miR-223-5p, miR-223-5p, miR-136-5p, miR-451a, miR-487b-3p, miR-370-3p, miR-410-3p, miR-431-3p, miR-4485-3p, miR-4485-5p, miR-127-5p, miR-409-3p, miR-338-3p, miR-559, miR-411-5p, miR-133a-5p, miR-143-3p, miR-376b-3p, miR-758-3p, miR-1, miR-101, miR-1180, miR-1236, miR-124-3p, miR-125b, miR-126, miR-1280, miR-133a, miR-133b, miR-141, miR-143, miR-144, miR-145, miR-155, miR-16, miR-18a, miR-192, miR-195, miR-200a, miR-200b, miR-200c, miR-203, miR-205, miR-214, miR-218, miR-23b, miR-26a, miR-29c, miR-320c, miR-34a, miR-370, miR-409-3p, miR-429, miR-451, miR-490-5p, miR-493, miR-576-3p, and/or miR-99a inserted into the 5' UTR or 3' UTR of one or more viral genes required for viral replication. This oncolytic virus may be used in methods and compositions for treating bladder cancer.

In some embodiments, a recombinant oncolytic virus comprises a plurality of copies of one or more tumor-suppressive miRNA target sequences for miR-1251-5p, miR-219a-5p, miR-219a-2-3p, miR-124-3p, miR-448, miR-138-2-3p, miR-490-5p, miR-129-1-3p, miR-1264, miR-3943, miR-490-3p, miR-383-5p, miR-133b, miR-129-2-3p, miR-128-2-5p, miR-133a-3p, miR-129-5p, miR-1-3p, miR-885-3p, miR-124-5p, miR-759, miR-7158-3p, miR-770-5p, miR-135a-5p, miR-885-5p, let-7g-5p, miR-100, miR-101, miR-106a, miR-124, miR-124a, miR-125a, miR-125a-5p, miR-125b, miR-127-3p, miR-128, miR-129, miR-136, miR-137, miR-139-5p, miR-142-3p, miR-143, miR-145, miR-146b-5p, miR-149, miR-152, miR-153, miR-195, miR-21, miR-212-3p, miR-219-5p, miR-222, miR-29b, miR-31, miR-3189-3p, miR-320, miR-320a, miR-326, miR-330, miR-331-3p, miR-340, miR-342, miR-34a, miR-376a, miR-449a, miR-483-5p, miR-503, miR-577, miR-663, miR-7, miR-7-5p, miR-873, let-7a, let-7f, miR-107, miR-122, miR-124-5p, miR-139, miR-146a, miR-146b, miR-15b, miR-16, miR-181a, miR-181a-1, miR-181a-2, miR-181b, miR-181b-1, miR-181b-2, miR-181c, miR-181d, miR-184, miR-185, miR-199a-3p, miR-200a, miR-200b, miR-203, miR-204, miR-205, miR-218, miR-23b, miR-26b, miR-27a, miR-29c, miR-328, miR-34c-3p, miR-34c-5p, miR-375, miR-383, miR-451, miR-452, miR-495, miR-584, miR-622, miR-656, miR-98, miR-124-3p, miR-181b-5p, miR-200b, and/or miR-3189-3p inserted into the 5' UTR or 3' UTR of one or more viral genes required for viral replication. This oncolytic virus may be used in methods and compositions for treating brain cancer. In certain embodiments, the brain cancer is astrocytoma, glioblastoma, or glioma.

In some embodiments, a recombinant oncolytic virus comprises a plurality of copies of one or more tumor-suppressive miRNA target sequences for miR-10b-5p, miR-126-3p, miR-145-3p, miR-451a, miR-199b-5p, miR-5683, miR-3195, miR-3182, miR-1271-5p, miR-204-5p, miR-409-5p, miR-136-5p, miR-514a-5p, miR-559, miR-483-3p, miR-1-3p, miR-6080, miR-144-3p, miR-10b-3p, miR-6130, miR-6089, miR-203b-5p, miR-4266, miR-4327, miR-5694, miR-193b, let-7a, let-7a-1, let-7a-2, let-7a-3, let-7b, let-7c, let-7d, let-7e, let-7f-1, let-7f-2, let-7g, let-7i, miR-100, miR-107, miR-10a, miR-10b, miR-122, miR-124, miR-1258, miR-125a-5p, miR-125b, miR-126, miR-127, miR-129, miR-130a, miR-132, miR-133a, miR-143, miR-145, miR-146a, miR-146b, miR-147, miR-148a, miR-149, miR-152, miR-153, miR-15a, miR-16, miR-17-5p, miR-181a, miR-1826, miR-183, miR-185, miR-191, miR-193a-3p, miR-195, miR-199b-5p, miR-19a-3p, miR-200a, miR-200b, miR-200c, miR-205, miR-206, miR-211, miR-216b, miR-218, miR-22, miR-26a, miR-26b, miR-300, miR-30a, miR-31, miR-335, miR-339-5p, miR-33b, miR-34a, miR-34b, miR-34c, miR-374a, miR-379, miR-381, miR-383, miR-425, miR-429, miR-450b-3p, miR-494, miR-495, miR-497, miR-502-5p, miR-517a, miR-574-3p, miR-638, miR-7, miR-720, miR-873, miR-874, miR-92a, miR-98, miR-99a, mmu-miR-290-3p, and/or mmu-miR-290-5p inserted into the 5' UTR or 3' UTR of one or more viral genes required for viral replication. This oncolytic virus may be used in methods and compositions for treating breast cancer.

In some embodiments, a recombinant oncolytic virus comprises a plurality of copies of one or more tumor-suppressive miRNA target sequences for miR-143, miR-145, miR-1'7-5p, miR-203, miR-214, miR-218, miR-335, miR-342-3p, miR-372, miR-424, miR-491-5p, miR-497, miR-7, miR-99a, miR-99b, miR-100, miR-101, miR-15a, miR-16, miR-34a, miR-886-5p, miR-106a, miR-124, miR-148a, miR-29a, and/or miR-375 inserted into the 5' UTR or 3' UTR of one or more viral genes required for viral replication. This oncolytic virus may be used in methods and compositions for treating cervical cancer.

In some embodiments, a recombinant oncolytic virus comprises a plurality of copies of one or more tumor-suppressive miRNA target sequences for miR-133a-5p, miR-490-5p, miR-124-3p, miR-137, miR-655-3p, miR-376c-3p, miR-369-5p, miR-490-3p, miR-432-5p, miR-487b-3p, miR-342-3p, miR-223-3p, miR-136-3p, miR-136-3p, miR-143-5p, miR-1-3p, miR-214-3p, miR-143-3p, miR-199a-3p, miR-199b-3p, miR-451a, miR-127-3p, miR-133a-3p, miR-145-5p, miR-145-3p, miR-199a-5p, let-7a-1, let-7a-2, let-7a-3, let-7b, let-7c, let-7d, let-7e, let-7f-1, let-7f-2, let-7g, let-7i, miR-100, miR-101, miR-126, miR-142-3p, miR-143, miR-145, miR-192, miR-200c, miR-21, miR-214, miR-215, miR-22, miR-25, miR-302a, miR-320, miR-320a, miR-34a, miR-34c, miR-365, miR-373, miR-424, miR-429, miR-455, miR-484, miR-502, miR-503, miR-93, miR-98, miR-186, miR-30a-5p, miR-627, let-7a, miR-1, miR-124, miR-125a, miR-129, miR-1295b-3p, miR-1307, miR-130b, miR-132, miR-133a, miR-133b, miR-137, miR-138, miR-139, miR-139-5p, miR-140-5p, miR-148a, miR-148b, miR-149, miR-150-5p, miR-154, miR-15a, miR-15b, miR-16, miR-18a, miR-191, miR-193a-5p, miR-194, miR-195, miR-196a, miR-198, miR-199a-5p, miR-203, miR-204-5p, miR-206, miR-212, miR-218, miR-224, miR-24-3p, miR-26b, miR-27a, miR-28-3p, miR-28-5p, miR-29b, miR-30a-3p, miR-30b, miR-328, miR-338-3p, miR-342, miR-345, miR-34a-5p, miR-361-5p, miR-375, miR-378, miR-378a-3p, miR-378a-5p, miR-409-3p, miR-422a, miR-4487, miR-483, miR-497, miR-498, miR-518a-3p, miR-551a, miR-5'74-5p, miR-625, miR-638, miR-7, miR-96-5p, miR-202-3p, miR-30a, and/or miR-451 inserted into the 5' UTR or 3' UTR of one or more viral genes required for viral replication. This oncolytic virus may be used in methods and compositions for treating colon or colorectal cancer.

In some embodiments, a recombinant oncolytic virus comprises a plurality of copies of one or more tumor-suppressive miRNA target sequences for miR-101, miR-130a, miR-130b, miR-134, miR-143, miR-145, miR-152, miR-205, miR-223, miR-301a, miR-301b, miR-30c, miR-34a, miR-34c, miR-424, miR-449a, miR-543, and/or miR-34b inserted into the 5' UTR or 3' UTR of one or more viral genes required for viral replication. This oncolytic virus may be used in methods and compositions for treating endometrial cancer.

In some embodiments, a recombinant oncolytic virus comprises a plurality of copies of one or more tumor-suppressive miRNA target sequences for miR-125b, miR-138, miR-15a, miR-15b, miR-16, miR-16-1, miR-16-1-3p, miR-16-2, miR-181a, miR-181b, miR-195, miR-223, miR-29b, miR-34b, miR-34c, miR-424, miR-10a, miR-146a, miR-150, miR-151, miR-155, miR-2278, miR-26a, miR-30e, miR-31, miR-326, miR-564, miR-27a, let-7b, miR-124a, miR-142-3p, let-7c, miR-17, miR-20a, miR-29a, miR-30c, miR-720, miR-107, miR-342, miR-34a, miR-202, miR-142-5p, miR-29c, miR-145, miR-193b, miR-199a, miR-214, miR-22, miR-137, and/or miR-197 inserted into the 5' UTR or 3' UTR of one or more viral genes required for viral replication. This oncolytic virus may be used in methods and compositions for treating hematologic cancer. In some embodiments, the hematologic cancer is leukemia, lymphoma, or myeloma.

In some embodiments, a recombinant oncolytic virus comprises a plurality of copies of one or more tumor-suppressive miRNA target sequences for miR-1, miR-145, miR-1826, miR-199a, miR-199a-3p, miR-203, miR-205, miR-497, miR-508-3p, miR-509-3p, let-7a, let-7d, miR-106a*, miR-126, miR-1285, miR-129-3p, miR-1291, miR-133a, miR-135a, miR-138, miR-141, miR-143, miR-182-5p, miR-200a, miR-218, miR-28-5p, miR-30a, miR-30c, miR-30d, miR-34a, miR-378, miR-429, miR-509-5p, miR-646, miR-133b, let-7b, let-7c, miR-200c, miR-204, miR-335, miR-377, and/or miR-506 inserted into the 5' UTR or 3' UTR of one or more viral genes required for viral replication. This oncolytic virus may be used in methods and compositions for treating kidney cancer.

In some embodiments, a recombinant oncolytic virus comprises a plurality of copies of one or more tumor-suppressive miRNA target sequences for let-7a-1, let-7a-2, let-7a-3, let-7b, let-7c, let-7d, let-7e, let-7f, let-7f-1, let-7f-2, let-7g, let-7i, miR-1, miR-100, miR-101, miR-105, miR-122, miR-122a, miR-1236, miR-124, miR-125b, miR-126, miR-127, miR-1271, miR-128-3p, miR-129-5p, miR-130a, miR-130b, miR-133a, miR-134, miR-137, miR-138, miR-139, miR-139-5p, miR-140-5p, miR-141, miR-142-3p, miR-143, miR-144, miR-145, miR-146a, miR-148a, miR-148b, miR-150-5p, miR-15b, miR-16, miR-181a-5p, miR-185, miR-188-5p, miR-193b, miR-195, miR-195-5p, miR-197, miR-198, miR-199a, miR-199a-5p, miR-199b, miR-199b-5p, miR-200a, miR-200b, miR-200c, miR-202, miR-203, miR-204-3p, miR-205, miR-206, miR-20a, miR-21, miR-21-3p, miR-211, miR-212, miR-214, miR-217, miR-218, miR-219-5p, miR-22, miR-223, miR-26a, miR-26b, miR-29a, miR-29b-1, miR-29b-2, miR-29c, miR-302b, miR-302c, miR-30a, miR-30a-3p, miR-335, miR-338-3p, miR-33a, miR-34a, miR-34b, miR-365, miR-370, miR-372, miR-375, miR-376a, miR-377, miR-422a, miR-424, miR-424-5p, miR-433, miR-4458, miR-448, miR-450a, miR-451, miR-485-5p, miR-486-5p, miR-497, miR-503, miR-506, miR-519d, miR-520a, miR-520b, miR-520c-3p, miR-582-5p, miR-590-5p, miR-610, miR-612, miR-625, miR-637, miR-675, miR-7, miR-877, miR-940, miR-941, miR-98, miR-99a, miR-132, and/or miR-31 inserted into the 5' UTR or 3' UTR of one or more viral genes required for viral replication. This oncolytic virus may be used in methods and compositions for treating liver cancer. In some embodiments, the liver cancer is hepatocellular carcinoma.

In some embodiments, a recombinant oncolytic virus comprises a plurality of copies of one or more tumor-suppressive miRNA target sequences for miR-143-3p, miR-126-3p, miR-126-5p, miR-1266-3p, miR-6130, miR-6080, miR-511-5p, miR-143-5p, miR-223-5p, miR-199b-5p, miR-199a-3p, miR-199b-5p, miR-451a, miR-142-5p, miR-144, miR-150-5p, miR-142-3p, miR-214-3p, miR-214-5p, miR-199a-5p, miR-145-3p, miR-145-5p, miR-1297, miR-141, miR-145, miR-16, miR-200a, miR-200b, miR-200c, miR-29b, miR-381, miR-409-3p, miR-429, miR-451, miR-511, miR-99a, let-7a-1, let-7a-2, let-7a-3, let-7b, let-7c, let-7d, let-7e, let-7f-1, let-7f-2, let-7g, let-7i, miR-1, miR-101, miR-133b, miR-138, miR-142-5p, miR-144, miR-1469, miR-146a, miR-153, miR-15a, miR-15b, miR-16-1, miR-16-2, miR-182, miR-192, miR-193a-3p, miR-194, miR-195, miR-198, miR-203, miR-217, miR-218, miR-22, miR-223, miR-26a, miR-26b, miR-29c, miR-33a, miR-34a, miR-34b, miR-34c, miR-365, miR-449a, miR-449b, miR-486-5p, miR-545, miR-610, miR-614, miR-630, miR-660, miR-7515, miR-9500, miR-98, miR-99b, miR-133a, let-7a, miR-100, miR-106a, miR-107, miR-124, miR-125a-3p, miR-125a-5p, miR-126, miR-126*, miR-129, miR-137, miR-140, miR-143, miR-146b, miR-148a, miR-148b, miR-149, miR-152, miR-154, miR-155, miR-17-5p, miR-181a-1, miR-181a-2, miR-181b, miR-181b-1, miR-181b-2, miR-181c, miR-181d, miR-184, miR-186, miR-193b, miR-199a, miR-204, miR-212, miR-221, miR-224, miR-27a, miR-27b, miR-29a, miR-30a, miR-30b, miR-30c, miR-30d, miR-30d-5p, miR-30e-5p, miR-32, miR-335, miR-338-3p, miR-340, miR-342-3p, miR-361-3p, miR-373, miR-375, miR-4500, miR-4782-3p, miR-497, miR-503, miR-512-3p, miR-520a-3p, miR-526b, miR-625*, and/or miR-96 inserted into the 5' UTR or 3' UTR of one or more viral genes required for viral replication. This oncolytic virus may be used in methods and compositions for treating lung cancer.

In some embodiments, a recombinant oncolytic virus comprises a plurality of copies of one or more tumor-suppressive miRNA target sequences for let-7b, miR-101, miR-125b, miR-1280, miR-143, miR-146a, miR-146b, miR-155, miR-17, miR-184, miR-185, miR-18b, miR-193b, miR-200c, miR-203, miR-204, miR-205, miR-206, miR-20a, miR-211, miR-218, miR-26a, miR-31, miR-33a, miR-34a, miR-34c, miR-376a, miR-376c, miR-573, miR-7-5p, miR-9, and/or miR-98 inserted into the 5' UTR or 3' UTR of one or more viral genes required for viral replication. This oncolytic virus may be used in methods and compositions for treating melanoma.

In some embodiments, a recombinant oncolytic virus comprises a plurality of copies of one or more tumor-suppressive miRNA target sequences for let-7d, miR-218, miR-34a, miR-375, miR-494, miR-100, miR-124, miR-1250, miR-125b, miR-126, miR-1271, miR-136, miR-138, miR-145, miR-147, miR-148a, miR-181a, miR-206, miR-220a, miR-26a, miR-26b, miR-29a, miR-32, miR-323-5p, miR-329, miR-338, miR-370, miR-410, miR-429, miR-433, miR-499a-5p, miR-503, miR-506, miR-632, miR-646, miR-668, miR-877, and/or miR-9 inserted into the 5' UTR or 3' UTR of one or more viral genes required for viral replication. This oncolytic virus may be used in methods and compositions for treating oral cancer.

In some embodiments, a recombinant oncolytic virus comprises a plurality of copies of one or more tumor-suppressive miRNA target sequences for let-7i, miR-100, miR-124, miR-125b, miR-129-5p, miR-130b, miR-133a, miR-137, miR-138, miR-141, miR-145, miR-148a, miR-152, miR-153, miR-155, miR-199a, miR-200a, miR-200b, miR-200c, miR-212, miR-335, miR-34a, miR-34b, miR-34c, miR-409-3p, miR-411, miR-429, miR-432, miR-449a, miR-494, miR-497, miR-498, miR-519d, miR-655, miR-9, miR-98, miR-101, miR-532-5p, miR-124a, miR-192, miR-193a, and/or miR-7 inserted into the 5' UTR or 3' UTR of one or more viral genes required for viral replication. This oncolytic virus may be used in methods and compositions for treating ovarian cancer.

In some embodiments, a recombinant oncolytic virus comprises a plurality of copies of one or more tumor-suppressive miRNA target sequences for miR-216a-5p, miR-802, miR-217, miR-145-3p, miR-143-3p, miR-451a, miR-375, miR-214-3p, miR-216b-3p, miR-432-5p, miR-216a-3p, miR-199b-5p, miR-199a-5p, miR-136-3p, miR-216b-5p, miR-136-5p, miR-145-5p, miR-127-3p, miR-199a-3p, miR-199b-3p, miR-559, miR-129-2-3p, miR-4507, miR-1-3p, miR-148a-3p, miR-101, miR-1181, miR-124, miR-1247, miR-133a, miR-141, miR-145, miR-146a, miR-148a, miR-148b, miR-150*, miR-150-5p, miR-152, miR-15a, miR-198, miR-203, miR-214, miR-216a, miR-29c, miR-335, miR-34a, miR-34b, miR-34c, miR-373, miR-375, miR-410, miR-497, miR-615-5p, miR-630, miR-96, miR-132, let-7a, let-7a-1, let-7a-2, let-7a-3, let-7b, let-7c, let-7d, let-7e, let-7f-1, let-7f-2, let-7g, let-7i, miR-126, miR-135a, miR-143, miR-144, miR-150, miR-16, miR-200a, miR-200b, miR-200c, miR-217, miR-218, miR-337, miR-494, and/or miR-98 inserted into the 5' UTR or 3' UTR of one or more viral genes required for viral replication. This oncolytic virus may be used in methods and compositions for treating pancreatic cancer.

In some embodiments, a recombinant oncolytic virus comprises a plurality of copies of one or more tumor-suppressive miRNA target sequences for let-7a-3p, let-7c, miR-100, miR-101, miR-105, miR-124, miR-128, miR-1296, miR-130b, miR-133a-1, miR-133a-2, miR-133b, miR-135a, miR-143, miR-145, miR-146a, miR-154, miR-15a, miR-187, miR-188-5p, miR-199b, miR-200b, miR-203, miR-205, miR-212, miR-218, miR-221, miR-224, miR-23a, miR-23b, miR-25, miR-26a, miR-26b, miR-29b, miR-302a, miR-30a, miR-30b, miR-30c-1, miR-30c-2, miR-30d, miR-30e, miR-31, miR-330, miR-331-3p, miR-34a, miR-34b, miR-34c, miR-374b, miR-449a, miR-4723-5p, miR-497, miR-628-5p, miR-642a-5p, miR-765, and/or miR-940 inserted into the 5' UTR or 3' UTR of one or more viral genes required for viral replication. This oncolytic virus may be used in methods and compositions for treating prostate cancer.

In some embodiments, a recombinant oncolytic virus comprises a plurality of copies of one or more tumor-suppressive miRNA target sequences for miR-101, miR-183, miR-204, miR-34a, miR-365b-3p, miR-486-3p, and/or miR-532-5p inserted into the 5' UTR or 3' UTR of one or more viral genes required for viral replication. This oncolytic virus may be used in methods and compositions for treating retinoblastoma.

In some embodiments, an oncolytic virus described herein is a herpes simplex virus and wherein the one or more viral genes required for viral replication is selected from the group consisting of UL1, UL5, UL6, UL7, UL8, UL9, UL11, UL12, UL14, UL15, UL17, UL18, UL19, UL20, UL22, UL25, UL26, UL26.5, UL27, UL28, UL29, UL30, UL31, UL32, UL33, UL34, UL35, UL36, UL37, UL38, UL39, UL40, UL42, UL48, UL49, UL52, UL53, UL54, ICP0, ICP4, ICP22, ICP27, ICP47, gamma-34.5, US3, US4, US5, US6, US7, USB, US9, US10, US11, and US12.

In some cases, the recombinant viral vector of the invention is a herpes simplex virus (HSV) and further comprises a deletion of the internal repeat (joint) region comprising one copy each of the diploid genes ICP0, ICP34.5, LAT, and ICP4 along with the promoter for the ICP47 gene.

In certain embodiments, the recombinant viral vector of the invention is an HSV that exhibits enhanced entry into cells, either through direct infection and/or lateral spread. In one aspect, HSV vectors of the present invention can directly infect cells through interaction with cell proteins other than typical mediators of HSV infection (e.g., other than nectin-1, HVEM, or heparan sulfate/chondroitin sulfate proteoglycans). In certain embodiments, the recombinant viral vector of the invention is an HSV and further comprises a mutation of the gB or gH gene that facilitates vector entry through non-canonical receptors. In another aspect, the invention provides an HSV vector further comprising mutant gH glycoproteins that exhibit lateral spread in cells typically resistant to HSV lateral spread, such as cells lacking gD receptors. In some embodiments, an HSV vector of the invention comprises one or more of the mutant gB or gH proteins as described in U.S. Patent Publication No. 2013/0096186, which is incorporated herein by reference in its entirety. In certain aspects, the mutant entry protein within an HSV vector is a glycoprotein involved with viral entry, such as gB, gH, and the mutant HSV vector can comprise mutated versions of both. However, the mutant entry protein can be any protein effecting entry of the HSV vector into cells. In certain embodiments, the mutant entry protein is other than gD, although the HSV vector can additionally comprise a mutant gD, such as containing a ligand or other desired mutation. Non-limiting mutations of gB or gH glycoprotein for use in the inventive HSV vector occur at one or more of the following residues: gB:D285, gB:A549, gB:S668, gH:N753, and gH:A778. In some embodiments, the inventive HSV vector comprises mutations at both gB:D285 and gB:A549, at both gH:N753 and gH:A778, and/or at each of gB:5668, gH:N753, and gH:A778. In certain embodiments, the HSV vector contains two or more of such mutations (e.g., 3 or more, 4 or more), and the HSV vector can comprise mutations in all five of these residues. In one embodiment, an HSV vector has mutations at gB:285, gB; 549, gH:753, and gH:778. The mutations are referred to herein relative to the codon (amino acid) numbering of the gD, gB, and gH genes of the HSV-1 strain KOS derivative K26GFP. The sequences for gB and gH of K26GFP differ from the sequences for gB as disclosed in GenBank (# AF311740 (incorporated herein by reference)) and for gH (GenBank # X03896 (incorporated herein by reference)) as reflected in the following table:

| | Amino acid position | AF311740 | K26GFP | Nucleotide position(s) | AF311740 | K26GFP |
|---|---|---|---|---|---|---|
| gB | 313 | T | S | 938-939 | ACG | AGC |
| | 315 | A | T | 943 | GCC | ACC |
| | 515 | H | R | 1,544 | CAC | CGC |
| | | | | X03896 | X03896 | |
| gH | 12 | I | L | 1,011 | ATT | CTT |
| | 110 | P | S | 1,305 | CCG | TCG |
| | 127 | T | I | 1,357 | ACC | ATC |
| | 138 | S | A | 1,389 | TCG | GCG |
| | 150 | A | T | 1,425 | GCC | ACC |
| | 532 | A | A | 2,573 | GCT | GCG |
| | 633 | R | R | 2,876 | CGT | CGC |

However, K26GFP may contain additional differences in the region of the gene corresponding to nucleotides 2,079-2,102 of GenBank X03896. Thus, it will be understood that the sequence of either KOS derivative K26GFP or GenBank Accession No. AF311740 can serve as a reference sequence for the gB mutations discussed herein. Also, the sequence of either KOS derivative K26GFP or GenBank Accession No. X03896 can serve as a reference sequence for the gH mutations discussed herein. However, HSV vectors of the invention may include homologous mutations in gB and gH of any HSV strain.

In some aspects, the mutation of the entry protein for inclusion in an HSV vector is a substitution mutation; however, mutations are not limited to substitution mutants. In certain embodiments, mutant gB or gH glycoproteins for use in an HSV vector are selected from the group of substitution mutations consisting of gB:D285N, gB:A549T, gB:S668N, gH:N753K, gH:A778V. In certain aspects, an HSV vector includes combinations of these substitutions (such as two or more of such substitutions (e.g., 3 or more, 4 or more, or all)), with the gB:D285N/gB:A549T double mutant, the gH:N753K/gH:A778V double mutant, and the gB:S668N/gH:N753K/gH:A778V triple mutant being examples of embodiments. In one embodiment, an HSV vector comprises gB:D285N/gB:A549T/gH:N753K/gH:A778V.

In certain aspects, an HSV vector comprises a mutant gB and/or a mutant gH glycoprotein, wherein the mutations in the glycoproteins are substitution mutations in at least two residues, wherein, when the vector is HSV-1 K26GFP, the at least two residues are selected from the group consisting of gB:D285, gB:A549, gB:S668, gH:N753, and gH:A778, or wherein when the vector is a homologous HSV, the at least two residues are selected from amino acids that correlate to gB:D285, gB:A549, gB:S668, gH:N753, and gH:A778 wherein the gB:D285 residue correlates to X in VYPYXEFVL (SEQ ID NO:1), the gB:A549 residue correlates to X in KLNPNXIAS (SEQ ID NO:2), the gB:S668 residue correlates to X in ITTVXTFID (SEQ ID NO:3) the gH:N753 residue correlates to X in VDTDXTQQQ (SEQ ID NO:4), and the gH:A778 residue correlates to X in VPSTXLLLF (SEQ ID NO:5); and wherein the HSV vector is an HSV-1 or HSV-2 vector.

In one aspect, the invention encompasses a recombinant oncolytic virus comprising at least one polynucleotide encoding a protein or an oligonucleotide (e.g., an shRNA, a decoy oligonucleotide, or an antagomir) that reduces the expression or inhibits the function of an miRNA, a gene, or a tissue inhibitor of metalloproteinases (TIMP). Such recombinant oncolytic viruses are referred to herein as "genome-editing" or "microenvironment-remodeling" viruses or vectors. The encoded protein or oligonucleotide may reduce expression or inhibit the function of a miRNA, gene, or TIMP in any number of ways including targeting the protein (e.g., a TIMP) for degradation (e.g., by ubiquitination and proteosomal degradation or targeting for lysosomal degradation), blocking interactions with cognate receptors (e.g., blocking antibodies or antigen binding fragments thereof or peptide inhibitors), degrading messenger RNA transcripts (e.g., a short interfering RNA or short hairpin RNA), and/or altering the genomic DNA sequence encoding the specific miR, gene, or protein (e.g., by an endonuclease).

In particular embodiments, the protein or oligonucleotide reduces the expression of a miR or a gene involved in carcinogenesis or metastasis (e.g., an oncogenic miR or an oncogene). In some embodiments, a recombinant oncolytic virus comprises at least one polynucleotide encoding a protein or an oligonucleotide that reduces the expression or function of an miRNA that is an oncogenic miRNA (e.g., one or more of the miRNAs listed in Table 4). In some embodiments, the recombinant oncolytic virus comprises at least 1, 2, 3, 4, 5, 6, 7, 8, 9, 10 or more polynucleotides encoding for a protein or oligonucleotide that reduces the expression or function of an oncogenic miRNA. In some embodiments, the recombinant oncolytic virus comprises at least 1, 2, 3, 4, 5, 6, 7, 8, 9, 10 or more polynucleotides encoding for a plurality of proteins or oligonucleotides that reduce the expression or function of a plurality of oncogenic miRNAs. In some embodiments, the protein or oligonucleotide reduces the expression of miR-17-92 and is used to treat lung cancer (e.g., small-cell lung cancer). In other embodiments, the protein or oligonucleotide reduces the expression of miR-221 and/or miR-21 and is used to treat glioblastoma. In certain embodiments, the protein or oligonucleotide reduces the expression of miR-155 and/or miR-17-92 and is used to treat lymphoma (e.g., Burkitt's lymphoma, diffuse large B cell lymphoma, marginal zone lymphoma, or chronic lymphocytic leukemia). In some embodiments, the protein or oligonucleotide reduces the expression of miR-221, miR-222, and/or miR-146 and is used to treat thyroid cancer. In some embodiments, the protein or oligonucleotide reduces the expression of miR-372 and/or miR-373 and is used to treat testicular cancer (e.g., testicular germ cell tumors). In some embodiments, the protein or oligonucleotide reduces the expression of miR-18 and/or miR-224 and is used to treat liver cancer (e.g., hepatocellular carcinoma).

In some embodiments, a recombinant viral vector described herein may be used to degrade the tumor extracellular matrix (ECM), which in some aspects leads to enhanced viral spread. Matrix metalloproteinases (MMPs) are zinc-dependent proteases that are classified, based on their activity, into collagenases, gelatinases, stromelysins and matrilysins. These proteases are generally secreted as pro-enzymes (zymogens) and are activated by proteolytic removal of the pro-peptide pro-domain. The primary role that MMPs play in cancer is in the degradation of the ECM, which facilitates tumor invasion and metastasis. MMPs are also involved in tumor progression, epithelial to mesenchymal transition (EMT), and angiogenesis. MMPs are regulated by miRNAs as well as TIMPs, which comprise a family of four protease inhibitors (TIMP1, TIMP2, TIMP3, and TIMP4). A broad array of tumor microenvironments can be degraded by disrupting miRNAs or TIMPs that negatively regulate the MMP family with the recombinant viral vectors of the invention. Examples of miRNA/MMP interactions are shown in Table 5. Many of these interactions show that multiple MMPs are regulated by a single miRNA: e.g. let-7 regulates MMP-2, MMP-9, and MMP-14; miR-143 regulates MMP-2, MMP-9, and MMP-13; miR-218 regulates MMP-2, MMP-7, and MMP-9. Furthermore, the vast majority of MMPs may be regulated by a single TIMP master switch: e.g. TIMP1 is known to inhibit most all of the known MMPs and also promotes cell proliferation in a wide range of cell types; TIMP2 interacts with MMP-14 and MMP-2.

In some embodiments, a recombinant oncolytic virus comprises at least one polynucleotide encoding a protein or an oligonucleotide that reduces the expression or function of an miRNA that is a microenvironment remodeling miRNA (e.g., one or more of the miRNAs listed in Table 5). In some embodiments, the protein or oligonucleotide reduces the expression or function of one microenvironment remodeling miRNA. In some embodiments, the protein or oligonucleotide reduces the expression or function of at least 2, 3, 4, 5, 6, 7, 8, 9, or 10 or more microenvironment remodeling miRNAs. In some embodiments, the recombinant oncolytic virus comprises a plurality of polynucleotides encoding a plurality of protein or oligonucleotides that reduce the expression or function of a plurality of microenvironment remodeling miRNAs. In some embodiments, strategies described herein may be utilized by recombinant viral vectors of the present invention to knockdown or disrupt expression or function of miRNAs or TIMPs which negatively regulate MMPs. In some embodiments, a recombinant oncolytic virus reduces the expression of a TIMP selected from TIMP1, TIMP2, TIMP3 and TIMP4.

In some embodiments, the recombinant oncolytic viruses described herein comprise at least one polynucleotide encoding a protein or an oligonucleotide that reduces the expression or function of a gene. In some aspects, the gene is an oncogenic gene (e.g., a gene selected from the genes listed in Table 7). In some aspects, the gene encodes an oncogenic miR (e.g., a miRNA listed in Table 4), a microenvironment remodeling miR (e.g., a miRNA listed in Table 5), or a negative regulator of ECM-degradation (e.g., a TIMP). Reduction of gene expression and/or function may be accomplished by at the level of transcription (e.g., mutating, deleting, or silencing the genomic DNA sequence) or at the level of translation (e.g., by inhibiting the production of the gene product through mRNA degradation). In some embodiments, the recombinant oncolytic viruses described herein comprise one or more polynucleotides that encode for nucleases that reduce the expression or function of a gene by enabling the mutation, deletion, or repression of transcription of a gene sequence. In specific embodiments, the nuclease is selected from a Clustered Regulatory Interspaced Short Palindromic Repeats (CRISPR)-associated endonuclease, a zinc-finger nuclease (ZFN) or a Transcription activator-like effector nuclease (TALEN). In non-limiting examples, a CRISPR-associated endonuclease is selected from SpCas9, SpCas9-HF1, SpCas9-HF2, SpCas9-HF3, SpCas9-HF4, SaCas9, FnCpf, FnCas9, eSpCas9, C2C1, C2C3, Cpf1, Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4.

Recombinant viral vectors of the invention may utilize the CRISPR (Clustered Regularly Interspaced Short Palindromic Repeats)/Cas (CRISPR Associated) nuclease system, which is an engineered nuclease system based on a bacterial system that can be used for mammalian genome engineering. Generally, the system comprises a Cas nuclease and a guide RNA (gRNA). The gRNA is comprised of two parts; a crispr-RNA (crRNA) that is specific for a target genomic DNA sequence, and a tracr RNA (trRNA) that facilitates Cas binding. The crRNA and trRNA may be present as separate RNA oligonucleotides, or may be present in the same RNA oligonucleotide, referred to as a single guide-RNA (sgRNA). As used herein, the term "guide RNA" or "gRNA" refers to either the combination of an individual trRNA and an individual crRNA or an sgRNA. See, e.g., Jinek et al. (2012) *Science* 337:816-821; Cong et al. (2013) *Science* 339:819-823; Mali et al. (2013) *Science* 339:823-826; Qi et al. (2013) *Cell* 152:1173-1183; Jinek et al. (2013), *eLife* 2:e00471; David Segal (2013) *eLife* 2:e00563; Ran et al. (2013) *Nature Protocols* 8(11):2281-2308; Zetsche et al. (2015) *Cell* 163 (3):759-771; PCT Publication Nos. WO 2007/025097, WO 2008/021207, WO 2010/011961, WO 2010/054108, WO 2010/054154, WO 2012/054726, WO 2012/149470, WO 2012/164565, WO 2013/098244, WO 2013/126794, WO 2013/141680, and WO 2013/142578; U.S. Patent Publication Nos. 2010-0093617, 2013-0011828, 2010-0257638, 2010-0076057, 2011-0217739, 2011-0300538, 2013-0288251, and 2012-0277120; and U.S. Pat. No. 8,546,553, each of which is incorporated herein by reference in its entirety.

Multiple class 1 CRISPR-Cas systems, which include the type I and type III systems, have been identified and functionally characterized in detail, revealing the complex architecture and dynamics of the effector complexes (Brouns et al., 2008, Marraffini and Sontheimer, 2008, Hale et al., 2009, Sinkunas et al., 2013, Jackson et al., 2014, Mulepati et al., 2014). In addition, several class 2-type II CRISPR-Cas systems that employ homologous RNA-guided endonucleases of the Cas9 family as effectors have also been identified and experimentally characterized (Barrangou et al., 2007, Garneau et al., 2010, Deltcheva et al., 2011, Sapranauskas et al., 2011, Jinek et al., 2012, Gasiunas et al., 2012). A second, putative class 2-type V CRISPR-Cas system has been recently identified in several bacterial genomes. The putative type V CRISPR-Cas systems contain a large, ~1,300 amino acid protein called Cpf1 (CRISPR from *Prevotella* and *Francisella* 1).

In some embodiments, an oncolytic virus described herein further comprises at least one polynucleotide encoding a tRNA and crRNA targeted to the miRNA or the TIMP. In some cases, the at least one polynucleotide encoding a tRNA and crRNA is inserted into a locus on the viral genome. In some embodiments, the polynucleotide is an insulated sequence comprising a synthetic insulator or a native viral (e.g., HSV) insulator. In certain embodiments, an oncolytic virus is a herpes simplex virus and the at least one polynucleotide encoding an RNA binding site is inserted into or between one or more loci including the internal repeat joint region (comprising one copy each of the diploid genes ICP0, ICP34.5, LAT, ICP4, and the ICP47 promoter), ICP0, LAT, UL1, UL5, UL6, UL7, UL8, UL9, UL11, UL12, UL14, UL15, UL17, UL18, UL19, UL20, UL22, UL25, UL26, UL26.5, UL27, UL28, UL29, UL30, UL31, UL32, UL33, UL34, UL35, UL36, UL37, UL38, UL39, UL40, UL42, UL48, UL49, UL52, UL53, UL54, ICP0, ICP4, ICP22, ICP27, ICP47, gamma-34.5, US3, US4, US5, US6, US7, US8, US9, US10, US11, and US12. In one embodiment, an oncolytic virus is a herpes simplex virus (HSV) and the at least one polynucleotide encoding an RNA binding site is inserted into a locus between the UL3 and the UL4 open reading frames (e.g., FIG. 45 and FIG. 46).

In some embodiments, the recombinant oncolytic virus comprises at least one polynucleotide encoding a protein that is a bispecific T-cell engager (BiTE), an anti-immunosuppressive protein, or an immunogenic antigen. As used herein an "anti-immunosuppressive protein" is a protein that inhibits an immunosuppressive pathway. The invention encompasses an oncolytic virus expressing an anti-immunosuppressive protein that is an anti-regulatory T-cell (Treg) protein or an anti-myeloid-derived suppressor cell (MDSC) protein. In some embodiments, the anti-immunosuppressive protein is a VHH-derived blocker or a VHH-derived BiTE. As used herein, an "immunogenic antigen" refers to a protein that increases an inflammatory or immunogenic immune response. In particular embodiments, the anti-immunosuppressive and immunogenic antigens induce an anti-tumor immune response. Examples of such proteins include antibody or antigen binding fragments thereof that bind to and inhibit immune checkpoint receptors (e.g. CTLA4, LAG3, PD1, PDL1, and others), pro-inflammatory cytokines (e.g., IFNγ, IFNα, IFNβ, TNFα, IL-12, IL-2, IL-6, IL-8, GM-CSF, and others), or proteins that binding to and activate an activating receptor (e.g., FcγRI, FcγIIa, FcγIIIa, costimulatory receptors, and others). In particular embodiments, the protein is selected from EpCAM, folate, IFNβ, anti-CTLA-4, anti-PD1, A2A, anti-FGF2, anti-FGFR/FGFR2b, anti-SEMA4D, CCL5, CD137, CD200, CD38, CD44, CSF-1R, CXCL10, CXCL13, endothelin B Receptor, IL-12, IL-15, IL-2, IL-21, IL-35, ISRE7, LFA-1, NG2 (also known as SPEG4), SMADs, STING, TGFβ, and VCAM1.

In certain embodiments, a polynucleotide encoding a protein or an oligonucleotide targeted to reduce expression of an miRNA, a gene, or a TIMP is inserted into a locus on the viral genome of a recombinant oncolytic virus. In some embodiments, the polynucleotide is an insulated sequence comprising a synthetic insulator or a native viral (e.g., HSV) insulator. In certain embodiments, the oncolytic virus is a herpes simplex virus and the at least one polynucleotide encoding an RNA binding site is inserted into or between one or more loci including the internal repeat joint region (comprising one copy each of the diploid genes ICP0, ICP34.5, LAT, ICP4, and the ICP47 promoter), ICP0, LAT, UL1, UL5, UL6, UL7, UL8, UL9, UL11, UL12, UL14, UL15, UL17, UL18, UL19, UL20, UL22, UL25, UL26, UL26.5, UL27, UL28, UL29, UL30, UL31, UL32, UL33, UL34, UL35, UL36, UL37, UL38, UL39, UL40, UL42, UL48, UL49, UL52, UL53, UL54, ICP0, ICP4, ICP22, ICP27, ICP47, gamma-34.5, US3, US4, US5, US6, US7, US8, US9, US10, US11, and US12. In one embodiment, the virus is a herpes simplex virus (HSV) and the at least one polynucleotide is inserted into a locus between the UL3 and the UL4 open reading frames (see, e.g., FIG. 45 and FIG. 46).

In some embodiments, the recombinant oncolytic virus comprises at least one protease-activated antibody. Protease-activated antibodies, such as those described by Metz et al. (Protein Eng Des Sel, 25(10):571-80, 2012) are activated and bind only to targets following protease cleavage of a protective cap. In some instances, tumor microenvironments possess an array of proteases that are well differentiated from surrounding healthy tissues. For example, the protease cathepsin B is overexpressed in numerous cancers, including breast, cervix, colon, colorectal, gastric, head and neck, liver, lung, melanoma, ovarian, pancreatic, prostate, and thyroid cancer. The human degradome, comprised of a complete list of proteases synthesized by human cells, is made up of at least 569 proteases that are distributed into five broad classes (in order from greatest to least number): metalloproteinases (MMPs), serine, cysteine, threonine, and aspartic proteases (Lopez-Otin et al., Nat Rev Cancer, 7(10):800-8, 2007). In particular, protease antibodies specifically cleaved by MMPs can serve as an excellent means of targeting the recombinant viral vectors described herein to the tumor microenvironment, as MMPs are found in the extracellular and pericellular areas of the cell. Table 6 summarizes proteases that are overexpressed in cancers which can be exploited to enable specific binding of recombinant viral vectors pseudotyped with protease-activated antibodies.

In certain embodiments, the protease-activated antibody is incorporated into the viral glycoprotein envelope. Protease-activated antibodies can be incorporated into the glycoprotein envelope of a recombinant viral vector of the invention (e.g., an HSV vector) to increase the therapeutic index and reduce off-target infection. In the case of an HSV vector, in some embodiments, the glycoprotein may be gC or gD. In some embodiments, the recombinant oncolytic viruses described herein comprise at least one polynucleotide encoding a protease-activated antibody. In certain embodiments, a protease-activated antibody is activated by a protease selected from a cysteine cathepsin, an aspartic cathepsin, a kallikrein (hK), a serine protease, a caspase, a matrix metalloproteinase (MMP), and a disintegrin and metalloproteinase (ADAM). In some embodiments, a protease is selected from cathepsin K, cathepsin B, cathepsin L, cathepsin E, cathepsin D, hK1, PSA (hK3), hK10, hK15, uPA, uPAR, MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19, MMP-20, MMP-21, MMP-23A, MMP-23B, MMP-24, MMP-25, MMP-26, MMP-27, MMP-28, or a protease listed in Table 6.

In some embodiments, the protease-activated antibody binds a protein expressed more highly by cancer cells or in cancer microenvironments than by non-cancer cells or in non-cancer microenvironments. In certain aspects, a protease-activated antibody binds NKG2D, c-met, HGFR, CD8, heparan sulfate, VSPG4 (also known as NG2), EGFR, EGFRvIII, CD133, CXCR4, carcinoembryonic antigen (CEA), CLC-3, annexin II, human transferrin receptor, or EpCAM. In certain instances, multiple protease activated antibodies may be incorporated into a single viral vector particle to ensure that diverse tumor histotypes are targeted. For example, at least 1, 2, 3, 4, 6, 7, 8, 9, 10, or more protease activated antibodies may be incorporated into the viral glycoprotein envelope. In some embodiments, the recombinant oncolytic virus comprises at least 1, 2, 3, 4, 5, 6, 7, 8, 9, 10, or more polynucleotides that encodes for at least 1, 2, 3, 4, 5, 6, 7, 8, 9, 10, or more protease activated antibodies. In some embodiments, an oncolytic virus comprises a first protease-activated antibody that binds a first protein expressed more highly by cancer cells or in cancer microenvironments than by non-cancer cells or in non-cancer microenvironments, and a second protease-activated antibody that binds a second protein expressed more highly by cancer cells or in cancer microenvironments than by non-cancer cells or in non-cancer microenvironments. In further embodiments, an oncolytic virus comprises a plurality of protease-activated antibodies binding a plurality of protein expressed more highly by cancer cells or in cancer microenvironments than by non-cancer cells or in non-cancer microenvironments. An oncolytic virus comprises, for example, a protease-activated antibody that is a human antibody, a humanized antibody or a chimeric antibody. In some embodiments, an oncolytic virus comprises an antibody that is a full-length immunoglobulin, an scFv, a Fab, a Fab', an F(ab')2, an Fv, a diabody, a triabody, a minibody, a single-domain antibody, or a multispecific antibody.

In some embodiments, a recombinant oncolytic virus comprises one or more of: one or more tumor-suppressive micro-RNA (miR) target sequences inserted into a locus of one or more viral genes required for viral replication; one or more polynucleotides encoding one or more proteins or oligonucleotides, wherein the proteins or oligonucleotides reduce the expression or inhibit the function of a miR, a gene, or a TIMP; at least one protease-activated antibody; and/or a polynucleotide encoding at least one protease activated antibody. In some embodiments, a recombinant oncolytic virus comprises: a plurality of copies of one or more tumor-suppressive miRNA target sequences inserted into a locus of a viral gene required for viral replication in non-cancerous cells; and/or a first polynucleotide encoding a protein or an oligonucleotide targeted to reduce expression of an oncogenic miRNA or an oncogenic gene; and/or a second polynucleotide encoding a protein or an oligonucleotide targeted to reduce expression of a microenvironment remodeling miRNA or a TIMP. In some embodiments, a recombinant oncolytic virus comprises: a plurality of copies of one or more tumor-suppressive miRNA target sequences inserted into a locus of a viral gene required for viral replication in non-cancerous cells; and/or a polynucleotide encoding a protein or an oligonucleotide targeted to reduce expression of an oncogenic miRNA or an oncogenic gene; and/or at least one protease-activated antibody. In further embodiments, a recombinant oncolytic virus comprises a plurality of copies of one or more tumor-suppressive miRNA target sequences inserted into a locus of a viral gene required for viral replication in non-cancerous cells; and/or a polynucleotide encoding a protein or an oligonucleotide targeted to reduce expression of a microenvironment remodeling miRNA or a TIMP; and/or at least one protease-activated antibody. In one embodiment, a recombinant oncolytic virus comprises a plurality of copies of one or more tumor-suppressive miRNA target sequences inserted into a locus of a viral gene required for viral replication in non-cancerous cells; and/or a first polynucleotide encoding a protein or an oligonucleotide targeted to reduce expression of an oncogenic miRNA or an oncogenic gene; and/or a second polynucleotide encoding a protein or an oligonucleotide targeted to reduce expression of a microenvironment remodeling miRNA or a TIMP; and/or at least one protease-activated antibody. In some specific embodiments, an oncolytic virus described in this paragraph is a herpes simplex virus and the viral gene required for viral replication in non-cancerous cells is UL1, UL5, UL6, UL7, UL8, UL9, UL11, UL12, UL14, UL15, UL17, UL18, UL19, UL20, UL22, UL25, UL26, UL26.5, UL27, UL28, UL29, UL30, UL31, UL32, UL33, UL34, UL35, UL36, UL37, UL38, UL39, UL40, UL42, UL48, UL49, UL52, UL53, UL54, ICP0, ICP4, ICP22, ICP27, ICP47, gamma-34.5, US3, US4, US5, US6, US7, USB, US9, US10, US11, and US12.

In certain aspects, the invention relates to a recombinant oncolytic virus comprising a first polynucleotide encoding a protein or an oligonucleotide targeted to reduce expression of an oncogenic miRNA or an oncogenic gene; and a second polynucleotide encoding a protein or an oligonucleotide targeted to reduce expression of a microenvironment remodeling miRNA or a TIMP. In other embodiments, a recombinant oncolytic virus comprises a polynucleotide encoding a protein or an oligonucleotide targeted to reduce expression of an oncogenic miRNA or an oncogenic gene; and at least one protease-activated antibody. In some embodiments, a recombinant oncolytic virus comprises a polynucleotide encoding a protein or an oligonucleotide targeted to reduce expression of a microenvironment remodeling miRNA or a TIMP; and at least one protease-activated antibody. In one embodiment, a recombinant oncolytic virus comprises a first polynucleotide encoding a protein or an oligonucleotide targeted to reduce expression of an oncogenic miRNA or an oncogenic gene; and/or a second polynucleotide encoding a protein or an oligonucleotide targeted to reduce expression of a microenvironment remodeling miRNA or a TIMP; and/or at least one protease-activated antibody.

In certain embodiments, an oncolytic virus described herein is a herpesvirus (for example, herpes simplex virus (e.g., HSV-1 or HSV-2)), an adenovirus, a polio virus, a vaccinia virus, a measles virus, a vesicular stomatitis virus, an orthomyxovirus, a parvovirus, a maraba virus or a coxsackievirus. HSV-based vectors and methods for their construction are described in, for example, U.S. Pat. Nos. 7,078,029, 6,261,552, 5,998,174, 5,879,934, 5,849,572, 5,849,571, 5,837,532, 5,804,413, and 5,658,724, and International Patent Applications WO 91/02788, WO 96/04394, WO 98/15637, and WO 99/06583, which are incorporated herein by reference in their entireties. The sequence of HSV is published (NCBI Accession No. NC_001806; see also McGoech et al., J. Gen. Virol, 69 (PT 7), 1531-1574 (1988)), which may facilitate designing HSV-based vectors of the invention.

The invention also encompasses a nucleic acid molecule encoding an oncolytic virus described herein.

Compositions and Methods of Use

Certain aspects of the invention relate to stocks and compositions comprising the oncolytic viruses described herein. In some aspects, the invention relates to a viral stock comprising an oncolytic virus described herein. In some embodiments, a viral stock is a homogeneous stock. The preparation and analysis of viral stocks is well known in the art. For example, a viral stock can be manufactured in roller bottles containing cells transduced with the viral vector. The viral stock can then be purified on a continuous nycodenze gradient, and aliquotted and stored until needed. Viral stocks vary considerably in titer, depending largely on viral genotype and the protocol and cell lines used to prepare them.

In particular embodiments, the titer of a viral stock (e.g., an HSV-based vector viral stock) contemplated herein is at least about $10^5$ plaque-forming units (pfu), such as at least about $10^6$ pfu or even more preferably at least about $10^7$ pfu. In certain embodiments, the titer can be at least about $10^8$ pfu, or at least about $10^9$ pfu, and high titer stocks of at least about $10^{10}$ pfu or at least about $10^{11}$ pfu are most preferred.

The invention further contemplates a composition comprising an oncolytic virus or a nucleic acid molecule described herein and a pharmaceutically acceptable carrier. The phrase "pharmaceutically-acceptable" refers to molecular entities and compositions that do not produce an allergic or similar untoward reaction when administered to a subject (e.g., a human). The term "composition" as used herein refers to a formulation of one or more oncolytic virus or a nucleic acid molecules described herein that is capable of being administered or delivered to a subject and/or a cell. Typically, formulations include all physiologically acceptable compositions including derivatives and/or prodrugs, solvates, stereoisomers, racemates, or tautomers thereof with any physiologically acceptable carriers, diluents, and/or excipients. A "therapeutic composition" or "pharmaceutical composition" (used interchangeably herein) is a composition of one or more agents capable of being administered or delivered to a patient and/or subject and/or cell for the treatment of a particular disease or disorder.

The compositions disclosed herein may be formulated in a neutral or salt form. "Pharmaceutically acceptable salt" includes both acid and base addition salts. Pharmaceutically-acceptable salts include the acid addition salts (formed with the free amino groups of the protein) and which are formed with inorganic acids such as, for example, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, ptoluenesulfonic acid, trifluoroacetic acid, undecylenic acid, and the like. Salts formed with the free carboxyl groups can also be derived from inorganic bases such as, for example, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

As used herein "pharmaceutically acceptable carrier" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, dispersion media, coatings, antibacterial and antifungal agents, isotonic and absorption delaying agents, and the like that are physiologically compatible, including pharmaceutically acceptable cell culture media and/or emulsifier which has been approved by the United States Food and Drug Administration as being acceptable for use in humans and/or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions;

and any other compatible substances employed in pharmaceutical formulations. Except insofar as any conventional media and/or agent is incompatible with the agents of the present disclosure, its use in therapeutic compositions is contemplated. Supplementary active ingredients also can be incorporated into the compositions.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In one embodiment, a composition comprising a carrier is suitable for parenteral administration, e.g., intravascular (intravenous or intraarterial), intraperitoneal or intramuscular administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with a viral vector or nucleic acid molecule, use thereof in the pharmaceutical compositions of the invention is contemplated.

The compositions of the invention may comprise one or more polypeptides, polynucleotides, vectors comprising same, infected cells, etc., as described herein, formulated in pharmaceutically-acceptable or physiologically-acceptable solutions for administration to a cell or an animal, either alone, or in combination with one or more other modalities of therapy. It will also be understood that, if desired, the compositions of the invention may be administered in combination with other agents as well, such as, e.g., cytokines, growth factors, hormones, small molecules or various pharmaceutically-active agents. There is virtually no limit to other components that may also be included in the compositions, provided that the additional agents do not adversely affect the ability of the composition to deliver the intended therapy.

In the pharmaceutical compositions of the invention, formulation of pharmaceutically-acceptable excipients and carrier solutions is well-known to those of skill in the art, as is the development of suitable dosing and treatment regimens for using the particular compositions described herein in a variety of treatment regimens. Upon formulation, solutions are administered in a manner compatible with the dosage formulation and in such amount as is therapeutically effective to result in an improvement or remediation of the symptoms. The formulations are easily administered in a variety of dosage forms such as ingestible solutions, drug release capsules and the like. Some variation in dosage can occur depending on the condition of the subject being treated. The person responsible for administration can, in any event, determine the appropriate dose for the individual subject. Moreover, for human administration, preparations meet sterility, general safety and purity standards as required by FDA Center for Biologics Evaluation and Research standards. The route of administration will vary, naturally, with the location and nature of the disease being treated, and may include, for example intradermal, transdermal, subdermal, parenteral, nasal, intravenous, intramuscular, intranasal, subcutaneous, percutaneous, intratracheal, intraperitoneal, intratumoral, perfusion, lavage, direct injection, and oral administration.

In certain circumstances it will be desirable to deliver the compositions, recombinant viral vectors, and nucleic acid molecules disclosed herein parenterally, intravenously, intramuscularly, or even intraperitoneally as described, for example, in U.S. Pat. Nos. 5,543,158; 5,641,515 and 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabenes, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., Remington: The Science and Practice of Pharmacy, 20th Edition. Baltimore, Md.: Lippincott Williams & Wilkins, 2000). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions can be prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain embodiments, the compositions may be delivered by intranasal sprays, inhalation, and/or other aerosol delivery vehicles. Methods for delivering polynucleotides and peptide compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

In certain embodiments, the delivery may occur by use of liposomes, nanocapsules, microparticles, microspheres, lipid particles, vesicles, optionally mixing with CPP polypeptides, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques. The formulations and compositions of the invention may comprise one or more polypeptides, polynucleotides, and small molecules, as described herein, formulated in pharmaceutically-acceptable or physiologically-acceptable solutions (e.g., culture medium) for administration to a cell or an animal, either alone, or in combination with one or more other modalities of therapy. It will also be understood that, if desired, the compositions of the invention may be administered in combination with other agents as well, such as, e.g., cells, other proteins or polypeptides or various pharmaceutically-active agents.

In a particular embodiment, a formulation or composition according to the present invention comprises a cell contacted with a combination of any number of polynucleotides or viral vectors, as contemplated herein.

In certain aspects, the present invention provides formulations or compositions suitable for the delivery of viral vector systems.

Exemplary formulations for ex vivo delivery may also include the use of various transfection agents known in the art, such as calcium phosphate, electroporation, heat shock and various liposome formulations (i.e., lipid-mediated transfection). Liposomes are lipid bilayers entrapping a fraction of aqueous fluid. DNA spontaneously associates to the external surface of cationic liposomes (by virtue of its charge) and these liposomes will interact with the cell membrane.

Particular embodiments of the invention may comprise other formulations, such as those that are well known in the pharmaceutical art, and are described, for example, in Remington: The Science and Practice of Pharmacy, 20th Edition. Baltimore, Md.: Lippincott Williams & Wilkins, 2000.

In certain aspects, the present invention provides pharmaceutically acceptable compositions which comprise a therapeutically effective amount of one or more viral vectors or polynucleotides, as described herein, formulated together with one or more pharmaceutically acceptable carriers (additives) and/or diluents (e.g., pharmaceutically acceptable cell culture medium). As used herein, a "therapeutically effective amount" refers to the amount of a composition or recombinant virus described herein required to achieve a desired physiologic and/or biological outcome. A "therapeutically effective amount" of a virus, a viral stock, or a composition may vary according to factors such as the disease state, age, sex, and weight of the individual, and the ability of the stem and progenitor cells to elicit a desired response in the individual. A therapeutically effective amount is also one in which any toxic or detrimental effects of the virus or transduced therapeutic cells are outweighed by the therapeutically beneficial effects. The term "therapeutically effective amount" includes an amount that is effective to "treat" a subject (e.g., a patient). The therapeutically effective amount may be quantified by the total number of plaque forming units (pfu) (e.g. at least $1e^1$ to at least $1e^{20}$, particularly about $1e^4$ to about $1e^{15}$ more particularly about $1e^6$ to about $1e^{12}$ pfu), or number of viral genomes (e.g. at least $1e^1$ to at least $1e^{20}$, particularly about $1e^4$ to about $1e^{15}$, more particularly about $1e^6$ to about $1e^{12}$ viral genomes). One of skill in the art will understand that the therapeutically effective amount will vary based on the type of virus being administered, nature of the formulation, route of administration, nature and/or severity of the disease to be treated, and/or general health and well-being of the subject.

Some aspects of the invention encompass a method of killing a cancerous cell, comprising exposing the cancerous cell to an oncolytic virus described herein or compositions thereof under conditions sufficient for the oncolytic virus to infect and replicate within said cancerous cell, and wherein replication of the oncolytic virus within the cancerous cell results in cell death. In certain embodiments, the cancerous cell has a reduced expression of a tumor-suppressive miR compared to a non-cancerous cell. In some embodiments, a cancerous cell killed by this method is in vivo. In certain embodiments, a cancerous cell killed by this method is within a tumor.

The invention relates to a method of treating cancer in a subject in need thereof, comprising administering a prophylactically effective amount or a therapeutically effective amount of an oncolytic virus, a viral stock, or a composition as described herein to the subject. A "subject," as used herein, includes any animal that exhibits a symptom of a disease, disorder, or condition that can be treated with the recombinant viral vectors, compositions, and methods disclosed herein. Suitable subjects (e.g., patients) include laboratory animals (such as mouse, rat, rabbit, or guinea pig), farm animals (such as horse or cow), and domestic animals or pets (such as cat or dog). Non-human primates and, preferably, human patients, are included.

"Administration" refers herein to introducing an oncolytic virus, a viral stock, or a composition thereof into a subject or contacting an oncolytic virus, a viral stock, or a composition thereof with a cell and/or tissue. Administration can occur by injection, irrigation, inhalation, consumption, electro-osmosis, hemodialysis, iontophoresis, and other methods known in the art. The route of administration will vary, naturally, with the location and nature of the disease being treated, and may include, for example auricular, buccal, conjunctival, cutaneous, dental, endocervical, endosinusial, endotracheal, enteral, epidural, interstitial, intra-articular, intra-arterial, intra-abdominal, intraauricular, intrabiliary, intrabronchial, intrabursal, intracavernous, intracerebral, intracisternal, intracorneal, intracronal, intracoronary, intracranial, intradermal, intradiscal, intraductal, intraduodenal, intraduodenal, intradural, intraepicardial, intraepidermal, intraesophageal, intragastric, intragingival, intrahepatic, intraileal, intralesional, intralingual, intraluminal, intralymphatic, intramammary, intramedulleray, intrameningeal, instramuscular, intranasal, intranodal, intraocular, intraomentum, intraovarian, intraperitoneal, intrapericardial, intrapleural, intraprostatic, intrapulmonary, intraruminal, intrasinal, intraspinal, intrasynovial, intratendinous, intratesticular, intratracheal, intrathecal, intrathoracic, intratubular, intratumoral, intratympanic, intrauterine, intraperitoneal, intravascular, intraventricular, intravesical, intravestibular, intravenous, intravitreal, larangeal, nasal, nasogastric, oral, ophthalmic, oropharyngeal, parenteral, percutaneous, periarticular, peridural, perineural, periodontal, respiratory, retrotubular, rectal, spinal, subarachnoid, subconjunctival, subcutaneous, subdermal, subgingival, sublingual, submucosal, subretinal, topical, transdermal, transendocardial, transmucosal, transplacental, trantracheal, transtympanic, ureteral, urethral, and/or vaginal perfusion, lavage, direct injection, and oral administration.

The term "treating" and "treatment" as used herein refers to administering to a subject a therapeutically effective amount of a recombinant virus or composition thereof as described herein so that the subject has an improvement in a disease or condition, or a symptom of the disease or condition. The improvement is any improvement or remediation of the disease or condition, or symptom of the disease or condition. The improvement is an observable or measurable improvement, or may be an improvement in the general feeling of well-being of the subject. Thus, one of skill in the art realizes that a treatment may improve the disease condition, but may not be a complete cure for the disease. A "prophylactically effective amount" refers to an amount of a virus, a viral stock, or a composition effective to achieve the desired prophylactic result. As used herein, "prophylaxis" can mean complete prevention of the symptoms of a disease, a delay in onset of the symptoms of a disease, or a lessening in the severity of subsequently developed disease symptoms. Typically, but not necessarily, since a prophylactic dose is used in subjects prior to or at an earlier stage of disease, the prophylactically effective amount is less than the therapeutically effective amount.

"Cancer" herein refers to or describes the physiological condition in mammals that is typically characterized by unregulated cell growth. Examples of cancer include but are not limited to carcinoma, lymphoma, blastoma, sarcoma (including liposarcoma, osteogenic sarcoma, angiosarcoma, endotheliosarcoma, leiomyosarcoma, chordoma, lymphangiosarcoma, lymphangioendotheliosarcoma, rhabdomyosarcoma, fibrosarcoma, myxosarcoma, chondrosarcoma), neuroendocrine tumors, mesothelioma, synovioma, schwannoma, meningioma, adenocarcinoma, melanoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, small cell lung carcinoma, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulvar cancer, thyroid cancer, hepatic carcinoma, anal carcinoma, penile carcinoma, testicular cancer, esophageal cancer, tumors of the biliary tract, Ewing's tumor, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, testicular tumor, lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, multiple myeloma, Waldenstrom's macroglobulinemia, myelodysplastic disease, heavy chain disease, neuroendocrine tumors, Schwannoma, and other carcinomas, as well as head and neck cancer.

In certain embodiments, an oncolytic virus (e.g., an HSV), a viral stock, or a composition as described herein are used to treat a cancer selected from lung cancer (e.g., small cell lung cancer or non-small cell lung cancer), breast cancer, ovarian cancer, cervical cancer, prostate cancer, testicular cancer, colorectal cancer, colon cancer, pancreatic cancer, liver cancer (e.g., hepatocellular carcinoma (HCC)), gastric cancer, head and neck cancer, thyroid cancer, malignant glioma, glioblastoma, melanoma, B-cell chronic lymphocytic leukemia, diffuse large B-cell lymphoma (DLBCL), and marginal zone lymphoma (MZL).

In certain aspects, the invention relates to an oncolytic viral vector as shown in any one of the figures or embodiments disclosed herein.

EXAMPLES

The following examples for the purpose of illustrating various embodiments of the invention and are not meant to limit the present invention in any fashion. The present examples, along with the methods described herein, are exemplary, and are not intended as limitations on the scope of the invention. Alterations, modifications, and other changes to the described embodiments which are encompassed within the spirit of the invention as defined by the scope of the claims are specifically contemplated.

Example 1—miR Sequence Analysis of Normal and Malignant Cells

Differential miR expression is a hallmark of many cancers (Lu et al, Nature, 2005). Experiments were performed to determine the miRs that were mostly highly differentially expressed in eight different cancer cells lines. Differential expression was determined by comparisons to non-cancerous control tissues. In total, 108 samples were sequenced. Sample details are provided in the following table.

| Cancer Type | # of Cancer Cell Lines | # of Control Tissue Samples |
|---|---|---|
| Bladder | 8 | 4 |
| Colon | 8 | 3 |
| Breast | 12 | 4 |
| Pancreatic | 7 | 3 |
| Lung | 8 | 5 |
| Head and Neck | 6 | 6 |
| Schwannoma | 7 | 4* |
| Glioblastoma | 14 | 4* |
| Additional Controls | | |
| Normal Liver | 3 | |
| Normal Bone Marrow | 3 | |

*Same control samples used for both Schwannoma and glioblastoma analysis

To facilitate the identification of appropriate miRNA target sequences suitable for HSV attenuation in select cell types, miRNA sequence profiling of cancer lines and non-cancer control tissue was performed. Sequencing libraries of dicer-processed RNAs were generated for cancer and non-cancer cells, including bladder, colon, breast, pancreas, lung, head and neck, schwannoma, glioblastoma, brain, liver, and bone marrow. These miRNA sequencing libraries were normalized to total RNA, and sequenced using a HiSeq 2500 ultra-high throughput sequencing system with HiSeq V4 chemistry reagents for sequencing reads up to $3e^8$ reads/run (Illumina). FASTQ files from sequencing runs were analyzed using the miRNAs Analysis tool in Basespace (Illumina). Rankings were made by calculating the mean of normal, the mean of cancer and sorting the ratio of normal/cancer from high to low. Heat maps were generated with natural logarithmic values with zero and negative values converted to zero (scale: black is high, white is low expression). Normalized data across samples were expressed as normalized miRNA read counts in a given sample. Normalization is related to total number of reads in a given sample relative to other samples in the comparison.

FIG. 1 exemplifies the miRNA expression profile heat map in non-cancerous and cancerous brain tissue of twenty-five miRNAs. Additional examples of miRNA expression profile heat maps are shown for non-cancerous and cancerous bladder (FIG. 2), breast (FIG. 3), colon (FIG. 4), brain (FIG. 5), head and neck (FIG. 6), lung (FIG. 7), pancreas (FIG. 8), and schwannoma (FIG. 9) tissue corresponding to twenty-five miRNAs in each example. FIG. 10 shows that miR-451a levels are down regulated in all tumor types compared to non-cancerous tissue, representing a pan-tumor suppressor miRNA. FIG. 11 shows that miR-1 is down-regulated in all tumor types tested, present at moderate levels in non-cancerous tissue, and present at high levels in head and neck tissue. FIG. 12 shows that miR-559 is down-regulated in all tumor types tested, present generally at low levels in non-cancerous tissue, and present at high levels in non-cancerous lung tissue. FIG. 13 shows that miR-145-5p is down-regulated in all tumor types tested and present generally at high levels in the majority of non-cancerous tissue types tested. FIG. 14 shows that miR-143-3p is down-regulated in colon, lung, and pancreatic tumors, and is present at high levels in all normal tissue types and some breast tumor lines. miRNA data analysis revealed at least eleven miRNAs that represent novel and unexpected miRNA expression profiles not previously identified in the literature.

Many of these identified miRNAs are pan- or multi-tumor specific. For example, expression of miR-451a, miR-559, miR-1, miR-145-3p, and miR143-3p were generally down-regulated across all cancer cell lines tested compared to control tissues. This was particularly notable for miR-451a, which was highly expressed in all normal tissue type and substantially down-regulated in all cancer types, thus representing a pan-specific tumor-suppressive miRNA. The expression of miR-559 was lower in normal tissue types, except for normal lung tissue, and expression of miR-1 and mir-145-3p in normal tissue was variable. Despite the variability in the magnitude of differences and absolute expression levels, mean expression of each miR in cancer cells lines was substantially lower compared to levels in the corresponding normal tissues. These miRNAs are candidates for generating pan-tumor HSV virions that are capable of broadly treating a variety of cancer types.

Although the mean expression for miR-451a, miR-559, miR-1, miR-145-3p, and miR143-3p was lower in cancer cell lines compared to normal controls, the decreased expression was not fully penetrant across all cancer cell lines. For example, ⅔ of the normal bladder samples tested showed increased expression of miR-145-3p, while expression in the remaining sample was substantially similar to the average observed in the cancer cell lines. Similar results were observed in breast cancer cell lines. Although the average read count for all breast cancer samples was 106, 5/12 samples had a normalized read count of >1000 counts, 2 of which were >40,000 counts.

These data indicate the potential to generate a single miR-attenuated oncolytic virus capable of targeting a broad array of tumor types. For example, a construct comprising target sequences for miR-124, miR-451a, miR-559, miR-1, and miR-145-3p may be used in the treatment of all the tumor types tested (e.g., bladder, colon, breast, pancreatic, lung, head and neck, Schwannoma, and glioblastoma). The variability in expression levels of miRs in different cancer types indicates the potential need to stratify patients by miR expression or through the use of an additional biomarker.

Example 2—Construction and Use of a Reporter System to Rapidly Assay miRNA-Based Gene Attenuation A reporter system was developed to assess miRNA-based gene attenuation using virtually any miRNA target sequence and cognate miRNA. In this system (shown in FIG. 15), the target sequence recognized by miRNAs (i.e. hsa-miR-122) was inserted into the 3' UTR of de-stabilized green fluorescent protein (dsGFP). The cognate miRNA was then expressed via a tetracycline (tet) inducible promoter using mCherry as a control for miRNA expression. All expression vectors were cloned into a tet repressible vector pcDNA5 Frt/To that also expresses mCherry (pTF002). All miRNAs for expression generated by gene synthesis from human genomic DNA and were cloned into pTF002. To generate attenuation reporter vectors, dsGFP was cloned into cDNA3.1+, generating vector pTF004. Attenuation vectors contain four tandem repeats of the reverse complement of the miRNA sequence of interest separated by 8-16 nucleotides. Plasmids were constructed by insertion of synthetically generated oligonucleotides into the 3'UTR of the dsGFP gene of pTF004 using standard molecular biology techniques. On day one, HEK293TetR cells were transfected with the miRNA attenuation and reporter expression plasmids (0.15 μg each, for a total of 0.3 μg of CMV promotor-containing plasmid) using Lipofectamine 2000 per manufacturers protocol (Invitrogen). On day two, cells were treated with Tetracycline at 5 ng/ml and allowed to incubate for up to 72 hours. After incubation, GFP and mCherry fluorescence signals were detected daily using a SpectraMax® i3x Minimax multi-mode microplate reader (Molecular Devices) and analyzed using Softmax Pro or Metamorph imaging software (Molecular Devices). Phase images were acquired with an exposure of 5-6 ms. Fluorescence images were acquired with a GFP (541 nm channel) exposure of 10 ms, and an mCherry (713 nm channel) of 200-1500 ms.

Figure 16:
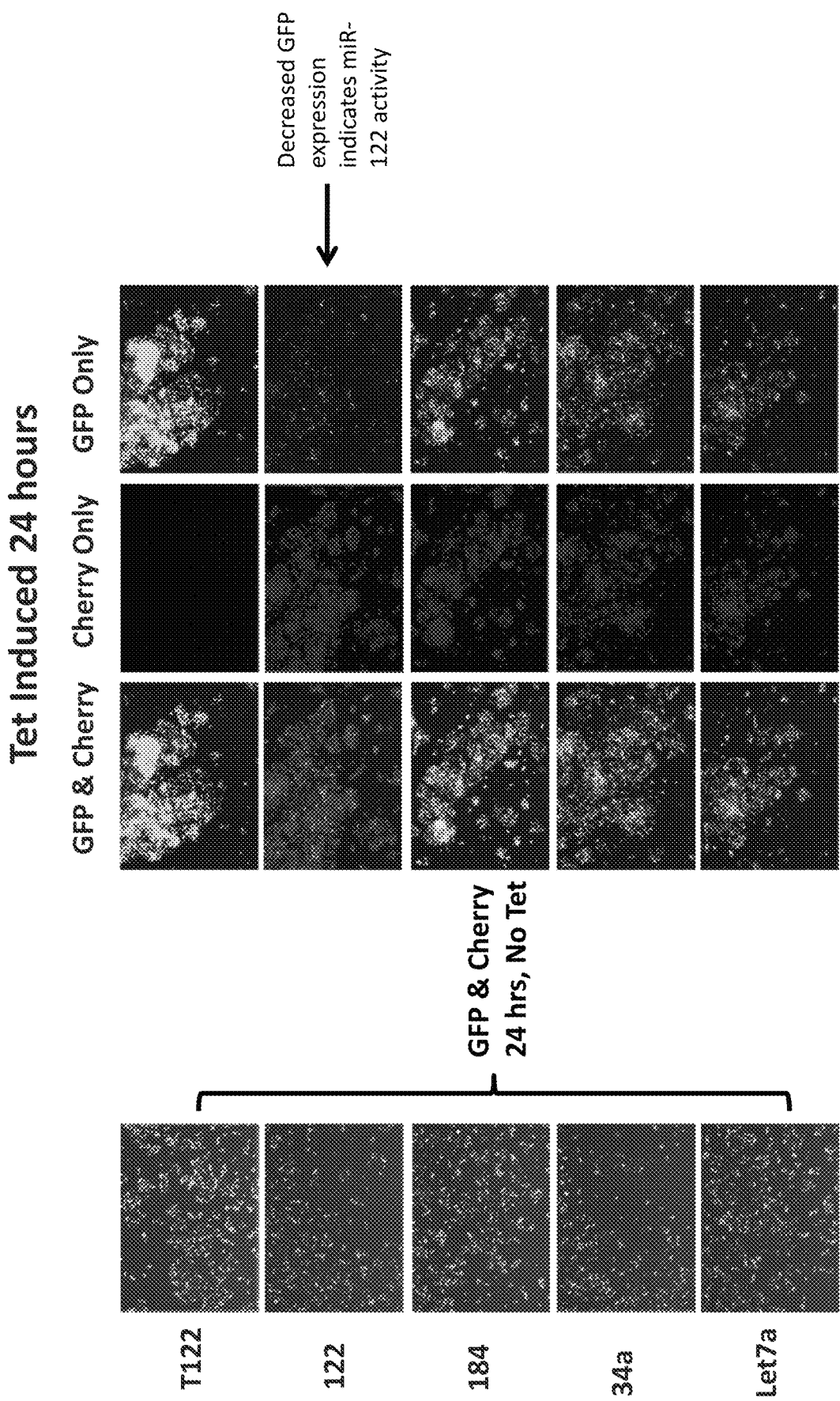
FIG. 16 illustrates miR-122 expression and attenuation using the reporter system shown in FIG. 15 and described in Example 2.
Figure 17:
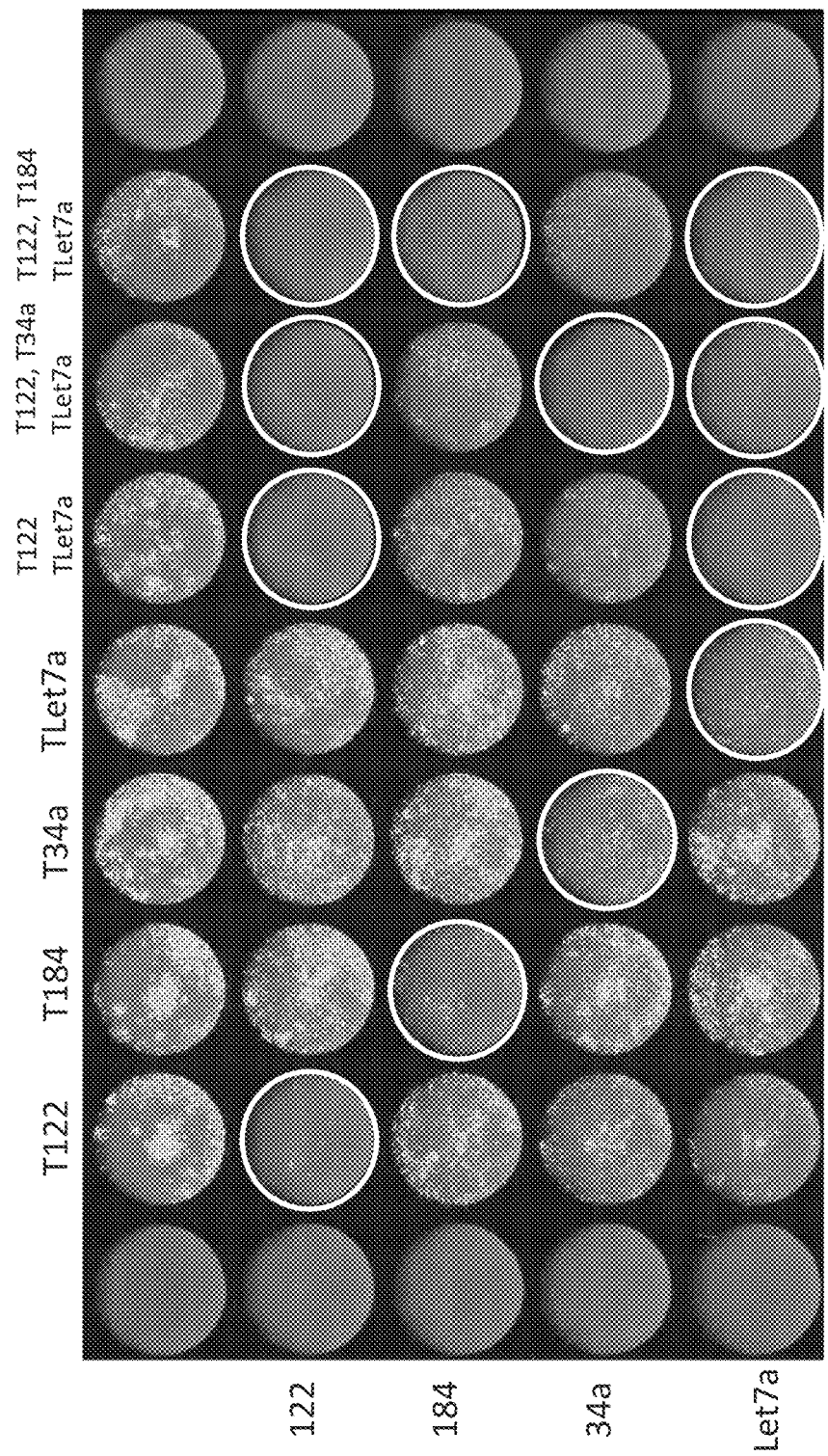
FIG. 17 illustrates miR-122, miR-184, miR-34a, and Let7a-mediated GFP attenuation using the reporter system shown in FIG. 15 and described in Example 2. Circled wells indicate reduced GFP expression levels.
Figure 18:
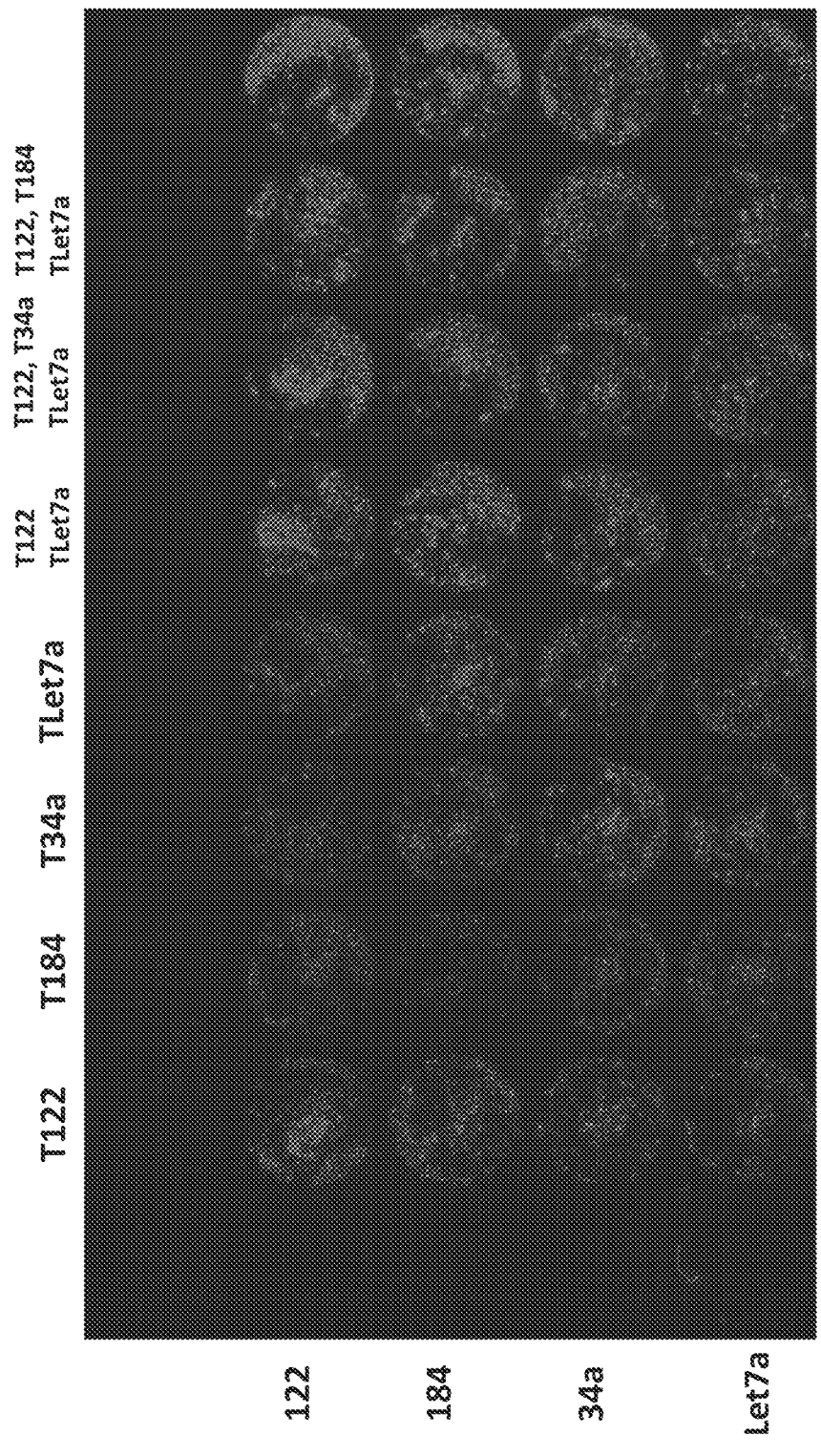
FIG. 18 illustrates expression of miR-122, miR-184, miR-34a, and Let7a, indicated by mCherry expression, using the reporter system shown in FIG. 15 and described in Example 2.

FIG. 16 exemplifies miR-122 mediated attenuation of GFP expression upon induction of miR-122 expression via tet at 24 hours. The control constructs miR-184, miR-34a, and Let7a do not attenuate GFP levels, nor is GFP attenuation observed in the absence of tet. FIG. 17 shows miR-122, miR-184, miR-34a, and Let7a expression and GFP attenuation using each miR target sequence individually and in cassette combinations of miR-122/Let7a, miR-122/Let7a/miR-34a, or miR-122/Let7a/miR-184. Decreased GFP is only observed when the appropriate miR and cognate target sequence are present together (circled wells). FIG. 18 serves as a non-attenuated control and shows miR-122, miR-184, miR-34a, and Let7a expression and mCherry expression.

Figure 19:
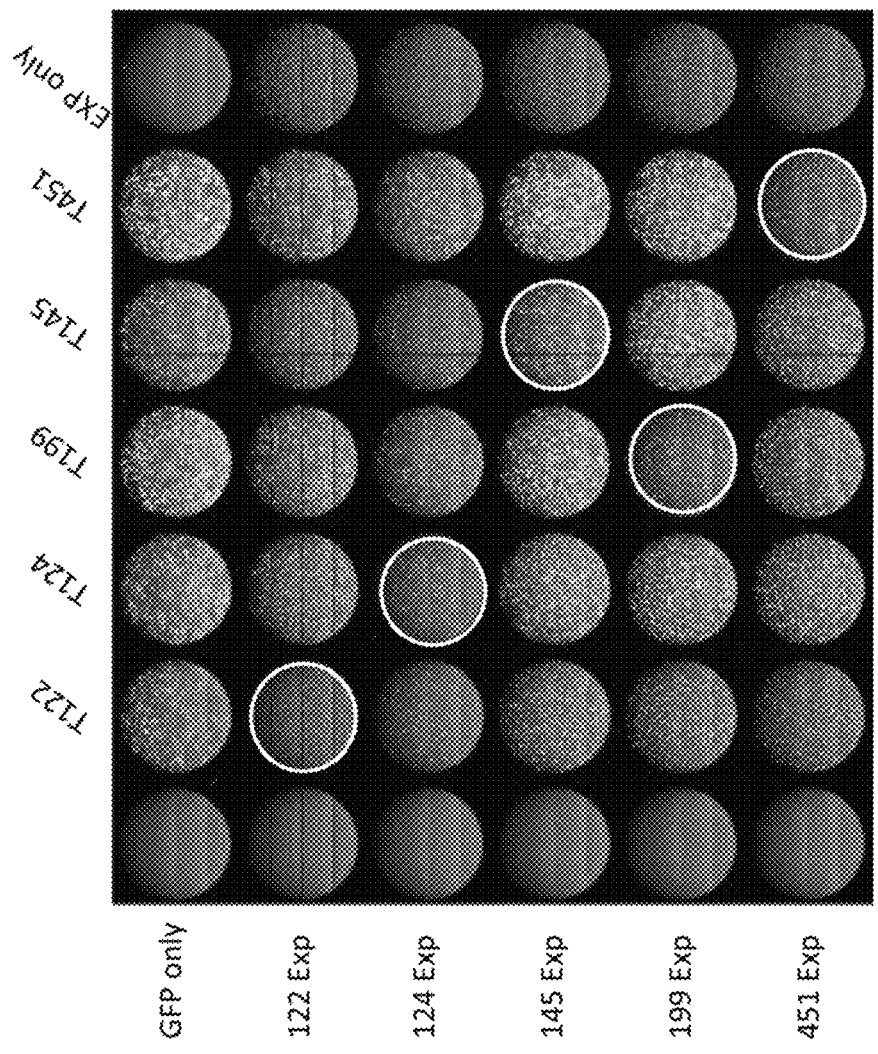
FIG. 19 illustrates miR-122, miR-124, miR-145, miR-199, and miR-451-mediated GFP attenuation using the reporter system shown in FIG. 15 and described in Example 2. Circled wells indicate reduced GFP expression levels.
Figure 20:
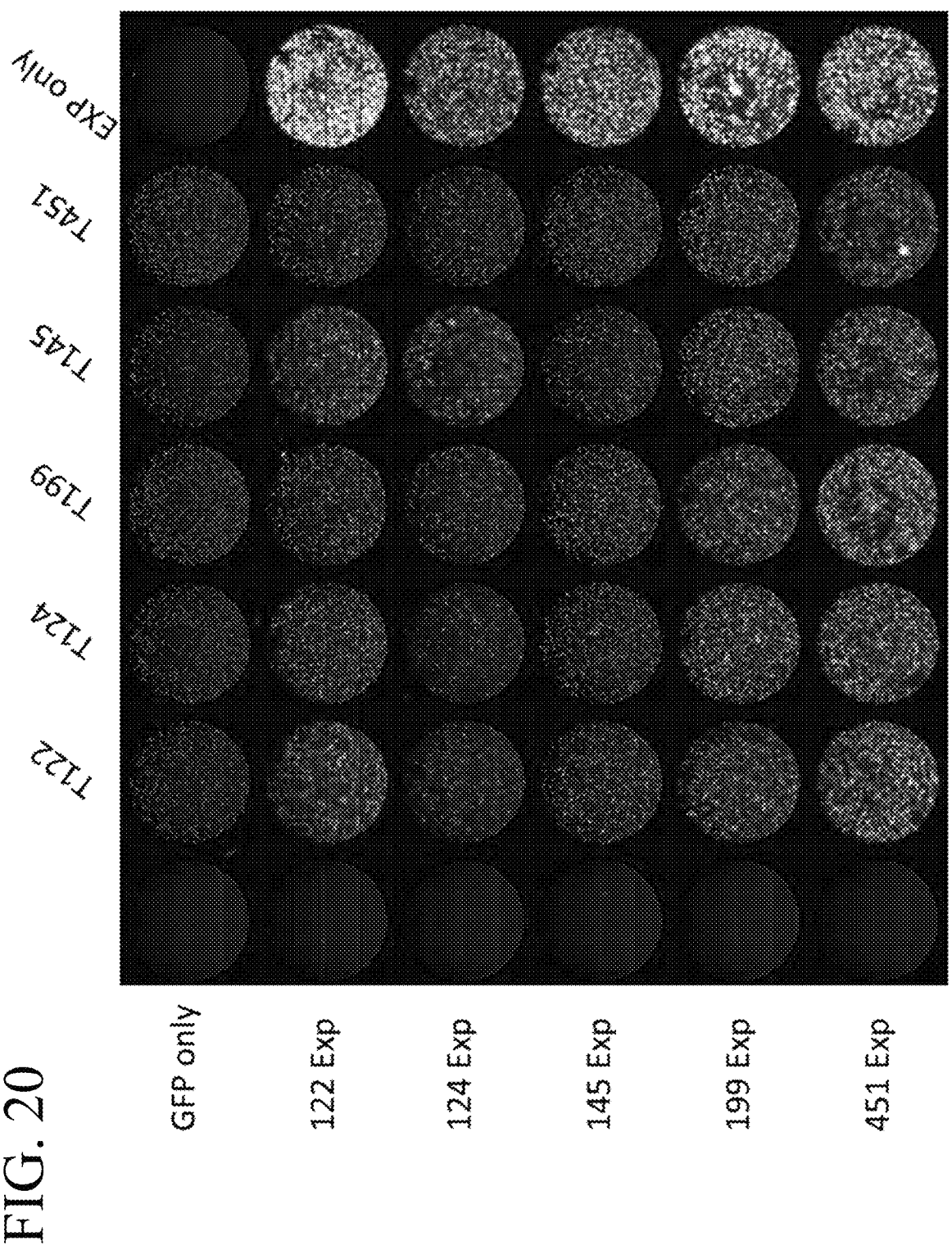
FIG. 20 illustrates expression of miR-122, miR-124, miR-145, miR-199, and miR-451, indicated by mCherry expression, using the reporter system shown in FIG. 15 and described in Example 2.
Figure 22:
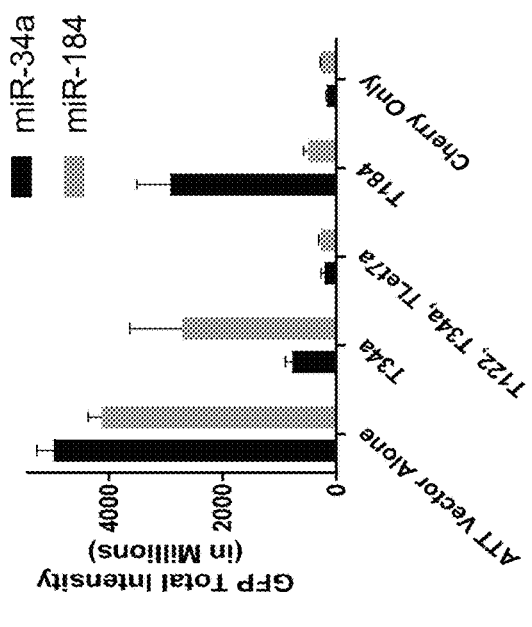
FIG. 22 shows quantitation of miR-34a and miR-184 attenuated GFP fluorescence.
Figure 21:
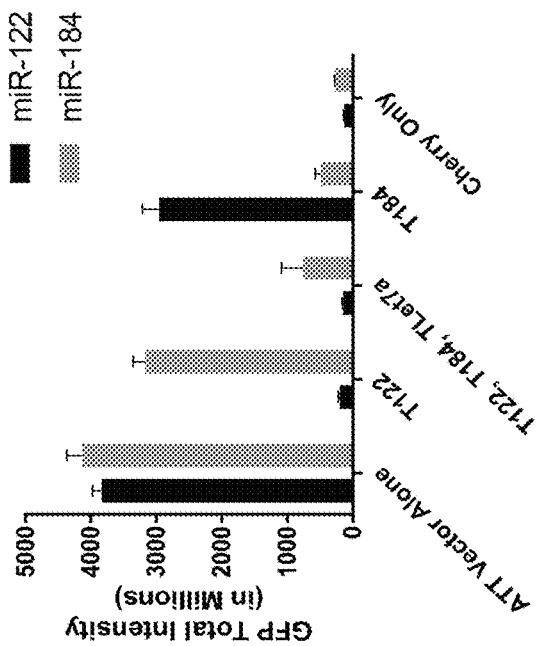
FIG. 21 shows quantitation of miR-122 and miR-184 attenuated GFP fluorescence.
Figure 23:
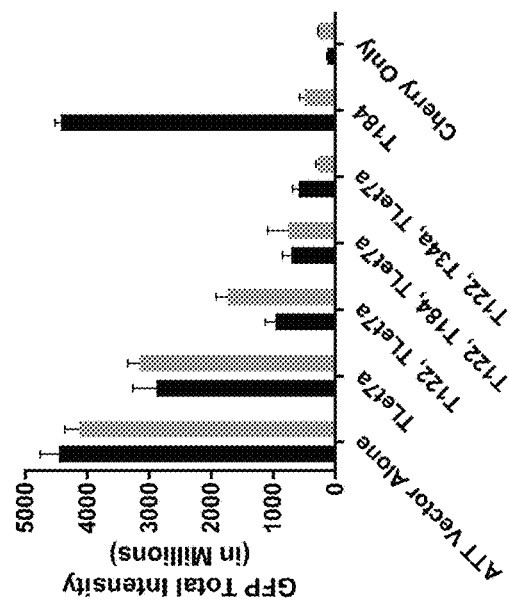
FIG. 23 shows quantitation of Let7a and miR-184 attenuated GFP fluorescence.
Figure 24:
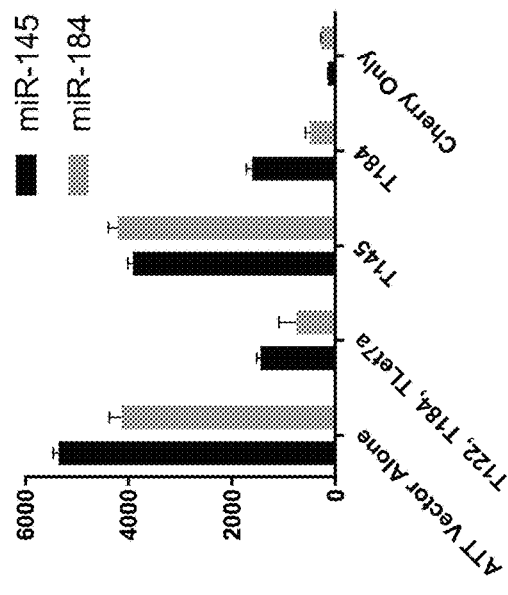
FIG. 24 shows quantitation of miR-124 and miR-184 attenuated GFP fluorescence.
Figure 25:
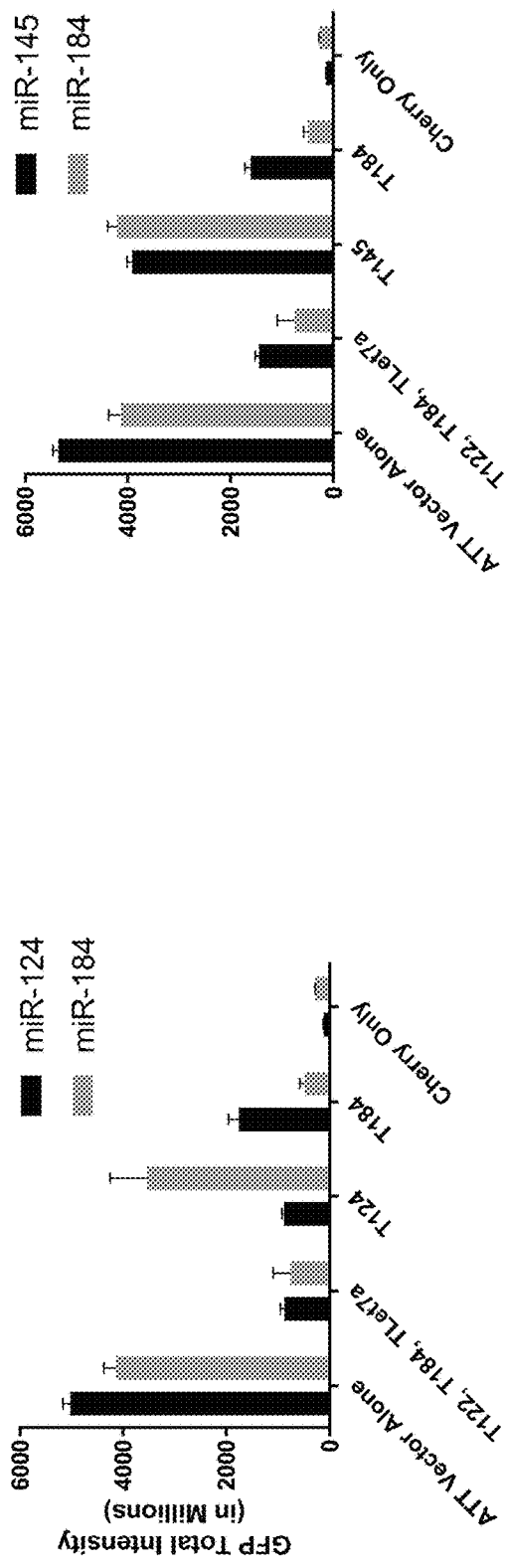
FIG. 25 shows quantitation of miR-145 and miR-184 attenuated GFP fluorescence.
Figure 26:
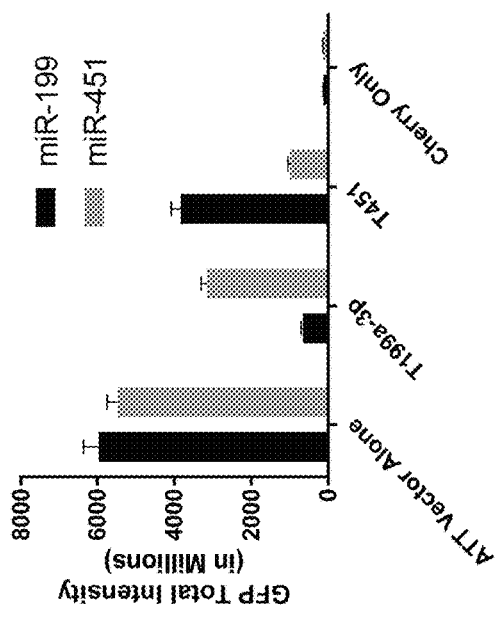
FIG. 26 shows quantitation of miR-199 and miR-451 attenuated GFP fluorescence.
Figure 28:
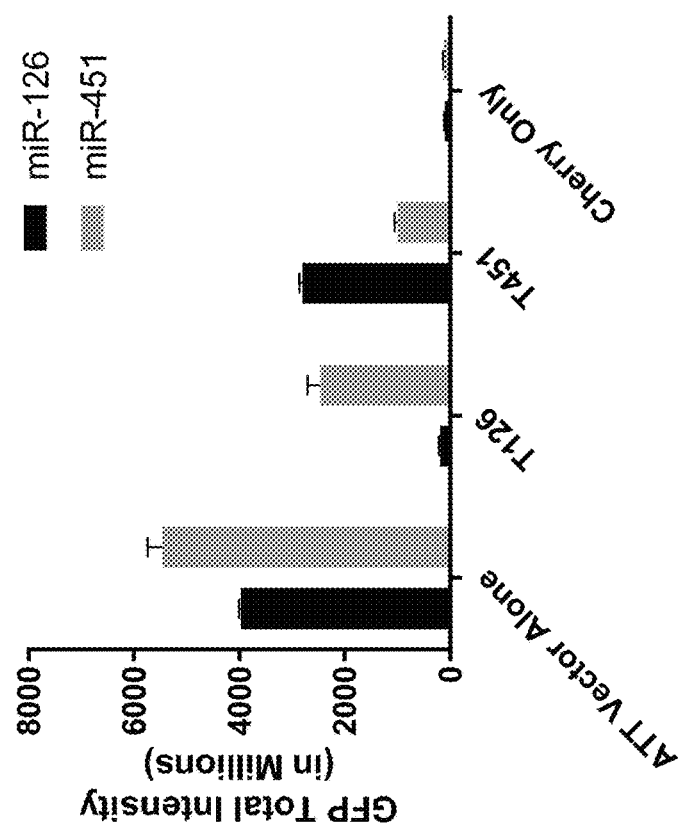
FIG. 28 shows quantitation of miR-126 and miR-451 attenuated GFP fluorescence.
Figure 27:
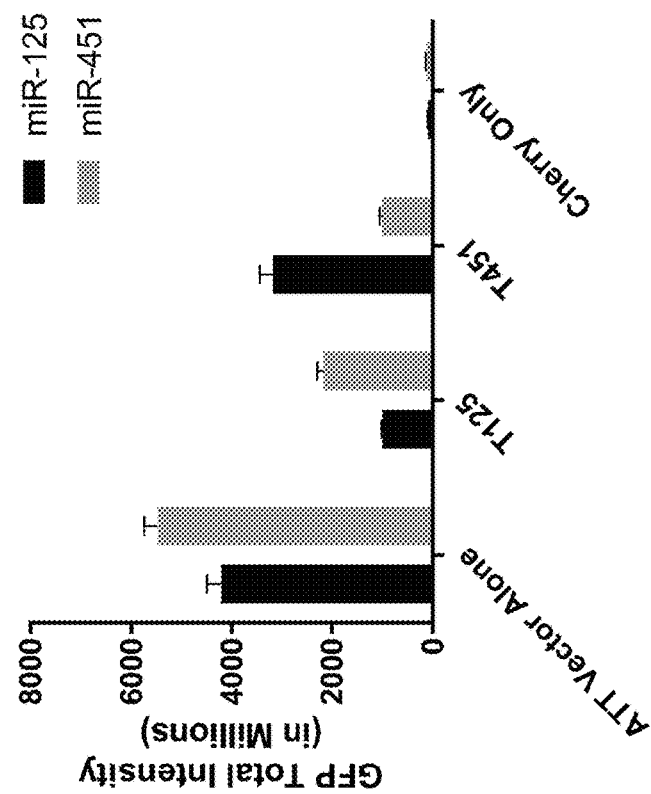
FIG. 27 shows quantitation of miR-125 and miR-451 attenuated GFP fluorescence.
Figure 29:
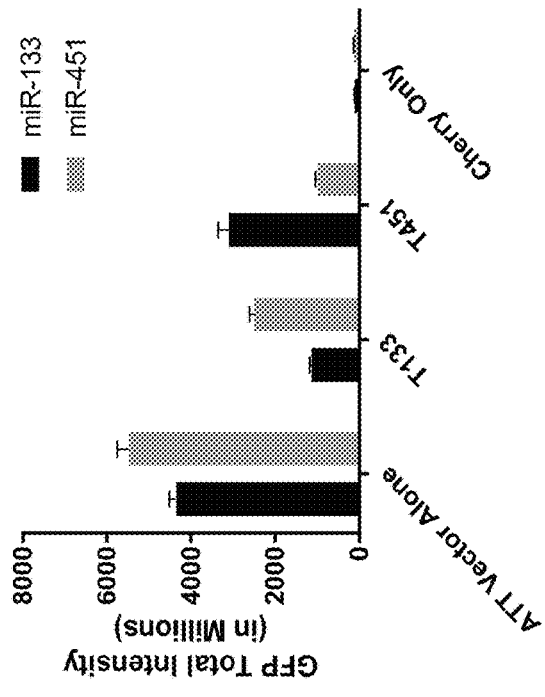
FIG. 29 shows quantitation of miR-127 and miR-451 attenuated GFP fluorescence.
Figure 30:
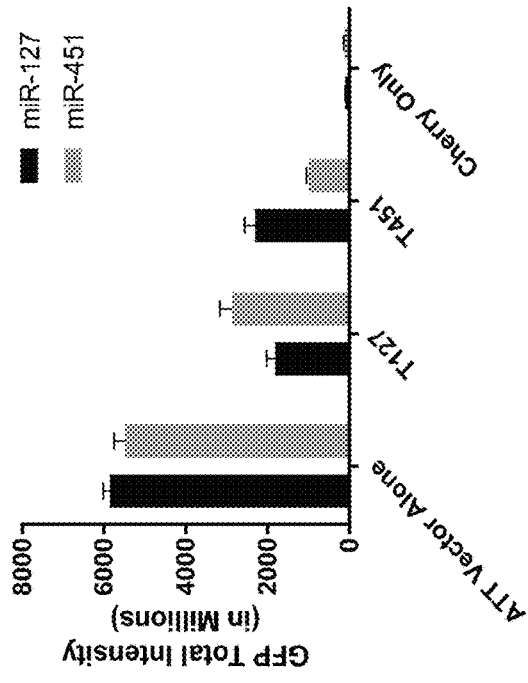
FIG. 30 shows quantitation of miR-133 and miR-451 attenuated GFP fluorescence.
Figure 31:
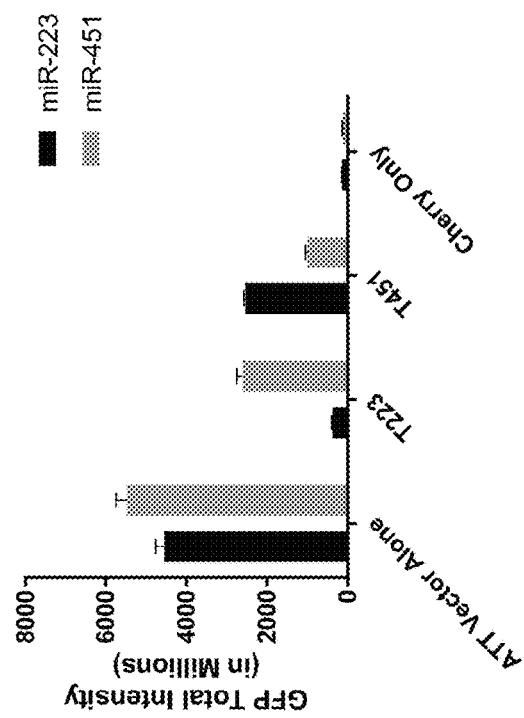
FIG. 31 shows quantitation of miR-223 and miR-451 attenuated GFP fluorescence.

FIG. 19 shows miR-122, miR-124, miR-145, miR-199, and miR-451 expression and GFP attenuation using each target sequence individually (circled wells). FIG. 20 serves as a non-attenuated control for the above example and shows miR-122, miR-124, miR-145, miR-199, and miR-451 expression and mCherry expression using each target sequence individually. FIG. 21 shows that miR-122 and miR-184 attenuate GFP fluorescence at 72 hours post transfection when the cognate miR-122 or miR-184 target sequences are present. FIG. 22 shows that miR-34a and miR-184 attenuate GFP fluorescence at 72 hours post transfection when the cognate miR-34a or miR-184 target sequences are present. FIG. 23 shows that Let-7a and miR-184 attenuate GFP fluorescence at 72 hours post transfection when the cognate Let-7a or miR-184 target sequences are present. FIG. 24 shows that miR-124 and miR-184 attenuate GFP fluorescence at 72 hours post transfection when the cognate miR-124 or miR-184 target sequences are present. FIG. 25 shows that miR-145 and miR-184 attenuate GFP fluorescence at 72 hours post transfection when the cognate miR-145 or miR-184 target sequences are present. FIG. 26 shows that miR-199 and miR-451 attenuate GFP fluorescence at 72 hours post transfection when the cognate miR-199 or miR-451 target sequences are present. FIG. 27 shows that miR-125 and miR-451 attenuate GFP fluorescence at 72 hours post transfection when the cognate miR-125 or miR-451 target sequences are present. FIG. 28 shows that miR-126 and miR-451 attenuate GFP fluorescence at 72 hours post transfection when the cognate miR-126 or miR-451 target sequences are present. FIG. 29 shows that miR-127 and miR-451 attenuate GFP fluorescence at 72 hours post transfection when the cognate miR-127 or miR-451 target sequences are present. FIG. 30 shows that miR-133 and miR-451 attenuate GFP fluorescence at 72 hours post transfection when the cognate miR-133 or miR-451 target sequences are present. FIG. 31 shows that miR-223 and miR-451 attenuate GFP fluorescence at 72 hours post transfection when the cognate miR-223 or miR-451 target sequences are present.

As such, these data indicate that miR expression can result in the specific attenuation of genes expressing the cognate miR target sequence.

Example 3—Generation of miRNA-Attenuated HSV

Following reporter gene-based validation of miRNA target sequences and cognate miRNA pairs, HSV-based viruses were generated containing miRNA attenuation cassettes. A series of modifications were made in KOS-37 BAC, a full-length genomic clone of the KOS strain of HSV-1 on a bacterial artificial chromosome (BAC) as described (Mazzacurati et al., Mol Ther., 2015). The product, KGBAC, was deleted for the internal repeat (joint) region containing one copy each of the diploid genes ICP0, ICP34.5, LAT and ICP4 along with the promoter for the ICP47 gene. This deletion facilitates manipulation of the remaining copies of the 4 deleted genes, provides abundant space for the potential incorporation of transgenes that enhance the oncolytic activity of the virus, and increases tumor specificity by reducing expression of the neurovirulence factor ICP34.5; elimination of ICP47 expression benefits immune recognition of infected cancer cells by virus-specific T cells. KGBAC also contains the GFP open reading frame (ORF) fused to the glycoprotein C (gC) ORF via a 2A peptide sequence to allow monitoring of late (post-replication) viral gene expression. Lastly, KGBAC contains a pair of mutations in the gB gene shown to enhance HSV entry through non-canonical receptors. The miRNA target sequence cassettes were recombined into the 3' UTR of the ICP4 and/or ICP27 genes of 2A5B-MMP9 to generate ONCR-003, ONCR-010, ONCR-011, ONCR-012, ONCR-013, ONCR-014, ONCR-015, ONCR-016, ONCR-017, ONCR-018, ONCR-019, ONCR-020, ONCR-021, and ONCR-022 as shown in FIG. 32. All BAC constructs were converted to virus particles with simultaneous removal of the BAC sequences located between loxP sites by transfection of Vero-Cre cells. Following plaque purification, virus stocks were prepared and titered on Vero cells.

Example 4—Viral Infectivity Assay Using miRNA-Attenuated HSV

To assay for viral infectivity and replication in normal and cancerous cells, miRNA-attenuated HSV particles were tested in the following in vitro assay. On day one, for each cell type infected, HSV particles were introduced to achieve a multiplicity of infection (moi) of 0.01. On days two through five, viral infectivity was assayed by GFP detection using a SpectraMax® i3x Minimax multi-mode microplate reader (Molecular Devices) and analyzed using Softmax Pro or Metamorph imaging software (Molecular Devices). Phase images were acquired with an exposure of 5-6 ms. Fluorescence images were acquired with a GFP (541 nm channel) exposure of 10 ms and an mCherry (713 nm channel) exposure of 200-1500 ms to evaluated any potential non-specific autofluorescence signal.

Figure 34:
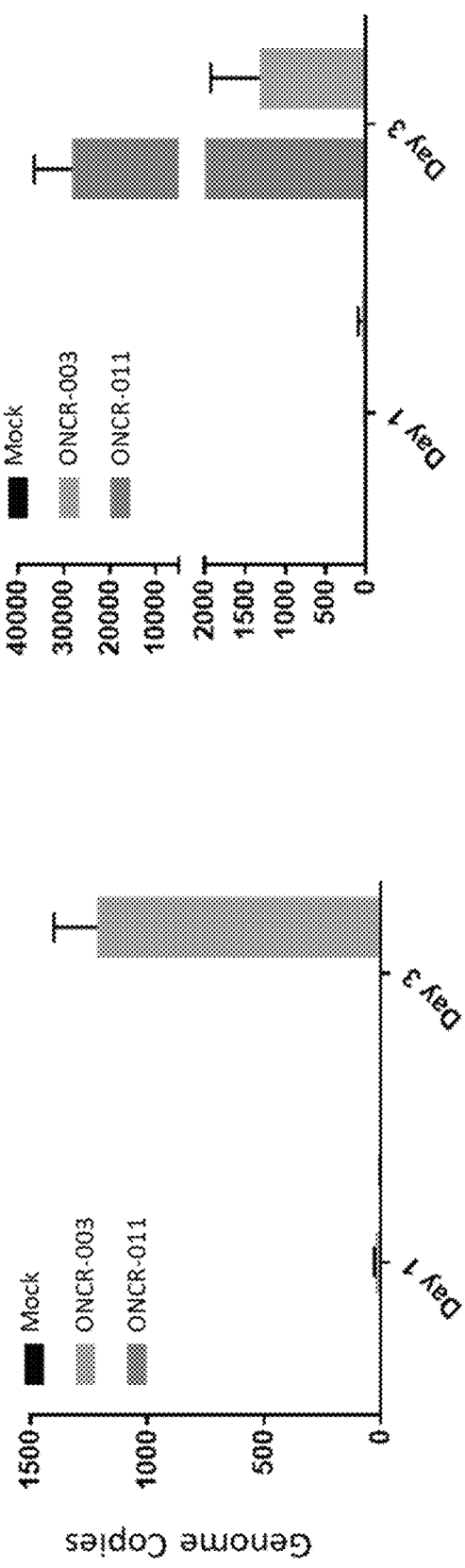
FIG. 34 shows qPCR-based quantitation of HSV attenuation by miR-125 in non-cancerous (PM Lung) and cancerous (A253) lung cells.
Figure 35:
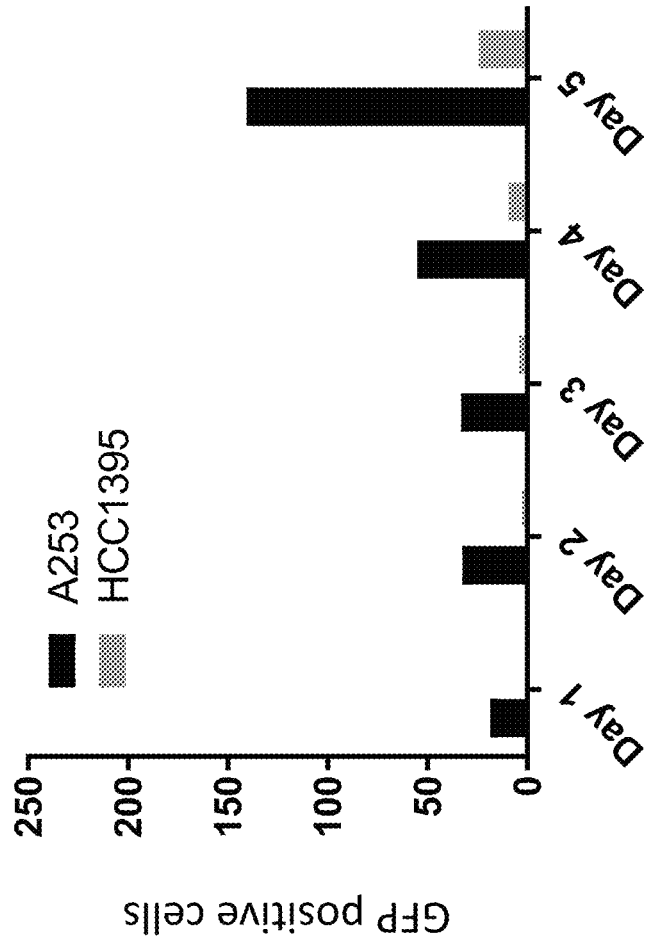
FIG. 35 illustrates fluorescence-based quantitation of HSV attenuation by miR-145 in HCC1395 vs. A253 cells.
Figure 36:
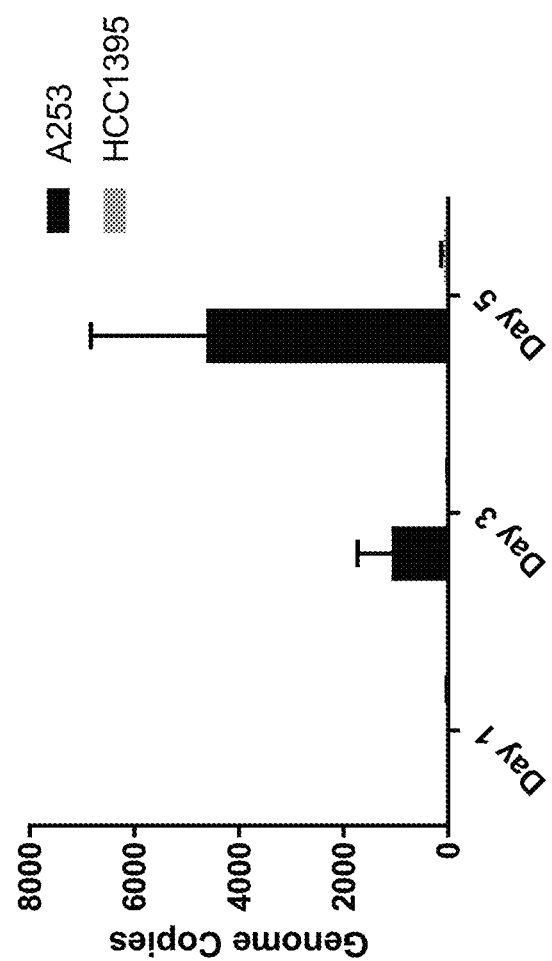
FIG. 36 shows qPCR-based quantitation of HSV attenuation by miR-145 in HCC1395 vs. A253 cells.
Figure 37:
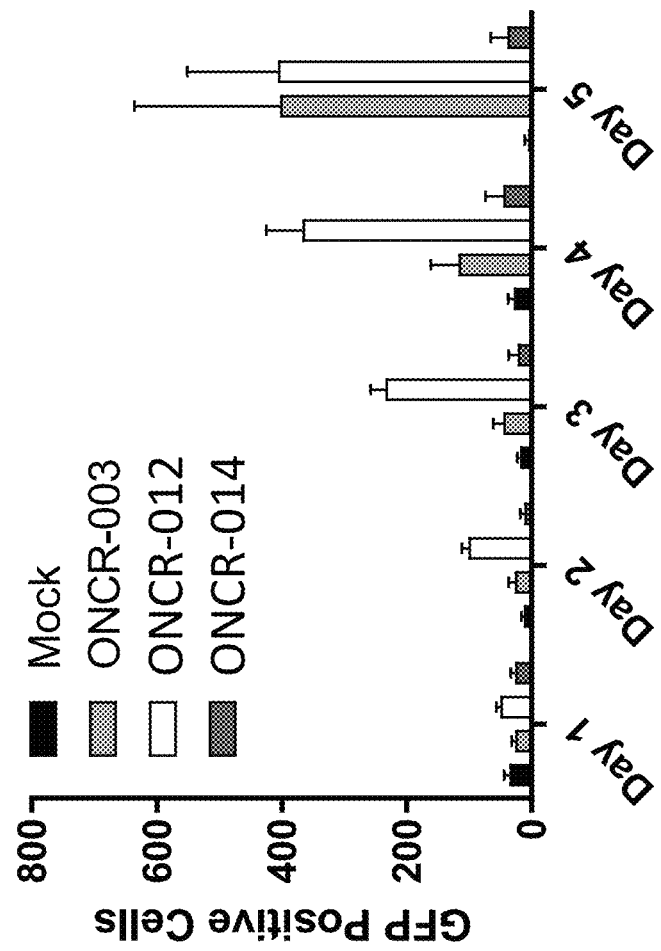
FIG. 37 illustrates fluorescence-based quantitation of HSV attenuation by miR-199a-5p vs. miR-143-3p in normal lung cells.
Figure 38:
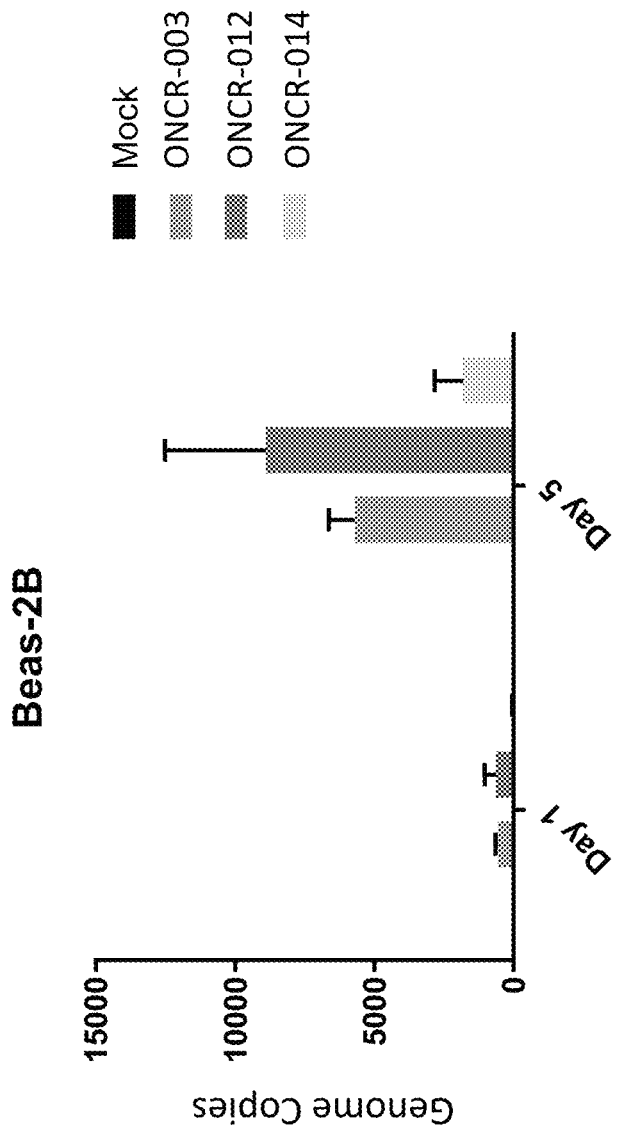
FIG. 38 shows qPCR-based quantitation of HSV attenuation in normal lung cells by miR-199a-5p vs. miR-143-3p.
Figure 39:
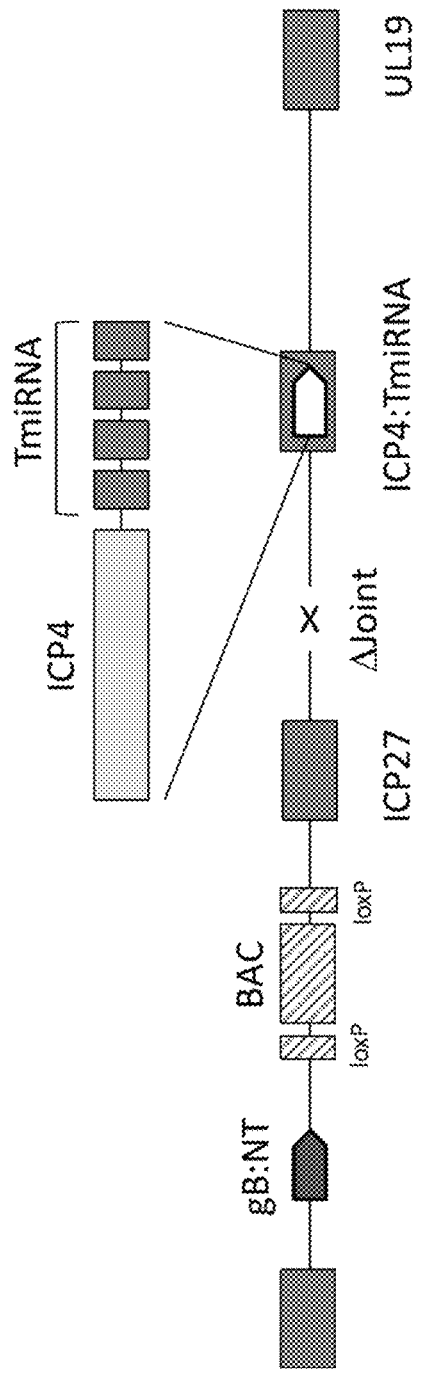
FIG. 39 illustrates a schematic of an ICP4-TmiRNA-attenuated HSV vector for the treatment of cancer or benign hyper-proliferative disorders.
Figure 40:
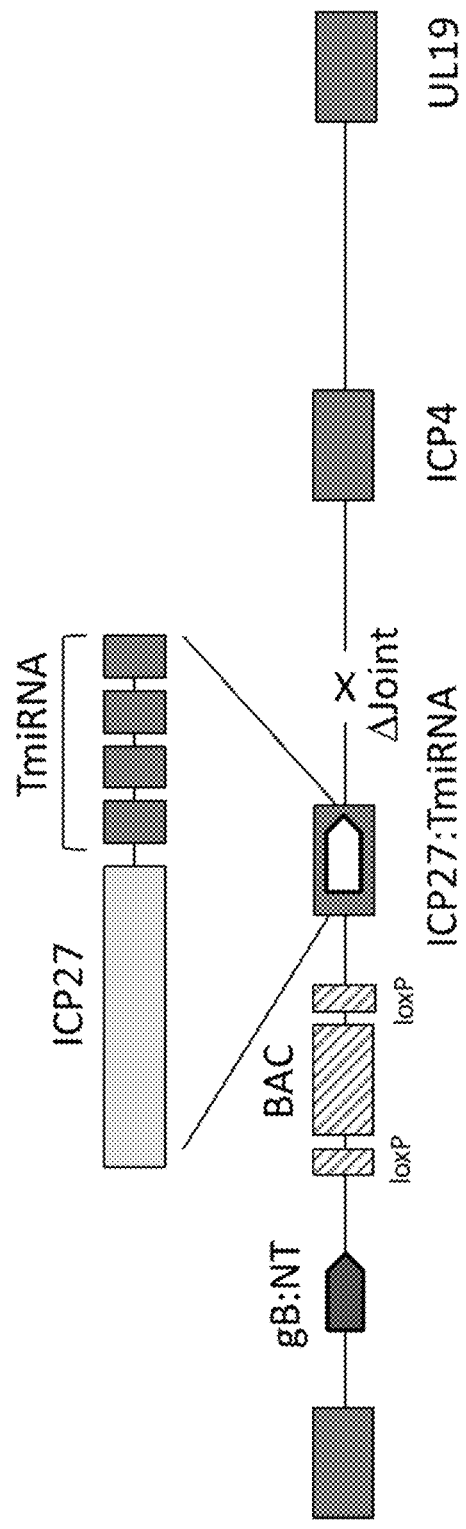
FIG. 40 shows a schematic of an ICP27-TmiRNA-attenuated HSV vector for the treatment of cancer or benign hyper-proliferative disorders.
Figure 42:
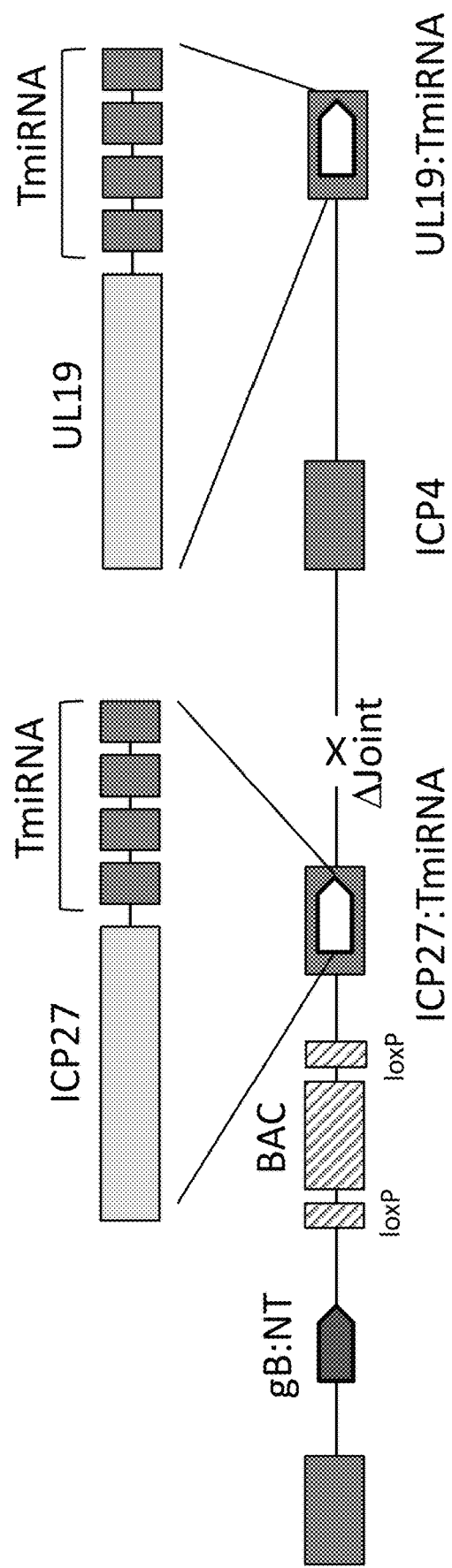
FIG. 42 shows a schematic of an UL19-TmiRNA and ICP27-TmiRNA-attenuated HSV vector for the treatment of cancer or benign hyper-proliferative disorders.
Figure 43:
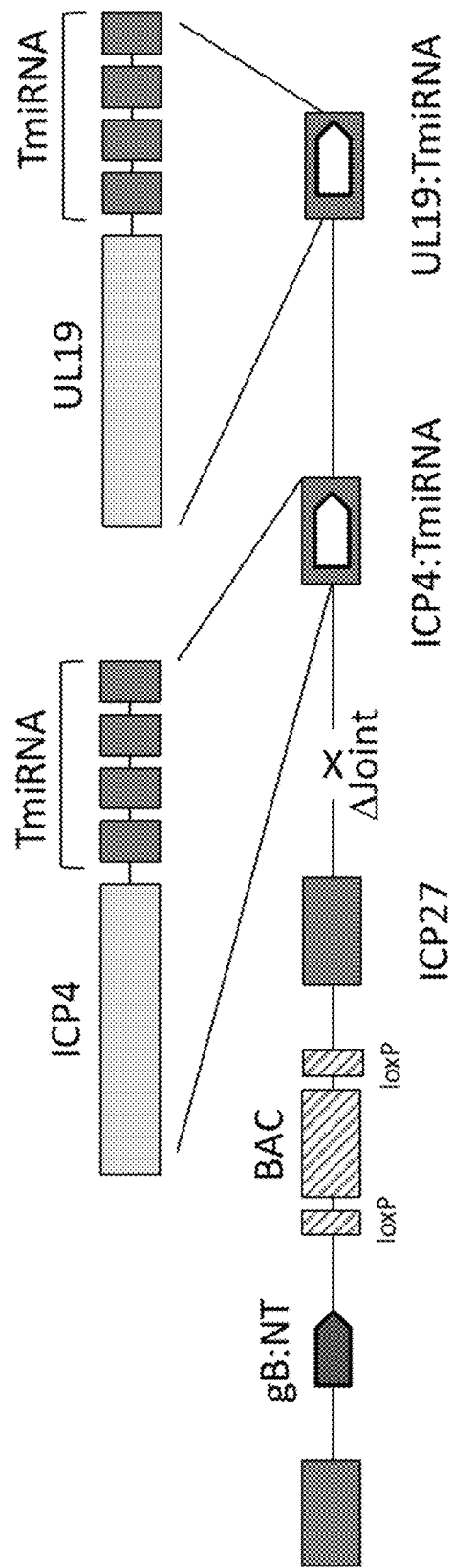
FIG. 43 shows a schematic of an UL19-TmiRNA and ICP4-TmiRNA-attenuated HSV vector for the treatment of cancer or benign hyper-proliferative disorders.

ONCR-011 replication was significantly attenuated in post-mitotic lung tissue due to the presence of the miR-125 cassette in the ICP27 gene and high levels of miR-125a (>3000 counts) in these cells, as shown in FIG. 33 (read out by GFP positive cell quantitation) and FIG. 34 (read out by quantitative PCR). Although ONCR-011 and the control virus, ONCR-003, contain miR-124 target sequences in the ICP4 gene, miR-124 is present at low levels (<100 counts) which were insufficient to attenuate viral replication. Both ONCR-011 and ONCR-003 replicated freely in head and neck cancer cells (A253) because these cells contain low levels of both miR-125a and miR-124 (<100 counts). ONCR-013 replication was significantly attenuated in HCC1395 cells, but not in A253 cells as shown in FIG. 35 (read out by GFP positive cell quantitation) and FIG. 36 (read out by quantitative PCR). ONCR-014 replication was significantly attenuated in non-cancerous lung tissue as shown in FIG. 37 (read out by GFP positive cell quantitation) and FIG. 38 (read out by quantitative PCR).

Figure 47:
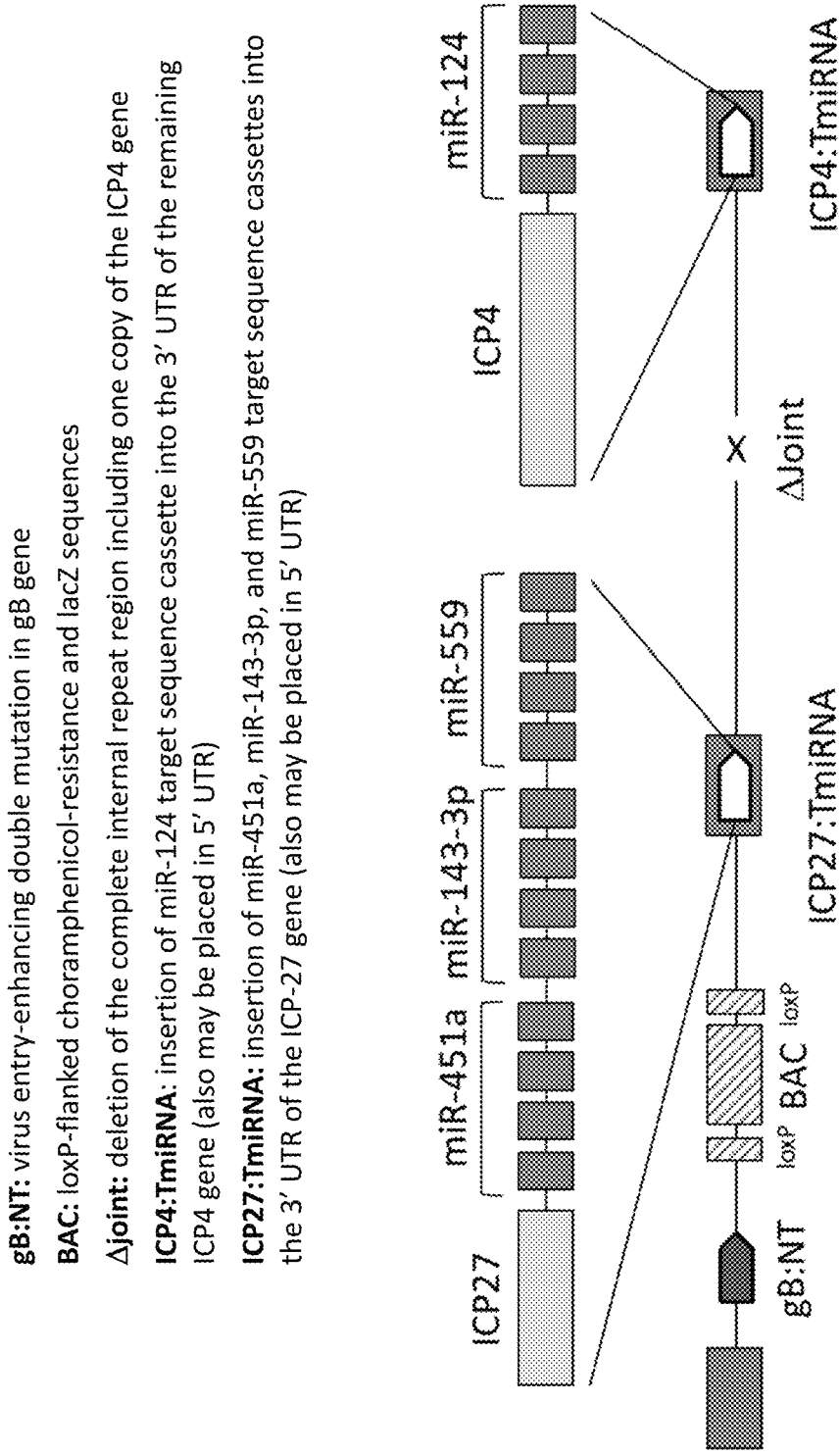
FIG. 47 shows a schematic of an ICP4-TmiRNA and ICP27-TmiRNA-attenuated HSV vector for the treatment of pancreatic, lung, and colon cancer.

Example 5—Treatment of a Patient Suffering from Pancreatic Cancer, Lung Cancer, or Colon Cancer A patient suffering from pancreatic cancer, lung cancer, or colon cancer is treated using the compositions and methods disclosed herein. HSV-based viral stocks may be generated that are attenuated by incorporating one or more miRNA target sequences into UL19, ICP4, ICP27 (or other viral genes) as shown in FIGS. 39-44. In some cases, genome-editing capabilities for tumor destruction and/or microenvironment remodeling are engineered into the virus in addition to miRNA target sequences, as shown in FIGS. 45-46. In a specific example, an HSV-based stock containing miR-124, miR-451a, miR-143-3p, and miR-559 attenuation cassettes incorporated into ICP4 and ICP27 is generated according to the methods described in Example 3. The miRNA target sequence cassettes are introduced into the 3' UTR of the ICP4 (miR-124) and ICP27 (miR-451a, miR-143-3p, miR-559) genes as shown in FIG. 47. BAC constructs are converted to virus particles with simultaneous removal of the BAC sequences located between loxP sites by transfection of Vero-Cre cells. Following plaque purification, virus stocks are further purified, buffer exchanged, and titered on Vero cells. For in vivo administration to a patient suffering from pancreatic cancer, lung cancer, or colon cancer, HSV particles are prepared in phosphate buffered solution (PBS) along with pharmaceutically acceptable stabilizing agents. On the day of treatment, $10^9$ vector genomes in a volume of 1.0 mL pharmaceutically acceptable carrier are administered via intra-tumoral infusion. The patient is monitored for tumor regression using standard of care procedures at an appropriate time interval based on that patient's particular prognosis.

Example 6—Treatment of a Patient Suffering from Brain Cancer, Bladder Cancer, Breast Cancer, or Head and Neck Cancer A patient suffering from brain cancer, bladder cancer, breast cancer, or head and neck cancer is treated using the compositions and methods disclosed herein. An HSV-based viral stock is generated containing miR-124, miR-451a, miR-145-3p, and miR-559 attenuation cassettes according to the methods described in Example 3. The miRNA target sequence cassettes are introduced into the 3' UTR of the ICP4 (miR-124) and ICP27 (miR-451a, miR-145-3p, miR-559) genes as shown in FIG. 48. BAC constructs are converted to virus particles with simultaneous removal of the BAC sequences located between loxP sites by transfection of Vero-Cre cells. Following plaque purification, virus stocks are further purified, buffer exchanged, and titered on Vero cells. For in vivo administration to a patient suffering from brain cancer, bladder cancer, breast cancer, or head and neck cancer, HSV particles are prepared in phosphate buffered solution (PBS) along with pharmaceutically acceptable stabilizing agents. On the day of treatment, $10^9$ vector genomes in a volume of 1.0 mL pharmaceutically acceptable carrier are administered via intra-tumoral infusion. The patient is monitored for tumor regression using standard of care procedures at an appropriate time interval based on that patient's particular prognosis.

Example 7—Treatment of a Patient Suffering from Schwannoma

A patient suffering from schwannoma is treated using the compositions and methods disclosed herein. An HSV-based viral stock is generated containing miR-124-3p, miR-205-5p, miR-141-5p, and miR-31-5p attenuation cassettes according to the methods described in Example 3. The miRNA target sequence cassettes were recombined into the 3' UTR of the ICP4 (miR-124) and ICP27 (miR-205-5p, miR-141-5p, miR-31-5p) genes as shown in FIG. 49. BAC constructs are converted to virus particles with simultaneous removal of the BAC sequences located between loxP sites by transfection of Vero-Cre cells. Following plaque purification, virus stocks were further purified, buffer exchanged, and titered on Vero cells. For in vivo administration to a patient suffering from schwannoma, HSV particles are prepared in phosphate buffered solution (PBS) along with pharmaceutically acceptable stabilizing agents. On the day of treatment, $10^9$ vector genomes in a volume of 1.0 mL pharmaceutically acceptable carrier are administered via intra-tumoral infusion. The patient is monitored for tumor regression using standard of care procedures at an appropriate time interval based on that patient's particular prognosis.

While preferred embodiments of the present invention are shown and described herein, it will be obvious to those skilled in the art that such embodiments are provided by way of example only. Numerous variations, changes, and substitutions can be implemented by those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

TABLE 1

Summary of relationships between 12 select oncomiRs (9 tumor suppressors and 3 oncogenic miRNAs) versus cancers.

| Malignancy | Down-regulated | | | | | | | | | Up-regulated | | |
| --- | --- | --- | --- | --- | --- | --- | --- | --- | --- | --- | --- | --- |
| | let-7 | miR-15a | miR-16 | miR-29a | miR-34a | miR-98 | miR-101 | miR-124 | miR-202 | miR-17 | miR-21 | miR-155 |
| acute lymphoblastic leukemia | X | | | | | | | X | | | | |
| acute myeloid leukemia | X | | X | | | | | | | | X | X |
| acute promyelocytic leukemia | X | | | | | | | | | | | |
| adrenal cortical carcinoma | | | | | | | | | | | X | |
| anaplastic astrocytoma | | | | | | | | X | | | | |
| anaplastic large-cell lymphoma | | | | | | | | | | | | X |
| astrocytoma | | | | | | | | X | | | | |

TABLE 1-continued

Summary of relationships between 12 select oncomiRs (9 tumor suppressors and 3 oncogenic miRNAs) versus cancers.

| Malignancy | Down-regulated | | | | | | | | | Up-regulated | | |
|---|---|---|---|---|---|---|---|---|---|---|---|---|
| | let-7 | miR-15a | miR-16 | miR-29a | miR-34a | miR-98 | miR-101 | miR-124 | miR-202 | miR-17 | miR-21 | miR-155 |
| B cell lymphoma | | | | | X | | | | | X | | |
| bladder cancer | | | X | | X | | X | X | | X | | X |
| breast cancer | X | X | X | X | X | X | | X | | X | | X |
| breast carcinoma | | | | | | | | | | X | | |
| bronchioloalveolar carcinoma | X | | | | | X | | | | | | |
| cervical cancer | | | | | | | | X | | X | | X |
| cervical carcinoma | | X | X | | X | | X | | | | | |
| cervical squamous cell carcinoma | | | | X | | | | X | | | | |
| cholangiocarcinoma | | | | | X | | X | | | X | | |
| chondrosarcoma | X | | | | | | | | | | | |
| chordoma | | | | | X | | | | | | | |
| choriocarcinoma | | | | | X | | | | | | | |
| chronic lymphocytic leukemia | | X | X | | | | | | | | | X |
| chronic myelogenous leukemia | | | X | | | | | | | | | X |
| clear cell renal cell cancer | | | | | X | | | | | | | X |
| colon cancer | X | | | | X | X | X | | | | | X |
| colorectal cancer | X | X | X | X | X | | X | X | X | X | | X |
| colorectal carcinoma | | | | | | | | | | X | | X |
| cutaneous T cell lymphoma | | | | | | | | | | | | X |
| diffuse large B cell lymphoma | | | | | | | | | | | | X |
| endometrial cancer | | | | | X | | X | X | | | | X |
| epithelial ovarian cancer | | | | | | | | X | | | | |
| esophageal cancer | | X | | | | | X | X | | | | |
| esophageal squamous cell carcinoma | X | | X | | X | X | X | | | X | | |
| extrahepatic cholangiocarcinoma | | | | | X | | | | | | | |
| follicular lymphoma | | | | | | | | | X | | | |
| gallbladder carcinoma | | | | | | | | | | | | X |
| gastric cancer | X | | | X | X | X | X | X | X | X | | X |
| glioblastoma | X | | | | X | | X | X | | | | |
| glioma | X | | X | | X | X | | X | | X | | X |
| head and neck cancer | | | | | | | | | | | | |
| head and neck squamous cell carcinoma | X | | X | X | X | | | | | | X | |
| hepatocellular carcinoma | X | | X | X | X | X | X | X | X | X | X | X |
| hypopharyngeal squamous cell carcinoma | | | | | | | | | | | X | |
| kidney cancer | | | | | | | | | | | X | |
| laryngeal carcinoma | | | X | | | | | | | | X | |
| laryngeal squamous cell carcinoma | | | | | | | X | | | | X | |
| liver cancer | | | | | | | X | | | | X | X |
| lung adenocarcinoma | | | X | | | | | | | | | X |
| lung cancer | X | X | X | | X | X | X | | | X | X | X |
| malignant melanoma | X | | | | X | X | X | | | X | X | X |
| malt lymphoma | | | | | | | | | | | | X |
| mantle cell lymphoma | | | | X | | | | X | | X | | X |
| medulloblastoma | | | | | | | | X | | X | | |
| mesenchymal cancer | | | | X | | | | | | | | |
| monocytic leukemia | | | | X | | | | | | | | |
| multiple myeloma | | | | | | | | | | | X | |
| nasopharyngeal cancer | | | | | | | | | | X | | |
| nasopharyngeal carcinoma | X | | | | | X | X | X | | | X | X |
| neuroblastoma | X | X | X | X | X | X | | X | | | | |
| non-small cell lung cancer | X | X | X | X | X | | X | X | | X | X | X |
| oral cancer | X | | | | X | | | | | | X | |
| oral squamous cell carcinoma | | | | X | | | | X | | | X | X |
| osteosarcoma | X | X | X | | X | | X | X | X | X | X | |
| ovarian cancer | X | | | | X | X | | X | | X | X | X |
| ovarian carcinoma | | | | | | | X | | | | | |
| pancreatic adenocarcinoma | | | | | X | | | | | | X | |
| pancreatic cancer | | X | | | | | X | X | | X | X | |
| pancreatic ductal adenocarcinoma | X | X | X | | X | X | | | | | X | |
| papillary thyroid carcinoma | X | | X | | X | | X | | | | X | X |
| pituitary carcinoma | | | | | | | | | | X | | |
| prostate cancer | X | X | X | | X | | X | X | | | X | |
| rectal cancer | | | | | X | | | | | | X | X |
| renal cell carcinoma | X | | X | | X | | | | | | X | |
| renal clear cell carcinoma | X | | | | | | | | | | | X |

TABLE 1-continued

Summary of relationships between 12 select oncomiRs (9 tumor suppressors and 3 oncogenic miRNAs) versus cancers.

| | Down-regulated | | | | | | | | Up-regulated | | |
|---|---|---|---|---|---|---|---|---|---|---|---|
| Malignancy | let-7 | miR-15a | miR-16 | miR-29a | miR-34a | miR-98 | miR-101 | miR-124 | miR-202 | miR-17 | miR-21 | miR-155 |
| retinoblastoma | | | | | X | | X | | | | X | |
| squamous carcinoma | | X | X | | X | | | | | | X | X |
| T cell lymphoblastic lymphoma | | | | | | | | | | X | | |
| uveal melanoma | | | | | X | | | | | | | |

TABLE 2

List of examples of oncomiR-cancer relationships.

| Malignancy | Down-regulated miRs | Up-regulated miRs |
|---|---|---|
| breast cancer | let-7a, let-7a-1, let-7a-2, let-7a-3, let-7b, let-7c, let-7d, let-7e, let-7f-1, let-7f-2, let-7g, let-7i, mir-100, mir-107, mir-10a, mir-10b, mir-122, mir-124, mir-1258, mir-125a-5p, mir-125b, mir-126, mir-127, mir-129, mir-130a, mir-132, mir-133a, mir-143, mir-145, mir-146a, mir-146b, mir-147, mir-148a, mir-149, mir-152, mir-153, mir-15a, mir-16, mir-17-5p, mir-181a, mir-1826, mir-183, mir-185, mir-191, mir-193a-3p, mir-193b, mir-195, mir-199b-5p, mir-19a-3p, mir-200a, mir-200b, mir-200c, mir-205, mir-206, mir-211, mir-216b, mir-218, mir-22, mir-26a, mir-26b, mir-300, mir-30a, mir-31, mir-335, mir-339-5p, mir-33b, mir-34a, mir-34b, mir-34c, mir-374a, mir-379, mir-381, mir-383, mir-425, mir-429, mir-450b-3p, mir-494, mir-495, mir-497, mir-502-5p, mir-517a, mir-574-3p, mir-638, mir-7, mir-720, mir-7515, mir-92a, mir-98, mir-99a, mmu-mir-290-3p, mmu-mir-290-5p | mir-10b, mir-125a, mir-135a, mir-140, mir-141, mir-142, mir-150, mir-155, mir-181a, mir-181b, mir-182, mir-18a, mir-18b, mir-191, mir-196a, mir-197, mir-19a, mir-19b, mir-200a, mir-200b, mir-200c, mir-203, mir-205, mir-20a, mir-20b, mir-21, mir-217, mir-221, mir-224, mir-23a, mir-24, mir-24-2-5p, mir-24-3p, mir-27a, mir-29a, mir-29b-1, mir-29b-2, mir-29c, mir-373, mir-378, mir-423, mir-429, mir-495, mir-503, mir-510, mir-520c, mir-526b, mir-96 |
| chondrosarcoma | let-7a, mir-100, mir-136, mir-145, mir-199a, mir-222, mir-30a, mir-335, mir-376a | |
| colorectal cancer | let-7a, mir-1, mir-100, mir-101, mir-124, mir-125a, mir-126, mir-129, mir-1295b-3p, mir-1307, mir-130b, mir-132, mir-133a, mir-133b, mir-137, mir-138, mir-139, mir-139-5p, mir-140-5p, mir-143, mir-145, mir-148a, mir-148b, mir-149, mir-150-5p, mir-154, mir-15a, mir-15b, mir-16, mir-18a, mir-191, mir-192, mir-193a-5p, mir-194, mir-195, mir-196a, mir-198, mir-199a-5p, mir-200c, mir-203, mir-204-5p, mir-206, mir-212, mir-215, mir-218, mir-22, mir-224, mir-24-3p, mir-26b, mir-27a, mir-28-3p, mir-28-5p, mir-29b, mir-30a-3p, mir-30b, mir-320a, mir-328, mir-338-3p, mir-342, mir-345, mir-34a, mir-34a-5p, mir-361-5p, mir-375, mir-378, mir-378a-3p, mir-378a-5p, mir-409-3p, mir-422a, mir-4487, mir-483, mir-497, mir-498, mir-518a-3p, mir-551a, mir-574-5p, mir-625, mir-638, mir-7, mir-96-5p | let-7a, mir-103, mir-106a, mir-10b, mir-1179, mir-1229, mir-1246, mir-125b-2*, mir-1269a, mir-130b, mir-133b, mir-135a, mir-135a-1, mir-135a-2, mir-135b, mir-139-3p, mir-145, mir-150, mir-150*, mir-155, mir-17, mir-181a, mir-182, mir-183, mir-18a, mir-191, mir-196a, mir-196b, mir-19a, mir-19b, mir-200b, mir-200c, mir-203, mir-204-5p, mir-20a, mir-20a-5p, mir-21, mir-210, mir-211, mir-221, mir-223, mir-224, mir-23a, mir-25, mir-27a, mir-29a, mir-301a, mir-31, mir-32, mir-320b, mir-326, mir-424, mir-429, mir-494, mir-497, mir-499-5p, mir-592, mir-630, mir-7-5p, mir-892a, mir-92, mir-92a, mir-93, mir-95, mir-96 |
| esophageal squamous cell carcinoma | let-7a, let-7a-1, let-7a-2, let-7a-3, let-7b, let-7c, let-7d, let-7e, let-7f-1, let-7f-2, let-7g, let-7i, mir-1, mir-100, mir-101, mir-126, mir-1294, mir-133a, mir-133b, mir-138, mir-143, mir-145, mir-150, mir-185, mir-195, mir-200b, mir-203, mir-21, mir-210, mir-214, mir-218, mir-22, mir-27a, mir-29b, mir-29c, mir-302b, mir-34a, mir-375, mir-494, mir-518b, mir-655, mir-98, mir-99a | mir-100, mir-1179, mir-1290, mir-130b, mir-145, mir-16, mir-17, mir-183, mir-18a, mir-19a, mir-19b, mir-208, mir-20a, mir-21, mir-218, mir-223, mir-25, mir-30a-5p, mir-31, mir-330-3p, mir-373, mir-9, mir-92a, mir-942 |
| gastric cancer | let-7a, let-7b, let-7g, mir-1, mir-101, mir-103a, mir-10a, mir-10b, mir-1207-5p, mir-122, mir-1228*, mir-124, mir-124-3p, mir-125a-3p, mir-126, mir-1266, mir-1271, mir-129-1-3p, mir-129-2-3p, mir-129-3p, mir-129-5p, mir-133a, mir-133b, mir-137, mir-141, mir-143, mir-144, mir-145, mir-146a, mir-146a-5p, mir-148a, | mir-100, mir-103, mir-106a, mir-106b, mir-107, mir-10a, mir-10b, mir-1259, mir-125b, mir-126, mir-1274a, mir-1303, mir-130b*, mir-135a-5p, mir-135b, mir-138, mir-143, mir-146a, mir-147, mir-148a, mir-150, mir-17, mir-17-5p, mir-181a, mir-181a-2*, mir-181a-5p, mir-181c, mir-183, mir-185, mir-18a, mir-191, |

TABLE 2-continued

List of examples of oncomiR-cancer relationships.

| Malignancy | Down-regulated miRs | Up-regulated miRs |
| --- | --- | --- |
| | mir-148b, mir-149, mir-152, mir-155, mir-155-5p, mir-181a, mir-181b, mir-182, mir-183, mir-185, mir-194, mir-195, mir-197, mir-199a-3p, mir-200b, mir-200c, mir-202-3p, mir-204, mir-204-5p, mir-205, mir-206, mir-210, mir-212, mir-217, mir-218, mir-22, mir-23b, mir-24, mir-26a, mir-29a, mir-29a-3p, mir-29b, mir-29b-1, mir-29b-2, mir-29c, mir-30a-5p, mir-30b, mir-31, mir-328, mir-329, mir-331-3p, mir-335-5p, mir-338, mir-338-3p, mir-34a, mir-34b, mir-34c, mir-361-5p, mir-367, mir-375, mir-378, mir-409-3p, mir-410, mir-429, mir-433, mir-449, mir-449a, mir-490-3p, mir-494, mir-497, mir-503, mir-506, mir-513b, mir-520d-3p, mir-542-3p, mir-622, mir-625, mir-638, mir-663, mir-7, mir-765, mir-9 | mir-192, mir-196a, mir-196a*, mir-196a-5p, mir-196b, mir-199a, mir-199a-3p, mir-199a-5p, mir-19a, mir-19b, mir-200b, mir-20a, mir-21, mir-214, mir-215, mir-221, mir-221*, mir-222, mir-223, mir-224, mir-23a, mir-23b, mir-27a, mir-27b, mir-296-5p, mir-301a, mir-302f, mir-337-3p, mir-340*, mir-34a, mir-362-3p, mir-370, mir-374a, mir-377, mir-421, mir-425, mir-500, mir-520c-3p, mir-544, mir-575, mir-601, mir-616*, mir-650, mir-92, mir-98, mir-99a |
| glioma | let-7a, let-7f, mir-106a, mir-107, mir-122, mir-124, mir-124-5p, mir-124a, mir-125b, mir-128, mir-136, mir-137, mir-139, mir-143, mir-145, mir-146a, mir-146b, mir-146b-5p, mir-152, mir-15b, mir-16, mir-181a, mir-181a-1, mir-181a-2, mir-181b, mir-181b-1, mir-181b-2, mir-181c, mir-181d, mir-184, mir-185, mir-195, mir-199a-3p, mir-200a, mir-200b, mir-203, mir-204, mir-205, mir-218, mir-219-5p, mir-23b, mir-26b, mir-27a, mir-29c, mir-320, mir-326, mir-328, mir-34a, mir-34c-3p, mir-34c-5p, mir-375, mir-383, mir-451, mir-452, mir-483-5p, mir-495, mir-584, mir-622, mir-656, mir-7, mir-98 | mir-106b, mir-106b-5p, mir-10b, mir-125b, mir-132, mir-155, mir-17, mir-181a, mir-182, mir-183, mir-193b, mir-19a, mir-19b, mir-20a, mir-210, mir-214, mir-221, mir-222, mir-224, mir-23a, mir-24, mir-24-3p, mir-25, mir-26a, mir-27a-3p, mir-27b, mir-30a-5p, mir-30e, mir-30e*, mir-328, mir-335, mir-33a, mir-372, mir-486, mir-494, mir-497, mir-566, mir-603, mir-650, mir-675, mir-9, mir-92b, mir-93, mir-96 |
| nasopharyngeal carcinoma | let-7a, let-7a-1, let-7a-2, let-7a-3, let-7b, let-7c, let-7d, let-7e, let-7f-1, let-7f-2, let-7g, let-7i, mir-1, mir-101, mir-124, mir-138, mir-143, mir-145, mir-148a, mir-200b, mir-204, mir-216b, mir-29c, mir-320a, mir-324-3p, mir-34c, mir-375, mir-378, mir-451, mir-506, mir-9, mir-98 | mir-10b, mir-144, mir-149, mir-155, mir-18a, mir-21, mir-214, mir-24, mir-421, mir-663, mir-7-5p, mir-93 |
| non-small cell lung cancer | let-7a, let-7c, mir-1, mir-100, mir-101, mir-106a, mir-107, mir-124, mir-125a-3p, mir-125a-5p, mir-126*, mir-129, mir-133a, mir-137, mir-138, mir-140, mir-143, mir-145, mir-146a, mir-146b, mir-148a, mir-148b, mir-149, mir-152, mir-153, mir-154, mir-155, mir-15a, mir-16, mir-17-5p, mir-181a-1, mir-181a-2, mir-181b, mir-181b-1, mir-181b-2, mir-181c, mir-181d, mir-184, mir-186, mir-193b, mir-195, mir-199a, mir-204, mir-212, mir-221, mir-224, mir-26b, mir-27a, mir-27b, mir-29a, mir-29b, mir-29c, mir-30a, mir-30b, mir-30c, mir-30d, mir-30d-5p, mir-30e-5p, mir-32, mir-335, mir-338-3p, mir-340, mir-342-3p, mir-34a, mir-34b, mir-361-3p, mir-365, mir-373, mir-375, mir-429, mir-449a, mir-4500, mir-451, mir-4782-3p, mir-497, mir-503, mir-512-3p, mir-520a-3p, mir-526b, mir-625*, mir-96, mir-99a | mir-10b, mir-125a-5p, mir-1280, mir-136, mir-140, mir-141, mir-142-3p, mir-145, mir-146a, mir-150, mir-18a, mir-196a, mir-19a, mir-200a, mir-200c, mir-205, mir-205-5p, mir-21, mir-212, mir-22, mir-221, mir-222, mir-24, mir-25, mir-29c, mir-31, mir-328, mir-330-3p, mir-339, mir-34a, mir-375, mir-494, mir-675-5p, mir-9, mir-92b, mir-93, mir-95 |
| osteosarcoma | let-7a, mir-1, mir-100, mir-101, mir-122, mir-124, mir-125b, mir-126, mir-127-3p, mir-132, mir-133a, mir-141, mir-142-3p, mir-142-5p, mir-143, mir-144, mir-145, mir-153, mir-16, mir-183, mir-194, mir-195, mir-199a-3p, mir-204, mir-212, mir-217, mir-218, mir-22, mir-23a, mir-24, mir-26a, mir-26b, mir-29b, mir-32, mir-320, mir-335, mir-33b, mir-340, mir-34a, mir-34b, mir-34c, mir-375, mir-376c, mir-382, mir-3928, mir-424, mir-429, mir-449a, mir-451, mir-454, mir-503, mir-519d, mir-646 | mir-128, mir-151-3p, mir-17, mir-181a, mir-181b, mir-181c, mir-18a, mir-191, mir-195-5p, mir-199a-3p, mir-19a, mir-19b, mir-20a, mir-21, mir-210, mir-214, mir-221, mir-27a, mir-300, mir-320a, mir-374a-5p, mir-720, mir-9, mir-92a |

TABLE 2-continued

List of examples of oncomiR-cancer relationships.

| Malignancy | Down-regulated miRs | Up-regulated miRs |
| --- | --- | --- |
| pancreatic ductal adenocarcinoma | let-7a, let-7a-1, let-7a-2, let-7a-3, let-7b, let-7c, let-7d, let-7e, let-7f-1, let-7f-2, let-7g, let-7i, mir-126, mir-135a, mir-143, mir-144, mir-145, mir-148a, mir-150, mir-15a, mir-16, mir-200a, mir-200b, mir-200c, mir-217, mir-218, mir-337, mir-375, mir-494, mir-615-5p, mir-98 | mir-10b, mir-186, mir-18a, mir-192, mir-194, mir-196a, mir-198, mir-203, mir-21, mir-212, mir-30b-5p, mir-31, mir-34a, mir-369-5p, mir-376a, mir-541 |
| renal cell carcinoma | let-7a, let-7d, mir-1, mir-106a*, mir-126, mir-1285, mir-129-3p, mir-1291, mir-133a, mir-133b, mir-135a, mir-138, mir-141, mir-143, mir-145, mir-182-5p, mir-199a-3p, mir-200a, mir-205, mir-218, mir-28-5p, mir-30a, mir-30c, mir-30d, mir-34a, mir-378, mir-429, mir-509-3p, mir-509-5p, mir-646 | mir-100, mir-1233, mir-1260b, mir-146a, mir-146b, mir-16, mir-193a-3p, mir-203a, mir-21, mir-210, mir-27a, mir-362, mir-572, mir-7 |
| bronchioloalveolar carcinoma | let-7a-1, let-7a-2, let-7a-3, let-7b, let-7c, let-7d, let-7e, let-7f-1, let-7f-2, let-7g, let-7i, mir-98 | |
| colon cancer | let-7a-1, let-7a-2, let-7a-3, let-7b, let-7c, let-7d, let-7e, let-7f-1, let-7f-2, let-7g, let-7i, mir-100, mir-101, mir-126, mir-142-3p, mir-143, mir-145, mir-192, mir-200c, mir-21, mir-214, mir-215, mir-25, mir-302a, mir-320, mir-320a, mir-34a, mir-34c, mir-365, mir-373, mir-424, mir-429, mir-455, mir-484, mir-502, mir-503, mir-93, mir-98 | mir-1290, mir-145, mir-155, mir-181a, mir-18a, mir-200c, mir-31, mir-675 |
| hepatocellular carcinoma | let-7a-1, let-7a-2, let-7a-3, let-7b, let-7c, let-7d, let-7e, let-7f, let-7f-1, let-7f-2, let-7g, let-7i, mir-1, mir-100, mir-101, mir-105, mir-122, mir-122a, mir-123 6, mir-124, mir-125b, mir-126, mir-127, mir-1271, mir-128-3p, mir-129-5p, mir-130a, mir-130b, mir-133a, mir-134, mir-137, mir-138, mir-139, mir-139-5p, mir-140-5p, mir-141, mir-142-3p, mir-143, mir-144, mir-145, mir-146a, mir-148a, mir-148b, mir-150-5p, mir-15b, mir-16, mir-181a-5p, mir-185, mir-188-5p, mir-193b, mir-195, mir-195-5p, mir-197, mir-198, mir-199a, mir-199a-5p, mir-199b, mir-199b-5p, mir-200a, mir-200b, mir-200c, mir-202, mir-203, mir-204-3p, mir-205, mir-206, mir-20a, mir-21, mir-21-3p, mir-211, mir-212, mir-214, mir-217, mir-218, mir-219-5p, mir-22, mir-26a, mir-26b, mir-29a, mir-29b-1, mir-29b-2, mir-29c, mir-302b, mir-302c, mir-30a, mir-30a-3p, mir-335, mir-338-3p, mir-33a, mir-34a, mir-34b, mir-365, mir-370, mir-372, mir-375, mir-376a, mir-377, mir-422a, mir-424, mir-424-5p, mir-433, mir-4458, mir-448, mir-450a, mir-451, mir-485-5p, mir-486-5p, mir-497, mir-503, mir-506, mir-519d, mir-520a, mir-520b, mir-520c-3p, mir-582-5p, mir-590-5p, mir-610, mir-612, mir-625, mir-637, mir-675, mir-7, mir-877, mir-940, mir-941, mir-98, mir-99a | mir-106b, mir-10b, mir-122, mir-1228, mir-1269, mir-128a, mir-130a, mir-130b, mir-146a, mir-153, mir-155, mir-17-5p, mir-181a, mir-181a-1, mir-181a-2, mir-181b, mir-181b-1, mir-181b-2, mir-181c, mir-181d, mir-182, mir-183, mir-184, mir-190b, mir-191, mir-20a, mir-20b, mir-21, mir-210, mir-214, mir-215, mir-216a, mir-217, mir-221, mir-222, mir-223, mir-224, mir-23a, mir-24, mir-25, mir-27a, mir-301a, mir-30d, mir-31, mir-3127, mir-32, mir-331-3p, mir-362-3p, mir-371-5p, mir-372, mir-373, mir-423, mir-429, mir-452, mir-483-3p, mir-483-5p, mir-485-3p, mir-490-3p, mir-494, mir-495, mir-500, mir-501-5p, mir-519d, mir-520g, mir-574-3p, mir-590-5p, mir-630, mir-650, mir-657, mir-664, mir-885-5p, mir-9, mir-92a, mir-96 |
| lung cancer | let-7a-1, let-7a-2, let-7a-3, let-7b, let-7c, let-7d, let-7e, let-7f-1, let-7f-2, let-7g, let-7i, mir-1, mir-101, mir-133b, mir-138, mir-142-5p, mir-144, mir-145, mir-1469, mir-146a, mir-153, mir-15a, mir-15b, mir-16-1, mir-16-2, mir-182, mir-192, mir-193a-3p, mir-194, mir-195, mir-198, mir-203, mir-217, mir-218, mir-22, mir-223, mir-26a, mir-26b, mir-29c, mir-33a, mir-34a, mir-34b, mir-34c, mir-365, mir-449a, mir-449b, mir-486-5p, mir-545, mir-610, mir-614, mir-630, mir-660, mir-7-5p, mir-9500, mir-98, mir-99b | mir-10b, mir-135b, mir-150, mir-155, mir-17, mir-182, mir-183-3p, mir-18a, mir-197, mir-19a, mir-19b, mir-205, mir-20a, mir-21, mir-210, mir-24, mir-30d, mir-4423, mir-5100, mir-570, mir-663, mir-7, mir-92a |
| neuroblastoma | let-7a-1, let-7a-2, let-7a-3, let-7b, let-7c, let-7d, let-7e, let-7f-1, let-7f-2, let-7g, let-7i, mir-124, mir-137, mir-145, mir-181c, mir-184, mir-200a, mir-29a, mir-335, mir-338-3p, mir-34a, mir-449a, mir-885-5p, mir-98 | mir-125b, mir-15a, mir-15b, mir-16-1, mir-16-2, mir-18a, mir-195, mir-19a, mir-23a, mir-421, mir-92 |

TABLE 2-continued

List of examples of oncomiR-cancer relationships.

| Malignancy | Down-regulated miRs | Up-regulated miRs |
| --- | --- | --- |
| prostate cancer | let-7a-3p, let-7c, mir-100, mir-101, mir-105, mir-124, mir-128, mir-1296, mir-130b, mir-133a-1, mir-133a-2, mir-133b, mir-135a, mir-143, mir-145, mir-146a, mir-154, mir-15a, mir-187, mir-188-5p, mir-199b, mir-200b, mir-203, mir-205, mir-212, mir-218, mir-221, mir-224, mir-23a, mir-23b, mir-25, mir-26a, mir-26b, mir-29b, mir-302a, mir-30a, mir-30b, mir-30c-1, mir-30c-2, mir-30d, mir-30e, mir-31, mir-330, mir-331-3p, mir-34a, mir-34b, mir-34c, mir-374b, mir-449a, mir-4723-5p, mir-497, mir-628-5p, mir-642a-5p, mir-720, mir-940 | mir-125b, mir-141, mir-153, mir-155, mir-181a-1, mir-181a-2, mir-181b, mir-181b-1, mir-181b-2, mir-181c, mir-181d, mir-182, mir-182-5p, mir-183, mir-18a, mir-204, mir-20a, mir-21, mir-221, mir-223-3p, mir-31, mir-429, mir-96 |
| acute lymphoblastic leukemia | let-7b, mir-124a, mir-142-3p | mir-128 |
| malignant melanoma | let-7b, mir-101, mir-125b, mir-1280, mir-143, mir-146a, mir-146b, mir-155, mir-17, mir-184, mir-185, mir-18b, mir-193b, mir-200c, mir-203, mir-204, mir-205, mir-206, mir-20a, mir-211, mir-218, mir-26a, mir-31, mir-33a, mir-34a, mir-34c, mir-376a, mir-376c, mir-573, mir-7, mir-9, mir-98 | mir-126, mir-141, mir-15b, mir-17, mir-17-5p, mir-182, mir-18a, mir-193b, mir-200a, mir-200b, mir-200c, mir-20a, mir-21, mir-210, mir-214, mir-221, mir-222, mir-429, mir-455-5p, mir-532-5p, mir-638, mir-92a |
| renal clear cell carcinoma | let-7b, let-7c, mir-138, mir-141, mir-200c, mir-204, mir-218, mir-335, mir-377, mir-506 | mir-122, mir-155, mir-630 |
| acute myeloid leukemia | let-7c, mir-17, mir-181a, mir-20a, mir-223, mir-26a, mir-29a, mir-30c, mir-7 | mir-125b, mir-126-5p, mir-128, mir-155, mir-29a, mir-32, mir-331, mir-370, mir-378 |
| acute promyelocytic leukemia | let-7c, mir-107, mir-342 | mir-181a, mir-181b, mir-92a |
| head and neck squamous cell carcinoma | let-7d, mir-1, mir-107, mir-128, mir-133a, mir-138, mir-149, mir-200c, mir-205, mir-218, mir-27a*, mir-29a, mir-29b-1, mir-29b-2, mir-29c, mir-300, mir-34a, mir-363, mir-375, mir-874 | mir-106b, mir-134, mir-16, mir-184, mir-196a, mir-21, mir-25, mir-30a-5p, mir-31, mir-372, mir-93 |
| oral cancer | let-7d, mir-218, mir-34a, mir-375, mir-494 | mir-10b, mir-196a-1, mir-196a-2, mir-196b, mir-21 |
| papillary thyroid carcinoma | mir-101, mir-130b, mir-138, mir-146a, mir-16, mir-195, mir-199a-3p, mir-204-5p, mir-219-5p, mir-26a, mir-34b, mir-613 | let-7e, mir-146b, mir-146b-5p, mir-151-5p, mir-155, mir-181a-1, mir-181a-2, mir-181b-1, mir-181b-2, mir-181c, mir-181d, mir-182, mir-183, mir-199b-5p, mir-21, mir-221, mir-222, mir-339-5p, mir-34a |
| glioblastoma | let-7g-5p, mir-100, mir-101, mir-106a, mir-124, mir-124a, mir-125a, mir-125a-5p, mir-125b, mir-127-3p, mir-128, mir-129, mir-13 6, mir-13 7, mir-139-5p, mir-142-3p, mir-143, mir-145, mir-146b-5p, mir-149, mir-152, mir-153, mir-195, mir-21, mir-212-3p, mir-219-5p, mir-222, mir-29b, mir-31, mir-3189-3p, mir-320, mir-320a, mir-326, mir-330, mir-331-3p, mir-340, mir-342, mir-34a, mir-376a, mir-449a, mir-483-5p, mir-503, mir-577, mir-663, mir-7, mir-744 | mir-10b, mir-125b, mir-127-3p, mir-148a, mir-18a, mir-196a, mir-196a-1, mir-196a-2, mir-196b, mir-21, mir-210, mir-210-3p, mir-223, mir-340, mir-576-5p, mir-626, mir-92b |
| ovarian cancer | let-7i, mir-100, mir-124, mir-125b, mir-129-5p, mir-130b, mir-133a, mir-137, mir-138, mir-141, mir-145, mir-148a, mir-152, mir-153, mir-155, mir-199a, mir-200a, mir-200b, mir-200c, mir-212, mir-335, mir-34a, mir-34b, mir-34c, mir-409-3p, mir-411, mir-429, mir-432, mir-449a, mir-494, mir-497, mir-498, mir-519d, mir-655, mir-9, mir-98 | mir-106a, mir-141, mir-148b, mir-181b, mir-182, mir-200a, mir-200c, mir-205, mir-20a, mir-21, mir-210, mir-214, mir-221, mir-224-5p, mir-23b, mir-25, mir-26a, mir-27a, mir-27b, mir-346, mir-378, mir-424, mir-503, mir-572, mir-9, mir-96 |
| bladder cancer | mir-1, mir-101, mir-1180, mir-1236, mir-124-3p, mir-125b, mir-126, mir-1280, mir-133a, mir-133b, mir-141, mir-143, mir-144, mir-145, mir-155, mir-16, mir-18a, mir-192, mir-195, mir-200a, mir-200b, mir-200c, mir-203, mir-205, mir-214, mir-218, mir-23b, mir-26a, mir-29c, mir-320c, mir-34a, mir-370, mir-409-3p, mir-429, mir-451, mir-490-5p, mir-493, mir-576-3p, mir-99a | mir-103a-3p, mir-10b, mir-135a, mir-137, mir-141, mir-155, mir-17-5p, mir-182, mir-182-5p, mir-183, mir-185, mir-19a, mir-203, mir-205, mir-210, mir-221, mir-222, mir-223, mir-23a, mir-23b, mir-26b, mir-639, mir-96 |

TABLE 2-continued

List of examples of oncomiR-cancer relationships.

| Malignancy | Down-regulated miRs | Up-regulated miRs |
|---|---|---|
| chordoma | mir-1, mir-222, mir-31, mir-34a, mir-608 | mir-140-3p, mir-148a |
| kidney cancer | mir-1, mir-145, mir-1826, mir-199a, mir-199a-3p, mir-203, mir-205, mir-497, mir-508-3p, mir-509-3p | mir-183, mir-21, mir-210, mir-223 |
| cervical carcinoma | mir-100, mir-101, mir-15a, mir-16, mir-34a, mir-886-5p, mir-99a, mir-99b | mir-133b, mir-21, mir-25, mir-373 |
| mesenchymal cancer | mir-100, mir-141, mir-199b-5p, mir-200a, mir-200b, mir-200c, mir-29a, mir-29b-1, mir-29b-1-5p, mir-29b-2, mir-29c, mir-335, mir-429, mir-99a | mir-125b-1-3p, mir-182 |
| oral squamous cell carcinoma | mir-100, mir-124, mir-1250, mir-125b, mir-126, mir-1271, mir-136, mir-138, mir-145, mir-147, mir-148a, mir-181a, mir-206, mir-220a, mir-26a, mir-26b, mir-29a, mir-32, mir-323-5p, mir-329, mir-338, mir-370, mir-410, mir-429, mir-433, mir-499a-5p, mir-503, mir-506, mir-632, mir-646, mir-668, mir-877, mir-9 | mir-125b, mir-126, mir-146a, mir-146b, mir-155, mir-181b, mir-196a-1, mir-196a-2, mir-196b, mir-21, mir-221, mir-222, mir-24, mir-27b, mir-31, mir-345 |
| ovarian carcinoma | mir-100, mir-101, mir-34b, mir-34c, mir-532-5p | mir-148b, mir-182 |
| cholangiocarcinoma | mir-101, mir-144, mir-200b, mir-200c | mir-17, mir-18a, mir-19a, mir-19b, mir-20a, mir-21, mir-26a, mir-92a |
| endometrial cancer | mir-101, mir-130a, mir-130b, mir-134, mir-143, mir-145, mir-152, mir-205, mir-223, mir-301a, mir-301b, mir-30c, mir-34a, mir-34c, mir-424, mir-449a, mir-543 | mir-106a, mir-145, mir-155, mir-182, mir-200b, mir-200c, mir-205, mir-21, mir-222-3p, mir-25, mir-93 |
| esophageal cancer | mir-124, mir-126, mir-140, mir-197, mir-203, mir-218, mir-223, mir-30b, mir-375, mir-454, mir-486, mir-574-3p | mir-101, mir-10b, mir-130a, mir-141, mir-143, mir-146b, mir-15a, mir-183, mir-196b, mir-200a, mir-203, mir-205, mir-21, mir-210, mir-221, mir-27a, mir-28-3p, mir-31, mir-452, mir-96, mir-99b |
| liver cancer | mir-101, mir-122, mir-132, mir-140-5p, mir-145, mir-148b, mir-31, mir-338-3p, mir-433 | mir-1301, mir-155, mir-21, mir-221, mir-27a, mir-525-3p |
| pancreatic cancer | mir-101, mir-1181, mir-124, mir-1247, mir-133a, mir-141, mir-145, mir-146a, mir-148a, mir-148b, mir-150*, mir-150-5p, mir-152, mir-15a, mir-198, mir-203, mir-214, mir-216a, mir-29c, mir-335, mir-34a, mir-34b, mir-34c, mir-373, mir-375, mir-410, mir-497, mir-615-5p, mir-630, mir-96 | mir-10a, mir-10b, mir-132, mir-15a, mir-17-5p, mir-181a, mir-18a, mir-191, mir-196a, mir-21, mir-212, mir-214, mir-222, mir-27a, mir-301a, mir-301a-3p, mir-367, mir-424-5p, mir-7, mir-92, mir-99a |
| retinoblastoma | mir-101, mir-183, mir-204, mir-34a, mir-365b-3p, mir-486-3p, mir-532-5p | mir-181b, mir-21 |
| cervical squamous cell carcinoma | mir-106a, mir-124, mir-148a, mir-214, mir-218, mir-29a, mir-375 | mir-205 |
| clear cell renal cell cancer | mir-106a-5p, mir-135a-5p, mir-206 | mir-142-5p, mir-155, mir-21-5p |
| laryngeal carcinoma | | mir-106b, mir-16, mir-21, mir-27a, mir-423-3p |
| medulloblastoma | mir-124, mir-128a, mir-199b-5p, mir-206, mir-22, mir-31, mir-383 | mir-106b, mir-17, mir-18a, mir-19a, mir-19b, mir-20a, mir-30b, mir-30d, mir-92 |
| pituitary carcinoma | | mir-106b, mir-122, mir-20a, mir-493 |
| prostate carcinoma | mir-107 | |
| cervical cancer | mir-143, mir-145, mir-17-5p, mir-203, mir-214, mir-218, mir-335, mir-342-3p, mir-3 72, mir-424, mir-491-5p, mir-497, mir-7, mir-99a, mir-99b | mir-10a, mir-155, mir-181a, mir-181b, mir-196a, mir-19a, mir-19b, mir-205, mir-20a, mir-21, mir-215, mir-224, mir-31, mir-494, mir-590-5p, mir-92a, mir-944 |
| chronic myelogenous leukemia | mir-10a, mir-146a, mir-150, mir-151, mir-155, mir-2278, mir-26a, mir-30e, mir-31, mir-326, mir-564 | mir-424, mir-96 |
| gastrointestinal cancer | mir-122a, mir-148a, mir-152 | |
| anaplastic astrocytoma | mir-124, mir-137 | |
| astrocytoma | mir-124-3p, mir-181b-5p, mir-200b, mir-3189-3p | mir-335 |
| epithelial ovarian cancer | mir-124a, mir-192, mir-193a, mir-7 | mir-372, mir-373 |

TABLE 2-continued

List of examples of oncomiR-cancer relationships.

| Malignancy | Down-regulated miRs | Up-regulated miRs |
| --- | --- | --- |
| mantle cell lymphoma | mir-142-3p, mir-142-5p, mir-150, mir-223, mir-29a, mir-29b, mir-29c | mir-124a, mir-155, mir-17, mir-18a, mir-19a, mir-19b, mir-20a, mir-92a |
| chronic lymphocytic leukemia | mir-125b, mir-138, mir-15a, mir-15b, mir-16, mir-16-1, mir-16-1-3p, mir-16-2, mir-181a, mir-181b, mir-195, mir-223, mir-29b, mir-34b, mir-34c, mir-424 | mir-150, mir-155 |
| follicular cancer | NA | mir-125b |
| malignant mesothelioma | mir-126 | |
| small cell lung cancer | mir-126, mir-138, mir-27a | mir-25 |
| meningioma | mir-128, mir-200a | mir-224, mir-335 |
| laryngeal squamous cell carcinoma | mir-129-5p, mir-203, mir-205, mir-206, mir-24, mir-370, mir-375 | mir-21, mir-9, mir-93 |
| medullary thyroid carcinoma | mir-129-5p | mir-183 |
| lung adenocarcinoma | mir-1297, mir-141, mir-145, mir-16, mir-200a, mir-200b, mir-200c, mir-29b, mir-381, mir-409-3p, mir-429, mir-451, mir-511, mir-99a | mir-150, mir-155, mir-31 |
| pancreatic carcinoma | mir-132, mir-375 | mir-301b |
| lung squamous cell carcinoma | mir-133a, mir-218 | |
| multiple myeloma | mir-137, mir-197, mir-214 | mir-21 |
| squamous carcinoma | mir-15a, mir-16, mir-203, mir-205, mir-375 | mir-137, mir-155, mir-184, mir-196a, mir-203, mir-21, mir-221, mir-27a, mir-34a |
| uveal melanoma | mir-137, mir-144, mir-145, mir-182, mir-34a, mir-34b, mir-34c, mir-9 | NA |
| anaplastic thyroid carcinoma | mir-138 | mir-146b, mir-221, mir-222 |
| colorectal carcinoma | mir-139, mir-143, mir-145, mir-202-3p, mir-30a, mir-338-3p, mir-429, mir-451, mir-93 | mir-17, mir-182, mir-191, mir-21, mir-95 |
| malt lymphoma | | mir-142-5p, mir-155 |
| thyroid cancer | mir-144, mir-886-3p | |
| primary cns lymphomas | mir-145, mir-193b, mir-199a, mir-214 | |
| follicular thyroid carcinoma | mir-199b | mir-146b, mir-183, mir-197, mir-221,mir-346 |
| gallbladder carcinoma | mir-146b-5p | mir-155, mir-182 |
| adult t-cell leukemia | | mir-150 |
| anaplastic large-cell lymphoma | | mir-155 |
| cutaneous t-cell lymphoma | | mir-155 |
| diffuse large B-cell lymphoma | | mir-155, mir-21 |
| rectal cancer | | mir-155, mir-200c, mir-21-5p, mir-34a |
| tongue cancer | mir-15b, mir-200b | |
| b-cell lymphoma | mir-34a | mir-17, mir-18a, mir-19a, mir-19b, mir-20a, mir-92a |
| breast carcinoma | | mir-17, mir-18a, mir-19a, mir-19b, mir-20a, mir-24, mir-92a |
| nasopharyngeal cancer | mir-218, mir-223, mir-29c | mir-17, mir-20a |
| gastric adenocarcinoma | mir-181b, mir-182, mir-200a, mir-302b, mir-449a, mir-9 | mir-23a, mir-27a, mir-373 |
| colorectal adenocarcinoma | | mir-182 |
| colon carcinoma | mir-186, mir-30a-5p | mir-221, mir-23a |
| adrenal cortical carcinoma | mir-195, mir-1974, mir-335, mir-497 | mir-21, mir-210, mir-483-3p, mir-483-5p |
| esophageal adenocarcinoma | mir-203 | mir-196a, mir-199a-3p, mir-199a-5p, mir-199b-3p, mir-200a, mir-223 |
| gastrointestinal stromal tumor | mir-218, mir-221, mir-222 | mir-196a |
| uterine leiomyoma | mir-197 | |
| choriocarcinoma | mir-199b, mir-218, mir-34a | |
| follicular lymphoma | mir-202 | |
| basal cell carcinoma | mir-203 | |
| hypopharyngeal cancer | | mir-203 |
| pancreatic adenocarcinoma | | mir-203, mir-301a |
| rhabdomyosarcoma | mir-203 | |

TABLE 2-continued

List of examples of oncomiR-cancer relationships.

| Malignancy | Down-regulated miRs | Up-regulated miRs |
| --- | --- | --- |
| head and neck cancer | NA | mir-21 |
| hypopharyngeal squamous cell carcinoma | mir-451a, mir-504 | mir-21 |
| t-cell lymphoma | mir-22 | |
| thyroid carcinoma | | mir-221, mir-222 |
| splenic marginal zone lymphoma | mir-223 | |
| laryngeal cancer | | mir-23a |
| primary thyroid lymphoma | mir-26a | |
| acute leukemia | mir-27a | |
| monocytic leukemia | mir-29a, mir-29b | |
| oral carcinoma | mir-375 | mir-31 |
| primary gallbladder carcinoma | mir-335 | |
| endometrial serous adenocarcinoma | mir-34b | |
| esophageal carcinoma | mir-451 | |
| hepatoblastoma | | mir-492 |
| colonic adenocarcinoma | mir-627 | |

TABLE 3

Complete list of tumor suppressive miRNAs and their relationship to cancer.

| Cancer | Down regulated tumor suppressive miR |
| --- | --- |
| acute leukemia | mir-27a |
| acute lymphoblastic leukemia | let-7b, mir-124a, mir-142-3p |
| acute myeloid leukemia | let-7c, mir-17, mir-181a, mir-20a, mir-223, mir-26a, mir-29a, mir-30c, mir-720 |
| acute promyelocytic leukemia | let-7c, mir-107, mir-342 |
| adrenal cortical carcinoma | mir-195, mir-1974, mir-335, mir-497 |
| anaplastic astrocytoma | mir-124, mir-137 |
| anaplastic thyroid carcinoma | mir-138 |
| astrocytoma | mir-124-3p, mir-181b-5p, mir-200b, mir-3189-3p |
| basal cell carcinoma | mir-203 |
| b-cell lymphoma | mir-34a |
| bladder cancer | mir-1, mir-101, mir-1180, mir-1236, mir-124-3p, mir-125b, mir-126, mir-1280, mir-133a, mir-133b, mir-141, mir-143, mir-144, mir-145, mir-155, mir-16, mir-18a, mir-192, mir-195, mir-200a, mir-200b, mir-200c, mir-203, mir-205, mir-214, mir-218, mir-23b, mir-26a, mir-29c, mir-320c, mir-34a, mir-370, mir-409-3p, mir-429, mir-451, mir-490-5p, mir-493, mir-576-3p, mir-99a |
| breast cancer | let-7a, let-7a-1, let-7a-2, let-7a-3, let-7b, let-7c, let-7d, let-7e, let-7f-1, let-7f-2, let-7g, let-7i, mir-100, mir-107, mir-10a, mir-10b, mir-122, mir-124, mir-1258, mir-125a-5p, mir-125b, mir-126, mir-127, mir-129, mir-130a, mir-132, mir-133a, mir-143, mir-145, mir-146a, mir-146b, mir-147, mir-148a, mir-149, mir-152, mir-153, mir-15a, mir-16, mir-17-5p, mir-181a, mir-1826, mir-183, mir-185, mir-191, mir-193a-3p, mir-193b, mir-195, mir-199b-5p, mir-19a-3p, mir-200a, mir-200b, mir-200c, mir-205, mir-206, mir-211, mir-216b, mir-218, mir-22, mir-26a, mir-26b, mir-300, mir-30a, mir-31, mir-335, mir-339-5p, mir-33b, mir-34a, mir-34b, mir-34c, mir-374a, mir-379, mir-381, mir-383, mir-425, mir-429, mir-450b-3p, mir-494, mir-495, mir-497, mir-502-5p, mir-517a, mir-574-3p, mir-638, mir-7, mir-720, mir-873, mir-874, mir-92a, mir-98, mir-99a, mmu-mir-290-3p, mmu-mir-290-5p |
| bronchioloalveolar carcinoma | let-7a-1, let-7a-2, let-7a-3, let-7b, let-7c, let-7d, let-7e, let-7f-1, let-7f-2, let-7g, let-7i, mir-98 |
| cervical cancer | mir-143, mir-145, mir-17-5p, mir-203, mir-214, mir-218, mir-335, mir-342-3p, mir-372, mir-424, mir-491-5p, mir-497, mir-7, mir-99a, mir-99b |
| cervical carcinoma | mir-100, mir-101, mir-15a, mir-16, mir-34a, mir-886-5p, mir-99a, mir-99b |
| cervical squamous cell carcinoma | mir-106a, mir-124, mir-148a, mir-214, mir-218, mir-29a, mir-375 |
| cholangiocarcinoma | mir-101, mir-144, mir-200b, mir-200c |
| chondrosarcoma | let-7a, mir-100, mir-136, mir-145, mir-199a, mir-222, mir-30a, mir-335, mir-376a |
| chordoma | mir-1, mir-222, mir-31, mir-34a, mir-608 |
| choriocarcinoma | mir-199b, mir-218, mir-34a |

TABLE 3-continued

Complete list of tumor suppressive miRNAs and their relationship to cancer.

| Cancer | Down regulated tumor suppressive miR |
| --- | --- |
| chronic lymphocytic leukemia | mir-125b, mir-138, mir-15a, mir-15b, mir-16, mir-16-1, mir-16-1-3p, mir-16-2, mir-181a, mir-181b, mir-195, mir-223, mir-29b, mir-34b, mir-34c, mir-424 |
| chronic myelogenous leukemia | mir-10a, mir-138, mir-146a, mir-150, mir-151, mir-155, mir-16, mir-2278, mir-26a, mir-30e, mir-31, mir-326, mir-564 |
| clear cell renal cell cancer | mir-106a-5p, mir-135a-5p, mir-206 |
| colon cancer | let-7a-1, let-7a-2, let-7a-3, let-7b, let-7c, let-7d, let-7e, let-7f-1, let-7f-2, let-7g, let-7i, mir-100, mir-101, mir-126, mir-142-3p, mir-143, mir-145, mir-192, mir-200c, mir-21, mir-214, mir-215, mir-22, mir-25, mir-302a, mir-320, mir-320a, mir-34a, mir-34c, mir-365, mir-373, mir-424, mir-429, mir-455, mir-484, mir-502, mir-503, mir-93, mir-98 |
| colon carcinoma | mir-186, mir-30a-5p |
| colonic adenocarcinoma | mir-627 |
| colorectal cancer | let-7a, mir-1, mir-100, mir-101, mir-124, mir-125a, mir-126, mir-129, mir-1295b-3p, mir-1307, mir-130b, mir-132, mir-133a, mir-133b, mir-137, mir-138, mir-139, mir-139-5p, mir-140-5p, mir-143, mir-145, mir-148a, mir-148b, mir-149, mir-150-5p, mir-154, mir-15a, mir-15b, mir-16, mir-18a, mir-191, mir-192, mir-193a-5p, mir-194, mir-195, mir-196a, mir-198, mir-199a-5p, mir-200c, mir-203, mir-204-5p, mir-206, mir-212, mir-215, mir-218, mir-22, mir-224, mir-24-3p, mir-26b, mir-27a, mir-28-3p, mir-28-5p, mir-29b, mir-30a-3p, mir-30b, mir-320a, mir-328, mir-338-3p, mir-342, mir-345, mir-34a, mir-34a-5p, mir-361-5p, mir-375, mir-378, mir-378a-3p, mir-378a-5p, mir-409-3p, mir-422a, mir-4487, mir-483, mir-497, mir-498, mir-518a-3p, mir-551a, mir-574-5p, mir-625, mir-638, mir-7, mir-96-5p |
| colorectal carcinoma | mir-139, mir-143, mir-145, mir-202-3p, mir-30a, mir-338-3p, mir-429, mir-451, mir-93 |
| endometrial cancer | mir-101, mir-130a, mir-130b, mir-134, mir-143, mir-145, mir-152, mir-205, mir-223, mir-301a, mir-301b, mir-30c, mir-34a, mir-34c, mir-424, mir-449a, mir-543 |
| endometrial serous adenocarcinoma | mir-34b |
| epithelial ovarian cancer | mir-124a, mir-192, mir-193a, mir-7 |
| esophageal adenocarcinoma | mir-203 |
| esophageal cancer | mir-124, mir-126, mir-140, mir-197, mir-203, mir-218, mir-223, mir-30b, mir-375, mir-454, mir-486, mir-574-3p |
| esophageal carcinoma | mir-451 |
| esophageal squamous cell carcinoma | let-7a, let-7a-1, let-7a-2, let-7a-3, let-7b, let-7c, let-7d, let-7e, let-7f-1, let-7f-2, let-7g, let-7i, mir-1, mir-100, mir-101, mir-126, mir-1294, mir-133a, mir-133b, mir-138, mir-143, mir-145, mir-150, mir-185, mir-195, mir-200b, mir-203, mir-21, mir-210, mir-214, mir-218, mir-22, mir-27a, mir-29b, mir-29c, mir-302b, mir-34a, mir-375, mir-494, mir-518b, mir-655, mir-98, mir-99a |
| follicular lymphoma | mir-202 |
| follicular thyroid carcinoma | mir-199b |
| gallbladder carcinoma | mir-146b-5p |
| gastric adenocarcinoma | mir-181b, mir-182, mir-200a, mir-302b, mir-449a, mir-9 |
| gastric cancer | let-7a, let-7b, let-7g, mir-1, mir-101, mir-103a, mir-10a, mir-10b, mir-1207-5p, mir-122, mir-1228*, mir-124, mir-124-3p, mir-125a-3p, mir-126, mir-1266, mir-127, mir-1271, mir-129-1-3p, mir-129-2-3p, mir-129-3p, mir-129-5p, mir-133a, mir-133b, mir-137, mir-141, mir-143, mir-144, mir-145, mir-146a, mir-146a-5p, mir-148a, mir-148b, mir-149, mir-152, mir-155, mir-155-5p, mir-181a, mir-181b, mir-182, mir-183, mir-185, mir-194, mir-195, mir-197, mir-199a-3p, mir-200b, mir-200c, mir-202-3p, mir-204, mir-204-5p, mir-205, mir-206, mir-210, mir-212, mir-217, mir-218, mir-22, mir-23b, mir-24, mir-26a, mir-29a, mir-29a-3p, mir-29b, mir-29b-1, mir-29b-2, mir-29c, mir-30a-5p, mir-30b, mir-31, mir-328, mir-329, mir-331-3p, mir-335-5p, mir-338, mir-338-3p, mir-34a, mir-34b, mir-34c, mir-361-5p, mir-367, mir-375, mir-378, mir-409-3p, mir-410, mir-429, mir-433, mir-449, mir-449a, mir-490-3p, mir-494, mir-497, mir-503, mir-506, mir-513b, mir-520d-3p, mir-542-3p, mir-622, mir-625, mir-638, mir-663, mir-7, mir-874, mir-9 |
| gastrointestinal cancer | mir-122a, mir-148a, mir-152 |
| gastrointestinal stromal tumor | mir-218, mir-221, mir-222 |
| glioblastoma | let-7g-5p, mir-100, mir-101, mir-106a, mir-124, mir-124a, mir-125a, mir-125a-5p, mir-125b, mir-127-3p, mir-128, mir-129, mir-136, mir-137, mir-139-5p, mir-142-3p, mir-143, mir-145, mir-146b-5p, mir-149, mir-152, mir-153, mir-195, mir-21, mir-212-3p, mir-219-5p, mir-222, mir-29b, mir-31, mir-3189-3p, mir-320, mir-320a, mir-326, mir-330, mir-331-3p, mir-340, mir-342, mir-34a, mir-376a, mir-449a, mir-483-5p, mir-503, mir-577, mir-663, mir-7, mir-7-5p, mir-873 |

TABLE 3-continued

Complete list of tumor suppressive miRNAs and their relationship to cancer.

| Cancer | Down regulated tumor suppressive miR |
|---|---|
| glioma | let-7a, let-7f, mir-106a, mir-107, mir-122, mir-124, mir-124-5p, mir-124a, mir-125b, mir-128, mir-136, mir-137, mir-139, mir-143, mir-145, mir-146a, mir-146b, mir-146b-5p, mir-152, mir-15b, mir-16, mir-181a, mir-181a-1, mir-181a-2, mir-181b, mir-181b-1, mir-181b-2, mir-181c, mir-181d, mir-184, mir-185, mir-195, mir-199a-3p, mir-200a, mir-200b, mir-203, mir-204, mir-205, mir-218, mir-219-5p, mir-23b, mir-26b, mir-27a, mir-29c, mir-320, mir-326, mir-328, mir-34a, mir-34c-3p, mir-34c-5p, mir-375, mir-383, mir-451, mir-452, mir-483-5p, mir-495, mir-584, mir-622, mir-656, mir-7, mir-98 |
| head and neck squamous cell carcinoma | let-7d, mir-1, mir-107, mir-128, mir-133a, mir-138, mir-149, mir-200c, mir-205, mir-218, mir-27a*, mir-29a, mir-29b-1, mir-29b-2, mir-29c, mir-300, mir-34a, mir-363, mir-375, mir-874 |
| hepatocellular carcinoma | let-7a-1, let-7a-2, let-7a-3, let-7b, let-7c, let-7d, let-7e, let-7f, let-7f-1, let-7f-2, let-7g, let-7i, mir-1, mir-100, mir-101, mir-105, mir-122, mir-122a, mir-1236, mir-124, mir-125b, mir-126, mir-127, mir-1271, mir-128-3p, mir-129-5p, mir-130a, mir-130b, mir-133a, mir-134, mir-137, mir-138, mir-139, mir-139-5p, mir-140-5p, mir-141, mir-142-3p, mir-143, mir-144, mir-145, mir-146a, mir-148a, mir-148b, mir-150-5p, mir-15b, mir-16, mir-181a-5p, mir-185, mir-188-5p, mir-193b, mir-195, mir-195-5p, mir-197, mir-198, mir-199a, mir-199a-5p, mir-199b, mir-199b-5p, mir-200a, mir-200b, mir-200c, mir-202, mir-203, mir-204-3p, mir-205, mir-206, mir-20a, mir-21, mir-21-3p, mir-211, mir-212, mir-214, mir-217, mir-218, mir-219-5p, mir-22, mir-223, mir-26a, mir-26b, mir-29a, mir-29b-1, mir-29b-2, mir-29c, mir-302b, mir-302c, mir-30a, mir-30a-3p, mir-335, mir-338-3p, mir-33a, mir-34a, mir-34b, mir-365, mir-370, mir-372, mir-375, mir-376a, mir-377, mir-422a, mir-424, mir-424-5p, mir-433, mir-4458, mir-448, mir-450a, mir-451, mir-485-5p, mir-486-5p, mir-497, mir-503, mir-506, mir-519d, mir-520a, mir-520b, mir-520c-3p, mir-582-5p, mir-590-5p, mir-610, mir-612, mir-625, mir-637, mir-675, mir-7, mir-877, mir-940, mir-941, mir-98, mir-99a |
| hypopharyngeal squamous cell carcinoma | mir-451a, mir-504 |
| kidney cancer | mir-1, mir-145, mir-1826, mir-199a, mir-199a-3p, mir-203, mir-205, mir-497, mir-508-3p, mir-509-3p |
| laryngeal squamous cell carcinoma | mir-129-5p, mir-203, mir-205, mir-206, mir-24, mir-370, mir-375 |
| liver cancer | mir-101, mir-122, mir-132, mir-140-5p, mir-145, mir-148b, mir-31, mir-338-3p, mir-433 |
| lung adenocarcinoma | mir-1297, mir-141, mir-145, mir-16, mir-200a, mir-200b, mir-200c, mir-29b, mir-381, mir-409-3p, mir-429, mir-451, mir-511, mir-99a |
| lung cancer | let-7a-1, let-7a-2, let-7a-3, let-7b, let-7c, let-7d, let-7e, let-7f-1, let-7f-2, let-7g, let-7i, mir-1, mir-101, mir-133b, mir-138, mir-142-5p, mir-144, mir-145, mir-1469, mir-146a, mir-153, mir-15a, mir-15b, mir-16-1, mir-16-2, mir-182, mir-192, mir-193a-3p, mir-194, mir-195, mir-198, mir-203, mir-217, mir-218, mir-22, mir-223, mir-26a, mir-26b, mir-29c, mir-33a, mir-34a, mir-34b, mir-34c, mir-365, mir-449a, mir-449b, mir-486-5p, mir-545, mir-610, mir-614, mir-630, mir-660, mir-7515, mir-9500, mir-98, mir-99b |
| lung squamous cell carcinoma | mir-133a, mir-218 |
| malignant melanoma | let-7b, mir-101, mir-125b, mir-1280, mir-143, mir-146a, mir-146b, mir-155, mir-17, mir-184, mir-185, mir-18b, mir-193b, mir-200c, mir-203, mir-204, mir-205, mir-206, mir-20a, mir-211, mir-218, mir-26a, mir-31, mir-33a, mir-34a, mir-34c, mir-376a, mir-376c, mir-573, mir-7-5p, mir-9, mir-98 |
| malignant mesothelioma | mir-126 |
| mantle cell lymphoma | mir-142-3p, mir-142-5p, mir-150, mir-223, mir-29a, mir-29b, mir-29c |
| medullary thyroid carcinoma | mir-129-5p |
| medulloblastoma | mir-124, mir-128a, mir-199b-5p, mir-206, mir-22, mir-31, mir-383 |
| meningioma | mir-128, mir-200a |
| mesenchymal cancer | mir-100, mir-141, mir-199b-5p, mir-200a, mir-200b, mir-200c, mir-29a, mir-29b-1, mir-29b-1-5p, mir-29b-2, mir-29c, mir-335, mir-429, mir-99a |
| monocytic leukemia | mir-29a, mir-29b |
| multiple myeloma | mir-137, mir-197, mir-214 |
| nasopharyngeal cancer | mir-218, mir-223, mir-29c |
| nasopharyngeal carcinoma | let-7a, let-7a-1, let-7a-2, let-7a-3, let-7b, let-7c, let-7d, let-7e, let-7f-1, let-7f-2, let-7g, let-7i, mir-1, mir-101, mir-124, mir-138, mir-143, mir-145, mir-148a, mir-200b, mir-204, mir-216b, mir-223, mir-29c, mir-320a, mir-324-3p, mir-34c, mir-375, mir-378, mir-451, mir-506, mir-9, mir-98 |
| neuroblastoma | let-7a-1, let-7a-2, let-7a-3, let-7b, let-7c, let-7d, let-7e, let-7f-1, let-7f-2, let-7g, let-7i, mir-124, mir-137, mir-145, mir-181c, mir-184, mir-200a, mir-29a, mir-335, mir-338-3p, mir-34a, mir-449a, mir-885-5p, mir-98 |

TABLE 3-continued

Complete list of tumor suppressive miRNAs and their relationship to cancer.

| Cancer | Down regulated tumor suppressive miR |
| --- | --- |
| non-small cell lung cancer | let-7a, let-7c, mir-1, mir-100, mir-101, mir-106a, mir-107, mir-124, mir-125a-3p, mir-125a-5p, mir-126, mir-126*, mir-129, mir-133a, mir-137, mir-138, mir-140, mir-143, mir-145, mir-146a, mir-146b, mir-148a, mir-148b, mir-149, mir-152, mir-153, mir-154, mir-155, mir-15a, mir-16, mir-17-5p, mir-181a-1, mir-181a-2, mir-181b, mir-181b-1, mir-181b-2, mir-181c, mir-181d, mir-184, mir-186, mir-193b, mir-195, mir-199a, mir-204, mir-212, mir-221, mir-224, mir-26b, mir-27a, mir-27b, mir-29a, mir-29b, mir-29c, mir-30a, mir-30b, mir-30c, mir-30d, mir-30d-5p, mir-30e-5p, mir-32, mir-335, mir-338-3p, mir-340, mir-342-3p, mir-34a, mir-34b, mir-361-3p, mir-365, mir-373, mir-375, mir-429, mir-449a, mir-4500, mir-451, mir-4782-3p, mir-497, mir-503, mir-512-3p, mir-520a-3p, mir-526b, mir-625*, mir-96, mir-99a |
| oral cancer | let-7d, mir-218, mir-34a, mir-375, mir-494 |
| oral carcinoma | mir-375 |
| oral squamous cell carcinoma | mir-100, mir-124, mir-1250, mir-125b, mir-126, mir-1271, mir-136, mir-138, mir-145, mir-147, mir-148a, mir-181a, mir-206, mir-220a, mir-26a, mir-26b, mir-29a, mir-32, mir-323-5p, mir-329, mir-338, mir-370, mir-410, mir-429, mir-433, mir-499a-5p, mir-503, mir-506, mir-632, mir-646, mir-668, mir-877, mir-9 |
| osteosarcoma | let-7a, mir-1, mir-100, mir-101, mir-122, mir-124, mir-125b, mir-126, mir-127-3p, mir-132, mir-133a, mir-141, mir-142-3p, mir-142-5p, mir-143, mir-144, mir-145, mir-153, mir-16, mir-183, mir-194, mir-195, mir-199a-3p, mir-204, mir-212, mir-217, mir-218, mir-22, mir-23a, mir-24, mir-26a, mir-26b, mir-29b, mir-32, mir-320, mir-335, mir-33b, mir-340, mir-34a, mir-34b, mir-34c, mir-375, mir-376c, mir-382, mir-3928, mir-424, mir-429, mir-449a, mir-451, mir-454, mir-503, mir-519d, mir-646 |
| ovarian cancer | let-7i, mir-100, mir-124, mir-125b, mir-129-5p, mir-130b, mir-133a, mir-137, mir-138, mir-141, mir-145, mir-148a, mir-152, mir-153, mir-155, mir-199a, mir-200a, mir-200b, mir-200c, mir-212, mir-335, mir-34a, mir-34b, mir-34c, mir-409-3p, mir-411, mir-429, mir-432, mir-449a, mir-494, mir-497, mir-498, mir-519d, mir-655, mir-9, mir-98 |
| ovarian carcinoma | mir-100, mir-101, mir-34b, mir-34c, mir-532-5p |
| pancreatic cancer | mir-101, mir-1181, mir-124, mir-1247, mir-133a, mir-141, mir-145, mir-146a, mir-148a, mir-148b, mir-150*, mir-150-5p, mir-152, mir-15a, mir-198, mir-203, mir-214, mir-216a, mir-29c, mir-335, mir-34a, mir-34b, mir-34c, mir-373, mir-375, mir-410, mir-497, mir-615-5p, mir-630, mir-96 |
| pancreatic carcinoma | mir-132, mir-375 |
| pancreatic ductal adenocarcinoma | let-7a, let-7a-1, let-7a-2, let-7a-3, let-7b, let-7c, let-7d, let-7e, let-7f-1, let-7f-2, let-7g, let-7i, mir-126, mir-135a, mir-143, mir-144, mir-145, mir-148a, mir-150, mir-15a, mir-16, mir-200a, mir-200b, mir-200c, mir-217, mir-218, mir-337, mir-375, mir-494, mir-615-5p, mir-98 |
| papillary thyroid carcinoma | mir-101, mir-130b, mir-138, mir-146a, mir-16, mir-195, mir-199a-3p, mir-204-5p, mir-219-5p, mir-26a, mir-34b, mir-613 |
| primary cns lymphomas | mir-145, mir-193b, mir-199a, mir-214 |
| primary gallbladder carcinoma | mir-335 |
| primary thyroid lymphoma | mir-26a |
| prostate cancer | let-7a-3p, let-7c, mir-100, mir-101, mir-105, mir-124, mir-128, mir-1296, mir-130b, mir-133a-1, mir-133a-2, mir-133b, mir-135a, mir-143, mir-145, mir-146a, mir-154, mir-15a, mir-187, mir-188-5p, mir-199b, mir-200b, mir-203, mir-205, mir-212, mir-218, mir-221, mir-224, mir-23a, mir-23b, mir-25, mir-26a, mir-26b, mir-29b, mir-302a, mir-30a, mir-30b, mir-30c-1, mir-30c-2, mir-30d, mir-30e, mir-31, mir-330, mir-331-3p, mir-34a, mir-34b, mir-34c, mir-374b, mir-449a, mir-4723-5p, mir-497, mir-628-5p, mir-642a-5p, mir-765, mir-940 |
| prostate carcinoma | mir-107 |
| renal cell carcinoma | let-7a, let-7d, mir-1, mir-106a*, mir-126, mir-1285, mir-129-3p, mir-1291, mir-133a, mir-135a, mir-138, mir-141, mir-143, mir-145, mir-182-5p, mir-199a-3p, mir-200a, mir-205, mir-218, mir-28-5p, mir-30a, mir-30c, mir-30d, mir-34a, mir-378, mir-429, mir-509-3p, mir-509-5p, mir-646 |
| renal clear cell carcinoma | let-7b, let-7c, mir-138, mir-141, mir-200c, mir-204, mir-218, mir-335, mir-377, mir-506 |
| retinoblastoma | mir-101, mir-183, mir-204, mir-34a, mir-365b-3p, mir-486-3p, mir-532-5p |
| rhabdomyosarcoma | mir-203 |
| small cell lung cancer | mir-126, mir-138, mir-27a |
| splenic marginal zone lymphoma | mir-223 |
| squamous carcinoma | mir-15a, mir-16, mir-203, mir-205, mir-375 |
| t-cell lymphoma | mir-22 |
| thyroid cancer | mir-144, mir-886-3p |
| tongue cancer | mir-15b, mir-200b |
| uterine leiomyoma | mir-197 |

TABLE 3-continued

Complete list of tumor suppressive miRNAs and their relationship to cancer.

| Cancer | Down regulated tumor suppressive miR |
|---|---|
| uveal melanoma | mir-137, mir-144, mir-145, mir-182, mir-34a, mir-34b, mir-34c, mir-9 |

TABLE 4

List of examples of oncogenic miRNA relationships to cancer.

| Cancer | miRNA |
|---|---|
| colorectal cancer | let-7a, mir-103, mir-106a, mir-10b, mir-1179, mir-1229, mir-1246, mir-125b-2*, mir-1269a, mir-130b, mir-133b, mir-135a, mir-135a-1, mir-135a-2, mir-135b, mir-139-3p, mir-145, mir-150, mir-150*, mir-155, mir-17, mir-181a, mir-182, mir-183, mir-18a, mir-191, mir-196a, mir-196b, mir-19a, mir-19b, mir-200b, mir-200c, mir-203, mir-204-5p, mir-20a, mir-20a-5p, mir-21, mir-210, mir-211, mir-221, mir-223, mir-224, mir-23a, mir-25, mir-27a, mir-29a, mir-301a, mir-31, mir-32, mir-320b, mir-326, mir-424, mir-429, mir-494, mir-497, mir-499-5p, mir-592, mir-630, mir-720, mir-892a, mir-92, mir-92a, mir-93, mir-95, mir-96 |
| papillary thyroid carcinoma | let-7e, mir-146b, mir-146b-5p, mir-151-5p, mir-155, mir-181a-1, mir-181a-2, mir-181b-1, mir-181b-2, mir-181c, mir-181d, mir-182, mir-183, mir-199b-5p, mir-21, mir-221, mir-222, mir-339-5p, mir-34a |
| esophageal squamous cell carcinoma | mir-100, mir-1179, mir-1290, mir-130b, mir-145, mir-16, mir-17, mir-183, mir-18a, mir-19a, mir-19b, mir-208, mir-20a, mir-21, mir-218, mir-223, mir-25, mir-30a-5p, mir-31, mir-330-3p, mir-373, mir-9, mir-92a, mir-942 |
| gastric cancer | mir-100, mir-103, mir-106a, mir-106b, mir-107, mir-10a, mir-10b, mir-1259, mir-125b, mir-126, mir-1274a, mir-1303, mir-130b*, mir-135a-5p, mir-135b, mir-138, mir-143, mir-146a, mir-147, mir-148a, mir-150, mir-17, mir-17-5p, mir-181a, mir-181a-2*, mir-181a-5p, mir-181c, mir-183, mir-185, mir-18a, mir-191, mir-192, mir-196a, mir-196a*, mir-196a-5p, mir-196b, mir-199a, mir-199a-3p, mir-199a-5p, mir-19a, mir-19b, mir-200b, mir-20a, mir-21, mir-214, mir-215, mir-221, mir-221*, mir-222, mir-223, mir-224, mir-23a, mir-23b, mir-25, mir-27a, mir-27b, mir-296-5p, mir-301a, mir-302f, mir-337-3p, mir-340*, mir-34a, mir-362-3p, mir-370, mir-374a, mir-377, mir-421, mir-425, mir-500, mir-520c-3p, mir-544, mir-575, mir-601, mir-616*, mir-650, mir-92, mir-98, mir-99a |
| renal cell carcinoma | mir-100, mir-1233, mir-1260b, mir-146a, mir-146b, mir-16, mir-193a-3p, mir-203a, mir-21, mir-210, mir-27a, mir-362, mir-572, mir-7 |
| esophageal cancer | mir-101, mir-10b, mir-130a, mir-141, mir-143, mir-146b, mir-15a, mir-183, mir-196b, mir-200a, mir-203, mir-205, mir-21, mir-210, mir-221, mir-27a, mir-28-3p, mir-31, mir-452, mir-96, mir-99b |
| bladder cancer | mir-103a-3p, mir-10b, mir-135a, mir-137, mir-141, mir-155, mir-17-5p, mir-182, mir-182-5p, mir-183, mir-185, mir-19a, mir-203, mir-205, mir-210, mir-221, mir-222, mir-223, mir-23a, mir-23b, mir-26b, mir-639, mir-96 |
| endometrial cancer | mir-106a, mir-145, mir-155, mir-182, mir-200b, mir-200c, mir-205, mir-21, mir-222-3p, mir-25, mir-93 |
| ovarian cancer | mir-106a, mir-141, mir-148b, mir-181b, mir-182, mir-200a, mir-200c, mir-205, mir-20a, mir-21, mir-210, mir-214, mir-221, mir-224-5p, mir-23b, mir-25, mir-26a, mir-27a, mir-27b, mir-346, mir-378, mir-424, mir-503, mir-572, mir-9, mir-96 |
| glioma | mir-106b, mir-106b-5p, mir-10b, mir-125b, mir-132, mir-155, mir-17, mir-181a, mir-182, mir-183, mir-193b, mir-19a, mir-19b, mir-20a, mir-210, mir-214, mir-221, mir-222, mir-224, mir-23a, mir-24, mir-24-3p, mir-25, mir-26a, mir-27a-3p, mir-27b, mir-30a-5p, mir-30e, mir-30e*, mir-328, mir-335, mir-33a, mir-372, mir-486, mir-494, mir-497, mir-566, mir-603, mir-650, mir-675, mir-9, mir-92b, mir-93, mir-96 |
| head and neck squamous cell carcinoma | mir-106b, mir-134, mir-16, mir-184, mir-196a, mir-21, mir-25, mir-30a-5p, mir-31, mir-372, mir-93 |
| hepatocellular carcinoma | mir-106b, mir-10b, mir-122, mir-1228, mir-1269, mir-128a, mir-130a, mir-130b, mir-146a, mir-153, mir-155, mir-17-5p, mir-181a, mir-181a-1, mir-181a-2, mir-181b, mir-181b-1, mir-181b-2, mir-181c, mir-181d, mir-182, mir-183, mir-184, mir-190b, mir-191, mir-20a, mir-20b, mir-21, mir-210, mir-214, mir-215, mir-216a, mir-217, mir-221, mir-222, mir-223, mir-224, mir-23a, mir-24, mir-25, mir-27a, mir-301a, mir-30d, mir-31, mir-3127, mir-32, mir-331-3p, mir-362-3p, mir-362-5p, mir-371-5p, mir-372, mir-373, mir-423, mir-429, mir-452, mir-483-3p, mir-483-5p, mir-485-3p, mir-490-3p, mir-494, mir-495, mir-500, mir-501, mir-501-5p, mir-519d, mir-520g, mir-574-3p, mir-590-5p, mir-630, mir-650, mir-657, mir-664, mir-885-5p, mir-9, mir-92a, mir-96 |
| laryngeal carcinoma | mir-106b, mir-16, mir-21, mir-27a, mir-423-3p |
| medulloblastoma | mir-106b, mir-17, mir-18a, mir-19a, mir-19b, mir-20a, mir-30b, mir-30d, mir-92 |

TABLE 4-continued

List of examples of oncogenic miRNA relationships to cancer.

| Cancer | miRNA |
| --- | --- |
| pituitary carcinoma | mir-106b, mir-122, mir-17-5p, mir-20a, mir-493 |
| cervical cancer | mir-10a, mir-155, mir-181a, mir-181b, mir-196a, mir-19a, mir-19b, mir-205, mir-20a, mir-21, mir-215, mir-224, mir-31, mir-494, mir-590-5p, mir-92a, mir-944 |
| pancreatic cancer | mir-10a, mir-10b, mir-132, mir-15a, mir-17-5p, mir-181a, mir-18a, mir-191, mir-196a, mir-21, mir-212, mir-214, mir-221, mir-222, mir-27a, mir-301a, mir-301a-3p, mir-367, mir-424-5p, mir-7, mir-92, mir-99a |
| breast cancer | mir-10b, mir-125a, mir-135a, mir-140, mir-141, mir-142, mir-150, mir-155, mir-17, mir-17-5p, mir-181a, mir-181b, mir-182, mir-18a, mir-18b, mir-191, mir-196a, mir-197, mir-19a, mir-19b, mir-200a, mir-200b, mir-200c, mir-203, mir-205, mir-20a, mir-20b, mir-21, mir-217, mir-221, mir-222, mir-224, mir-23a, mir-24, mir-24-2-5p, mir-24-3p, mir-27a, mir-29a, mir-29b-1, mir-29b-2, mir-29c, mir-373, mir-378, mir-423, mir-429, mir-495, mir-503, mir-510, mir-520c, mir-526b, mir-96 |
| glioblastoma | mir-10b, mir-125b, mir-127-3p, mir-148a, mir-18a, mir-196a, mir-196a-1, mir-196a-2, mir-196b, mir-21, mir-210, mir-210-3p, mir-223, mir-340, mir-576-5p, mir-626, mir-92b |
| lung cancer | mir-10b, mir-135b, mir-150, mir-155, mir-17, mir-182, mir-183-3p, mir-18a, mir-197, mir-19a, mir-19b, mir-205, mir-20a, mir-21, mir-210, mir-24, mir-30d, mir-4423, mir-5100, mir-570, mir-663, mir-7, mir-92a |
| nasopharyngeal carcinoma | mir-10b, mir-144, mir-149, mir-155, mir-18a, mir-21, mir-214, mir-24, mir-421, mir-663, mir-744, mir-93 |
| non-small cell lung cancer | mir-10b, mir-125a-5p, mir-1280, mir-136, mir-140, mir-141, mir-142-3p, mir-145, mir-146a, mir-150, mir-18a, mir-196a, mir-19a, mir-200a, mir-200c, mir-205, mir-205-3p, mir-205-5p, mir-21, mir-212, mir-22, mir-221, mir-222, mir-24, mir-25, mir-29c, mir-31, mir-328, mir-330-3p, mir-339, mir-34a, mir-375, mir-494, mir-675-5p, mir-9, mir-92b, mir-93, mir-95 |
| oral cancer | mir-10b, mir-196a-1, mir-196a-2, mir-196b, mir-21 |
| pancreatic ductal adenocarcinoma | mir-10b, mir-186, mir-18a, mir-192, mir-194, mir-196a, mir-198, mir-203, mir-21, mir-212, mir-30b-5p, mir-31, mir-34a, mir-369-5p, mir-376a, mir-541 |
| renal clear cell carcinoma | mir-122, mir-155, mir-210, mir-630 |
| mantle cell lymphoma | mir-124a, mir-155, mir-17, mir-18a, mir-19a, mir-19b, mir-20a, mir-92a |
| acute myeloid leukemia | mir-125b, mir-126-5p, mir-128, mir-155, mir-29a, mir-32, mir-331, mir-370, mir-378 |
| follicular cancer | mir-125b |
| neuroblastoma | mir-125b, mir-15a, mir-15b, mir-16-1, mir-16-2, mir-18a, mir-195, mir-19a, mir-23a, mir-421, mir-92 |
| oral squamous cell carcinoma | mir-125b, mir-126, mir-146a, mir-146b, mir-155, mir-181b, mir-196a-1, mir-196a-2, mir-196b, mir-21, mir-221, mir-222, mir-24, mir-27b, mir-31, mir-345 |
| prostate cancer | mir-125b, mir-141, mir-153, mir-155, mir-181a-1, mir-181a-2, mir-181b, mir-181b-1, mir-181b-2, mir-181c, mir-181d, mir-182, mir-182-5p, mir-183, mir-18a, mir-204, mir-20a, mir-21, mir-221, mir-223-3p, mir-31, mir-429, mir-96 |
| mesenchymal cancer | mir-125b-1-3p, mir-182 |
| malignant melanoma | mir-126, mir-141, mir-15b, mir-17, mir-17-5p, mir-182, mir-18a, mir-193b, mir-200a, mir-200b, mir-200c, mir-20a, mir-21, mir-210, mir-214, mir-221, mir-222, mir-429, mir-455-5p, mir-532-5p, mir-638, mir-92a |
| acute lymphoblastic leukemia | mir-128 |
| osteosarcoma | mir-128, mir-151-3p, mir-17, mir-181a, mir-181b, mir-181c, mir-18a, mir-191, mir-195-5p, mir-199a-3p, mir-19a, mir-19b, mir-20a, mir-21, mir-210, mir-214, mir-221, mir-27a, mir-300, mir-320a, mir-374a-5p, mir-802, mir-9, mir-92a |
| colon cancer | mir-1290, mir-145, mir-155, mir-181a, mir-18a, mir-200c, mir-31, mir-675 |
| liver cancer | mir-1301, mir-155, mir-21, mir-221, mir-27a, mir-525-3p |
| cervical carcinoma | mir-133b, mir-21, mir-25, mir-373 |
| squamous carcinoma | mir-137, mir-155, mir-184, mir-196a, mir-203, mir-21, mir-221, mir-27a, mir-34a |
| chordoma | mir-140-3p, mir-148a |
| clear cell renal cell cancer | mir-142-5p, mir-155, mir-21-5p |
| malt lymphoma | mir-142-5p, mir-155 |
| anaplastic thyroid carcinoma | mir-146b, mir-221, mir-222 |
| follicular thyroid carcinoma | mir-146b, mir-183, mir-197, mir-221, mir-346 |
| primary thyroid lymphoma | mir-146b |
| ovarian carcinoma | mir-148b, mir-182 |
| adult t-cell leukemia | mir-150 |
| chronic lymphocytic leukemia | mir-150, mir-155 |

TABLE 4-continued

List of examples of oncogenic miRNA relationships to cancer.

| Cancer | miRNA |
| --- | --- |
| lung adenocarcinoma | mir-150, mir-155, mir-31 |
| anaplastic large-cell lymphoma | mir-155 |
| cutaneous t-cell lymphoma | mir-155 |
| diffuse large B-cell lymphoma | mir-155, mir-21 |
| gallbladder carcinoma | mir-155, mir-182 |
| rectal cancer | mir-155, mir-200c, mir-21-5p, mir-34a |
| b-cell lymphoma | mir-17, mir-18a, mir-19a, mir-19b, mir-20a, mir-92a |
| breast carcinoma | mir-17, mir-18a, mir-19a, mir-19b, mir-20a, mir-24, mir-92a |
| cholangiocarcinoma | mir-17, mir-18a, mir-19a, mir-19b, mir-20a, mir-21, mir-26a, mir-92a |
| colorectal carcinoma | mir-17, mir-182, mir-191, mir-21, mir-95 |
| nasopharyngeal cancer | mir-17, mir-20a |
| acute promyelocytic leukemia | mir-181a, mir-181b, mir-92a |
| retinoblastoma | mir-181b, mir-21 |
| colorectal adenocarcinoma | mir-182 |
| kidney cancer | mir-183, mir-21, mir-210, mir-223 |
| medullary thyroid carcinoma | mir-183 |
| esophageal adenocarcinoma | mir-196a, mir-199a-3p, mir-199a-5p, mir-199b-3p, mir-200a, mir-223 |
| gastrointestinal stromal tumor | mir-196a |
| hypopharyngeal cancer | mir-203 |
| pancreatic adenocarcinoma | mir-203, mir-301a |
| cervical squamous cell carcinoma | mir-205 |
| adrenal cortical carcinoma | mir-21, mir-210, mir-483-3p, mir-483-5p |
| head and neck cancer | mir-21 |
| hypopharyngeal squamous cell carcinoma | mir-21 |
| laryngeal squamous cell carcinoma | mir-21, mir-9, mir-93 |
| multiple myeloma | mir-21 |
| colon carcinoma | mir-221, mir-23a |
| thyroid carcinoma | mir-221, mir-222 |
| meningioma | mir-224, mir-335 |
| gastric adenocarcinoma | mir-23a, mir-27a, mir-373 |
| laryngeal cancer | mir-23a |
| small cell lung cancer | mir-25 |
| pancreatic carcinoma | mir-301b |
| oral carcinoma | mir-31 |
| astrocytoma | mir-335 |
| epithelial ovarian cancer | mir-372, mir-373 |
| chronic myelogenous leukemia | mir-424, mir-96 |
| hepatoblastoma | mir-492 |

TABLE 5

Summary of microRNA/MMP linked interactions in cancer.

| microRNA | MMP Type and target molecule | Cancer type | Phenotype | Pathway |
| --- | --- | --- | --- | --- |
| let-7 | MMP-9 | Melanoma | Cell proliferation and migration | — |
| let-7 | MMP-14, ERK1/2 activation | Pancreatic ductal adenocarcinoma | NA | ERK1/2 activation, TGF-β1 signaling |
| let-7 | Focal adhesion kinase (FAK), AKT, ERK, MMP-2 and MMP-9 | Glioblastoma | Migration and invasion | AKT and ERK |
| miR-9 | MMP-2, MMP-9 and VEGFA | Uveal melanoma | Migration and invasion | NF-κB1 signaling |

TABLE 5-continued

Summary of microRNA/MMP linked interactions in cancer.

| microRNA | MMP Type and target molecule | Cancer type | Phenotype | Pathway |
|---|---|---|---|---|
| miR-9 | MMP-14 | Neuroblastoma | Invasion, metastasis, and angiogenesis | — |
| miR-10b | MMP-9, E-cadherin and vimentin | Nasopharyngeal carcinoma cells | Proliferation, migration, invasion | — |
| miR-10b | MMP-14 and uPAR | Glioma | Cell invasiveness | — |
| miR-10b | MMP-2, EGFR. | Glioblastoma multiforme | Apoptosis invasion and migration | EGFR pathways |
| miR-15b | MMP-3 | Glioma | Cell invasiveness | MEK-ERK pathway |
| miR-17 | MMP-3 | Hepatocellular carcinoma | Migration and invasion | p-AKT |
| miR-21 | RECK, MMP-9 | Prostate cancer | NA | — |
| miR-21 | Phospho-c-Jun, MMP-2, MMP-9 | Hepatocellular carcinoma | Migration and invasion | — |
| miR-21 | RECK, MMP-2 | Glioma | Apoptosis, migration, and invasiveness | — |
| miR-21 | MMP-2, EGFR. | Glioblastoma multiforme | Apoptosis invasion and migration | EGFR pathways |
| miR-26a | MMP-2 | Lung cancer | Migration, invasion and metastasis | AKT phosphorylation |
| miR-29b | MMP-2 | Colon cancer | Migration | — |
| miR-29b | MMP-2 | Hepatocellular carcinoma | Tumor angiogenesis, invasion, and metastasis | VEGFR-2-signaling |
| miR-29b | MMP-2, Mcl-1, COL1A1, and COL4A1 | Prostate cancer | invasion and metastasis | — |
| miR-29c | MMP-2 | Nerve sheath tumours | Cell invasion and migration | — |
| miR-30d | SOCS1, phospho-STAT3, MMP-2 and MMP-9 | Prostate cancer | Proliferation and invasion | STAT3 signalling |
| miR-34a | Fra-1, p53 MMP-1 and MMP-9 | Colon cancer | Migration and invasion | — |
| miR-92a | MMP-2 and -9 | Lung cancer | Migration and invasion | STAT3 signaling |
| miR-101 | Enhancer of zeste homolog 2 (EZH2), CDH1 and MMP-2 | Lung cancer | Cell invasiveness | — |
| miR-106b | MMP-2 | Breast cancer | Migration and invasion | ERK signaling cascade |
| miR-125b | MMP-2 and MMP-9 | Glioblastoma | Invasion | — |
| miR-133 | MMP-14 | Lung cancer | Cell proliferation, migration and invasion | — |
| miR-138 | RhoC, MMP-2 and MMP-9 | Cholangiocarcinoma | Proliferation, migration and invasion | p-ERK signaling |
| miR-139 | IGF-IR and MMP-2 | Colorectal cancer | Migration, invasion and metastasis | IGF-IR/MEK/ERK signaling |
| miR-143 | MMP-13 | Prostate cancer | Migration and invasion | — |
| miR-143 | MMP-2 and MMP-9 | Pancreatic cancer | Migration and invasion | — |
| miR-143 | MMP-13 | Osteosarcoma | Cell invasiveness | — |
| miR-145 | Ets1, MMP-1 and -9 | Gastric cancer | Invasion, metastasis, and angiogenesis | — |
| miR-146a | MMP-1, uPA, and uPAR | Brain cancer | Migration, invasion and metastasis | — |
| miR-146a | MMP-16 | Colon cancer | Invasion | — |
| miR-149 | MMP-2 and CyclinD1 | Glioma | Proliferation and invasion | AKT signaling |
| miR-152 | MMP-3 | Glioma | Cell invasiveness | MEK-ERK pathway |
| miR-181b | MMP-2 and MMP-9 | Hepatocellular carcinomas | Migration and invasion | TGF-β, Smad signaling |
| miR-182 | MMP-9, RECK | Breast cancer | cell invasion and colony formation ability | — |
| miR-196b | Vimentin, MMP-2 and MMP-9 | Gastric cancer | Migration and invasion | — |
| miR-203 | MMP-9 and Robo1 | Glioblastoma | Proliferation, migration, and invasion | ERK phosphorylation |
| miR-206 | MMP-2 and MMP-9 | Breast cancer | Invasion and migration | — |
| miR-211 | MMP-9 | Glioblastoma multiforme | Cell invasion and migration | — |
| miR-218 | LEF1, MMP-2, -7 and -9 | Glioblastoma multiforme | Invasion | — |
| miR-218 | MMP-9 | Gliomas | Cell invasiveness | IKK-β/NF-κB pathway |
| miR-224 | MMP-9 via targeting HOXD10 | Human hepatocellular carcinoma | Migration and invasion | — |
| miR-338-3p | SMO and MMP-9 | Hepatocellular carcinoma | Invasion and metastasis | — |
| miR-340 | MMP-2 and MMP-9 | Breast cancer | Tumor cell growth, migration, and invasion | — |
| miR-430 | ERK, MMP-2 and MMP-9 | Bladder cancer | Proliferation, migration and colony formation ability | — |

TABLE 5-continued

Summary of microRNA/MMP linked interactions in cancer.

| microRNA | MMP Type and target molecule | Cancer type | Phenotype | Pathway |
|---|---|---|---|---|
| miR-451 | Akt1, CyclinD1, MMP-2, MMP-9 and Bcl-2 | Glioblastoma | Proliferation, invasion and apoptosis | PI3K/AKT signaling |
| miR-491 | MMP-9 | Hepatocellular carcinoma | Migration | — |
| miR-491-5p | MMP-9 | Glioblastoma multiforme | Invasion | — |
| miRNA-590-3p | PI3K, Akt, MMP-2 and MMP-9 | Bladder cancer | Proliferation, migration and colony-formation | PI3K, Akt signaling |
| miR-874 | MMP-2 and -9, Aquaporin-3 | Human gastric cancer | Cell migration and invasion assays and in vivo tumorigenicity | — |
| miR-874 | MMP-2 and uPA | Non-small cell lung cancer | Tumor cell invasiveness and in vivo tumor growth | — |
| miR-885-5p | MMP-9 | Glioblastoma multiforme | Invasion | — |

TABLE 6

Target proteases and cancers associated with their overexpression.

| Family | Protease | Location | Cancer |
|---|---|---|---|
| Cysteine Cathepsins | General | Intracellular, lysosomes | Most |
|  | Cathepsin K | Extracellular, bone | Breast |
|  | Cathepsin B | Extracellular and pericellular under pathological conditions | Breast, cervix, colon, colorectal, gastric, head and neck, liver, lung, melanoma, ovarian, pancreatic, prostate, thyroid |
|  | Cathepsin L |  | Breast, colorectal |
| Aspartic Cathepsins | Cathepsin E | Endosomal structures, ER, Golgi | Cervical, gastric, lung, pancreas adenocarcinomas |
|  | Cathepsin D | Lysosome | Breast, colorectal, ovarian |
| Kallikreins (hK) | General hK1 | Intracellular, secreted | Most |
|  | PSA (hK 3) |  | Prostate, ovarian |
|  | hK10 |  | Colon, ovarian, pancreatic, head and neck |
|  | hK15 |  | Ovarian, prostate |
| Serine Proteases | uPA, uPAR | Membrane, Pericellular | Cervical, colorectal, gastric, prostate |
| Caspases |  | Intracellular |  |
| MMPs | General | Extracellular | Most |
|  | MMP-1, -8, -13 |  | Breast |
|  | MMP-2, -9 |  | Breast, colorectal, lung, malignant gliomas, ovarian |
|  | MMP-14 | Membrane | Breast |
| ADAM |  | Extracellular |  |

TABLE 7

List of selected oncogenes associated with human malignancy

| Gene Name | Gene Locus | Malignancies associated with | Comments |
|---|---|---|---|
| ABL1 (ABL) | 9q34.1 | Chronic myeloid leukemia | see tyrosine kinase Abelson murine leukemia protein |
| ABL2 (ABLL, ARG) | 1q24-q25 | acute myeloid leukemia | Member of the tyrosine kinase family. Important for synapse assembly and remodeling |
| AKAP13 (HT31, LBC. BRX) | 15q24-q25 | breast cancer | Blast crisis oncogene |
| ARAF1 | Xp11.4-p11.2 | angioimmunoblastic lymphadenopathy with dysproteinemia | Serine/threonine kinase |
| ARHGEF5 (TIM) | 7q33-q35 | Breast cancer | Codes for protein that controls cytoskeletal organization through regulation of small GTP-binding proteins |
| ATF1 | 12q13 | ATF1/EWS fusion gene associated with malignant melanoma of soft parts (MMSP) ATF1/FUS with histiocytoma. | Codes for cAMP-dependent transcription factor-1 |

TABLE 7-continued

List of selected oncogenes associated with human malignancy

| Gene Name | Gene Locus | Malignancies associated with | Comments |
| --- | --- | --- | --- |
| AXL | 19q13.1-q13.2 | Chronic myelogenous leukemia | transforming gene to acute leukemia |
| BCL2 | 18q21.3 | Burkitt lymphoma, follicular lymphoma | Mediator of apoptosis. Translocation is marker of poorer therapeutic response |
| BRAF (BRAF1, RAFB1) | 7q34 | Hairy cell leukemia, Malignant melanoma, thyroid papillary cancer, thyroid anaplastic carcinoma, bowel cancer, adenocarcinoma of lung, non-Hogkins lymphoma | see proto-oncogenes |
| BRCA1 | 17q21 | Hereditary breast-ovarian cancer syndrome. Familial Breast cancer, Papillary serous carcinoma of the peritoneum (PSCP), Prostate cancer | see BRCA1. |
| BRCA2(FANCD1) | 13q12.3 | Familial Breast cancer, prostate cancer, pancreatic cancer | see BRCA2 |
| BRIP1 | 17q22.2 | Ovarian cancer, breast cancer | BRCA1 interacting protein C-terminal helicase 1 which is important in normal double-strand break repair |
| CBL (CBL2) | 11q23.3 | | see proto-oncogenes |
| CSF1R (CSF-1, FMS, MCSF) | 5q33.2-q33.3 | Type M4 acute myeloblastic leukemia and chronic myelomonocytic leukemia | Codes for colony-stimulating factor-1 receptor, otherwise known as macrophage colony-stimulating factor |
| DAPK1 (DAPK) | 9q34.1 | Bladder cancer | Codes for death-associated protein kinase a positive mediators of apoptosis induced by gamma-interferon. |
| DEK (D6S231E) | 6p23 | DEK/NUP214(DEK/CAN) fusion gene associated with acute myeloid leukemia | Codes for DNA binding protein involved in transcriptional regulation and signal transduction as a component of the splicing complex that remains associated with spliced exons. |
| DUSP6 (MKP3, PYST1) | 12q22-q23 | Non-small cell lung cancer, pancreatic cancer | Codes for member of mitogen-activated protein (MAP) kinase family and has key role in cellular signal transduction |
| EGF | | | see proto-oncogenes |
| EGFR (ERBB, ERBB1) | | | see proto-oncogenes |
| ERBB3 (HER3) | 12q13 | Non-small cell lung cancer | elevated ERBB3 mRNA levels in breast cancer |
| ERG | | | see proto-oncogenes |
| ETS1 | | | see proto-oncogenes |
| ETS2 | | Acute myeloid leukemia | Codes for a transcription factor |
| EWSR1 (EWS, ES, PNE,) | 22q12 | EWS/ERG in Ewing sarcoma, esthesioneuroblastoma EWS/FEV fusion gene in Ewing sarcoma, EWS/ZNF278 in small round cell sarcoma, EWS/FLI1 in Ewing sarcoma, EWS/ATF1 in malignant melanoma of soft parts (MMSP) EWS/WT1 in desmoplastic small round cell tumor | Ewing sarcoma breakpoint 1 gene |
| FES (FPS) | 15q26.1 | B cell lymphoma, acute promyelocytic leukemia, bladder carcinoma, lung cancer, breast cancer, colon cancer, neuroblastoma, pre-B lymphocyte neoplasm, plasmacytoma, multiple myeloma, T cell lymphoma, sarcoma | Codes for a tyrosine-specific protein kinase with a role in regulating immune response |
| FGF4 (HSTF1, KFGF) | 11q13 | Stomach cancer, kaposi sarcoma | A fibroblast growth factor Important in limb development. |
| FGFR1 | | | see proto-oncogenes |
| FGFR1OP (FOP) | 6q27 | FGFR1/FGFR1OP2 fusion gene in non-Hodgkin lymphoma | |
| FLCN | 17p11.2 | Renal cancer, bowel cancer | see FFCN |
| FOS (c-fos) | 14q24.3 | | see proto-oncogenes |
| FRAP1 | | | see tumor suppressors |
| FUS (TLS) | 16p11.2 | | see proto-oncogenes |

TABLE 7-continued

List of selected oncogenes associated with human malignancy

| Gene Name | Gene Locus | Malignancies associated with | Comments |
|---|---|---|---|
| HRAS | 11p15.5 | | see proto-oncogenes. |
| GLI1 | 12q13.2-q13.3 | Glioma, myxoid liposarcoma, salivary gland tumor | Codes for a Kruppel (Kr) zinc finger protein |
| GLI2 | 2q14 | Glioma | Codes for a Kruppel (Kr) zinc finger protein |
| GPC3 | Xq26 | Germ cell cancer, Hepatocellular cancer | see GPC3 |
| HER2 (ERBB2, TKR1, NEU) | 17q21.1 | Breast cancer, lung cancer | see HER2. Targeted by Trastuzumab. |
| HGF (SF) | 7q21.1 | Prostate cancer, renal cancer | Codes for hepatocyte growth factor (hepatopoietin A, scatter factor) which is upregulated in many malignancies |
| IRF4 (LSIRF, MUM1) | 6p25-p23 | B-cell lymphoma, B-cell leukemia, Multiple myeloma | Codes for an interferon regulatory factor essential for lymphocyte function |
| JUNB | 19p13.2 | | see proto-oncogenes |
| KIT(SCFR) | 4q12 | Gastrointestinal stromal tumor (GISTs), mast cell leukemia, mastocytosis, seminoma and dysgerminoma | Transmembrane tyrosine kinase receptor for stem cell factor (SCFR) is required for haematopoiesis, melanogenesis and gametogenesis. Mutations cause piebaldism. |
| KRAS2 (RASK2) | 12p12.1 | | see proto-oncogenes. |
| LCK | 1p35-p34.3 | Non-small cell lung cancer, Neuroblastoma, non-Hodgkin lymphoma | codes for lymphocyte specific protein tyrosine kinase |
| LCO | 2q14-q21 | Hepatocellular carcinoma | |
| MAP3K8(TPL2, COT, EST) | 10p11.2 | Ewings sarcoma, adenocarcinoma of lung, thyroid carcinoma | Codes for a serine-threonine protein kinase. |
| MCF2 (DBL) | Xq27 | Breast cancer | Codes for a GDP-GTP exchange factor that modulates the activity of small GTPases of the Rho family |
| MDM2 | 12q14.3-q15 | Multiple | MDM2 acts as a major regulator of the tumor suppressor p53 by targeting its destruction. Direct association of p53 with the protein MDM2 results in ubiquitination and subsequent degradation of p53 |
| MET(HGFR, RCCP2) | 7q31 | | see proto-oncogenes |
| MLH type genes | | | see proto-oncogenes |
| MMD | 17q | Non small cell lung cancer, hepatocellular carcinoma, colon cancer | Codes for monocyte to macrophage differentiation associated protein. |
| MOS (MSV) | 8q11 | Burkitt lymphoma, acute myeloblastic leukemia | Function in man unknown. Above associations indirect but analogous gene to Moloney murine sarcoma virus. |
| MRAS (RRAS3) | 3q22.3 | Activated in many tumors | Codes for a RAS GTP-binding protein membrane-anchored, intracellular signal transducer |
| MSH type genes | | | see proto-oncogenes |
| MYB (AMV) | 6q22 | Alterations found in more than a third of human solid tumor lines | Encodes for proteins critical to hematopoietic cell proliferation and development |
| MYC | 8q24.12-q24.13 | Burkitt lymphoma Over expression in many malignancies, possibly associated with angiogenic, invasive promoting properties in excess. | A transcription factor that promotes cell proliferation |
| MYCL1 (LMYC) | 1p34.3 | Small cell lung cancer, adenocarcinoma of lung, neuroblastoma | |
| MYCN | 2p24.1 | Neuroblastomas | Overlaps with NMYC and is transcribed from opposite DNA strand |

TABLE 7-continued

List of selected oncogenes associated with human malignancy

| Gene Name | Gene Locus | Malignancies associated with | Comments |
|---|---|---|---|
| NCOA4 (ELE1, ARA70, PTC3) | 10q11.2 | Prostate cancer | Interacts with the androgen receptor in presence of dihydrotestosterone. |
| NF1 type genes | | | see tumor suppressors |
| NMYC | 2p24 | Neuroblastomas, retinoblastoma | Overlaps with MYCN and is transcribed from opposite DNA strand. Probably a DNA-binding protein. |
| NRAS | 1p13.2 | | see proto-oncogenes. |
| NTRK1 (IRK, TRKA) | 1q21-q22 | | see proto-oncogenes. |
| NUP214 (CAN, D9S46E) | 9q34.1 | NUP214/DEK fusion gene associated with acute myeloid leukemia, NUP214/ABL1 associated with T-cell acute lymphoblastic leukemia (T-ALL). | Codes for nucleoporin component of the vertebrate nuclear pore complex. |
| OVC | 9p24 | Ovarian adenocarcinoma | Abnormal in about 40% ovarian adenocarcinoma |
| TP53 (P53) | 17p13.1 | | see tumor suppressors |
| PALB2 | 16p12 | Breast cancer | see PALB2 |
| PAX3 (HUP2) STAT1 | 2q35 | Alveolar rhabdomyosarcoma | Transcriptions factor, causes some forms of Waardenburg syndrome and regulates RET. |
| PDGFB (SIS) | | | see proto-oncogenes |
| PIM genes | | | see proto-oncogenes |
| PML (MYL) | 15q22 | | see tumour suppressors |
| PMS (PMSL) genes | | | see tumour suppressors |
| PPM1D (WIP1) | 17q22-q23 | Breast cancer, Osteosarcoma | Codes for a serine/threonine protein phosphatase that attenuates apoptosis and facilitates transformation of primary cells in cooperation with RAS |
| PTEN (MMAC1) | 10q23.31 | | see tumor suppressors |
| PVT1 | 8q24 | Burkitt lymphoma | |
| RAF1 (CRAF) | 3p25 | Stomach cancer, renal cancer, glioblastoma, laryngeal cancer | A regulator of endothelial cell survival during angiogenesis. Activated RAF counteracts apoptosis by suppressing the activation of mammalian sterile 20-like kinase (MST2). |
| RB1 (RB) | 13q14.1-q14.2 | Retinoblastoma, osteogenic sarcoma, small cell carcinoma of lung, bladder cancer | see RB1 |
| RET | 10q11.2 | Multiple endocrine neoplasia type 2a and 2b and Medullary thyroid carcinoma | see RET |
| RRAS2 (TC21) | 11pter-p15.5 | Teratocarcinoma, ovarian cancer | Single point mutation activates its oncogene potential |
| ROS1 (ROS, MCF3) | 6q22 | Glioblastoma and probably others | ROS1/FIG fusion protein is a tyrosine kinase found in astrocytoma |
| SMAD type genes | | | see tumor suppressors |
| SMARCB1 (SNF5, INI1) | 22q11 | | see tumor suppressors |
| SMURF1 | 7q21.1-q31.1 | Pancreatic cancer | Codes for a HECT domain E3 ubiquitin ligase that regulates tumor cell plasticity and motility through degradation of RhoA |
| SRC (AVS) | 20q12-q13 | hepatic metastatic bowel cancer, colon cancer, leukemia | Intracellular communication regulator protein. Mutations are activating, transforming, tumorigenic, and metastasis-promoting |
| STAT1 | 2q32.2-q32.3 | Non-small cell lung cancer | see STAT1 |
| STAT3 | 17q21 | Epithelial cancers | Codes signal protein that induces cell transformation through a combined inhibition of apoptosis and cell-cycle activation |

TABLE 7-continued

List of selected oncogenes associated with human malignancy

| Gene Name | Gene Locus | Malignancies associated with | Comments |
| --- | --- | --- | --- |
| STAT5 | 17q11.2 | Permissive for a wide range of malignancies | Codes signal protein that induces cell transformation through a combined inhibition of apoptosis and cell-cycle activation |
| TDGF1 (CRGF) | 3p23-p21 | teratocarcinoma | Probably codes for signaling protein for mesoderm development |
| TGFBR2 | 3p22 | | see proto-oncogenes |
| THRA (ERBA, EAR7 etc) | | | see proto-oncogenes |
| TFG (TRKT3) | 3q11-q12 | Papillary thyroid carcinoma | Chimeric oncogene with NTRK1 proto-oncogene |
| TIF1 (TRIM24, TIF1A) | 7q32-q34 | Fusion genes associated with papillary thyroid carcinoma and myeloproliferative disorder. | Codes for transcriptional intermediary factor 1 |
| TNC (TN, HXB) | 9q33 | Neurofibromatosis type 1, Pancreatic cancer | see TNC |
| TRK | 1q21-q22 | | see proto-oncogenes |
| TUSC3 | 8p22 | | see tumor suppressors |
| USP6 (TRE2) | 17p13 | Multiple cancers | Codes for a ubiquitin-specific protease found only in primates |
| WNT1 (INT1) | 12q12-q13 | | see proto-oncogenes |
| WT1 | 11p13 | Wilms tumour, over expressed in breast and lung cancer, myelodysplastic syndrome and acute myeloid leukemia | A zinc finger DNA-binding protein acting as a transcriptional activator or repressor depending on intracellular context |
| VHL | 3p26-p25 | | see tumor suppressors |

TABLE 8

Tumor suppresor miRs that are downregulated in specific cancer types

| Cancer | miRNA |
| --- | --- |
| Bladder | mir-1; mir-101; mir-1180; mir-1236; mir-124-3p; mir-125b; mir-126; mir-1280; mir-133a; mir-133b; mir-141; mir-143; mir-144; mir-145; mir-155; mir-16; mir-18a; mir-192; mir-195; mir-200a; mir-200b; mir-200c; mir-203; mir-205; mir-214; mir-218; mir-23b; mir-26a; mir-29c; mir-320c; mir-34a; mir-370; mir-409-3p; mir-429; mir-451; mir-490-5p; mir-493; mir-576-3p; mir-99a |
| Brain (Astrocytoma, Glioblastoma, Glioma) | let-7g-5p; mir-100; mir-101; mir-106a; mir-124; mir-124a; mir-125a; mir-125a-5p; mir-125b; mir-127-3p; mir-128; mir-129; mir-136; mir-137; mir-139-5p; mir-142-3p; mir-143; mir-145; mir-146b-5p; mir-149; mir-152; mir-153; mir-195; mir-21; mir-212-3p; mir-219-5p; mir-222; mir-29b; mir-31; mir-3189-3p; mir-320; mir-320a; mir-326; mir-330; mir-331-3p; mir-340; mir-342; mir-34a; mir-376a; mir-449a; mir-483-5p; mir-503; mir-577; mir-663; mir-7; mir-7-5p; mir-873; let-7a; let-7f; mir-107; mir-122; mir-124-5p; mir-139; mir-146a; mir-146b; mir-15b; mir-16; mir-181a; mir-181a-1; mir-181a-2; mir-181b; mir-181b-1; mir-181b-2; mir-181c; mir-181d; mir-184; mir-185; mir-199a-3p; mir-200a; mir-200b; mir-203; mir-204; mir-205; mir-218; mir-23b; mir-26b; mir-27a; mir-29c; mir-328; mir-34c-3p; mir-34c-5p; mir-375; mir-383; mir-451; mir-452; mir-495; mir-584; mir-622; mir-656; mir-98; mir-124-3p; mir-181b-5p; mir-200b; mir-3189-3p |
| Breast | mir-193b; let-7a; let-7a-1; let-7a-2; let-7a-3; let-7b; let-7c; let-7d; let-7e; let-7f-1; let-7f-2; let-7g; let-7i; mir-100; mir-107; mir-10a; mir-10b; mir-122; mir-124; mir-1258; mir-125a-5p; mir-125b; mir-126; mir-127; mir-129; mir-130a; mir-132; mir-133a; mir-143; mir-145; mir-146a; mir-146b; mir-147; mir-148a; mir-149; mir-152; mir-153; mir-15a; mir-16; mir-17-5p; mir-181a; mir-1826; mir-183; mir-185; mir-191; mir-193a-3p; mir-195; mir-199b-5p; mir-19a-3p; mir-200a; mir-200b; mir-200c; mir-205; mir-206; mir-211; mir-216b; mir-218; mir-22; mir-26a; mir-26b; mir-300; mir-30a; mir-31; mir-335; mir-339-5p; mir-33b; mir-34a; mir-34b; mir-34c; mir-374a; mir-379; mir-381; mir-383; mir-425; mir-429; mir-450b-3p; mir-494; mir-495; mir-497; mir-502-5p; mir-517a; mir-574-3p; mir-638; mir-7; mir-720; mir-873; mir-874; mir-92a; mir-98; mir-99a; mmu-mir-290-3p; mmu-mir-290-5p |
| Cervical | mir-143; mir-145; mir-17-5p; mir-203; mir-214; mir-218; mir-335; mir-342-3p; mir-372; mir-424; mir-491-5p; mir-497; mir-7; mir-99a; mir-99b; mir-100; mir-101; mir-15a; mir-16; mir-34a; mir-886-5p; mir-106a; mir-124; mir-148a; mir-29a; mir-375 |

TABLE 8-continued

Tumor suppresor miRs that are downregulated in specific cancer types

| Cancer | miRNA |
| --- | --- |
| Colon/Colorectal | let-7a-1; let-7a-2; let-7a-3; let-7b; let-7c; let-7d; let-7e; let-7f-1; let-7f-2; let-7g; let-7i; mir-100; mir-101; mir-126; mir-142-3p; mir-143; mir-145; mir-192; mir-200c; mir-21; mir-214; mir-215; mir-22; mir-25; mir-302a; mir-320; mir-320a; mir-34a; mir-34c; mir-365; mir-373; mir-424; mir-429; mir-455; mir-484; mir-502; mir-503; mir-93; mir-98; mir-186; mir-30a-5p; mir-627; let-7a; mir-1; mir-124; mir-125a; mir-129; mir-1295b-3p; mir-1307; mir-130b; mir-132; mir-133a; mir-133b; mir-137; mir-138; mir-139; mir-139-5p; mir-140-5p; mir-148a; mir-148b; mir-149; mir-150-5p; mir-154; mir-15a; mir-15b; mir-16; mir-18a; mir-191; mir-193a-5p; mir-194; mir-195; mir-196a; mir-198; mir-199a-5p; mir-203; mir-204-5p; mir-206; mir-212; mir-218; mir-224; mir-24-3p; mir-26b; mir-27a; mir-28-3p; mir-28-5p; mir-29b; mir-30a-3p; mir-30b; mir-328; mir-338-3p; mir-342; mir-345; mir-34a-5p; mir-361-5p; mir-375; mir-378; mir-378a-3p; mir-378a-5p; mir-409-3p; mir-422a; mir-4487; mir-483; mir-497; mir-498; mir-518a-3p; mir-551a; mir-574-5p; mir-625; mir-638; mir-7; mir-96-5p; mir-202-3p; mir-30a; mir-451 |
| Endometrial | mir-101; mir-130a; mir-130b; mir-134; mir-143; mir-145; mir-152; mir-205; mir-223; mir-301a; mir-301b; mir-30c; mir-34a; mir-34c; mir-424; mir-449a; mir-543; mir-34b |
| Hematologic (Leukemia, Lymphoma, Myeloma) | mir-125b; mir-138; mir-15a; mir-15b; mir-16; mir-16-1; mir-16-1-3p; mir-16-2; mir-181a; mir-181b; mir-195; mir-223; mir-29b; mir-34b; mir-34c; mir-424; mir-10a; mir-146a; mir-150; mir-151; mir-155; mir-2278; mir-26a; mir-30e; mir-31; mir-326; mir-564; mir-27a; let-7b; mir-124a; mir-142-3p; let-7c; mir-17; mir-20a; mir-29a; mir-30c; mir-720; mir-107; mir-342; mir-34a; mir-202; mir-142-5p; mir-29c; mir-145; mir-193b; mir-199a; mir-214; mir-22; mir-137; mir-197 |
| Kidney | mir-1; mir-145; mir-1826; mir-199a; mir-199a-3p; mir-203; mir-205; mir-497; mir-508-3p; mir-509-3p; let-7a; let-7d; mir-106a*; mir-126; mir-1285; mir-129-3p; mir-1291; mir-133a; mir-135a; mir-138; mir-141; mir-143; mir-182-5p; mir-200a; mir-218; mir-28-5p; mir-30a; mir-30c; mir-30d; mir-34a; mir-378; mir-429; mir-509-5p; mir-646; mir-133b; let-7b; let-7c; mir-200c; mir-204; mir-335; mir-377; mir-506 |
| Liver (Hepatocellular Carcinoma) | mir-137; mir-138; mir-139; mir-139-5p; mir-140-5p; mir-141; mir-142-3p; mir-143; mir-144; mir-145; mir-146a; mir-148a; mir-148b; mir-150-5p; mir-15b; mir-16; mir-181a-5p; mir-185; mir-188-5p; mir-193b; mir-195; mir-195-5p; mir-197; mir-198; mir-199a; mir-199a-5p; mir-199b; mir-199b-5p; mir-200a; mir-200b; mir-200c; mir-202; mir-203; mir-204-3p; mir-205; mir-206; mir-20a; mir-21; mir-21-3p; mir-211; mir-212; mir-214; mir-217; mir-218; mir-219-5p; mir-22; mir-223; mir-26a; mir-26b; mir-29a; mir-29b-1; mir-29b-2; mir-29c; mir-302b; mir-302c; mir-30a; mir-30a-3p; mir-335; mir-338-3p; mir-33a; mir-34a; mir-34b; mir-365; mir-370; mir-372; mir-375; mir-376a; mir-377; mir-422a; mir-424; mir-424-5p; mir-433; mir-4458; mir-448; mir-450a; mir-451; mir-485-5p; mir-486-5p; mir-497; mir-503; mir-506; mir-519d; mir-520a; mir-520b; mir-520c-3p; mir-582-5p; mir-590-5p; mir-610; mir-612; mir-625; mir-637; mir-675; mir-7; mir-877; mir-940; mir-941; mir-98; mir-99a; mir-132; mir-31 |
| Lung | mir-1297; mir-141; mir-145; mir-16; mir-200a; mir-200b; mir-200c; mir-29b; mir-381; mir-409-3p; mir-429; mir-451; mir-511; mir-99a; let-7a-1; let-7a-2; let-7a-3; let-7b; let-7c; let-7d; let-7e; let-7f-1; let-7f-2; let-7g; let-7i; mir-1; mir-101; mir-133b; mir-138; mir-142-5p; mir-144; mir-1469; mir-146a; mir-153; mir-15a; mir-15b; mir-16-1; mir-16-2; mir-182; mir-192; mir-193a-3p; mir-194; mir-195; mir-198; mir-203; mir-217; mir-218; mir-22; mir-223; mir-26a; mir-26b; mir-29c; mir-33a; mir-34a; mir-34b; mir-34c; mir-365; mir-449a; mir-449b; mir-486-5p; mir-545; mir-610; mir-614; mir-630; mir-660; mir-7515; mir-9500; mir-98; mir-99b; mir-133a; let-7a; mir-100; mir-106a; mir-107; mir-124; mir-125a-3p; mir-125a-5p; mir-126; mir-126*; mir-129; mir-137; mir-140; mir-143; mir-146b; mir-148a; mir-148b; mir-149; mir-152; mir-154; mir-155; mir-17-5p; mir-181a-1; mir-181a-2; mir-181b; mir-181b-1; mir-181b-2; mir-181c; mir-181d; mir-184; mir-186; mir-193b; mir-199a; mir-204; mir-212; mir-221; mir-224; mir-27a; mir-27b; mir-29a; mir-30a; mir-30b; mir-30c; mir-30d; mir-30d-5p; mir-30e-5p; mir-32; mir-335; mir-338-3p; mir-340; mir-342-3p; mir-361-3p; mir-373; mir-375; mir-4500; mir-4782-3p; mir-497; mir-503; mir-512-3p; mir-520a-3p; mir-526b; mir-625*; mir-96 |
| Melanoma | let-7b; mir-101; mir-125b; mir-1280; mir-143; mir-146a; mir-146b; mir-155; mir-17; mir-184; mir-185; mir-18b; mir-193b; mir-200c; mir-203; mir-204; mir-205; mir-206; mir-20a; mir-211; mir-218; mir-26a; mir-31; mir-33a; mir-34a; mir-34c; mir-376a; mir-376c; mir-573; mir-7-5p; mir-9; mir-98 |
| Oral Cancer | let-7d; mir-218; mir-34a; mir-375; mir-494; mir-100; mir-124; mir-1250; mir-125b; mir-126; mir-1271; mir-136; mir-138; mir-145; mir-147; mir-148a; mir-181a; mir-206; mir-220a; mir-26a; mir-26b; mir-29a; mir-32; mir-323-5p; mir-329; mir-338; mir-370; mir-410; mir-429; mir-433; mir-499a-5p; mir-503; mir-506; mir-632; mir-646; mir-668; mir-877; mir-9 |

TABLE 8-continued

Tumor suppresor miRs that are downregulated in specific cancer types

| Cancer | miRNA |
|---|---|
| Ovarian | let-7i; mir-100; mir-124; mir-125b; mir-129-5p; mir-130b; mir-133a; mir-137; mir-138; mir-141; mir-145; mir-148a; mir-152; mir-153; mir-155; mir-199a; mir-200a; mir-200b; mir-200c; mir-212; mir-335; mir-34a; mir-34b; mir-34c; mir-409-3p; mir-411; mir-429; mir-432; mir-449a; mir-494; mir-497; mir-498; mir-519d; mir-655; mir-9; mir-98; mir-101; mir-532-5p; mir-124a; mir-192; mir-193a; mir-7 |
| Pancreatic | mir-101; mir-1181; mir-124; mir-1247; mir-133a; mir-141; mir-145; mir-146a; mir-148a; mir-148b; mir-150*; mir-150-5p; mir-152; mir-15a; mir-198; mir-203; mir-214; mir-216a; mir-29c; mir-335; mir-34a; mir-34b; mir-34c; mir-373; mir-375; mir-410; mir-497; mir-615-5p; mir-630; mir-96; mir-132; let-7a; let-7a-1; let-7a-2; let-7a-3; let-7b; let-7c; let-7d; let-7e; let-7f-1; let-7f-2; let-7g; let-7i; mir-126; mir-135a; mir-143; mir-144; mir-150; mir-16; mir-200a; mir-200b; mir-200c; mir-217; mir-218; mir-337; mir-494; mir-98 |
| Prostate | let-7a-3p; let-7c; mir-100; mir-101; mir-105; mir-124; mir-128; mir-1296; mir-130b; mir-133a-1; mir-133a-2; mir-133b; mir-135a; mir-143; mir-145; mir-146a; mir-154; mir-15a; mir-187; mir-188-5p; mir-199b; mir-200b; mir-203; mir-205; mir-212; mir-218; mir-221; mir-224; mir-23a; mir-23b; mir-25; mir-26a; mir-26b; mir-29b; mir-302a; mir-30a; mir-30b; mir-30c-1; mir-30c-2; mir-30d; mir-30e; mir-31; mir-330; mir-331-3p; mir-34a; mir-34b; mir-34c; mir-374b; mir-449a; mir-4723-5p; mir-497; mir-628-5p; mir-642a-5p; mir-765; mir-940 |
| Retinoblastoma | mir-101; mir-183; mir-204; mir-34a; mir-365b-3p; mir-486-3p; mir-532-5p |

The invention claimed is:

1. A recombinant herpes simplex virus (HSV) comprising at least one copy of a micro-RNA (miR)-124 target sequence inserted into the ICP4 locus of the recombinant HSV genome and at least one copy of a miR-122 target sequence inserted into the ICP27 locus of the recombinant HSV genome.

2. The recombinant HSV of claim 1, wherein the at least one miR-124 target sequence and the at least one miR-122 target sequence are inserted into the 5' untranslated region (UTR) or 3' UTR of the ICP4 locus or ICP27 locus, respectively.

3. The recombinant HSV of claim 1, wherein two or more miR-124 target sequences are inserted into the ICP4 locus of the recombinant HSV genome.

4. The recombinant HSV of claim 1, wherein two or more miR-122 target sequences are inserted into the ICP27 locus of the recombinant HSV genome.

5. The recombinant HSV of claim 1, further comprising at least one additional miR target sequence incorporated into the ICP4 locus, wherein the additional miR target sequence is a sequence other than a miR-124 or a miR-122 target sequence.

6. The recombinant HSV of claim 1, further comprising at least one additional miR target sequence incorporated into the ICP27 locus, wherein the additional miR target sequence is a sequence other than a miR-124 or a miR-122 target sequence.

7. The recombinant HSV of claim 1, further comprising a heterologous polynucleotide sequence encoding a human IL-12 protein inserted into the recombinant HSV genome.

8. The recombinant HSV of claim 1, wherein four miR-124 target sequences are inserted into the ICP4 locus of the recombinant HSV genome.

9. The recombinant HSV of claim 1, wherein four miR-122 target sequences are inserted into the ICP27 locus of the recombinant HSV genome.

10. The recombinant HSV of claim 1, further comprising a deletion in the internal repeat joint region such that the recombinant HSV genome comprises one copy of each of the ICP0, γ34.5, LAT, and ICP4 genes.

11. A composition comprising the recombinant HSV of claim 1 and a pharmaceutically-acceptable carrier.

12. A recombinant herpes simplex virus (HSV) comprising:
at least one copy of a micro-RNA (miR)-124 target sequence inserted into the ICP4 locus of the recombinant HSV genome and at least one copy of a miR-122 target sequence inserted into the ICP27 locus of the recombinant HSV genome;
at least one additional miR target sequence incorporated into the ICP4 locus or the ICP27, wherein the additional miR target sequence is a sequence other than a miR-124 or a miR-122 target sequence; and
a heterologous polynucleotide sequence encoding a human IL-12 protein.

13. The recombinant HSV of claim 12, wherein the at least one miR-124 target sequence and the at least one miR-122 target sequence are inserted into the 5' untranslated region (UTR) or 3' UTR of the ICP4 locus or the ICP27 locus, respectively.

14. The recombinant HSV of claim 12, wherein two or more miR-124 target sequences are inserted into the ICP4 locus of the recombinant HSV genome.

15. The recombinant HSV of claim 12, wherein two or more miR-122 target sequences are inserted into the ICP27 locus of the recombinant HSV genome.

16. The recombinant HSV of claim 12, wherein four miR-124 target sequences are inserted into the ICP4 locus of the recombinant HSV genome.

17. The recombinant HSV of claim 12, wherein four miR-122 target sequences are inserted into the ICP27 locus of the recombinant HSV genome.

18. The recombinant HSV of claim 12, further comprising a deletion in the internal repeat joint region such that the recombinant HSV genome comprises one copy of each of the ICP0, γ34.5, LAT, and ICP4 genes.

19. A composition comprising the recombinant HSV of claim 12 and a pharmaceutically-acceptable carrier.

20. A method of treating a cancer in a subject in need thereof,
comprising administering a recombinant herpes simplex virus (HSV) to the subject, wherein the recombinant HSV comprises:
at least one copy of a micro-RNA (miR)-124 target sequence inserted into the ICP4 locus of the recombinant HSV genome and at least one copy of a miR-122 target sequence inserted into the ICP27 locus of the recombinant HSV genome; and
a heterologous polynucleotide sequence encoding a human IL-12 protein,
thereby treating the cancer.

21. The method of claim 20, wherein the subject is a human.

22. The method of claim 20, wherein the cancer is selected from the group consisting of melanoma, colon cancer, pancreatic cancer, head and neck cancer, breast cancer, liver cancer, and lung cancer.

23. The method of claim 20, wherein the recombinant HSV further comprises at least one additional miR target sequence incorporated into the ICP4 locus, wherein the additional miR target sequence is a sequence other than a miR-124 or a miR-122 target sequence.

24. The method of claim 20, wherein the recombinant HSV further comprises at least one additional miR target sequence incorporated into the ICP27 locus, wherein the additional miR target sequence is a sequence other than a miR-124 or a miR-122 target sequence.

25. The method of claim 20, wherein the recombinant HSV further comprises a deletion in the internal repeat joint region such that the recombinant HSV genome comprises one copy of each of the ICP0, γ34.5, LAT, and ICP4 genes.

26. A method of treating a cancer in a subject in need thereof,
comprising administering a recombinant herpes simplex virus (HSV) to the subject, wherein the recombinant HSV comprises at least one copy of a micro-RNA (miR)-124 target sequence inserted into the ICP4 locus of the recombinant HSV genome and at least one copy of a miR-122 target sequence inserted into the ICP27 locus of the recombinant HSV genome, thereby treating the cancer.

27. The method of claim 26, wherein the subject is a human.

28. The method of claim 26, wherein the recombinant HSV further comprises at least one additional miR target sequence incorporated into the ICP4 locus, wherein the additional miR target sequence is a sequence other than a miR-124 or a miR-122 target sequence.

29. The method of claim 26, wherein the recombinant HSV further comprises at least one additional miR target sequence incorporated into the ICP27 locus, wherein the additional miR target sequence is a sequence other than a miR-124 or a miR-122 target sequence.

30. The method of claim 26, wherein the recombinant HSV further comprises a heterologous polynucleotide sequence encoding a human IL-12 protein.

31. The method of claim 26, wherein the recombinant HSV further comprises a deletion in the internal repeat joint region such that the recombinant HSV genome comprises one copy of each of the ICP0, γ34.5, LAT, and ICP4 genes.

* * * * *

SEQUENCE LISTING

```
<160> NUMBER OF SEQ ID NOS: 5

<210> SEQ ID NO 1
<211> LENGTH: 9
<212> TYPE: PRT
<213> ORGANISM: Artificial Sequence
<220> FEATURE:
<223> OTHER INFORMATION: Mutated gB glycoprotein
<220> FEATURE:
<221> NAME/KEY: MISC_FEATURE
<222> LOCATION: (5)..(5)
<223> OTHER INFORMATION: Position of gB substitution mutation, D to N

<400> SEQUENCE: 1

Val Tyr Pro Tyr Xaa Glu Phe Val Leu
1               5

<210> SEQ ID NO 2
<211> LENGTH: 9
<212> TYPE: PRT
<213> ORGANISM: Artificial Sequence
<220> FEATURE:
<223> OTHER INFORMATION: Mutated gB glycoprotein
<220> FEATURE:
<221> NAME/KEY: MISC_FEATURE
<222> LOCATION: (6)..(6)
<223> OTHER INFORMATION: Position of gB substitution mutation, A to T

<400> SEQUENCE: 2

Lys Leu Asn Pro Asn Xaa Ile Ala Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Mutated gB glycoprotein
<220> FEATURE:
<221> NAME/KEY: MISC_FEATURE
<222> LOCATION: (5)..(5)
```

```
<223> OTHER INFORMATION: Position of gB substitution mutation, S to N

<400> SEQUENCE: 3

Ile Thr Thr Val Xaa Thr Phe Ile Asp
1               5

<210> SEQ ID NO 4
<211> LENGTH: 9
<212> TYPE: PRT
<213> ORGANISM: Artificial Sequence
<220> FEATURE:
<223> OTHER INFORMATION: Mutated gB glycoprotein
<220> FEATURE:
<221> NAME/KEY: MISC_FEATURE
<222> LOCATION: (5)..(5)
<223> OTHER INFORMATION: Position of gH substitution mutation, N to K

<400> SEQUENCE: 4

Val Asp Thr Asp Xaa Thr Gln Gln Gln
1               5

<210> SEQ ID NO 5
<211> LENGTH: 9
<212> TYPE: PRT
<213> ORGANISM: Artificial Sequence
<220> FEATURE:
<223> OTHER INFORMATION: Mutated gB glycoprotein
<220> FEATURE:
<221> NAME/KEY: MISC_FEATURE
<222> LOCATION: (5)..(5)
<223> OTHER INFORMATION: Position of gH substitution mutation, A to V

<400> SEQUENCE: 5

Val Pro Ser Thr Xaa Leu Leu Leu Phe
1               5
```